(12) United States Patent
Fearon et al.

(10) Patent No.: US 8,003,115 B2
(45) Date of Patent: Aug. 23, 2011

(54) CHIMERIC IMMUNOMODULATORY COMPOUNDS AND METHODS OF USING THE SAME

(75) Inventors: Karen L. Fearon, Lafayette, CA (US); Dino Dina, Oakland, CA (US); Stephen F. Tuck, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 340 days.

(21) Appl. No.: 11/891,624

(22) Filed: Aug. 10, 2007

(65) Prior Publication Data
US 2008/0181909 A1    Jul. 31, 2008

Related U.S. Application Data

(62) Division of application No. 10/176,883, filed on Jun. 21, 2002, now Pat. No. 7,255,868.

(60) Provisional application No. 60/299,883, filed on Jun. 21, 2001, provisional application No. 60/375,253, filed on Apr. 23, 2002.

(51) Int. Cl.
*A61K 45/00* (2006.01)
(52) U.S. Cl. .................................... 424/280.1
(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. |
| 4,587,329 A | 5/1986 | Tomalia et al. |
| 4,650,675 A | 3/1987 | Borel et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,162,515 A | 11/1992 | Conrad et al. |
| 5,171,264 A | 12/1992 | Merrill |
| 5,338,532 A | 8/1994 | Tomalia et al. |
| 5,391,723 A | 2/1995 | Priest |
| 5,453,496 A | 9/1995 | Caruthers et al. |
| 5,460,831 A | 10/1995 | Kossovsky et al. |
| 5,484,596 A | 1/1996 | Hanna, Jr. et al. |
| 5,495,006 A | 2/1996 | Climie et al. |
| 5,552,391 A | 9/1996 | Coutts et al. |
| 5,627,025 A | 5/1997 | Steinman et al. |
| 5,661,025 A | 8/1997 | Szoka, Jr. et al. |
| 5,663,153 A | 9/1997 | Hutcherson et al. |
| 5,668,265 A | 9/1997 | Nadeau et al. |
| 5,674,683 A | 10/1997 | Kool |
| 5,677,439 A | 10/1997 | Weis et al. |
| 5,679,555 A | 10/1997 | Goodchild et al. |
| 5,723,335 A | 3/1998 | Hutcherson et al. |
| 5,795,582 A | 8/1998 | Wright |
| 5,849,719 A | 12/1998 | Carson et al. |
| 5,856,462 A | 1/1999 | Agrawal |
| 5,912,332 A | 6/1999 | Agrawal et al. |
| 5,948,648 A | 9/1999 | Khan et al. |
| 6,031,091 A | 2/2000 | Arnold, Jr. et al. |
| 6,090,791 A | 7/2000 | Sato et al. |
| 6,117,657 A | 9/2000 | Usman et al. |
| 6,127,173 A | 10/2000 | Eckstein et al. |
| 6,156,501 A | 12/2000 | McGall et al. |
| 6,160,103 A | 12/2000 | Marchand et al. |
| 6,172,208 B1 | 1/2001 | Cook |
| 6,174,872 B1 | 1/2001 | Carson et al. |
| 6,177,414 B1 | 1/2001 | Tomalia et al. |
| 6,183,959 B1 | 2/2001 | Thompson |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,426,334 B1 | 7/2002 | Agrawal et al. |
| 6,426,336 B1 | 7/2002 | Carson et al. |
| 6,429,199 B1 | 8/2002 | Krieg et al. |
| 6,476,000 B1 | 11/2002 | Agrawal |
| 6,524,613 B1 | 2/2003 | Steer et al. |
| 6,531,591 B1 | 3/2003 | Fensholdt |
| 6,589,940 B1 | 7/2003 | Raz et al. |
| 6,683,167 B2 | 1/2004 | Metelev et al. |
| 6,815,429 B2 | 11/2004 | Agrawal |
| 7,045,609 B2 | 5/2006 | Metelev et al. |
| 7,074,768 B2 | 7/2006 | Agrawal |
| 7,115,579 B2 | 10/2006 | Agrawal |
| 7,157,437 B2 | 1/2007 | Van Nest |

(Continued)

FOREIGN PATENT DOCUMENTS

CA    2 423 487 A1    4/2002

(Continued)

OTHER PUBLICATIONS

Agrawal, S. et al. (1986). "Efficient Methods for Attaching Non-Radioactive Labels to the 5' ends of Synthetic Oligodeoxyribonucleotides," *Nucleic Acids Res.* 14(15):6227-6245.
Agrawal, S. et al. (2001). "Antisense and/or Immunostimulatory Oligonucleotide," *Current Cancer Drug Target* 1(3):197-209.
Agrawal, S. (2002). "Medicinal Chemistry and Therapeutic Potential of CpG DNA," *Trends In Molecular Medicine* 8(3):114-121.
Ahmeida, E.T.S. Ben et al. (1993). "Immunopotentiation of Local and Systemic Humoral Immune Responses by ISCOMs, Liposomes and FCA: Role in Protection Against Influenza A in Mice," *Vaccine* 11(13):1302-1309.
Altmann, S. et al. (1995). "NMR Studies of DNA Duplexes Singly Cross-Linked by Different Synthetic Linkers," *Nucleic Acids Res.* 23(23):4827-4835.
Amendment in Response to Non-Final Office Action mailed on Feb. 10, 2006, for U.S. Appl. No. 10/177,826, filed Jun. 21, 2002, 28 pages.
Amendment in Response to Non-Final Office Action mailed on Oct. 10, 2006, for U.S. Appl. No. 10/176,883, filed Jun. 21, 2002, 14 pages.

(Continued)

*Primary Examiner* — Nita M Minnifield
*Assistant Examiner* — Brian J Gangle
(74) *Attorney, Agent, or Firm* — Morrison & Foerster LLP

(57) ABSTRACT

The invention provides immunomodulatory compounds and methods for immunomodulation of individuals using the immunomodulatory compounds.

6 Claims, 11 Drawing Sheets

U.S. PATENT DOCUMENTS

| | | |
|---|---|---|
| 7,223,398 B1 | 5/2007 | Tuck et al. |
| 7,250,403 B2 | 7/2007 | Van Nest et al. |
| 7,255,868 B2 | 8/2007 | Fearon et al. |
| 7,262,286 B2 | 8/2007 | Kandimalla et al. |
| 7,276,489 B2 | 10/2007 | Agrawal et al. |
| 7,329,648 B2 | 2/2008 | Agrawal |
| 7,354,907 B2 | 4/2008 | Agrawal et al. |
| 7,407,944 B2 | 8/2008 | Agrawal et al. |
| 7,517,862 B2 | 4/2009 | Agrawal et al. |
| 7,560,436 B2 | 7/2009 | Raz et al. |
| 7,569,553 B2 | 8/2009 | Krieg |
| 7,576,066 B2 | 8/2009 | Krieg |
| 7,605,138 B2 | 10/2009 | Krieg |
| 7,625,872 B2 | 12/2009 | Fearon |
| 7,723,500 B2 | 5/2010 | Krieg et al. |
| 7,785,610 B2 | 8/2010 | Fearon et al. |
| 2002/0132995 A1 | 9/2002 | Agrawal et al. |
| 2002/0137714 A1 | 9/2002 | Kandimalla et al. |
| 2003/0049266 A1 | 3/2003 | Fearon et al. |
| 2003/0059773 A1 | 3/2003 | Van Nest et al. |
| 2003/0133988 A1 | 7/2003 | Fearon et al. |
| 2003/0175731 A1 | 9/2003 | Fearon et al. |
| 2003/0199466 A1 | 10/2003 | Fearon et al. |
| 2003/0212026 A1 | 11/2003 | Krieg et al. |
| 2003/0225016 A1 | 12/2003 | Fearon et al. |
| 2004/0006034 A1 | 1/2004 | Raz et al. |
| 2004/0097719 A1 | 5/2004 | Agrawal et al. |
| 2004/0132677 A1 | 7/2004 | Fearon et al. |
| 2004/0136948 A1 | 7/2004 | Fearon |
| 2004/0156825 A1 | 8/2004 | Agrawal et al. |
| 2004/0198680 A1 | 10/2004 | Krieg |
| 2004/0198685 A1 | 10/2004 | Agrawal et al. |
| 2005/0009773 A1 | 1/2005 | Kandimalla et al. |
| 2005/0026861 A1 | 2/2005 | Kandimalla et al. |
| 2005/0130911 A1 | 6/2005 | Uhlmann et al. |
| 2005/0130918 A1 | 6/2005 | Agrawal et al. |
| 2005/0222072 A1 | 10/2005 | Wang et al. |
| 2005/0256073 A1 | 11/2005 | Lipford et al. |
| 2006/0014713 A1 | 1/2006 | Agrawal et al. |
| 2006/0019909 A1 | 1/2006 | Agrawal et al. |
| 2006/0019918 A1 | 1/2006 | Agrawal et al. |
| 2006/0019919 A1 | 1/2006 | Agrawal et al. |
| 2006/0025365 A1 | 2/2006 | Agrawal et al. |
| 2006/0074040 A1 | 4/2006 | Kandimalla et al. |
| 2006/0094681 A1 | 5/2006 | Agrawal et al. |
| 2006/0098680 A1 | 5/2006 | Kelesoglu et al. |
| 2006/0211641 A1 | 9/2006 | Agrawal et al. |
| 2006/0217328 A1 | 9/2006 | Kandimalla et al. |
| 2006/0241076 A1 | 10/2006 | Uhlmann et al. |
| 2006/0287261 A1 | 12/2006 | Agrawal et al. |
| 2006/0287262 A1 | 12/2006 | Agrawal et al. |
| 2007/0049550 A1 | 3/2007 | Fearon et al. |
| 2007/0066554 A1 | 3/2007 | Krieg et al. |
| 2007/0089883 A1 | 4/2007 | Patton et al. |
| 2007/0173469 A1 | 7/2007 | Agrawal et al. |
| 2007/0179103 A1 | 8/2007 | Agrawal et al. |
| 2007/0219153 A1 | 9/2007 | Kandimalla et al. |
| 2008/0152662 A1 | 6/2008 | Agrawal et al. |
| 2009/0017075 A1 | 1/2009 | Van Nest et al. |
| 2009/0068208 A1 | 3/2009 | Hessel et al. |
| 2009/0196915 A1 | 8/2009 | Van Nest et al. |
| 2009/0317480 A1 | 12/2009 | Fearon et al. |

FOREIGN PATENT DOCUMENTS

| | | |
|---|---|---|
| EP | 0 313 219 A2 | 4/1989 |
| EP | 0 313 219 A3 | 4/1989 |
| EP | 0 313 219 B1 | 4/1989 |
| EP | 0 468 520 A2 | 1/1992 |
| EP | 0 468 520 A3 | 1/1992 |
| EP | 1 393 745 A1 | 7/2003 |
| JP | 11-507027 A | 6/1999 |
| JP | 2004-509970 A | 4/2004 |
| WO | WO-89/02439 A1 | 3/1989 |
| WO | WO-91/10426 A1 | 7/1991 |
| WO | WO-93/02093 A1 | 2/1993 |
| WO | WO-95/07073 A1 | 3/1995 |
| WO | WO-96/02555 A1 | 2/1996 |
| WO | WO-96/40197 A1 | 12/1996 |
| WO | WO-96/40273 A2 | 12/1996 |
| WO | WO-96/40273 A3 | 12/1996 |
| WO | WO-97/28259 A1 | 8/1997 |
| WO | WO-97/29757 A1 | 8/1997 |
| WO | WO-97/46251 A1 | 12/1997 |
| WO | WO-98/16247 A1 | 4/1998 |
| WO | WO-98/18810 A1 | 5/1998 |
| WO | WO-98/37919 A1 | 9/1998 |
| WO | WO-98/40100 A1 | 9/1998 |
| WO | WO-98/52581 A1 | 11/1998 |
| WO | WO-98/52581 C2 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55495 B1 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/11275 C2 | 3/1999 |
| WO | WO-99/22770 A1 | 5/1999 |
| WO | WO-99/33488 A2 | 7/1999 |
| WO | WO-99/33488 A3 | 7/1999 |
| WO | WO-99/33868 A2 | 7/1999 |
| WO | WO-99/33868 A3 | 7/1999 |
| WO | WO-99/45964 A1 | 9/1999 |
| WO | WO-99/51259 A2 | 10/1999 |
| WO | WO-99/51259 A3 | 10/1999 |
| WO | WO-99/56755 A1 | 11/1999 |
| WO | WO-99/58118 A2 | 11/1999 |
| WO | WO-99/58118 A3 | 11/1999 |
| WO | WO-99/61056 A2 | 12/1999 |
| WO | WO-99/61056 A3 | 12/1999 |
| WO | WO-99/61056 C2 | 12/1999 |
| WO | WO-99/62923 A2 | 12/1999 |
| WO | WO-99/62923 A3 | 12/1999 |
| WO | WO-00/06588 A1 | 2/2000 |
| WO | WO-00/06588 B1 | 2/2000 |
| WO | WO-00/16804 A1 | 3/2000 |
| WO | WO-00/21556 A1 | 4/2000 |
| WO | WO-00/21556 C2 | 4/2000 |
| WO | WO-00/34231 A1 | 6/2000 |
| WO | WO-00/34296 A2 | 6/2000 |
| WO | WO-00/34296 A3 | 6/2000 |
| WO | WO-00/54803 A2 | 9/2000 |
| WO | WO-00/54803 A3 | 9/2000 |
| WO | WO-00/61151 A2 | 10/2000 |
| WO | WO-00/61151 A3 | 10/2000 |
| WO | WO-00/67023 A1 | 11/2000 |
| WO | WO-00/67787 A2 | 11/2000 |
| WO | WO-00/67787 A3 | 11/2000 |
| WO | WO-00/75105 A1 | 12/2000 |
| WO | WO-01/12223 A2 | 2/2001 |
| WO | WO-01/12223 A3 | 2/2001 |
| WO | WO-01/12804 A2 | 2/2001 |
| WO | WO-01/12804 A3 | 2/2001 |
| WO | WO-01/15726 A2 | 3/2001 |
| WO | WO-01/15726 A3 | 3/2001 |
| WO | WO-01/22972 A2 | 4/2001 |
| WO | WO-01/22972 A3 | 4/2001 |
| WO | WO-01/22972 C2 | 4/2001 |
| WO | WO-01/22990 A2 | 4/2001 |
| WO | WO-01/22990 A3 | 4/2001 |
| WO | WO-01/35991 A2 | 5/2001 |
| WO | WO-01/35991 A3 | 5/2001 |
| WO | WO-01/45750 A1 | 6/2001 |
| WO | WO-01/51500 A1 | 7/2001 |
| WO | WO-01/54720 A1 | 8/2001 |
| WO | WO-01/55341 A2 | 8/2001 |
| WO | WO-01/55341 A3 | 8/2001 |
| WO | WO-01/55370 A2 | 8/2001 |
| WO | WO-01/55370 A3 | 8/2001 |
| WO | WO-01/55370 C2 | 8/2001 |
| WO | WO-01/62207 A2 | 8/2001 |
| WO | WO-01/62207 A3 | 8/2001 |
| WO | WO-01/68077 A2 | 9/2001 |
| WO | WO-01/68077 A3 | 9/2001 |
| WO | WO-01/68078 A2 | 9/2001 |
| WO | WO-01/68078 A3 | 9/2001 |

| | | |
|---|---|---|
| WO | WO-01/68103 A2 | 9/2001 |
| WO | WO-01/68103 A3 | 9/2001 |
| WO | WO-01/68103 C2 | 9/2001 |
| WO | WO-01/68116 A2 | 9/2001 |
| WO | WO-01/68116 A3 | 9/2001 |
| WO | WO-01/68117 A2 | 9/2001 |
| WO | WO-01/68117 A3 | 9/2001 |
| WO | WO-01/68143 A2 | 9/2001 |
| WO | WO-01/68143 A3 | 9/2001 |
| WO | WO-01/68144 A2 | 9/2001 |
| WO | WO-01/68144 A3 | 9/2001 |
| WO | WO-01/72123 A1 | 10/2001 |
| WO | WO-01/72123 C2 | 10/2001 |
| WO | WO-01/76642 A1 | 10/2001 |
| WO | WO-01/83503 A2 | 11/2001 |
| WO | WO-01/83503 A3 | 11/2001 |
| WO | WO-01/93902 A2 | 12/2001 |
| WO | WO-01/93902 A3 | 12/2001 |
| WO | WO-02/09766 A1 | 2/2002 |
| WO | WO-02/26757 A2 | 4/2002 |
| WO | WO-02/26757 A3 | 4/2002 |
| WO | WO-02/27315 A2 | 4/2002 |
| WO | WO-02/27315 A3 | 4/2002 |
| WO | WO-02/052002 A2 | 7/2002 |
| WO | WO-02/052002 A3 | 7/2002 |
| WO | WO-02/069369 A2 | 9/2002 |
| WO | WO-02/069369 A3 | 9/2002 |
| WO | WO-02/074922 A2 | 9/2002 |
| WO | WO-02/074922 A3 | 9/2002 |
| WO | WO-03/000922 A2 | 1/2003 |
| WO | WO-03/000922 A3 | 1/2003 |
| WO | WO-03/014316 A2 | 2/2003 |
| WO | WO-03/014316 A3 | 2/2003 |
| WO | WO-03/035836 A2 | 5/2003 |
| WO | WO-03/057822 A2 | 7/2003 |
| WO | WO-03/057822 A3 | 7/2003 |
| WO | WO-03/057822 C2 | 7/2003 |
| WO | WO-2004/047742 A2 | 6/2004 |
| WO | WO-2004/047742 A3 | 6/2004 |
| WO | WO-2004/064782 A2 | 8/2004 |
| WO | WO-2004/064782 A3 | 8/2004 |
| WO | WO-2004/103301 A2 | 12/2004 |
| WO | WO-2004/103301 A3 | 12/2004 |
| WO | WO-2005/009355 A2 | 2/2005 |
| WO | WO-2005/009355 A3 | 2/2005 |
| WO | WO-2005/081847 A2 | 9/2005 |
| WO | WO-2005/081847 A3 | 9/2005 |
| WO | WO-2007/084237 A2 | 7/2007 |
| WO | WO-2007/084237 A3 | 7/2007 |
| WO | WO-2008/073661 A2 | 6/2008 |
| WO | WO-2008/073661 A3 | 6/2008 |
| WO | WO-2010/002940 A2 | 1/2010 |
| WO | WO-2010/002940 A3 | 1/2010 |

OTHER PUBLICATIONS

Amendment in Response to Non-Final Office Action mailed on Nov. 3, 2006, for U.S. Appl. No. 10/177,826, filed Jun. 21, 2002, 29 pages.
Amendment in Response to Final Office Action mailed on Feb. 26, 2007, for U.S. Appl. No. 10/176,883 filed, Jun. 21, 2002, 18 pages.
Amendment in Response to Non-Final Office Action submitted on Jul. 7, 2008, for U.S. Appl. No. 10/328,578, filed Dec. 23, 2002, 9 pages.
Aramaki, Yukihito et al. (1995). "Interferon-γ Inductive Effect of Liposomes as an Immunoadjuvant," *Vaccine* 13(18):1809-1814.
Asanuma, H. et al. (1995). "Cross-Protection Against Influenza Virus Infection in Mice Vaccinated by Combined Nasal-Subcutaneous Administration," *Vaccine* 13(1):3-5.
Asensio, J. L. et al. (1998). "Comparison of the Solution Structures of Intramolecular DNA Triple Helices Containing Adjacent and Non-Adjacent CG-C+ Triplets," *Nucleic Acids Res.* 26(16):3677-3686.
Atherton, E. et al. (Jul. 1981). "Synthesis of a 21-Residue Fragment of Human Proinsulin by the Polyamide Solid Phase Method," *Hoppe-Seylers Z. Physiol. Chem.* 372:833-839.
Ballas, Z. K. et al. (1996). "Induction of NK Activity in Murine and Human Cells by CpG Motifs in Oligodeoxynucleotides and Bacterial DNA," *J. Immunol.* 157:1840-1845.

Bartley, J. P. et al. (1997). "Solution Conformation of an Intramolecular DNA Triplex Containing a Nonnucleotide Linker: Comparison with the DNA Duplex," *Biochemistry* 36(47):14502-14511.
Beaucage, S. L. (1993). "Oligodeoxyribonucleotide Synthesis," Chapter 3 In *Protocols for Oligonucleotides and Analogs, Synthesis and Properties*, Sudhir Agrawal, ed., Humana Press, Totowa, NJ., 20:33-61.
Benoit, R. et al. (1987). "Peptides. Strategies for Antibody Production and Radioimmunoassays,"*In Neuromethods*, Alan A. Boulton et al., eds., Humana Press, Clifton, NJ 6:43-72.
Bhagat, L. et al. (2003). "CpG Penta and Hexadeoxyribonucleotides as Potent Immunomodulatory Agents," *Biochem. and Biophys. Res. Comm.* 300(4):853-861.
Bischoff, R. et al. (1987). "Introduction of 5'-Terminal Functional Groups into Synthetic Oligonucleotides for Selective Immobilization," *Anal. Bioch.* 164:336-344.
Blanks, R. et al. (1988). "An Oligodeoxynucleotide Affinity Column for the Isolation of Sequence Specific DNA Binding Proteins," *Nucleic Acids Res.* 16(21):10283-10299.
Bohle, B. et al. (1999). "Oligodeoxynucleotides Containing CpG Motifs Induce IL-12, IL-18, and IFN-γ Production in Cells from Allergic Individuals and Inhibit IgE Snthesis In Vitro," *Eur. J. Immunol*, 29:2344-2353.
Borel, H. et al. (1990). "A Novel Technique to Link Either Proteins or Peptides to Gammaglobulin to Construct Tolerogens," *Immunol. Methods* 126:159-168.
Borel, Y. et al. (1995). "Food Allergens Transformed Into Tolerogens," *Int. Arch. Allergy Immunol.* 107:264-267.
Borel, Y. et al. (1996). "Parenteral and Oral Administation of Tolerogens: Protein-IgG Conjugats," Vol. 778 in Oral Tolerance: Mechanisms an Applications *Ann. N.Y. Acad. Sci.* pp. 80-87.
Boujard, N. et al. (Jun. 1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *P NAS USA* 90:5728-5731.
Bousquet, Y. et al. (1999). "Molecular Mechanisms of the Adsorption of a Model Protein (Human Serum Albumin) on Poly(Methylidene Malonate 2.1.2) Nanoparticles," *Pharm. Res.* 16(1):141-147.
Branda, R. F. et al. (1993). "Immune Stimulation by an Antisense Oligomer Complementary to the *rev* Gene of HIV-1," *Biochem. Pharmacol.* 45(10):2037-2043.
Branda, R. F. et al. (1996). "Amplification of Antibody Production by Phosphorothioate Oligodeoxynucleotides," *J. Lab. Clin. Med.* 138(3):329-338.
Braun, R. P. and Lee, J. S. (1988). "Immunogenic Duplex Nucleic Acids are Nuclease Resistant," *J. Immunol.* 141(6):2084-2089.
Brazolot-Milan, C. L. et al. (1998). "CpG DNA Can Induce Strong Th1 Humoral and Cell-Mediated Immune Responses Against Hepatitis B Surface Antigen in Young Mice," *P NAS USA* 95:15553-15558.
Breiteneder, H. et al. (1989). "The Gene Coding for the Major Birch Pollen Allergen *Betvl*, is Highly Homologous to a Pea Disease Resistance Response Gene," *EMBO J.* 8(7):1935-1938.
Broide, D. et al. (1998). "Immunostimulatory DNA Sequences Inhibit IL-5, Eosinophilic Inflammation, and Airway Hyperresponsiveness in Mice," *J. Immunol.* 161:7054-7062.
Broide, D. et al. (1999). "DNA-Based Immunization for Asthma," *Int. Arch. Allergy Immunol.* 118:453-456.
Carson, D. A. et al. (1997). "Oligonucleotide Adjuvants for T Helper 1 (Th1)-Specific Vaccination,"*J. Exp. Med.* 186(10):1621-1622.
Chace, J. H. et al. (1997). "Bacterial DNA-Induced NK Cell IFN-γ Production is Dependent on Macrophage Secretin of IL-12," *Clin. Immunol. and Immunopathol.* 84(2):185-193.
Charoenvit, Y. et al. (2004). "CEL-1000-A Peptide With Adjuvant Activity for Th1 Immune Responses," *Vaccine* 22:2368-2373.
Chaturvedi, S. et al. (1996). "Stabilization of Triple-Stranded Oligonucleotide Complexes: Use of Probes Containing Alternating Phosphodiester and Stereo-Uniform Cationic Posphoramidate Linkages," *Nucleic Acids Res.* 24(12):2318-2323.
Chavany, C. et al. (1992). "Polyalkylcyanoacrylate Nanoparticles as Polymeric Carriers for Antisense Oligonucleotides," *Pharm. Res.* 9(4):441-449.

Chavany, C. et al. (1994). "Adsorption of Oligonucleotides onto Polyisohexylcyanoacrylate Nanoparticles Protects Them Against Nucleases and Increases their Cellular Uptake." *Pharm. Res.* 11(9):1370-1378.

Chem Genes Corporation. Bio Technology Products & Manufacturer of DNA-RNA Intermediates Section 10: Chromophores and Ligands.

Chen, Z. et al. (1999). "Enhanced Protection Against a Lethal Influenza Virus Challenge by Immunization with Both Hemagglutinin- and Neuraminidase-Expressing DNAs," *Vaccine* 17:653-659.

Cho, H. J. et al. (May 2000). "Immunostimulatory DNA-Based Vaccines Induce Cytotoxic Lymphocyte Activity by a T-Helper Cell-Independent Mechanism," *Nature Biotechnol.* 18:509-514.

Chu, R. S. et al. (Nov. 1997). "CpG Oligodeoxynucleotides Act as Adjuvants that Switch on T Helper 1 (Th1) Immunity," *J. Exp. Med.* 186(10):1623-1631.

Cload, S. T. et al. (1991)."Polyether Tethered Oligonucleotide Probes," *J. Am. Chem. Soc.* 113(16):632-6326.

Coligan, J. E. et al., eds. (1998). *Current Protocols in Immunology*, vol. 1, John Wiley & Sons, Inc: pp. 1-9.

Connolly, B. A. (1985). "Chemical Synthesis of Oligonucleotides Containing a Free Sulphydryl Group and Subsequent Attachment of Thiol Specific Probes," *Nucleic Acids Res.* 13(12):4485-4502.

Connolly, B. A. (1987). "The Synthesis of Oligonucleotides Containing a Primary Amino Group at the 5'-Terminus," *Nucleic Acids Res.* 15(7):3131-3139.

Corey, D. R. et al. (Dec. 1987). "Generation of a Hybrid Sequence-Specific Single-Stranded Deoxyribonuclease," *Science* 238:1401-1403.

Cowdery, J. S. et al. (1996). "Bacterial DNA Induces NK Cells to Produce IFN-γ In Vivo and Increases the Toxicity of Lipopolysaccharides." *J. Immunol.* 156:4570-4575.

Dagneaux, C. et al. (1996). "Parallel and Antiparallel A-A-T Intramolecular Tipe Helices," *Nucleic Acids. Res.* 24(22):4506-4512.

De Martino, M. et al. (Aug. 1999). "Low IgG3 and High IgG4 Subclass Levels in Children with Advanced Human Immunodeficiency Virus-Type 1 Infection and Elevated IgE Levels," *Annals of Allergy, Asthma & Immunol,* 3:160-164.

Douglas, S. J. et al. (1987). "Nanoparticles in Drug Delivery," *Crit. Rev. Ther. Drug. Carrier Syst.* 3(3):233-261.

Dumas, V. et al. (1995). "Induction of Tolerance by Administration of Hapten-Immunoglobulin Conjugates is Associated with Decreased Il-2 and IL-4 Production," *Arch. Dermatol. Res.* 287:123-128.

Durand, M. et al. (1990). "Circular Dichroism Studies of an Oligodeoxyribonucleotide Containing a Hairpin Loop Made of a Hexaethylene Glycol Chain: Conformation and Stability," *Nucleic Acids Res.* 18(21):6353-6359.

Elkins, K. L. et al. (1999). "Bacterial DNA Containing CpG Motifs Stimulates Lymphocyte—Dependent Protection of Mice Against Lethal Infection with Intracellular Bacteria," *J. Immunol.* 162:2291-2298.

Final Office Action mailed on Dec. 26, 2006, for U.S. Appl. No. 10/176,883, filed Jun. 21, 2002, 10 pages.

Final Office Action mailed on Sep. 21, 2007, for U.S. Appl. No. 10/177,826, filed Jun. 21, 2002, 15 pages.

Fornadley, J. (1998). "Allergy Immunotherapy," *Otolaryngol. Clin. North Am.* 31(1):111-127.

Gais, H.-J. et al. (1991). "Structure of a Free, Unassociated Alkyl-Substituted α-Sulfonyl Carbanion: Isolation and X-ray Crystal Structure Analysis of the Inclusive Lithium Ctyptate (Me$_2$CSO$_2$Ph) (Li[2.1.1]cryptad)," *J. Am. Chem. Soc.* 113:4002-4003.

Gall, J. G. et al. (1969). "Formation and Detection of RNA-DNA Hybrid Molecules in Cytological Preparations," *PNAS USA* 63:378-383.

Gamper, H. B. et al. (1993). "Facile Preparation of Nuclease Resistant 3' Modified Oligodeoxynucleotides," *Nucleic Acids Research* 21(1):145-150.

Gao, H. et al. (1995). "Circularization of Oligonucleotides by Disulfide Bridge Formation," *Nucleic Acids Res.* 23(11):2025-2029.

Geoghegan, K.F. et al. (1992). "Site-Directed Conjugation of Nonpeptide Groups to Peptides and Proteins Via Periodate Oxidatio of a 2-Amino Alcohol. Application to Modification at N-Terminal Serine," *Bioconjug. Chem.* 3(2):138-146.

Glenn Research Products for DNA Research. "5'-OR 3'-Modifiers" Catalog Table of Contents (p. 1) and pp. 27-29.

Glen Research, 2000 Catalog, "Spacer Modifiers, Dendrimers" located at <www.glenres.com>, Table of Content, pp. 35-36.

Gnanou, Y. et al. (1988). "Synthesis of Star-Shaped Poly(ethylene oxide)," *Makromol.Chem.* 189:2885-2892.

Godard, G. et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

Goodchild, J. (May/Jun. 1990). "Conjugates of Oligonucleotides and Modified Oligonucleotides: A Review of Their Synthesis and Properties," *Bioconjug. Chem.* 1(3):165-187.

Govorkova, E. A. et al. (1997). "Cross-Protection of Mice Immunized with Different Influenza A (H2) Strains and Challenged with Viruses of the Same HA Subtype," *Acta Virol.* 41:251-257.

Grabarek, Z. et al. (1990). "Zero-Length Crosslinking Procedure with the Use of Active Esters," *Anal. Biochem.* 185:131-135.

Gramzinski, R. A. et al. (Feb. 1998). "Immune Response to a Hepatitis B DNA Vaccine in *Aotus* Monkeys: A Comparison of Vaccine Formulation, Route, and Method of Administration," *Mol. Med.* 4:109-118.

Granoff, D. M. et al. (1993). "Effect of Immunity to the Carrier Protein on Antibody Responses to *Haemophilus influenzae* type B Conjugate Vaccines," *Vaccine* 11: Suppl.1:46-51.

Hagiwara, A. et al. (1987). "A New Drug-Delivery-System of Anticancer Agents: Activated Carbon Particles Adsorbing Anticancer Agents," In Vivo 1:241-252.

Haralambidis, J. et al. (1990a). "The Synthesis of Polyamide-Oligonucleotide Conjugate Molecules," *Nucleic Acids Res.* 18(3):493-499.

Haralambidis, J. et al. (1990b). "The Preparation of Polyamide-Oligonucleotide Probes Containing Multiple Non-Radioactive Labels," *Nucleic Acids Res.* 18(3):501-505.

Hartmann, G. et al. (2000). "Delineation of a CpG Phosphorothioate Oligodeoxynucleotide for Activating Primate Immune Responsed In Vitro and InVivo," *J. Immunol.* 164(3):1617-1624.

Hendry, P et al. (1994). "Using Linkers to Investigate the Spatial Separation of the Conserved Nucleotides $A_9$ and $G_{1,2}$ in the Hammerhead Ribozyme," *Biochimica et Biophysica Acta* 1219:405-412.

Hengge, U. R. et al. (Oct. 2001). "Topical Immunomodulators—Progress Towards Treating Inflammation, Infection, and Cancer," *Lancet Infectious Diseases* 1:189-198.

Horner, A. A. et al. (1998). "Immunostimulatory DNA is a Potent Mucosal Adjuvant," *Cell. Immunol.* 190:77-82.

Inman, J. K. (Feb. 1975). "Thymus-Independent Antigens: The Preparation of Convalent, Hapten-Ficall Conjugates," *J. Immunol.* 114(2,Part1):704-709.

Iyer, R. P. et al. (1990). "The Automated Synthesis of Sulfar-Containing Oligodeoxyribonucleotides Using 3 *H*-1,2-Benxodtihiol-3-one 1,1-Dioxide as a Sulfur-Transfer Reagent," *J. Org. Chem.* 55(15):4693-4699.

Jäger, A. et al. (1988). "Oligonucleotide *N*-Alkylphosphoramidates: Synthesis and Binding to Polynucleotides," *Biochem.* 27(19):7237-7246.

Jakob, T. et al. (1998). "Activation of Cutaneous Dendritic Cells by CpG-Containing Oligodeoxynucleotides: A Role for Dendritic Cells in the Augmentation of Th1 Responses by Immunostimulatory DNA," *J. Immunol.* 151:3042-3049.

Jäschke, A. et al. (1993). "Automated Incorporation of Polyethylene Glycol into Synthetic Oligonucleotides," *Tetraheddron Letters* 34(2);301-304.

Kandimalla, E. R.et al. (2001). "Effect of Chemical Modifications of Cytosine and Guanine in a CpG-Motif of Oligonucleotides: Structure-Immunostimulatory Activity Relationships" *Bioorg. Med. Chem.* 9:807-813.

Kandimalla, E. R. et al. (2002). "Conjugation of Ligands at the 5'-end of CpG DNA Affects Immunostimulatory Activity," *Bioconj. Chem.* 13(5):966-974.

Kandimalla, E. R. (2002). "Towards Optimal Design of Second-Generation Immunodulatory Oligonucleotides," *Curr. Opin. Mol. Therap.* 4(2):122-129.

Kandimalla, E. R. et al. (2003). "Divergent Synthetic Nucleotide Motif Recognition Pattern: Design and Development of Potent Immunomodulatory Oligodeoxyribonucleotide Agents With Distinct Cytokine Induction Profiles," *Nucleic Acids Research* 31(9):2393-2400.

Kandimalla, E. R. et al. (2003). "Secondary Structures in CpG Oligonucleotides Affect Immunostimulatory Activity," *Biochemical and Biophysical Research Communications* 306:948-953.

Kataoka, T. et al. (1992). "Antitumor Activity of Synthetic Oligonucleotides with Sequences from cDNA Encoding Proteins of *Mycobacterium bovis* BCG," *Jpn. J. Cancer Res.* 83:244-247.

Kessler, C. (Dec. 1992). "Nonradioactive Labeling Methods for Nucleic Acids,". Chapter 2 *In Nonisotopic DNA Probe Techniques*, Larry J. Kricka, ed., Academic Press, Inc.: pp. 29-92.

Kikuta, K. et al. (1990). "Cross-Protection Against Influenza B Type Virus Infection by Intranasal Inoculation of the HA Vaccines Combined with Cholera Toxin B Subunit," *Vaccine* 9:595-599.

Kimura, Y. et al. (1994). "Binding of Oligoguanylate to Scavenger Receptors is Required for Oligonucleotides to Augment NK Cell Activity and Induce IFN." *J. Biochem.* 116(5):991-994.

Kline, J. N. et al. (Mar. 1997). "Immune Redirection by CpG Oligonucleotides Conversion of a Th2 Response to a Th1 Response in a Murine Model of Asthma," *J. Invest. Med.* 45(3):282A.

Klinman, D. M. et al. (Apr. 1996). "CpG Motifs Present in Bacterial DNA Rapidly Induce Lymphocytes to Secrete Interleukin 6, Interleukin 12, and Interferon γ," *PNAS USA* 93:2879-2883.

Klinman, D. M. et al. (1997). "Contribution of CpG Motifs to the Immunogenicity of DNA Vaccines," *J. Immunol.* 158:3635-3639.

Kodihalli, S. et al. (May 1997). "Cross-Protection Among Lethal H5N2 Influenza Viruses Induced by DNA Vaccine to the Hemagglutinin," *J. Virol.* 71(5):3391-3396.

Kovarik, J. et al. (1999). "CpG Oligodeoxynucleotides Can Circumvent the Th2 Polarization of Neonatal Responoses to Vaccines But May Fail to Fully Redirect Th2 Responses Established by Neonatal Priming," *J. Immunol.* 162:1611-1617.

Kremsky, J. N. et al. (1987). "Immobilization of DNA via Oligonucleotides Containing an Aldehyde or Carboxylic Acid Group at the 5'Terminus," *Nucleic Acids Res.* 15(7)2891-2909.

Krieg, A. M. et al. (Oct. 1989). "A Role for Endogenous Retroviral Sequences in the Regulaton of Lymphocyte Activation," *J. Immunol.* 143(6):2448-2451.

Krieg, A. M. et al. (Apr. 1995). "CpG Motifs in Bacterial DNA Trigger Direct B-Cell Activation," *Nature* 374:546-549.

Krieg, A. M. (Feb. 1996). "Lymphocyte Activation by CpG Dinucleotide Motifs in Prokaryotic DNA," *Trends Microbiol.* 4(2):73-77.

Krieg, A. M. et al. (1996). "Oligodeoxynucleotide Modifications Determine the Magnitude of B Cell Stimulation by CpG Motifs," *Antisense Nucleic Acid Drug Dev.* 6:133-139.

Krieg, A. M. (1998). "Leukocyte Stimulation by Oligodeoxynucleotides," Chapter 24 *In Applied Antisense Oligonucleotide Technology*, C.A. Stein and Arthur M. Krieg, eds., Wiley-Liss, Inc.: pp. 431-448.

Krieg, A. M. et al. (Jan. 1998a). "The Role of CpG Dinucleotides in DNA Vaccines," *Trends Microbiol.* 6(1):23-27.

Krieg, A. M. et al. (1998b). "CpG Dna Induces Sustained IL12 Expression In Vivo and Resistance to *Listeria monocytogenes* Challenge," *J. Immunol.* 161:2428-2434.

Krieg, A. M. et al. (Oct. 1998c). "Sequence Motifs in Adenoviral DNA Block Immune Activation by Stimulatory CpG Motifs," *PNAS USA* 95:12631-12636.

Krieg, A. M. (Feb. 1999). "CpG DNA: A Novel Immunomodulator," *Trends Microbiol.* 7(2):64-65.

Krieg, A. M. (1999). "Mechanisms and Applications of Immune Stimulatory CpG Oligodeoxynucleotides," *Biochimica et Biophysica Acta* 1489:107-116.

Krug, A. et al. (2001). "Identification of CpG Oligonucleotide Sequences With High Induction of IFN-α/β in Plasmadytoid Dendritic Cells," *Eur. J. Immunol.* 31:2154-2163.

Lambert, G. et al. (1998). "Effect of Polyisobutylcyanoacrylate Nanoparticles and Lipofectin® Loaded with Oligonucleotides on Cell Viability and PKCα Neosynthesis in HepG2 Cells," *Biochimie* 80:969-976.

Langenberg, A. G. M. (Jun. 1995). "A Recombinant Glycoprotein Vaccine for Herpes Simplex Type 2: Safety and Efficacy," *Ann. Intern. Med.* 122(12):889-898.

Latimer, L. J. P. et al. (1995). "Specificity of Monoclonal Antibodies Produced Against Phosphorothioate and Ribo Modified DNAs," *Mol. Immunol.* 32(14/15):1057-1064.

Lea, I. A. et al., (1996). "Cloning and Sequencing of cDNAs Encoding the Human Sperm Protein, Sp17," *Biochim. et Biophys. Acta* 1307:263-266.

Leclerc, C. et al. (1997). "The Preferential Induction of a Th1 Immune Response by DNA-Based Immunization is Mediated by the Immunostimulatory Effect of Plasmid DNA," *Cell. Immunol.* 179:97-106.

Lee, A. C. J. et al. (1980). "A Method for Preparing β-hCG COOH Peptide-Carrier Conjugates of Predictable Composition," *Mol. Immunol.* 17:749-756.

Lee, S. W. et al. (Oct. 2000). "Effects of a Hexameric Deoxyriboguanosine Run Conjugation into CpG Oligodeoxynucleotides on Their Immunostimulatory Potentials," *J. Immunol.* 165(7):3631-3639.

Li, S.F.Y.ed. (1992). "Electrolyte Systems" Chapter 5 *In Capillary Electrophoresis, Principles and Practice and Application*. Elsevier Science Publishers, Amsterdxam, The Netherlands, pp. 201-226.

Liang, H. et al. (1996). "Activation of Human B Cells by Phosphorothioate Oligodeoxynucleotides," *J. Clin. Invest.* 98(5):1119-1129.

Lipford, G. B. et al. (1997a). "CpG-Containing Synthetic Oligonucleotides Promote B and Cytotoxic T Cell Responses to Protein Antigen: A New Class of Vaccine Adjuvants," *Eur. J. Immunol.* 27:2340-2344.

Lipford, G. B. et al. (1997b). "Immunostimulatory DNA: Sequence-Dependent Production of Potentially Harmful or Useful Cytokines," *Eur. J. Immunol.* 27:3420-3426.

Liu, H-M. et al. (1998). "Immunostimulatory CpG Oligodeoxynucleotides Enhance the Immune Response to Vaccine Strategies Involving Granulocyte-Macrophage Colony-Stimulating Factor," *Blood* 92(10):3730-3736.

Ma, M. Y-X. et al. (1993). "Design and Synthesis of RNA Miniduplexes via a Synthetic Linker Approach," *Biochemistry* 32(7):1751-1758.

Ma, M. Y-X. et al. (1993). "Design and Synthesis of RNA Miniduplexes Via A Synthetic Linker Approach.2. Generation of covalently Closed, Double-Stranded Cyclic HIV-1 TAR RNA Analogs with High Tat-Binding Affinity," *Nucleic Acids Res.* 21(11):2585-2589.

MacFarlane, D. E. et al. (1997). "Unmethylated CpG-Containing Oligonucleotides Inhibit Apoptosis in WEHI 231 B Lymphocytes Induced by Several Agents: Evidence for Blockade of Apoptosis at a Distal Signalling Step," *Immunology* 91:586-593.

Manzel, L. et al. (1999). "Lack of Immune Stimulation by Immobilized CpG-Oligonucleotide," *Antisense Nucl. Acid Drug Dev.* 9:459-464.

Marshall, J. D. et al. (2003). "Novel Chimeric Immunomodulatory Compounds Containing Short CpG Oligodeoxyribonucleotides Have Differential Activities in Human Cell," *Nucleic Acids Research* 31(17):5122-5133.

Marshall, J. D. et al. (Jun. 2003). "Identification of a Novel CpG DNA Class and Motif that Optimally Stimulate B Cell and Plasmacytoid Dendritic Cell Functions," *J. Leukoc. Biol.* 73:781-792.

Martin-Orozco, E. et al. (1999). "Enhancement of Antigen-Presenting Cell Surface Molecules Involved in Cognate Interactions by Immunostimulatory DNA Sequences," *Int. Immunol.* 11(7):1111-1118.

Matteucci, M. (1997). "Oligonucleotide Analogs: An Overview," *In Oligonucleotides as Therapeutic Agents*. D.J. Chadwick and G. Cardew, eds., John Wiley and Sons. New York, NY., pp. 5-18.

Mbawuike, I. N. et al. (1994). "Influenza: A Subtype Cross-Protection After Immunization of Outbred Mice with a Purified Chimeric $NS_1/HA_2$ Influenza Virus Protein," *Vaccine* 12(14):1340-1348.

McCluskie, M. J. et al. (1998). "CpG DNA is a Potent Enhancer of Systemic and Mucosal Immune Responses Against Hepatitis B Surface Antigen with Intransal Administration to Mice," *J. Immunol.* 151:4463-4466.

McCurdy, S. et al. (1991)."Deoxyoligonucleotides with Inverted Polarity: Aynthesis and Use in Triple-Helix Formation," *Nucleosides & Nucleotides* 10(1-3):287-290.

Miller, P. S. et al. (1971). "Syntheses and Properties of Adenine and Thymine Nucleoside Alkyl Phosphotriesters, the Neutral Analogs of Dinucleoside Monophosphates," *JACS* 93(24):6647-6665.

Mitragotri, S. et al. (Aug. 1995). "Ultrasound-Mediated Transdermal Protein Delivery," *Science* 269:850-853.

Mojcik, C. F. et al. (May 1993). "Administration of a Phosphorothioate Oligonucleotide Antisense to Murine Endogenous Retroviral MCF Env Causes Immune Effects In Vivo in a Sequence-Specific Manner," *Clin. Immunol. and Immunopathol.* 67(2):130-136.

Moldoveanu, Z. et al. (1998). "CpG DNA, A Novel Immune Enhancer for Systemic and Mucosal Immunization with Influenza Virus," *Vaccine* 16(11/12):1216-1224.

Nelson, J. S. et al. (1996). "Incorporation of a Non-Nucleotide Bridge into Hairpin Oligonucleotides Capable of High-Affinity Binding to the Rev Protein of HIV-1," *Biochemistry* 35(16):5339-5344.

Nelson, J. S. et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.

Nelson, P. S. et al. (1989). "Bifunctional Oligonucleotide Probes Synthesized Using a Novel CPG Support are able to Detect Single Base Pair Mutations," *Nucleic Acids Res.* 17(18):7187-7194.

Non-Final Office Action mailed on Aug. 11, 2005, for U.S. Appl. No. 10/177,826, filed Jun. 21, 2002, 29 pages.

Non-Final Office Action mailed on Apr. 7, 2006, for U.S. Appl. No. 10/176,883, filed Jun. 21, 2002, 14 pages.

Non-Final Office Action mailed on May 3, 2006, for U.S. Appl. No. 10/177,826, filed Jun. 21, 2002, 23 pages.

Non-Final Office Action mailed on Jul. 28, 2006, for U.S. Appl. No. 10/623,371, filed Jul. 18, 2003, 9 pages.

Non-Final Office Action mailed on Feb. 5, 2008, for U.S. Appl. No. 10/328,578, filed Dec. 23, 2002, 7 pages.

Non-Final Office Action mailed on Jul. 9, 2008, for U.S. Appl. No. 10/177,826, filed Jun. 21, 2002, 14 pages.

Notice of Allowance mailed on Apr. 4, 2007, for U.S. Appl. No. 10/176,883, filed Jun. 21, 2002, 5 pages.

O'Shannessy, D. J. et al. (1985). "Specific Conjugation Reactions of the Oligosaccharide Moieties of Immunoglobulins," *J. Applied Biochem.* 7:347-355.

Ono, A. et al. (1991). "DNA Triplex Formation of Oligonucleotide Analogues Consisting of Linker Groups and Octamer Segments That Have Opposite Sugar-Phosphate Backbone Polarites," *Biochemistry* 30(41):9914-9921.

Pertmer, T. M. et al. (Sep. 1996). "Influenza Virus Nucleoprotein-Specific Immunoglobulin G Subclass and Cytokine Responses Elicited by DNA Vaccination are Dependent on the Route of Vector DNA Delivery," *J. Virol.* 70(9):6119-6125.

Peyrottes, S. et al. (1996). "Oligodeoxynucleoside Phosphoramidates ($P-NH_2$): Synthesis and Thermal Stability of Duplexes with DNA and RNA Targets," *Nucleic Acids Res.* 24(10):1841-1848.

Pichyangkul, S. et al. (Jan. 2001). "Whole Blood Cultures to Assess the Immunostimulatory Activities of CpG Oligodeoxynucleotides," *J. Immunol. Methods* 247(1-2):83-94.

Pierce Enodogen Brands of QB Perbio (2001-2002). "Bringing You the Best Life Science Tools for Protein Chemistry Immunology & Proteomics," Catalog. p. 324-325 and 329.

Pils, W. et al. (May 2000). "Flexible Non-Nucleotide Linkers as Loop Replacements in Short Double Helical RNAs," *Nucleic Acids Res.* 28(9):1859-1863.

Pisetsky, D. S. et al. (1994). "Stimulation of Murine Lymphocyte Proliferation by a Phosphorothioate Oligonucleotide with Antisense Activity for Herpes Simplex Virus." *Life Sci.* 54(2):101-107.

Pisetsky, D. S. et al. (1995). "Immunological Properties of Bacterial DNA," *Ann. N. Y. Acad. Sci.* 772:152-163.

Pisetsky, D. S. (Jan. 1996a). "The Immunologic Properties of DNA," *J. Immunol.* 156(2):421-423.

Pisetsky, D. S. (Oct. 1996b). "Immune Activation by Bacterial DNA: A New Genetic Code," *Immunity* 5:303-310.

Pisetsky, D. S. et al. (1998). "The Influence of Base Sequence on the Immunological Properties of Defined Oligonucleotides," *Immunopharmacology* 40:199-208.

Raz, E. et al. (Sep. 1994). "Intradermal Gene Immunization: The Possible Role of DNA Uptake in the Induction of Cellular Immunity to Viruses," *PNAS USA* 91:9519-9523.

Raz, E. et al. (May 1996). "Preferential Induction of a $Th_1$ Immune Response and Inhibition of Specific IgE Antibody Formation by Plasmid DNA Immunization," *PNAS USA* 93:5141-5145.

Redford, T. W. et al. (1998). "Cyclosporin A Enhances IL-12 Production by CpG Motifs in Bacterial DNA and Synthetic Oligodeoxynucleotides." *J. Immunol.* 151:3930-3935.

Rein, D. et al. (1993). "New Developments in Synthesis of Star Polymers with Poly(ethylene oxide) Arms," *Acta Polymer* 44:225-229.

Reynolds, M. A. et al. (1996). "Antisense Oligonucleotides Containing an Internal, Non-Nucleotied-Based Linker Promote Site-Specific Cleavage of RNA." *Nucleic Acids Res.* 24(4):760-765.

Rhodes, A. J. et al., eds. (1953). "Fundamental Characteristics and Technical Methods and Apparatus" *In Textbook of Virology for Students and Practioners of Medicine.* 2nd ed., Williams and Wilkins Company, Baltimore, MD. pp. 66-69.

Richardson, P. L. and Schepartz, A. (1991). "Tethered Oligonucleotide Probes. A Strategy for the Recognition of Structured RNA," *J. Am. Chem. Soc.* 113:5109-5111.

Roget, A. et al. (1989). "Synthesis and Use of Labelled Nucleoside Phosphoramidite Building Blocks Bearing a Reporter Group: Biotinyl, Dinitrophenyl, Pyrenyl and Dsnsyl," *Nucleic Acids Res.* 17(19):7643-7651.

Romagnani, S. (Jul. 2000). "T-Cell Subsets (Th1 versus Th2)," *Ann. Allergy, Asthma, and Immunol.* 85(1):9-18.

Roman, M. et al. (Aug. 1997). "Immunostimulatory DNA Sequences Function as T Helper-1-Promoting Adjuvants," *Nature Med.* 3(3):849-854.

Ruth, J. L. (1991). "Oligodeoxynucleotides with Reporter Groups Attached to the Base," Chapter 11 *In Oligonucleotides and Analogues: A Practical Approach*, F. Eckstein, ed., IRL Press: pp. 255-282.

Salunkhe, M. et al. (1992). "Control of Folding and Binding of Oligonucleotides by Use of a Nonnucleotide Linker," *J. Am. Chem. Soc.* 114(23):8768-8772.

Sato, Y. et al. (Jul. 1996). "Immunostimulatory DNA Sequences Necessary for Effective Intradermal Gene Immunization," *Science* 273:352-354.

Scaringe, S. A.et al. (1990). "Chemical Synthesis of Biologically Active Oligoribonucleotides Using β-Cyanoethyl Protected Ribonucleoside Phosphramidites," *Nucleic Acids Res.* 18(18):5433-5441.

Schacht, E. et al. (Oct. 1996). "Biomedical Applications of Degradable Polyphosphazenes," *Biotechnol. Bioeng.* 52:102-108.

Scheerens, H. et al. (2001). "Characterzation of Chemokines and Chemokine Receptors in Two Murine Models of Inflammatory Bowel Disease: $IL-10^{-/-}$ Mice and $Rag\ 2^{-/-}$ Mice Reconstituted with $CD4^+\ CD45RB^{high}$ T Cells," *Eur. J. Immunology* 31:1465-1474.

Scherle, P. A. et al. (Oct. 1986). "Functional Analysis of Influenza Specific- Helper T Cell Clones In Vivo," *J. Exp. Med.* 164:1114-1128.

Scherle, P. A. et al. (Jun. 1988). "Differential Ability of B Cells Specific for External vs. Internal Influenza Virus Proteins to Respond to Help from Influenza Virus-Specific T-cell Clones In Vivo," *PNAS USA* 85:4446-4450.

Scheule, R. K. (Nov. 2000). "The Role of CpG Motifs in Immunostimulation and Gene Therapy," *Adv. Drug Deliv. Rev.* 44(2-3):119-134.

Schroeder, U. et al. (1998). "Efficacy of Oral Dalargin-Loaded nanoparticle Delivery Across the Blood-Brain Barrier," *Peptides* 19(4):777-780.

Schultz, R. G. et al. (Jul. 1996). "Oligo-2'-Fluoro-2'-Deoxynucleotide N3'→P5' Phosphoramidates: Synthesis and Properties," *Nucleic Acids Res.* 24(15):2966-2973.

Schwartz, D. A. et al. (1997). "CpG Motifs in Bacterial DNA Cause Inflammation in the Lower Respiratory Tract." *J. Clin. Invest.* 100(1):68-73.

Seela, F. et al. (1987). "Oligodeoxyribonucleotides Containing 1,3-Propanediol as Nucleoside Substitute," *Nucleic Acids Res.* 15(7):3113-3129.

Shearwater Polymers, Inc. Catalog Polyethylene Glycol Derivatives (1997-1998). Functionalized Biocompatible Polymers for Research and Pharmaceuticals. Star PEGs and Branched PEGs. p. 8.

Shimada, S. et al. (Aug. 1986). "In Vivo Augmentation of Natural Killer Cell Activity with a Deoxyribonucleic Acid Fraction of BCG," *Jpn. J. Cancer Res.* 77:808-816.

Sinha, N. D. et al. (1991). "Oligonucleotides with Reporter Groups Attached to the 5'-Terminus," Chapter 8 In *Oligonucleotide Analogues: A practical Approach*, F. Eckstein, ed., IRL Press: pp. 185-210.

Shchepinov et al. (1999). "Oligonucleotide Dendrimers: Stable Nano-Structures," *Nucleic Acid Research* 27(15):3035-3041.

Sonehara, K. et al. (1996). "Hexamer Palindromic Oligonucleotides with 5'-CG-3' Motif(s) Induce Production of Interferon," *J. Interferon and Cytokine Res.* 16:799-803.

Sparwasser, T. et al. (1997). "Macrophages Sense Pathogens Via DNA Motifs: Induction of Tumor Necrosis Factor-$\alpha$-Mediated Shock," *Eur. J. Immunol.* 27:1671-1679.

Spiegelberg, H.L. et al. (1998). "Inhibition of IgE Formation and Allergic Inflammation by Allergen Gene Immunization and by CpG Motif Immunostimulatory Oligodeoxynucleotides," *Allergy* 53:93-97.

Spiegelberg, H. L. et al. (1999). "Inhibition of Allergic Inflammation in the Lung by Plasmid DNA Allergen Immunization," *Pediatr. Pulmonol. Suppl.* 18:118-121.

Stacey, K. J. et al. (1996). "Macrophages Ingest and are Activated by Bacterial DNA," *J. Immunol.* 157:2116-2122.

Staros, J. V. et al. (1986). "Enhancement by *N*-Hydroxysulfosuccinimide of Water-Soluble Carbodiimide-Mediated Coupling Reactions," *Anal. Biochem.* 156:220-222.

Stein, C. A. et al. (1997). "Non-Antisense Effects of Oligodeoxynucleotides," Chapter 11 In *Antisense Technology*, C. Lichtenstein and W. Nellen, eds., IRL Press: pp. 241-264.

Stirchak, E. P. et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.

Takahashi, H. et al. (Apr. 1990). "Induction of CD8$^+$ Cytotoxic T Cells by Immunization with Purified HIV-1 Envelope Protein in ISCOMs," *Nature* 344:873-875.

Tamura, S-I. et al. (1992). "Superior Cross-Protective Effect of Nasal Vaccination to Subcutaneous Inoculation with Influenza Hemagglutinin Vaccine," *Eur. J. Immunol.* 22:477-481.

Tamura, S-I. et al. (1994). "Formulation of Inactivated Influenza Vaccines for Providing Effective Cross-Protection by intranasal Vaccination in Mice," *Vaccine* 12(4):310-316.

Tang, J-Y. et al. (2000). "Large-Scale Synthesis of Oligonucleotide Phosphorothiotes Usin 3-Amino-1,2,4-Dithiazole-Thione as an Efficient Sulfur-Transfer Reagent," *Org. Process Res. Dev.* 4(3):194-198.

Thomson, J. B. et al. (1993). "Activity of Hammerhead Ribozymes Contaiing Non-Nucleotidic Linkers," *Nucleic Acids Res.* 21(24):5600-5603.

Tokunaga, T. et al. (1992). "Synthetic Oligonucleotides with Particular Base Sequences from the cDNA Encoding Proteins of *Mycobacterium bovis* BCG Induce Interferons and Activate Natural Killer Cells," *Microbiol. Immunol.* 36(1):55-66.

Tomalia, D. A et al. (1990). "Starburst Dendrimers: Molecular-Level Control of Size, Shape, Surface Chemistry, Topology, and Flexibility from Atoms to Macroscopic Matter," *Angew Chem. Intl. Ed. Engl.* 29:138-175.

Tung, C-H. et al. (1991). "Preparation of Oligonucleotide-Peptide Conjugates," *Bioconjug. Chem.* 2:464-465.

U.S. Appl. No. 60/235,452, filed Sep. 26, 2000, by Agrawal.

U.S. Appl. No. 60/235,453, filed Sep. 26, 2000, by Agrawal.

U.S. Appl. No. 09/712,898, filed Nov. 15, 2000, by Kandimalla et al.

Usman, N. et al. (1987). "Automated Chemical Synthesis of Long Oligoribonucleotides Using 2'-O-Silylated Ribonucleoside 3'-O-Phosphoramidites on Sequence Similar to the 3'-Half Molecule of an *Escherichia coli* Formylmethionine tRNA," *J. Am. Chem. Soc.* 109(25):7845-7854.

Vailes, L. D. et al. (Feb. 1998). "High-Level Expression of Cockroach Allergen, Bla g 4, in *Pichia pastoris*," *J. Allergy Clin. Immunol.* 101(2 part 1):274-280.

Verthelyi, D. et al. (2001). "Human Peripheral Blood Cells Differentially Recognize and Respond to Two Distinct CpG Motifs," *J. Immunol.* 166(4):2372-2377.

Walker, P. S. et al. (Jun. 1999). "Immunostimulatory Oligodeoxynucleotides Promote Protective Immunity and Provide Systemic Therapy for Leishmaniasis Via IL-12- and IFN-$\gamma$-Dependent Mechanisms," *PNAS USA* 96(12):6970-6975.

Wang, S. et al. (1994). "Circular RNA Oligonucleotides. Synthesis, Nucleic Acid Binding Properties, and a Comparison with Circular DNAs," *Nucleic Acids Res.* 22(12):2326-2333.

Warner, B. D. et al. (1984). "Laboratory Methods: Construction and Evaluation of an Instrument for the Automated Synthesis of Oligodeoxyribonucleotides," *DNA* 3(5)401-411.

Watwe, R. M. et al. (Apr. 1995). "Manufacture of Liposomes: A Review," *Current Science* 68(7):715-724.

Weeratna, R. et al. (1998). "Reduction of Antigen Expression from DNA Vaccines by Coadministered Oligobeoxynucleotides," *Anti. and Nucleic Acid Drug Develop.* 8:351-356.

Weiner, G. J. et al. (Sep. 1997). "Immunostimulatory Oligodeoxynucleotides Containing the CpG Motif are Effective as Immune Adjuvants in Tumor Antigen Immunization," *PNAS USA* 94:10833-10837.

Widhe, M. et al. (1998). "IgG Subclasses in Lyme Borreliosis: A Study of Specific IgG Subclass Distribution in an Interferon-$\gamma$-Predominated Disease," *Scand. J. Immunol.* 47:575-581.

Williams, J. D. et al. (1996). "Thermodynamic Comparison of the Salt Dependence of Natural RNA Hairpins and RNA Hair[oms with Non-Nucleotide Spaces," *Biochemistry* 35(46):14665-14670.

Wooldridge, J. E. et al. (Apr. 1997). "Immunostimulatory Oligodeoxynucleotides Containing CpG Motifs Enhance the Efficacy of Monoclonal Antibody Therapy of Lymphoma," *Blood* 89(8):2994-2998.

Wyrzkiewicz, T. K. et al. (1994). "Efficiency of Sulfurization in the Synthesis of Oligodeoxyribonucleotide Phosphorothioates Utilizing Various Sulfurizing Reagents," *Bioorg. & Med. Chem. Lett.* 4912):1519-1522.

Yamamoto, S. et al. (Jun. 1992). "Unique Palindromic Sequences in Synthetic Oligonucleotides are Required to Induce INF and Augment INF-Mediated Natural Killer Activity," *J. Immunol*148(12):4072-4076.

Yamamoto, T. et al. (1994a). "Ability of Oligonucleotides with Certain Palindromes to Induce Interferon Production and Augment Natural Killer Cell Activity is Associated with Their Base Length," *Anti. Res. and Develop.* 4:119-122.

Yamamoto, T. et al. (1994b). "Synthetic Oligonucleotides with Certain Palindromes Stimulate Interferon Production of Human Peripheral Blood Lymphocytes In Vitro," *Jpn. J. Cancer Res.* 85:775-779.

Yamana, K. et al. (1999). "Synthesis of Oligonucleotides Containing a New Azobenzene Fragment with Efficient Photoisomerizability," *Bioorg. and Med. Chem.* 7:2977-2983.

Yanagawa, H. et al. (Feb. 1988). "Analysis of Superhelical Structures of Nucleic Acid-Lipid Conjugates by Image Processing," *Nucleic Acids Symp. Series* 19:189-192.

Yi, A-K. et al. (Jan. 1996). "IFN-$\gamma$ Promotes IL-6 and IgM Secretion in Response to CpG Motifs In Bacterial DNA and Oligodeoxynucleotides," *J. Immunol.* 156(2):558-564.

Yi, A-K. et al. (Feb. 1998a). "CpG DNA Rescue from Anti-IgM-Induced WEHI-231 B Lymphoma Apoptosis Via Modulation of I$\kappa$B$\alpha$ and I$\kappa$B$\gamma$ and Sustained Activation of Nuclear Factor-$\kappa$B/c-Rel," *J. Immunol.* 16(3):1240-1245.

Yi, A-K. et al. (May 1, 1998b). "CpG Motifs in Bacterial DNA Activate Leukocytes Through the Ph-Dependent Generation of Reactive Oxygen Species," *J. Immunol.* 160(10):4755-4761.

Yi, A-K. et al. (Jun. 1998c). "CpG Oligodeoxyribonucleotides Rescue Mature Spleen B Cells from Spontaneous Apoptosis and Promote Cell Cycle Entry," *J. Immunol.* 160(12):5898-5906.

Yi, A-K. et al. (1998d). "Rapid Induction of Mitogen-Activated Protein Kinases by Immune Stimulatory CpG DNA," *J. Immunol.* 161(9):4493-4497.

Yu, D. et al. (2000). "Accessible 5'-End of CpG-Containing Phosphorothioate Oligodeoxynucleotides is Essential for Immunostimulatory Activity," *Bioorg. Med. Chem. Lett.* 10(23):2585-2588.

Yu, D. et al. (2002). "Potent CpG Oligonucleotides Containing Phosphodiester Linkages: In Vitro and In Vivo Immunostimulatory Properties," *Biochem and Biophy. Res. Comm.* 297(1):83-90.

Yu, D. et al. (2002). "Design, Synthesis, and Immunostimulatory Properties of CpG DNAs Containing Alkyl-Linker Substitutions: Role of Nucleosides in the Flanking Sequences." *J. of Med. Chem.* 45(20):4540-4548.

Yu, D. et al. (2002). "Immunomers' -Novel 3'-3' -Linked CpG Oligonucleotides as Potent Immunomodulatory Agents," *Nucleic Acids Res.* 30(20):4460-4469.

Yu, D. et al. (2003). "Requirement of Nucleobase Proximal to CpG Dinucloetide for Immunostimulatory Activity of Synthetic," *Bioorg. Med. Chem.* 11(3):459-464.

Zhao, Q. et al. (1996). "Effect of Different Chemically Modified Oligodeoxynucleotides on Immune Stimulation," *Biochem. Pharmacol.* 51(2):173-182.

Zhao, Q. et al. (Dec. 1999). "Site of Chemical Modifications in CpG Containing Phosphorothiaote Oligodeoxynucleotide Modulates its Immunostimulatory Activity," *Bioorg. Med. Chem. Lett.* 9(24):3453-3458.

Zhou, P. et al. (Mar. 6, 1998). "Solution Structure of the Core NFATC1/DNA Complex," *Cell* 92:687-696.

Zimmermann, S. et al. (1998). "CpG Oligodeoxynucleotides Trigger Protective and Curative Th1 Responses in Lethal Murine Leishmaniasis," *J. Immunol.* 160(8):3627-3630.

Zon, G. (1993). "Oligonucleoside Phosphorothioates," Chapter 8 *In Protocols for Oligonucleotides and Analogs, Synthesis and Properties*, Sudhir Agrawal, ed., Humana Press, Totowa, N.J., pp. 165-189.

Zuckermann, R. et al. (1987). "Efficient Methods for Attachment of Thiol Specific Probes to the 3'-Ends of Synthetic Oligodeoxyribonucleotides," *Nucleic Acids Res.* 15(13):5305-5321.

Agrawal, S. et al. (1995). "Modified Oligonucleotides as Therapeutic and Diagnostic Agents," *Current Opinion in Biotechnology* 6:12-19.

Agrawal, S. et al. (2003). "Modulation of Toll-Like Receptor 9 Responses Through Synthetic Immunostimulatory Motifs of DNA," *Ann. N.Y. Acad. Sci.* 1002:30-42.

Amendment in Response to Non-Final Office Action submitted on Jan. 9 2009, for U.S. Appl. No. 10/177,826, filed Jun. 21, 2002, 14 pages.

Amendment in Response to the Final Office Action submitted on May 5, 2009, for U.S. Appl. No. 10/328,578, filed Dec. 23, 2002, 10 pages.

Bitton, R.J. (2004). "Cancer Vaccines: A Critical Review on Clinical Impact," *Current Opinion in Molecular Therapeutics* 6(1):17-26.

Bjersing, J.L. (Jun. 2004). "Impact of Site-Specific Nucleobse Deletions on the Arthritogenicity of DNA," *Inflammation* 28(3):159-168.

Degruijl, T.D. et al. (Oct. 1999). "Cancer Vaccine Strategies Get Bigger and Better," *Nature Medicine* 5(10):1124-1125.

Donnelly, J. (Nov. 2003). "Cancer Vaccine Targets Leukemia," *Nature Medicine* 9(11):1354-1356.

Ex-Parte Quayle Action mailed on Aug. 5, 2009, for U.S. Appl. No. 10/328,578, filed Dec. 23, 2002, 4 pages.

Final Office Action mailed on Nov. 5, 2008, for U.S. Appl. No. 10/328,578, filed Dec. 23, 2002, 9 pages.

Final Office Action mailed on Apr. 3, 2009, for U.S. Appl. No. 10/177,826, filed Jun. 21, 2002, 13 pages.

Grunanthan, S. et al. (2000). "DNA Vaccines: Immunology, Application, and Optimization," *Annual Review of Immunology* 18:927-974.

Jones, D.S. et al. (1994). "Conjugates of Double-Stranded Oligonucloetides with Poly(ethyleneglycol) and Keyhole Limpet Hemocyanin: A Model for Treating Systemic Lupus Erythematosus," *Bioconjugate Chemistry* 5:390-399.

Kandimalla, E.R. et al. (Nov. 25, 2003). "A Dinucleotide Motif in Oligonucleotides Shows Potent Immunomodulatory Activity and Overrides Species-Specific Recognition Observed with CpG Motif," *PNAS* 100(24):14303-14308.

Kandimalla, E.R. et al. (May 10, 2005). "Immunomodulatory Oligonucleotides Containing a Cytosine-Phosphate-2'-Deoxy-7-Deazaguanosine Motif as Potent Toll-Like Receptor 9 Agonists," *PNAS* 102(19):6925-6930.

Kawaguchi, T. et al. (1995). "Stability, Specific Binding Activity, and Plasma Concentration in Mice of an Oligodeoxynucleotide Modified at 5'-Terminal with Poly(ethylene glycol)," *Bio. Pharm. Bull.* 18(3):474-476.

Klinman, D.M. (Apr. 1998). "Therapeutic Applications of CpG-Containing Oligodeoxynucleotides," *Antisense & Nucleic Acid Drug Development* 8(2):181-184.

Kreig, A.M. et al. (1999). "Mechanisms and Therapeutic Applications of Immune Stimulatory CpG Dna," *Pharmacology and Therapeutics* 84:113-120.

Li, Y. et al. (2005). "Oligodeoxynucleotides Containing Synthetic Immunostimulatory Motifs Augment Potent Th1 Immune Responses to HBsAg in Mice," *International Immunopharmacology* 5:981-991.

Liang, H. et al. (2000). "The Role of Cell Surface Receptors in the Activation of Human B Cells by Phsophorothioate Oligonucleotides," *The Journal of Immunology* 165:1438-1445.

Williams, D.J. et al. (1996). "RNA Hairpins with Non-nucleotide Spacers Bind Efficiently to the Human U1A Protein," *Journal of Molecular Biology* 257:265-275.

Wongratancheewin, S. et al. (Aug. 2004). "Immunostimulatory CpG Oligodeoxynucleotide Confers Protection in a Murine Model of Infection with *Burkholderia pseudomallei*," *Infection and Immunity* 72(8):4494-4502.

Yu, D. et al. (2001). "Immunostimulatory Activity of CpG Oligonucleotides Containing Non-Ionic Methylphosphonate Linkages," Bioorganic & Medicinal Chemistry 9:2803-2808.

Zhu, F-G. (2004). "Modulation of Ovalbumin-Induced Th2 Responses by Second-Generation Immunomodulatory Oligonuicelotides in Mice," *International Immunopharmacology* 4:951-862.

Final Office Action mailed on Nov. 5, 2008, for U.S. Appl. No. 10/328,578, filed Dec. 23, 2002, 9 pages.

Amendment with RCE in Response to Final Office Action submitted on Oct. 5, 2009, for U.S. Appl. No. 10/328,578, filed Dec. 23, 2002, 5 pages.

Higgins, D. et al. (2007). "Immunostimulatory DNA as a Vaccine Adjuvant," *Expert Rev. Vaccines* 6(5):747-759.

Horner, A.A. et al. (Sep. 2002). "Optimized Conjugation Ratios Lead to Allergen Immunostimulatory Oligodeoxynucleotide Conjugates with Retained Immunogenicity and Minimal Anaphylactogenicity," *J. Allergy and Clinical Immunology* 110(3):413-420.

Non-Final Office Action mailed on Oct. 2, 2009, for U.S. Appl. No. 11/590,150, filed Oct. 30, 2006, 7 pages.

Tighe, H. et al. (Jul. 2000). "Conjugation of Immunostimulatory DNA to the Short Ragweed Allergen Amb a 1 Enhances its Immunogenicity and Reduces its Allergenicity," *J. Allergy and Clinical Immunology* 106(1 Part 1):123-134.

Alvarez-Salas, L.M. (2008). "Nucleic Acids as Therapeutic Agents," *Current Topics in Medicinal Chemistry* 8(15):1379-1404.

Amendment in Response to Non-Final Office Action submitted on Apr. 2, 2010, for U.S. Appl. No. 11/590,150, filed Oct. 30, 2006, 10 pages.

Amendment in Response to Final Action submitted on Sep. 23, 2010, for U.S. Appl. No. 11/590,150, filed Oct. 30, 2006, 8 pages.

Final Office Action mailed on Jun. 23, 2010, for U.S. Appl. No. 11/590,150, filed Oct. 30, 2006, 8 pages.

Non-Final Office Action mailed on Nov. 10, 2010, for U.S. Appl. No. 12/243,915, filed Oct. 1, 2008, 7 pages.

1a: R = (CH$_2$CH$_2$O)$_5$-CH$_2$CH$_2$
1b: R = (CH$_2$)$_3$
1c: R = (CH$_2$CH$_2$O)$_2$-CH$_2$CH$_2$
1d: R = CH$_2$CH(CH$_2$OH)
1e: R = (CH$_2$)$_4$
1f: R = 1',2'-dideoxyribose
1g: R = (CH$_2$)$_6$ 1a-g

HO-(CH2)6-S-S-(CH2)6-O-P-(O)(S)-O-5'-TCGTCGA-3'

4

TCEP →

HS-(CH2)6-O-P-(O)(S)-O-5'-TCGTCGA-3'

5

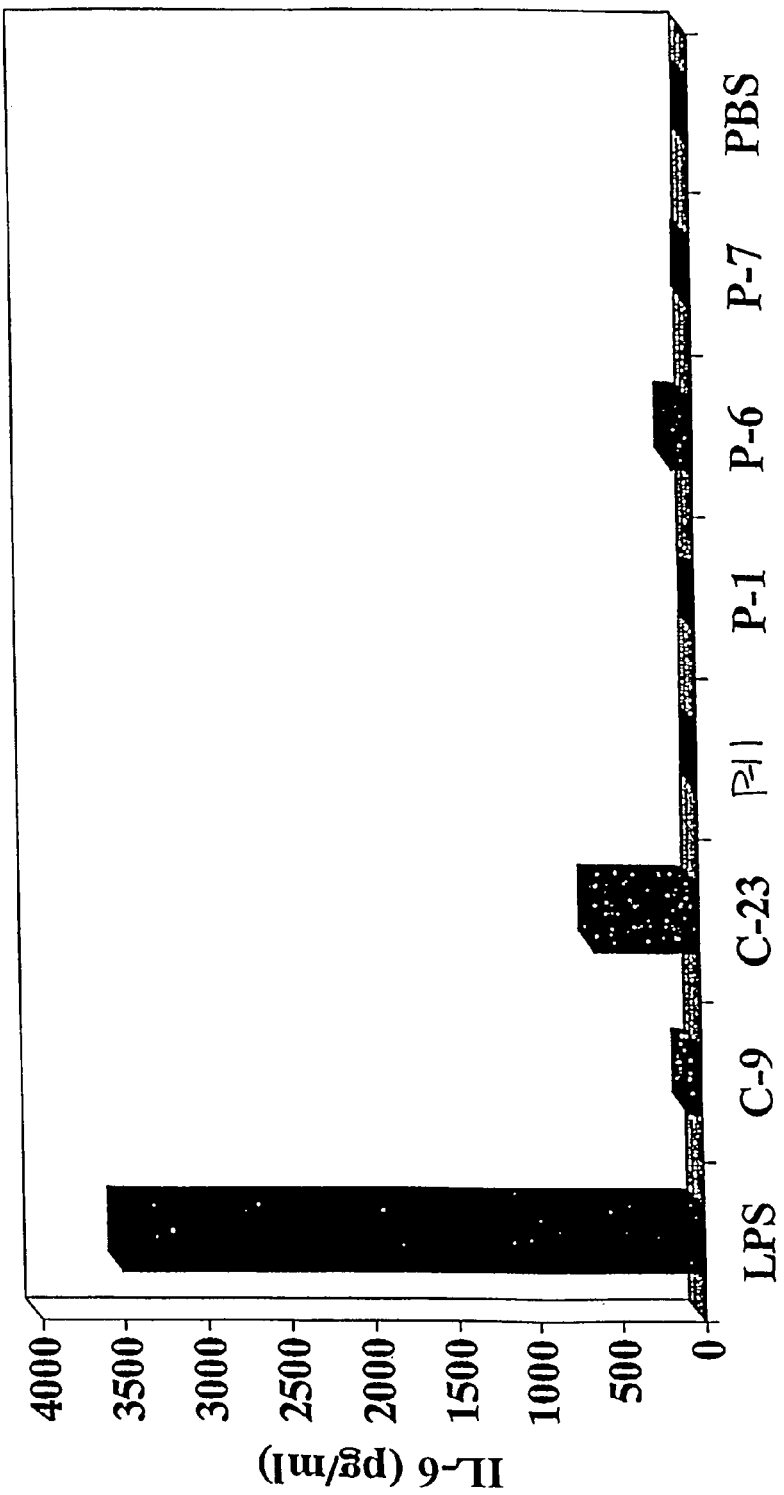

SEQUENCE LISTING

```
<160> NUMBER OF SEQ ID NOS: 141

<210> SEQ ID NO 1
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: (5)...(24)
<223> OTHER INFORMATION: n = any nucleotide
<220> FEATURE:
<221> NAME/KEY: variation
<222> LOCATION: (5)...(24)
<223> OTHER INFORMATION: n's may or may not be present
```

```
<400> SEQUENCE: 1
tcgannnnnn nnnnnnnnnn nnnn                                          24

<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2
tgactgtgaa cgttcgagat ga                                            22

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
tgactgtgaa ccttagagat ga                                            22

<210> SEQ ID NO 4
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1
<223> OTHER INFORMATION: n = t, g, c, or 5-bromocytosine
<220> FEATURE:
<221> NAME/KEY: variation
<222> LOCATION: 2
<223> OTHER INFORMATION: n = t, g, a, or u
<220> FEATURE:
<221> NAME/KEY: variation
<222> LOCATION: 4
<223> OTHER INFORMATION: n = t, a, or c
<220> FEATURE:
<221> NAME/KEY: variation
<222> LOCATION: 7
<223> OTHER INFORMATION: n = t, g, or u

<400> SEQUENCE: 4 nnancgntcg                                                          10

<210> SEQ ID NO 5
<211> LENGTH: 10
<212> TYPE: DNA
<213> ORGANISM: Artificial Sequence
<220> FEATURE:
<223> OTHER INFORMATION: Synthetic construct

<400> SEQUENCE: 5
tgaacgttcg                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthetic construct

<400> SEQUENCE: 6
ggaacgttcg                                                          10
```

<210> SEQ ID NO 7
<211> LENGTH: 10
<212> TYPE: DNA
<213> ORGANISM: Artificial Sequence
<220> FEATURE:
<223> OTHER INFORMATION: Synthetic construct

<400> SEQUENCE: 7
tgaacgutcg                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthetic construct

<400> SEQUENCE: 8
tgaccgttcg                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic construct

<400> SEQUENCE: 9
tgatcggtcg                                                          10

<210> SEQ ID NO 10
<211> LENGTH: 10
<212> TYPE: DNA
<213> ORGANISM: Artificial Sequence
<220> FEATURE:
<223> OTHER INFORMATION: Synthetic construct

<400> SEQUENCE: 10
tgatcgttcg                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic construct

<400> SEQUENCE: 11
tgaacggtcg                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic construct

<400> SEQUENCE: 12
gtaacgttcg                                                          10

<210> SEQ ID NO 13
<211> LENGTH: 10
<212> TYPE: DNA
<213> ORGANISM: Artificial Sequence
<220> FEATURE:
<223> OTHER INFORMATION: Synthetic construct

```
<400> SEQUENCE: 13
gtatcggtcg                                                              10

<210> SEQ ID NO 14
<211> LENGTH: 10
<212> TYPE: DNA
<213> ORGANISM: Artificial Sequence
<220> FEATURE:
<223> OTHER INFORMATION: Synthetic construct

<400> SEQUENCE: 14
gtaccgttcg                                                              10

<210> SEQ ID NO 15
<211> LENGTH: 10
<212> TYPE: DNA
<213> ORGANISM: Artificial Sequence
<220> FEATURE:
<223> OTHER INFORMATION: Synthetic construct

<400> SEQUENCE: 15
gaaccgttcg                                                              10

<210> SEQ ID NO 16
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1
<223> OTHER INFORMATION: n = 5-bromocytosine

<400> SEQUENCE: 16 ngaccgttcg                                                              10

<210> SEQ ID NO 17
<211> LENGTH: 10
<212> TYPE: DNA
<213> ORGANISM: Artificial Sequence
<220> FEATURE:
<223> OTHER INFORMATION: Synthetic construct

<400> SEQUENCE: 17
cgaacgttcg                                                              10

<210> SEQ ID NO 18
<211> LENGTH: 10
<212> TYPE: DNA
<213> ORGANISM: Artificial Sequence
<220> FEATURE:
<223> OTHER INFORMATION: Synthetic construct

<400> SEQUENCE: 18
cgaccgttcg                                                              10

<210> SEQ ID NO 19
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1
<223> OTHER INFORMATION: n = 5-bromocytosine
```

```
<400> SEQUENCE: 19 ngaacgttcg                                                              10

<210> SEQ ID NO 20
<211> LENGTH: 10
<212> TYPE: DNA
<213> ORGANISM: Artificial Sequence
<220> FEATURE:
<223> OTHER INFORMATION: Synthetic construct

<400> SEQUENCE: 20
ttaacgutcg                                                              10

<210> SEQ ID NO 21
<211> LENGTH: 10
<212> TYPE: DNA
<213> ORGANISM: Artificial Sequence
<220> FEATURE:
<223> OTHER INFORMATION: Synthetic construct

<400> SEQUENCE: 21
tuaacgutcg                                                              10

<210> SEQ ID NO 22
<211> LENGTH: 10
<212> TYPE: DNA
<213> ORGANISM: Artificial Sequence
<220> FEATURE:
<223> OTHER INFORMATION: Synthetic construct

<400> SEQUENCE: 22
ttaacgttcg                                                              10

<210> SEQ ID NO 23
<211> LENGTH: 24
<212> TYPE: DNA
<213> ORGANISM: Artificial Sequence
<220> FEATURE:
<223> OTHER INFORMATION: Synthetic construct

<400> SEQUENCE: 23
tcgtcgaacg ttcgttaacg ttcg                                              24

<210> SEQ ID NO 24
<211> LENGTH: 22
<212> TYPE: DNA
<213> ORGANISM: Artificial Sequence
<220> FEATURE:
<223> OTHER INFORMATION: Synthetic construct

<400> SEQUENCE: 24
tgactgtgaa cgutcgagat ga                                                22

<210> SEQ ID NO 25
<211> LENGTH: 24
<212> TYPE: DNA
<213> ORGANISM: Artificial Sequence
<220> FEATURE:
<223> OTHER INFORMATION: Synthetic construct

<400> SEQUENCE: 25
tcgtcgaucg utcgttaacg utcg                                              24

<210> SEQ ID NO 26
<211> LENGTH: 24
<212> TYPE: DNA
```

```
<213> ORGANISM: Artificial Sequence
<220> FEATURE:
<223> OTHER INFORMATION: Synthetic construct

<400> SEQUENCE: 26
tcgtcgaucg ttcgtuaacg utcg                                              24

<210> SEQ ID NO 27
<211> LENGTH: 24
<212> TYPE: DNA
<213> ORGANISM: Artificial Sequence
<220> FEATURE:
<223> OTHER INFORMATION: Synthetic construct

<400> SEQUENCE: 27
tcgtcguacg utcgttaacg utcg                                              24

<210> SEQ ID NO 28
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 7
<223> OTHER INFORMATION: n = 2-amino-adenine

<400> SEQUENCE: 28
tcgtcgnacg utcgttaacg utcg                                              24

<210> SEQ ID NO 29
<211> LENGTH: 24
<212> TYPE: DNA
<213> ORGANISM: Artificial Sequence
<220> FEATURE:
<223> OTHER INFORMATION: Synthetic construct

<400> SEQUENCE: 29
tgatcgaacg ttcgttaacg ttcg                                              24

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
tgactgtgaa cgutcggtat ga                                                22

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
tgactgtgac cgttcggtat ga                                                22

<210> SEQ ID NO 32
<211> LENGTH: 22
<212> TYPE: DNA
<213> ORGANISM: Artificial Sequence
<220> FEATURE:
<223> OTHER INFORMATION: Synthetic construct
```

<400> SEQUENCE: 32
tgactgtgat cggtcggtat ga                                              22

<210> SEQ ID NO 33
<211> LENGTH: 16
<212> TYPE: DNA
<213> ORGANISM: Artificial Sequence
<220> FEATURE:
<223> OTHER INFORMATION: Synthetic construct

<400> SEQUENCE: 33
tcgtcgaacg ttcgtt                                                     16

<210> SEQ ID NO 34
<211> LENGTH: 22
<212> TYPE: DNA
<213> ORGANISM: Artificial Sequence
<220> FEATURE:
<223> OTHER INFORMATION: Synthetic construct

<400> SEQUENCE: 34
tcgtcgtgaa cgttcgagat ga                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic construct

<400> SEQUENCE: 35
tcgtcggtat cggtcggtat ga                                              22

<210> SEQ ID NO 36
<211> LENGTH: 18
<212> TYPE: DNA
<213> ORGANISM: Artificial Sequence
<220> FEATURE:
<223> OTHER INFORMATION: Synthetic construct

<400> SEQUENCE: 36
cttcgaacgt tcgagatg                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic construct

<400> SEQUENCE: 37
ctgtgatcgt tcgagatg                                                   18

<210> SEQ ID NO 38
<211> LENGTH: 22
<212> TYPE: DNA
<213> ORGANISM: Artificial Sequence
<220> FEATURE:
<223> OTHER INFORMATION: Synthetic construct

<400> SEQUENCE: 38
tgactgtgaa cggtcggtat ga                                              22

<210> SEQ ID NO 39
<211> LENGTH: 22
<212> TYPE: DNA

<213> ORGANISM: Artificial Sequence
<220> FEATURE:
<223> OTHER INFORMATION: Synthetic construct

<400> SEQUENCE: 39
tcgtcggtac cgttcggtat ga					22

<210> SEQ ID NO 40
<211> LENGTH: 22
<212> TYPE: DNA
<213> ORGANISM: Artificial Sequence
<220> FEATURE:
<223> OTHER INFORMATION: Synthetic construct

<400> SEQUENCE: 40
tcgtcggaac cgttcggaat ga					22

<210> SEQ ID NO 41
<211> LENGTH: 19
<212> TYPE: DNA
<213> ORGANISM: Artificial Sequence
<220> FEATURE:
<223> OTHER INFORMATION: Synthetic construct

<400> SEQUENCE: 41
tcgtcgaacg ttcgagatg					19

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
tcgtcgtaac gttcgagatg					20

<210> SEQ ID NO 43
<211> LENGTH: 22
<212> TYPE: DNA
<213> ORGANISM: Artificial Sequence
<220> FEATURE:
<223> OTHER INFORMATION: Synthetic construct

<400> SEQUENCE: 43
tgactgtgac cgttcggaat ga					22

<210> SEQ ID NO 44
<211> LENGTH: 22
<212> TYPE: DNA
<213> ORGANISM: Artificial Sequence
<220> FEATURE:
<223> OTHER INFORMATION: Synthetic construct

<400> SEQUENCE: 44
tcgtcgaacg ttcgaacgtt cg					22

<210> SEQ ID NO 45
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 5
<223> OTHER INFORMATION: n = 5-bromocytosine

```
<400> SEQUENCE: 45
tngtngaacg ttcgagatg                                               19

<210> SEQ ID NO 46
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 46
tcgtngaacg ttcgagatg                                               19

<210> SEQ ID NO 47
<211> LENGTH: 20
<212> TYPE: DNA
<213> ORGANISM: Artificial Sequence
<220> FEATURE:
<223> OTHER INFORMATION: Synthetic construct

<400> SEQUENCE: 47
tcgtcgaccg ttcggaatga                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2,5
<223> OTHER INFORMATION: n = 5-bromocytosine

<400> SEQUENCE: 48
tngtngaccg ttcggaatga                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 49
tcgtngaccg ttcggaatga                                              20

<210> SEQ ID NO 50
<211> LENGTH: 22
<212> TYPE: DNA
<213> ORGANISM: Artificial Sequence
<220> FEATURE:
<223> OTHER INFORMATION: Synthetic construct

<400> SEQUENCE: 50
ttcgaacgtt cgttaacgtt cg                                           22

<210> SEQ ID NO 51
<211> LENGTH: 18
<212> TYPE: DNA
```

```
<213> ORGANISM: Artificial Sequence
<220> FEATURE:
<223> OTHER INFORMATION: Synthetic construct
<220> FEATURE:
<221> NAME/KEY: variation
<222> LOCATION: 4
<223> OTHER INFORMATION: n = 5-bromocystosine

<400> SEQUENCE: 51
cttngaacgt tcgagatg                                                   18

<210> SEQ ID NO 52
<211> LENGTH: 22
<212> TYPE: DNA
<213> ORGANISM: Artificial Sequence
<220> FEATURE:
<223> OTHER INFORMATION: Synthetic construct

<400> SEQUENCE: 52
tgatcgtcga acgttcgaga tg                                              22

<210> SEQ ID NO 53
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1
<223> OTHER INFORMATION: n = t, g, c, or 5-bromocytosine
<220> FEATURE:
<221> NAME/KEY: variation
<222> LOCATION: 2
<223> OTHER INFORMATION: n = t, g, a, or u
<220> FEATURE:
<221> NAME/KEY: variation
<222> LOCATION: 4
<223> OTHER INFORMATION: n = t, a, or c
<220> FEATURE:
<221> NAME/KEY: variation
<222> LOCATION: 5
<223> OTHER INFORMATION: n = 5-bromocytosine
<220> FEATURE:
<221> NAME/KEY: variation
<222> LOCATION: 7
<223> OTHER INFORMATION: n = t, g, or u

<400> SEQUENCE: 53 nnanngntcg                                                            10

<210> SEQ ID NO 54
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 54 tgaangttcg                                                            10

<210> SEQ ID NO 55
<211> LENGTH: 10
<212> TYPE: DNA
<213> ORGANISM: Artificial Sequence
<220> FEATURE:
<223> OTHER INFORMATION: Synthetic construct
<220> FEATURE:
```

```
<221> NAME/KEY: variation
<222> LOCATION: 5
<223> OTHER INFORMATION: n = 5-bromocytosine

<400> SEQUENCE: 55 tgaangutcg                                                              10

<210> SEQ ID NO 56
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 56 tgacngttcg                                                              10

<210> SEQ ID NO 57
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 57 tgatnggtcg                                                              10

<210> SEQ ID NO 58
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 58 gtatnggtcg                                                              10

<210> SEQ ID NO 59
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 59 gtacngttcg                                                              10

<210> SEQ ID NO 60
<211> LENGTH: 10
<212> TYPE: DNA
<213> ORGANISM: Artificial Sequence
<220> FEATURE:
<223> OTHER INFORMATION: Synthetic construct
<220> FEATURE:
```

```
<221> NAME/KEY: variation
<222> LOCATION: 5
<223> OTHER INFORMATION: n = 5-bromocytosine

<400> SEQUENCE: 60 gaacngttcg                                                          10

<210> SEQ ID NO 61
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 61 gaaangutcg                                                          10

<210> SEQ ID NO 62
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1, 5
<223> OTHER INFORMATION: n = 5-bromocytosine

<400> SEQUENCE: 62 ngacngttcg                                                          10

<210> SEQ ID NO 63
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 63 cgaangttcg                                                          10

<210> SEQ ID NO 64
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 1, 5
<223> OTHER INFORMATION: n = 5-bromocytosine

<400> SEQUENCE: 64 ngaangttcg                                                          10

<210> SEQ ID NO 65
<211> LENGTH: 10
<212> TYPE: DNA
<213> ORGANISM: Artificial Sequence
<220> FEATURE:
<223> OTHER INFORMATION: Synthetic construct
<220> FEATURE:
```

```
<221> NAME/KEY: variation
<222> LOCATION: 1, 5
<223> OTHER INFORMATION: n = 5-bromocytosine

<400> SEQUENCE: 65 ngaangutcg                                                              10

<210> SEQ ID NO 66
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 66 ttaangutcg                                                              10

<210> SEQ ID NO 67
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 67 tuaangutcg                                                              10

<210> SEQ ID NO 68
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 68 ttaangttcg                                                              10

<210> SEQ ID NO 69
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 69
tgactgtgaa ngutcgagat ga                                                22

<210> SEQ ID NO 70
<211> LENGTH: 24
<212> TYPE: DNA
<213> ORGANISM: Artificial Sequence
<220> FEATURE:
<223> OTHER INFORMATION: Synthetic construct
<220> FEATURE:
```

```
<221> NAME/KEY: variation
<222> LOCATION: 9, 19
<223> OTHER INFORMATION: n= 5-bromocytosine

<400> SEQUENCE: 70
tcgtcgaang ttcgttaang ttcg                                              24

<210> SEQ ID NO 71
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 71
tgactgtgaa ngutcggtat ga                                                22

<210> SEQ ID NO 72
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 72
tgactgtgaa ngutcggaat ga                                                22

<210> SEQ ID NO 73
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 73
tcgtcggaaa ngutcggaat ga                                                22

<210> SEQ ID NO 74
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5, 9
<223> OTHER INFORMATION: n = 5-bromocytosine

<400> SEQUENCE: 74
tcgtngaang utcggaatga                                                   20

<210> SEQ ID NO 75
<211> LENGTH: 10
<212> TYPE: DNA
<213> ORGANISM: Artificial Sequence
<220> FEATURE:
<223> OTHER INFORMATION: Synthetic construct
<220> FEATURE:
```

-continued

```
<221> NAME/KEY: variation
<222> LOCATION: 1
<223> OTHER INFORMATION: n = t, c, or 5-bromocytosine
<220> FEATURE:
<221> NAME/KEY: variation
<222> LOCATION: 2
<223> OTHER INFORMATION: n = t, g, a, or u
<220> FEATURE:
<221> NAME/KEY: variation
<222> LOCATION: 4
<223> OTHER INFORMATION: n = t, a, or c
<220> FEATURE:
<221> NAME/KEY: variation
<222> LOCATION: 7
<223> OTHER INFORMATION: n = t, g, or u

<400> SEQUENCE: 75 nnancgntcg                                                                10

<210> SEQ ID NO 76
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 76
tgactgtgaa ngttcgagat ga                                                  22

<210> SEQ ID NO 77
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11, 15
<223> OTHER INFORMATION: n = 5-bromocytosine

<400> SEQUENCE: 77
tgactgtgaa ngttngagat ga                                                  22

<210> SEQ ID NO 78
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 78
tgactgtgaa ngttccagat ga                                                  22

<210> SEQ ID NO 79
<211> LENGTH: 22
<212> TYPE: DNA
<213> ORGANISM: Artificial Sequence
<220> FEATURE:
<223> OTHER INFORMATION: Synthetic construct

<400> SEQUENCE: 79
tgactgtgaa cgtucgagat ga                                                  22
```

```
<210> SEQ ID NO 80
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 13
<223> OTHER INFORMATION: n = 5-bromouracil

<400> SEQUENCE: 80
tgactgtgaa cgntcgagat ga                                              22

<210> SEQ ID NO 81
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 81
tgactgtgaa ngttcgtuat ga                                              22

<210> SEQ ID NO 82
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 11
<223> OTHER INFORMATION: n = 5-bromocytosine

<400> SEQUENCE: 82
tgactgtgaa ngttcggtat ga                                              22

<210> SEQ ID NO 83
<211> LENGTH: 18
<212> TYPE: DNA
<213> ORGANISM: Artificial Sequence
<220> FEATURE:
<223> OTHER INFORMATION: Synthetic construct

<400> SEQUENCE: 83
ctgtgaacgt tcgagatg                                                   18

<210> SEQ ID NO 84
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 5
<223> OTHER INFORMATION: n = 5-bromocytosine

<400> SEQUENCE: 84
tngtngtgaa cgttcgagat ga                                              22

<210> SEQ ID NO 85
<211> LENGTH: 22
<212> TYPE: DNA
```

```
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 85
tcgtngtgaa cgttcgagat ga                                                   22

<210> SEQ ID NO 86
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 13
<223> OTHER INFORMATION: n = 4-thio-thymine

<400> SEQUENCE: 86
tgactgtgaa cgntcgagat ga                                                   22

<210> SEQ ID NO 87
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 12, 16
<223> OTHER INFORMATION: n = 6-thio-guanine

<400> SEQUENCE: 87
tgactgtgaa cnttcnagat ga                                                   22

<210> SEQ ID NO 88
<211> LENGTH: 22
<212> TYPE: DNA
<213> ORGANISM: Artificial Sequence
<220> FEATURE:
<223> OTHER INFORMATION: Synthetic construct

<400> SEQUENCE: 88
tgactgtgaa cgttcgtuat ga                                                   22

<210> SEQ ID NO 89
<211> LENGTH: 22
<212> TYPE: DNA
<213> ORGANISM: Artificial Sequence
<220> FEATURE:
<223> OTHER INFORMATION: Synthetic construct

<400> SEQUENCE: 89
tgactgtgaa cgttcgttat ga                                                   22

<210> SEQ ID NO 90
<211> LENGTH: 24
<212> TYPE: DNA
<213> ORGANISM: Artificial Sequence
<220> FEATURE:
<223> OTHER INFORMATION: Synthetic construct

<400> SEQUENCE: 90
tcgttcaacg ttcgttaacg ttcg                                                 24
```

```
<210> SEQ ID NO 91
<211> LENGTH: 24
<212> TYPE: DNA
<213> ORGANISM: Artificial Sequence
<220> FEATURE:
<223> OTHER INFORMATION: Synthetic construct

<400> SEQUENCE: 91
tgattcaacg ttcgttaacg ttcg                                              24

<210> SEQ ID NO 92
<211> LENGTH: 18
<212> TYPE: DNA
<213> ORGANISM: Artificial Sequence
<220> FEATURE:
<223> OTHER INFORMATION: Synthetic construct

<400> SEQUENCE: 92
ctgtcaacgt tcgagatg                                                     18

<210> SEQ ID NO 93
<211> LENGTH: 20
<212> TYPE: DNA
<213> ORGANISM: Artificial Sequence
<220> FEATURE:
<223> OTHER INFORMATION: Synthetic construct

<400> SEQUENCE: 93
tcgtcggaac gttcgagatg                                                   20

<210> SEQ ID NO 94
<211> LENGTH: 19
<212> TYPE: DNA
<213> ORGANISM: Artificial Sequence
<220> FEATURE:
<223> OTHER INFORMATION: Synthetic construct

<400> SEQUENCE: 94
tcgtcggacg ttcgagatg                                                    19

<210> SEQ ID NO 95
<211> LENGTH: 19
<212> TYPE: DNA
<213> ORGANISM: Artificial Sequence
<220> FEATURE:
<223> OTHER INFORMATION: Synthetic construct

<400> SEQUENCE: 95
tcgtcgtacg ttcgagatg                                                    19

<210> SEQ ID NO 96
<211> LENGTH: 19
<212> TYPE: DNA
<213> ORGANISM: Artificial Sequence
<220> FEATURE:
<223> OTHER INFORMATION: Synthetic construct

<400> SEQUENCE: 96
tcgtcgttcg ttcgagatg                                                    19

<210> SEQ ID NO 97
<211> LENGTH: 13
<212> TYPE: DNA
<213> ORGANISM: Artificial Sequence
<220> FEATURE:
<223> OTHER INFORMATION: Synthetic construct
```

```
<400> SEQUENCE: 97
tcgtgaacgt tcg                                                      13

<210> SEQ ID NO 98
<211> LENGTH: 14
<212> TYPE: DNA
<213> ORGANISM: Artificial Sequence
<220> FEATURE:
<223> OTHER INFORMATION: Synthetic construct

<400> SEQUENCE: 98
tcgtcgaacg ttcg                                                     14

<210> SEQ ID NO 99
<211> LENGTH: 13
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine

<400> SEQUENCE: 99
tngtgaacgt tcg                                                      13

<210> SEQ ID NO 100
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 5
<223> OTHER INFORMATION: n = 5-bromocytosine

<400> SEQUENCE: 100
tngtngaacg ttcg                                                     14

<210> SEQ ID NO 101
<211> LENGTH: 13
<212> TYPE: DNA
<213> ORGANISM: Artificial Sequence
<220> FEATURE:
<223> OTHER INFORMATION: Synthetic construct

<400> SEQUENCE: 101
tcgttaacgt tcg                                                      13

<210> SEQ ID NO 102
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(6)
<223> OTHER INFORMATION: tcg may or may not be present
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7, 8
<223> OTHER INFORMATION: n's may or may not be present
<220> FEATURE:
```

```
<221> NAME/KEY: variation
<222> LOCATION: 10
<223> OTHER INFORMATION: n = t, a, or c
<220> FEATURE:
<221> NAME/KEY: variation
<222> LOCATION: 13
<223> OTHER INFORMATION: n = t, g, or u

<400> SEQUENCE: 102
tcgtcgnnan cgntcg                                                    16

<210> SEQ ID NO 103
<211> LENGTH: 11
<212> TYPE: DNA
<213> ORGANISM: Artificial Sequence
<220> FEATURE:
<223> OTHER INFORMATION: Synthetic construct

<400> SEQUENCE: 103
tcgaacgttc g                                                         11

<210> SEQ ID NO 104
<211> LENGTH: 14
<212> TYPE: DNA
<213> ORGANISM: Artificial Sequence
<220> FEATURE:
<223> OTHER INFORMATION: Synthetic construct

<400> SEQUENCE: 104
tcgtcgaacg ttcg                                                      14

<210> SEQ ID NO 105
<211> LENGTH: 13
<212> TYPE: DNA
<213> ORGANISM: Artificial Sequence
<220> FEATURE:
<223> OTHER INFORMATION: Synthetic construct

<400> SEQUENCE: 105
tcgtgaacgt tcg                                                       13

<210> SEQ ID NO 106
<211> LENGTH: 13
<212> TYPE: DNA
<213> ORGANISM: Artificial Sequence
<220> FEATURE:
<223> OTHER INFORMATION: Synthetic construct

<400> SEQUENCE: 106
tcggtatcgg tcg                                                       13

<210> SEQ ID NO 107
<211> LENGTH: 13
<212> TYPE: DNA
<213> ORGANISM: Artificial Sequence
<220> FEATURE:
<223> OTHER INFORMATION: Synthetic construct

<400> SEQUENCE: 107
tcggtaccgt tcg                                                       13

<210> SEQ ID NO 108
<211> LENGTH: 13
<212> TYPE: DNA
<213> ORGANISM: Artificial Sequence
<220> FEATURE:
<223> OTHER INFORMATION: Synthetic construct
```

```
<400> SEQUENCE: 108
tcggaaccgt tcg                                                    13

<210> SEQ ID NO 109
<211> LENGTH: 12
<212> TYPE: DNA
<213> ORGANISM: Artificial Sequence
<220> FEATURE:
<223> OTHER INFORMATION: Synthetic construct

<400> SEQUENCE: 109
tcggaacgtt cg                                                     12

<210> SEQ ID NO 110
<211> LENGTH: 15
<212> TYPE: DNA
<213> ORGANISM: Artificial Sequence
<220> FEATURE:
<223> OTHER INFORMATION: Synthetic construct

<400> SEQUENCE: 110
tcgtcggaac gttcg                                                  15

<210> SEQ ID NO 111
<211> LENGTH: 12
<212> TYPE: DNA
<213> ORGANISM: Artificial Sequence
<220> FEATURE:
<223> OTHER INFORMATION: Synthetic construct

<400> SEQUENCE: 111
tcgtaacgtt cg                                                     12

<210> SEQ ID NO 112
<211> LENGTH: 11
<212> TYPE: DNA
<213> ORGANISM: Artificial Sequence
<220> FEATURE:
<223> OTHER INFORMATION: Synthetic construct

<400> SEQUENCE: 112
tcgaccgttc g                                                      11

<210> SEQ ID NO 113
<211> LENGTH: 14
<212> TYPE: DNA
<213> ORGANISM: Artificial Sequence
<220> FEATURE:
<223> OTHER INFORMATION: Synthetic construct

<400> SEQUENCE: 113
tcgtcgaccg ttcg                                                   14

<210> SEQ ID NO 114
<211> LENGTH: 13
<212> TYPE: DNA
<213> ORGANISM: Artificial Sequence
<220> FEATURE:
<223> OTHER INFORMATION: Synthetic construct

<400> SEQUENCE: 114
tcgttaacgt tcg                                                    13

<210> SEQ ID NO 115
<211> LENGTH: 16
<212> TYPE: DNA
```

```
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine
<220> FEATURE:
<221> NAME/KEY: variation
<222> LOCATION: 5
<223> OTHER INFORMATION: n = 5-bromocytosine
<220> FEATURE:
<221> NAME/KEY: variation
<222> LOCATION: 4-6
<223> OTHER INFORMATION: tng may or may not be present
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7, 8
<223> OTHER INFORMATION: n's may or may not be present
<220> FEATURE:
<221> NAME/KEY: variation
<222> LOCATION: (10)...(10)
<223> OTHER INFORMATION: n = t, a, or c
<220> FEATURE:
<221> NAME/KEY: variation
<222> LOCATION: (13)...(13)
<223> OTHER INFORMATION: n = t, g, or u

<400> SEQUENCE: 115
tngtngnnan cgntcg                                                16

<210> SEQ ID NO 116
<211> LENGTH: 13
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine

<400> SEQUENCE: 116
tngtgaacgt tcg                                                   13

<210> SEQ ID NO 117
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 5
<223> OTHER INFORMATION: n = 5-bromocytosine

<400> SEQUENCE: 117
tngtngtgaa cgttcg                                                16

<210> SEQ ID NO 118
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine
```

```
<400> SEQUENCE: 118
tngaacgttc g                                                        11

<210> SEQ ID NO 119
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine

<400> SEQUENCE: 119
tngaccgttc g                                                        11

<210> SEQ ID NO 120
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 5
<223> OTHER INFORMATION: n = 5-bromocytosine

<400> SEQUENCE: 120
tngtngaccg ttcg                                                     14

<210> SEQ ID NO 121
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7, 8
<223> OTHER INFORMATION: n's may or may not be present
<220> FEATURE:
<221> NAME/KEY: variation
<222> LOCATION: 10
<223> OTHER INFORMATION: n = t, a, or c
<220> FEATURE:
<221> NAME/KEY: variation
<222> LOCATION: 13
<223> OTHER INFORMATION: n = t, u, or g

<400> SEQUENCE: 121
tcgtngnnan cgntcg                                                   16

<210> SEQ ID NO 122
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine
```

```
<400> SEQUENCE: 122
tcgtngtgaa cgttcg                                              16

<210> SEQ ID NO 123
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 123
tcgtngaacg ttcg                                                14

<210> SEQ ID NO 124
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine

<400> SEQUENCE: 124
tcgtngaccg ttcg                                                14

<210> SEQ ID NO 125
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(6)
<223> OTHER INFORMATION: tcg may or may not be present
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7, 8
<223> OTHER INFORMATION: n's may or may not be present
<220> FEATURE:
<221> NAME/KEY: variation
<222> LOCATION: 10
<223> OTHER INFORMATION: n = t, a, or c
<220> FEATURE:
<221> NAME/KEY: variation
<222> LOCATION: 11
<223> OTHER INFORMATION: n = 5-bromocytosine
<220> FEATURE:
<221> NAME/KEY: variation
<222> LOCATION: (13)...(13)
<223> OTHER INFORMATION: n = t, g, or u

<400> SEQUENCE: 125
tcgtcgnnan ngntcg                                              16

<210> SEQ ID NO 126
<211> LENGTH: 13
<212> TYPE: DNA
<213> ORGANISM: Artificial Sequence
<220> FEATURE:
<223> OTHER INFORMATION: Synthetic construct
<220> FEATURE:
```

```
<221> NAME/KEY: variation
<222> LOCATION: 8
<223> OTHER INFORMATION: n = 5-bromocytosine

<400> SEQUENCE: 126
tcggaaangt tcg                                                          13

<210> SEQ ID NO 127
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 6
<223> OTHER INFORMATION: n = 5-bromocytosine

<400> SEQUENCE: 127
tcgaangttc g                                                            11

<210> SEQ ID NO 128
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2
<223> OTHER INFORMATION: n = 5-bromocytosine
<220> FEATURE:
<221> NAME/KEY: variation
<222> LOCATION: (4)...(6)
<223> OTHER INFORMATION: tng may or may not be present
<220> FEATURE:
<221> NAME/KEY: variation
<222> LOCATION: 5
<223> OTHER INFORMATION: n = 5-bromocytosine
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7,8
<223> OTHER INFORMATION: n's may or may not be present
<220> FEATURE:
<221> NAME/KEY: variation
<222> LOCATION: (10)...(10)
<223> OTHER INFORMATION: n = t, a, or c
<220> FEATURE:
<221> NAME/KEY: variation
<222> LOCATION: (13)...(13)
<223> OTHER INFORMATION: n = t, g, or u

<400> SEQUENCE: 128
tngtngnnan ngntcg                                                       16

<210> SEQ ID NO 129
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 6
<223> OTHER INFORMATION: n = 5-bromocytosine

<400> SEQUENCE: 129
tngaangutc g                                                            11
```

```
<210> SEQ ID NO 130
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 2, 6
<223> OTHER INFORMATION: n = 5-bromocytosine

<400> SEQUENCE: 130
tngaangttc g                                                          11

<210> SEQ ID NO 131
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5
<223> OTHER INFORMATION: n = 5-bromocytosine
<220> FEATURE:
<221> NAME/KEY: variation
<222> LOCATION: 7, 8
<223> OTHER INFORMATION: n = any nucleotide
<220> FEATURE:
<221> NAME/KEY: variation
<222> LOCATION: 7, 8
<223> OTHER INFORMATION: n's may or may not be present
<220> FEATURE:
<221> NAME/KEY: variation
<222> LOCATION: 10
<223> OTHER INFORMATION: n = t, a, c
<220> FEATURE:
<221> NAME/KEY: variation
<222> LOCATION: 11
<223> OTHER INFORMATION: n = 5-bromocytosine
<220> FEATURE:
<221> NAME/KEY: variation
<222> LOCATION: (13)...(13)
<223> OTHER INFORMATION: n = t, g, or u

<400> SEQUENCE: 131
tcgtngnnan ngntcg                                                     16

<210> SEQ ID NO 132
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5, 9
<223> OTHER INFORMATION: n = 5-bromocytosine

<400> SEQUENCE: 132
tcgtngaang utcg                                                       14

<210> SEQ ID NO 133
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: variation
<222> LOCATION: 5, 9
<223> OTHER INFORMATION: n = 5-bromocytosine
```

```
<400> SEQUENCE: 133
tcgtngaang ttcg                                                        14

<210> SEQ ID NO 134
<211> LENGTH: 22
<212> TYPE: DNA
<213> ORGANISM: Artificial Sequence
<220> FEATURE:
<223> OTHER INFORMATION: Synthetic construct

<400> SEQUENCE: 134
tgactgtgaa cgttcgagat ga                                               22

<210> SEQ ID NO 135
<211> LENGTH: 22
<212> TYPE: DNA
<213> ORGANISM: Artificial Sequence
<220> FEATURE:
<223> OTHER INFORMATION: Synthetic construct

<400> SEQUENCE: 135
tgactgtgaa ccttagagat ga                                               22

<210> SEQ ID NO 136
<211> LENGTH: 22
<212> TYPE: DNA
<213> ORGANISM: Artificial Sequence
<220> FEATURE:
<223> OTHER INFORMATION: Synthetic construct

<400> SEQUENCE: 136
tgactgtgaa ggttagagat ga                                               22

<210> SEQ ID NO 137
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 1
<223> OTHER INFORMATION: n = thymine attached to a reactive linking
      group

<400> SEQUENCE: 137
ngactgtgaa ccttagagat ga                                               22

<210> SEQ ID NO 138
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 1
<223> OTHER INFORMATION: n = thymine attached to a reactive linking
      group

<400> SEQUENCE: 138
ngactgtgaa ccttagagat ga                                               22

<210> SEQ ID NO 139
<211> LENGTH: 66
<212> TYPE: DNA
<213> ORGANISM: Artificial Sequence
<220> FEATURE:
```

```
<223> OTHER INFORMATION: Synthetic construct

<400> SEQUENCE: 139
tgactgtgaa cgttcgagat gatgactgtg aacgttcgag atgatgactg tgaacgttcg    60
agatga                                                               66

<210> SEQ ID NO 140
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 1
<223> OTHER INFORMATION: n = thymine attached to a reactive linking
      group

<400> SEQUENCE: 140
ngactgtgaa cgttcgagat ga                                             22

<210> SEQ ID NO 141
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 1
<223> OTHER INFORMATION: n = thymine attached to a reactive linking
      group

<400> SEQUENCE: 141
ngactgtgaa cgttcgagat ga                                             22
```

CHIMERIC IMMUNOMODULATORY COMPOUNDS AND METHODS OF USING THE SAME

CROSS-REFERENCE TO RELATED APPLICATIONS

This application is a divisional patent application of U.S. application Ser. No. 10/176,883, filed on Jun. 21, 2002, now U.S. Pat. No. 7,255,868, which claims the benefit of U.S. provisional patent application No. 60/299,883, filed Jun. 21, 2001 and U.S. provisional patent application No. 60/375,253, filed Apr. 23, 2002, the entire contents of which are hereby incorporated by reference for all purposes.

TECHNICAL FIELD

The present invention relates to chimeric immunomodulatory compounds ("CICs") containing nucleic acid and non-nucleic acid moieties, and to the use of such compounds to modulate an immune response. The invention finds use in the fields of biomedicine and immunology.

BACKGROUND

Reference to a publication in this section should not be construed as an indication that the publication is prior art to the present invention.

The type of immune response generated by infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

It has been recognized for some time that a Th1-type immune response can be induced in mammals by administration of certain immunomodulatory polynucleotides. The immunomodulatory polynucleotides include sequences referred to as immunostimulatory sequences ("ISS"), often including a CG dinucleotide. See, e.g., PCT Publications WO 98/55495, WO 97/28259, U.S. Pat. Nos. 6,194,388 and 6,207, 646; and Krieg et al. (1995) *Naure* 374:546-49. For many infectious diseases, such as tuberculosis and malaria, Th2-type responses are of little protective value against infection. Protein-based vaccines typically induce Th2-type immune responses, characterized by high titers of neutralizing antibodies but without significant cell-mediated immunity. Moreover, some types of antibody responses are inappropriate in certain indications, most notably in allergy where an IgE antibody response can result in anaphylactic shock.

In view of the need for improved methods of immunotherapy, a need exists for identification of compounds useful for modulation of an immune response.

DISCLOSURE OF THE INVENTION

In an aspect, the invention is directed to a chimeric compound having immunomodulatory activity. The chimeric immunomodulatory compound ("CIC") generally comprises one or more nucleic acid moieties and one or more non-nucleic acid moieties. The nucleic acid moieties in a CIC with more than one nucleic acid moiety may be the same or different. The non-nucleic acid moieties in a CIC with more than one non-nucleic acid moiety may be the same or different. Thus, in one embodiment the CIC comprises two or more nucleic acid moieties and one or more non-nucleic acid spacer moieties, where at least one non-nucleic acid spacer moiety is covalently joined to two nucleic acid moieties. In an embodiment, at least one nucleic acid moiety comprises the sequence 5'-CG-3'. In an embodiment, at least one nucleic acid moiety comprises the sequence 5'-TCG-3'.

In one aspect, the invention provides a chimeric immunomodulatory compound that has a core structure with the formula "$N_1$—$S_1$—$N_2$", where $N_1$ and $N_2$ are nucleic acid moieties and $S_1$ is a non-nucleic acid spacer moiety, and where the CIC exhibits immunomodulatory activity. In one embodiment, the core structure is "$N_1$—$S_1$—$N_2$—$S_2$—$N_3$", where $N_3$ is a nucleic acid moiety and $S_2$ is a non-nucleic acid spacer moiety. In one embodiment, the CIC has the core structure "$N_1$—$S_1$—$N_2$—$S_2$—$[N_v$—$S_v]_A$", where A is an integer between 1 and 100, and $[N_v$—$S_v]_A$ indicates A additional iterations of nucleic acid moieties conjugated to non-nucleic acid spacer moieties, where S and N are independently selected in each iteration of "$[N_v$—$S_v]$". In an embodiment, A is at least 2, and at least 4 nucleic acid moieties in the CIC have different sequences.

In an aspect, the CIC comprises a core structure with the formula $N_1$—$S_1$—$N_2$ or $N_1$—$S_1$—$N_2$—$S_2$—$N_3$ (wherein $N_1$, $N_2$, and $N_3$ are nucleic acid moieties, $S_1$ and $S_2$ are non-nucleic acid spacer moieties, and $S_1$ and $S_2$ are covalently bound to exactly two nucleic acid moieties). Examples of such CICs are CICs with core structures of the formula (5'-$N_1$-3')-$S_1$—$N_2$. In one embodiment, $N_1$ has the sequence 5'-TCGAX-3', wherein X is 0 to 20 nucleotide bases (SEQ ID NO:1). In one embodiment, X is 0 to 3 nucleotide bases. In one embodiment, X is CGT. In another embodiment $N_1$ has the sequence 5'-TCGTCGA-3'. In an embodiment, the CIC has the structure $N_1$—$S_1$—$N_2$—$S_2$—$[N_v$—$S_v]_A$ (wherein A is an integer between 1 and 100, and $[N_v$—$S_v]_A$ indicates "A" additional iterations of nucleic acid moieties conjugated to non-nucleotide spacer moieties, where S and N are independently selected in each iteration of $[N_v$—$S_v]$). In an embodiment, A is 1 to 3.

In another aspect, the invention provides a CIC that has a core structure with the formula $[N_v]_A$—$S_p$, where $S_p$ is a multivalent spacer covalently bonded to the quantity "A" independently selected nucleic acid moieties, $N_v$, where A is at least 3, and where the CIC exhibits immunomodulatory activity. In one embodiment, the CIC has the core sequence $[S_v$—$N_v]_A$—$S_p$ where $S_p$ is a multivalent spacer covalently bonded to the quantity "A" independently selected elements $[S_v$—$N_v]$, and independently selected element $[S_v$—$N_v]$ includes a spacer moiety covalently bound to a nucleic acid moiety, and wherein A is at least 3. In one embodiment, A is from 3 to 50. In a different embodiment, A is greater than 50.

In an embodiment, at least 2, at least 3 or at least 4 nucleic acid moieties in the CIC have different sequences.

In an aspect, the CIC comprises a core structure with the formula $[N_v]_A$—$S_p$ or $[S_v$—$N_v]_A$—$S_p$ (where $S_p$ is a multivalent spacer covalently bonded to the quantity "A" independently selected nucleic acid moieties, $N_v$, or independently selected elements $[S_v$—$N_v]$, each independently selected element $[S_v$—$N_v]$ comprising a spacer moiety covalently bound to a nucleic acid moiety, wherein A is at least 3. In embodiments, A is from 3 to about 50 or from about 50 to about 500. In an embodiment, $S_p$ comprises a dendrimer. In an embodiment, a nucleic acid moiety of the CIC has a sequence selected from TCGXXXX, TCGAXXX, XTCGXXX, XTCGAXX, TCGTCGA, TCGACGT, TCGAACG, TCGAGAT, TCGACTC, TCGAGCG, TCGATTT, TCGCTTT, TCGGTTT, TCGTTTT, TCGTCGT, ATCGATT, TTCGTTT, TTCGATT, ACGTTCG, AACGTTC, TGACGTT, TGTCGTT, TCGXXX, TCGAXX, TCGTCG, AACGTT, ATCGAT, GTCGTT, GACGTT, TCGXX, TCGAX, TCGAT, TCGTT, TCGTC, TCGA, TCGT, TCGX, or TCG (where "X" is any nucleotide).

In another aspect, the invention provides a CIC that has a core structure with the formula "$N_1$—$S_1$", where $N_1$ is a nucleic acid moiety and $S_1$ is a non-nucleic acid spacer moiety, and the CIC exhibits immunomodulatory activity.

The CIC may comprise non-nucleotide spacer moieties comprising, for example, triethylene glycol, hexaethylene glycol, a polymer comprising phosphodiester and/or phosphorothioate linked oligoethylene glycol moieties, $C_2$-$C_{10}$ alkyl (e.g., propyl, butyl, hexyl), glycerol or a modified glycerol (e.g., glycerol derivatized at the 1, 2 or 3 hydroxy-position; e.g., 3-levulinyl-glycerol), pentaerythritol or modified pentaerythritol (pentaerythritol modified at any hydroxy position(s), e.g., "trebler"), 2-(hydroxymethyl)ethyl, 1,3-diamino-2-propanol, an abasic nucleotide, a polysaccharide (e.g., a cross-linked polysaccharide), a dendrimer, and/or other spacer moiety components disclosed herein, in various combinations.

In various embodiments, a CIC described above has one or more of the following characteristics: (i) the CIC includes at least one nucleic acid moiety less than 8 nucleotides (or base pairs) in length, or, alternatively, less than 7 nucleotides in length (ii) all of the nucleic acid moieties of the CIC are less than 8 nucleotides in length, or, alternatively, less than 7 nucleotides in length, (iii) the CIC includes at least one nucleic acid moiety that includes the sequence 5'-CG-3' (e.g., 5'-TCG-3'), (iv) the CIC includes at least two nucleic acid moieties having different sequences, (v) all of the nucleic acid moieties of the CIC have the same sequence, (vi) the CIC includes at least one non-nucleic acid spacer moiety that is or comprises triethylene glycol, hexaethylene glycol, propyl, butyl, hexyl, glycerol or a modified glycerol (e.g., glycerol derivatized at the 1, 2 or 3 hydroxy-position; e.g., 3-levulinyl-glycerol), pentaerythritol or modified pentaerythritol (pentaerythritol modified at any hydroxy position(s), e.g., "trebler"), 2-(hydroxymethyl)ethyl, 1,3-diamino-2-propanol, an abasic nucleotide, a polysaccharide (e.g., a cross-linked polysaccharide), or a dendrimer. In some embodiments, the spacer moiety is not a polypeptide.

In various embodiments, a CIC described herein has one or more of the following characteristics: (vii) the CIC includes at least one nucleic acid moiety of the CIC that does not have "isolated immunomodulatory activity," (viii) the CIC does not include any nucleic acid moiety with "isolated immunomodulatory activity," (ix) the CIC includes at least one nucleic acid moiety of the CIC that has "inferior isolated immunological activity." "Isolated immunomodulatory activity" and "inferior isolated immunological activity" are described herein. In various embodiments a CIC described herein includes at least one nucleic acid moiety that is double-stranded or partially double-stranded. CICs can be designed with self-complementary nucleic acid moieties such that duplexes can be formed. See, e.g., C-84, C-85, and C-87.

Thus, in various aspects, the invention provides a CIC comprising two or more nucleic acid moieties and one or more non-nucleic acid spacer moieties, wherein at least one spacer moiety is covalently joined to two nucleic acid moieties and at least one nucleic acid moiety comprises the sequence 5'-CG-3', and wherein said CIC has immunomodulatory activity. The CIC may comprise at least three nucleic acid moieties, wherein each nucleic acid moiety is covalently joined to at least one non-nucleic acid spacer moiety. The CIC may have at least one immunomodulatory activity such as (a) the ability to stimulate IFN-γ production by human peripheral blood mononuclear cells; (b) the ability to stimulate IFN-α production by human peripheral blood mononuclear cells; and/or (c) the ability to stimulate proliferation of human B cells.

One or more nucleic acid moieties of the CIC can comprise a sequence such as 5'-TCGA-3',5'-TCGACGT-3',5'-TCGTCGA-3' and 5'-ACGTTCG-3'. In an embodiment, one or more nucleic acid moieties of the CIC can have the sequence 5'-$X_1X_2$CG$X_3X_4$-3' (where $X_1$ is zero to ten nucleotides; $X_2$ is absent or is A, T, or U; $X_3$ is absent or is A; and $X_4$ is zero to ten nucleotides, and wherein the nucleic acid moiety is conjugated to a spacer moiety, for example at the 3' end). In an embodiment, the sum of nucleotides in $X_1$, $X_2$, $X_3$, and $X_4$ can be less than 8, less than 7, less than 6, less than 5 or less than 4. In some embodiments, one or more nucleic acid moieties of the CIC can have a nucleic acid sequence such as TCGXXXX, TCGAXXX, XTCGXXX, XTCGAXX, TCGTCGA, TCGACGT, TCGAACG, TCGAGAT, TCGACTC, TCGAGCG, TCGATTT, TCGCTTT, TCGGTTT, TCGTTTT, TCGTCGT, ATCGATT, TTCGTTT, TTCGATT, ACGTTCG, AACGTTC, TGACGTT, TGTCGTT, TCGXXX, TCGAXX, TCGTCG, AACGTT, ATCGAT, GTCGTT, GACGTT, TCGXX, TCGAX, TCGAT, TCGTT, TCGTC, TCGA, TCGT, TCGX, or TCG (where "X" is any nucleotide).

In one embodiment, one or more nucleic acid moieties comprises 3 to 7 bases. In one embodiment, the nucleic acid moiety comprises 3 to 7 bases and has the sequence 5'-$[(X)_{0-2}]$TCG$[(X)_{2-4}]$-3', or 5'-TCG$[(X)_{2-4}]$-3', or 5'-TCG(A/T)$[(X)_{1-3}]$-3', or 5'-TCG(A/T)CG(A/T)-3', or 5'-TCGACGT-3' or 5'-TCGTCGA-3', wherein each X is an independently selected nucleotide. In some embodiments, the CIC contains at least 3, at least 10, at least 30 or at least 100 nucleic acid moieties having a sequence described above.

The CIC can include at least one nucleic acid moiety that is less than 8 nucleotides in length. Optionally all the nucleic acid moieties in the CIC are less than 8 nucleotides in length. In some embodiments, all the nucleic acid moieties in the CIC that comprise the sequence 5'-CG-3' are less than 8 nucleotides in length. The CIC can include at least 2 nucleic acid moieties having different sequences. The CIC can contain at least one nucleic acid moiety does not comprise the sequence 5'-CG-3'. The CIC may include at least one nucleic acid moiety that does not have isolated immunological activity or has inferior isolated immunological activity. Optionally no nucleic acid moiety of the CIC has isolated immunomodulatory activity. The linkages between the nucleotides of the nucleic acid moieties may include phosphodiester, phosphorothioate ester, phosphorodithioate ester, other covalent linkages, and mixtures thereof. Similarly, the linkages between nucleic acid moieties and spacer moieties or between components of spacer moieties may include phosphodiester, phosphorothioate ester, phosphorodithioate ester, other linkages, and mixtures thereof.

In an embodiment, the CIC includes a reactive linking group (e.g., a reactive thio group). The CIC may be linked or noncovalently associated with a polypeptide, e.g., a polypeptide antigen.

The invention also provides compositions comprising a CIC along with a pharmaceutically acceptable excipient and/or an antigen and/or a cationic microcarrier (such as a polymer of lactic acid and glycolic acid). The composition can be essentially endotoxin-free.

In an aspect, the invention provides a composition containing a CIC described herein and a pharmaceutically acceptable excipient, an antigen (e.g., an antigen to which an immune response is desired), or both. In an embodiment, the composition is formulated under GMP standards. In an embodiment, the composition is prepared by a process that includes assaying the composition for the presence of endotoxin. In an embodiment, the composition is essentially endotoxin-free. In an embodiment, the composition does not contain liposomes.

In an aspect, the invention provides the use of a CIC as described herein for the manufacture of a medicament.

In an aspect, the invention provides a method of modulating an immune response in an individual by administering an chimeric immunomodulatory compound or composition as described herein an amount sufficient to modulate an immune response in the individual. In one embodiment, the individual suffers from a disorder associated with a Th2-type immune response, for example, an allergy or allergy-induced asthma. In one embodiment, the individual has an infectious disease.

In an aspect, the invention provides a method of increasing interferon-gamma (IFN-γ) in an individual by administering a CIC or composition as described herein, in an amount sufficient to increase IFN-γ in the individual. In an embodiment, the individual has an inflammatory disorder. In an embodiment, the individual has idiopathic pulmonary fibrosis.

In an aspect, the invention provides a method of increasing interferon-alpha (IFN-α) in an individual, by administering a CIC or composition as described herein, in an amount sufficient to increase IFN-α in the individual. In an embodiment, the individual has a viral infection.

In an aspect, the invention provides a method of ameliorating a symptom of an infectious disease in an individual, by administering an effective amount of a CIC or composition, as described herein, to the individual, where the effective amount is an amount sufficient to ameliorate a symptom of the infectious disease.

In an aspect, the invention provides a method of ameliorating an IgE-related disorder in an individual, by administering an effective amount of a CIC or composition described herein to an individual having an IgE-related disorder, where an effective amount is an amount sufficient to ameliorate a symptom of the IgE-related disorder. In an embodiment, the IgE-related disorder is allergy or an allergy-related disorder.

The invention further provides a method of modulating an immune response in an individual by administering to an individual a CIC in an amount sufficient to modulate an immune response in said individual. In embodiments, the individual has cancer and/or suffers from a disorder associated with a Th2-type immune response (e.g., an allergy or allergy-induced asthma) and/or has an infectious disease.

BRIEF DESCRIPTION OF THE FIGURES

FIGS. 6A-C show the effect of CICs on levels of IL-12 p40 (FIG. 6A), IL-6 (FIG. 6B), and TNF-alpha (FIG. 6C).

MODES FOR CARRYING OUT THE INVENTION

I. General Methods

Figure 1:
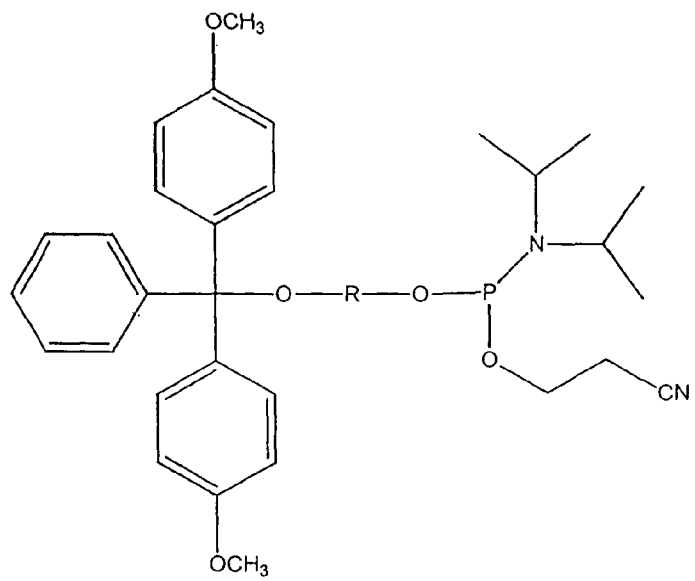
FIG. 1 shows the structure of certain reagents useful for synthesis of non-nucleic acid spacer moieties of CICs. Shown are dimethoxytrityl-protected phosphoramidite spacer moiety precursors for hexaethylene glycol ("HEG"), propyl, triethyleneglycol ("TEG"), 2-hydroxymethylethyl ("HME"), butyl, and abasic spacer moieties.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning. A Laboratory Manual*, second edition (Sambrook et al., 1989) and *Molecular Cloning: A Laboratory Manual*, third edition (Sambrook and Russel, 2001), jointly and individually referred to herein as "Sambrook"). *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane (1988) *Antibodies, A Laboratory Manual*, Cold Spring Harbor Publications, New York, and Harlow and Lane (1999) *Using Antibodies. A Laboratory Manual* Cold Spring Harbor Laboratory Press, Cold Spring Harbor, N.Y. (jointly, and individually referred to herein as "Harlow and Lane"), Beaucage et al. eds., *Current Protocols in Nucleic Acid Chemistry* John Wiley & Sons, Inc., New York, 2000); and Agrawal, ed., *Protocols for Oligonucleotides and Analogs, Synthesis and Properties* Humana Press Inc., New Jersey, 1993).

II. Definitions

As used herein, the singular form "a", "an", and "the" includes plural references unless otherwise indicated or clear from context. For example, as will be apparent from context, "a" chimeric immunostimulatory compound ("CIC") can include one or more CICs. Similarly, reference in the singular form of a component element of a CIC (i.e., nucleic acid moiety or non-nucleic acid spacer moiety) can include multiple elements. For example, a description of "a nucleic acid moiety" in a CIC can also describe two or more "nucleic acid moieties" in the CIC.

As used interchangeably herein, the terms "polynucleotide," "oligonucleotide" and "nucleic acid" include single-stranded DNA (ssDNA), double-stranded DNA (dsDNA), single-stranded RNA (ssRNA) and double-stranded RNA (dsRNA), modified oligonucleotides and oligonucleosides, or combinations thereof. The nucleic acid can be linearly or circularly configured, or the oligonucleotide can contain both linear and circular segments. Nucleic acids are polymers of nucleosides joined, e.g., through phosphodiester linkages or alternate linkages, such as phosphorothioate esters. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

An element, e.g., region, portion, non-nucleic acid spacer moiety, nucleic acid moiety, or sequence is "adjacent" to another element, e.g., region, portion, non-nucleic acid spacer moiety, nucleic acid moiety, or sequence, when it directly abuts that region, portion, spacer or sequence.

The term "CIC-antigen conjugate" refers to a complex in which a CIC and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with a CIC includes any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in *Hemophilus influenza* vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant peptides, crude peptide extracts, or peptides in a partially purified or unpurified active state (such as peptides that are part of attenuated or inactivated viruses, cells, micro-organisms), or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of a CIC, CIC-antigen mixture, or CIC-antigen conjugate to a particular site and/or with respect to particular timing. A delivery vehicle may or may not additionally stimulate an immune response.

An "allergic response to antigen" means an immune response generally characterized by the generation of eosinophils (usually in the lung) and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited to, histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Formadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

The term "microcarrier" refers to a particulate composition which is insoluble in water and which has a size of less than about 150, 120 or 100 μm, more commonly less than about 50-60 μm, and may be less than about 10 μm or even less than about 5 μm. Microcarriers include "nanocarriers", which are microcarriers have a size of less than about 1 μm, preferably less than about 500 nm. Microcarriers include solid phase particles such a particles formed from biocompatible naturally occurring polymers, synthetic polymers or synthetic copolymers, although microcarriers formed from agarose or cross-linked agarose may be included or excluded from the definition of microcarriers herein as well as other biodegradable materials known in the art. Solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., ellipsoidal, rod-shaped, etc.). Due to their insoluble nature, solid phase microcarriers are filterable from water and water-based (aqueous) solutions (e.g., using a 0.2 micron filter).

The term "nonbiodegradable", as used herein, refers to a microcarrier which is not degraded or eroded under normal mammalian physiological conditions. Generally, a microcarrier is considered nonbiodegradable if it not degraded (i.e., loses less than 5% of its mass or average polymer length) after a 72 hour incubation at 37° C. in normal human serum.

A microcarrier is considered "biodegradable" if it is degradable or erodible under normal mammalian physiological conditions. Generally, a microcarrier is considered biodegradable if it is degraded (i.e., loses at least 5% of its mass or average polymer length) after a 72 hour incubation at 37° C. in normal human serum.

The term "CIC/microcarrier complex" or "CIC/MC complex" refers to a complex of a CIC and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the CIC.

An "individual" or "subject" is a vertebrate, such as avian, preferably a mammal, such as a human. Mammals include, but are not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and, as such, an "effective amount" depends upon the context in which it is being applied. In the context of administering a composition that modulates an immune response to a co-administered antigen, an effective amount of a CIC and antigen is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response. Similarly, "stimulation" of a cytokine or cell type (such as CTLs) means an increase in the amount or level of cytokine or cell type.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by a CIC and antigen refers to the amount of a given antibody measured at a time point after administration of the CIC and antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in humans, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a composition comprising a CIC and antigen which suppresses histamine release reduces histamine release as compared to, for example, histamine release induced by antigen alone. As another example, a composition comprising a CIC and antigen which suppresses antibody production reduces extent and/or levels of antibody as compared to, for example, extent and/or levels of antibody produced by antigen alone.

As used herein manufactured or formulated "under GMP standards," when referring to a pharmaceutical composition means the composition is formulated as sterile, substantially isotonic and in full compliance with all Good Manufacturing Practice (GMP) regulations of the U.S. Food and Drug Administration.

As used herein, the term "immunogenic" has the normal meaning in the art and refers to an agent (e.g., polypeptide) that elicits an adaptive immune response upon injection into a person or animal. The immune response may be B cell (humoral) and/or T cell (cellular).

All ranges are intended to be inclusive of the terminal values. Thus, a polymer of "from 2 to 7 nucleotides" or "between 2 and 7 nucleotides" includes polymers of 2 nucleotides and polymers of 7 nucleotides. Where a lower limit and an independently selected upper limit are described, it is understood that the upper limit is higher than the lower limit.

III. Chimeric Immunomodulatory Compounds

The invention provides chimeric immunomodulatory compounds ("CICs") useful, inter alia, for modulating an immune response in individuals such as mammals, including humans. The present invention is based, in part, on the discovery that some chimeric molecules containing nucleic acid moieties covalently bound to non-nucleic acid spacer moieties have immunomodulatory activity, particularly in human cells. Surprisingly, this activity is manifest even in cases in which the nucleic acid moieties have a sequence that, if presented as an isolated polynucleotide, do not exhibit significant immunomodulatory activity.

Thus, the invention provides new reagents and methods for modulating an immune response, including treatment and prophylaxis of disease in humans and other animals.

The following sections describe the structure and properties of the CICs of the invention, as well as the structure and properties of the component nucleic acid moieties and non-nucleic acid spacer moieties.

1. Core Structure of CIC

CICs of the present invention contain one or more nucleic acid moieties and one or more non-nucleic acid spacer moieties. CICs having a variety of structures are contemplated. For illustration, exemplary CICs have core structures described in formulas I-VII, below. Formulas I-III show core sequences for "linear CICs." Formulas IV-VI show core sequences for "branched CICs." Formula VII shows a core structure for "single-spacer CICs."

In each formula provided below, "N" designates a nucleic acid moiety (oriented in either a 5'→3' or 3'→5' orientation) and "S" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("---") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures.

A. Linear CICs

In one embodiment, the CIC comprises the core structure $$N_1-S_1-N_2 \tag{I}$$

In one embodiment, the CIC comprises the core structure $$N_1-S_1-N_2-S_2-N_3 \tag{II}$$

In one embodiment, the CIC comprises the core structure $$N_1-S_1-N_2-S_2-[N_v-S_v]_A \tag{III}$$

where A is an integer between 1 and about 100 and $[N_v-S_v]$ indicates A additional iterations of nucleic acid moieties conjugated to non-nucleic acid spacer moieties. The subscript "v" indicates that N and S are independently selected in each iteration of "$[N_v-S_v]$." "A" is sometimes between 1 and about 10, sometimes between 1 and 3, sometimes exactly 1, 2, 3, 4 or 5. In some embodiments, A is an integer in a range defined by a lower limit of 1, 2, 3, 4, or 5, and an independently selected upper limit of 10, 20, 50 or 100 (e.g., between 3 and 10).

In some embodiments of the invention, the CIC has the structure of formula I, II or III. However, according to the invention, in some embodiments, linear CICs comprise, but are not necessarily limited to, the structures provided in formulas I-III. That is, formulas I, II, and III define core structures in which the non-nucleic acid spacer moieties in the core structure are covalently bound to no more than two nucleic acid moieties. However, it is contemplated that, in many embodiments, additional chemical moieties (e.g., phosphate, mononucleotide, additional nucleic acid moieties, alkyl, amino, thio or disulfide groups or linking groups, and/or spacer moieties) are covalently bound at the termini of the core structures. For example, if all nucleic acid moieties in a CIC are 5'-TCGTCGA-3', and spacer moieties are selected from HEG, a phosphorothioate-linked multimer of HEG, and glycerol, CICs having a core structure of formula I include each of the following formulas:

```
TCGTCGA-HEG-TCGTCGA-OH              (Ia)

TCGTCGA-HEG-TCGTCGA-PO4             (Ib)

TCGTCGA-HEG-TCGTCGA-HEG             (Ic)

HEG-TCGTCGA-HEG-TCGTCGA-HEG         (Id)
```

-continued

| | |
|---|---|
| TCGTCGA-HEG-TCGTCGA-HEG-TCGTCGA | (Ie) |
| TCGTCGA-HEG-TCGTCGA-(HEG)4-TCGTCGA | (If) |
| (TCGTCGA)2-glycerol-TCGTCGA-HEG-TCGTCGA | (Ig) |
| PO4-TCGTCGA-HEG-TCGTCGA | (Ih) |
| TCGTCGA-(HEG)15-T | (Ii) |
| (TCGTCGA-HEG)2-glycerol-HEG-TCGTCGA | (Ij) |
| TCGTCGA-HEG-T-HEG-T | (Ik) |

It will be immediately apparent that the genus of CICs comprising a core structure of formula I encompasses CICs comprising a core structure of formula II or III.

In some embodiments, one or more spacers comprises smaller units (e.g., HEG, TEG, glycerol, C3 alkyl, and the like) linked together. In one embodiment, the linkage is an ester linkage (e.g., phosphodiester or phosphorothioate ester) or other linkage, e.g., as described infra.

In certain embodiments, the terminal structures of the CIC are covalently joined (e.g., nucleic acid moiety-to-nucleic acid moiety; spacer moiety-to-spacer moiety, or nucleic acid moiety-to-spacer moiety), resulting in a circular conformation.

B. Branched CICs

In one embodiment, the CIC comprises the core structure $$[N_v]_A\text{—}S_p \qquad (IV)$$

where $S_p$ is a multivalent spacer covalently bonded to the quantity "A" independently selected nucleic acid moieties $N_v$, and where A is at least 3, e.g., exactly 3, 4, 5, 6, or 7 or more than 7. In various embodiments, A is an integer between 3 and 100 (inclusive). In some embodiments, A is an integer in a range defined by a lower limit of about 3, 5, 10, 50, or 100 and an independently selected upper limit of about 5, 7, 10, 50, 100, 150, 200, 250, or 500. It is also contemplated that in some embodiments, A is greater than about 500.

In a related embodiment, the CIC comprises the core structure $$[S_v\text{—}N_v]_A\text{—}S_p \qquad (V)$$

where $S_p$ is a multivalent spacer covalently bonded to the quantity "A" independently selected elements, $S_v$—$N_v$, comprising a spacer moiety covalently bound to a nucleic acid moiety, and where A is at least 3. In various embodiments, A is an integer between 3 and 100 (inclusive). In some embodiments, A is an integer in a range defined by a lower limit of 5, 10, 50, or 100 and an independently selected upper limit of 10, 50, 100, 250, or 500. It is also contemplated that in some embodiments, A is greater than 500. In a related embodiment, the CIC comprises the core structure:

$$(S_1\text{—}N_1)\text{—}S_p\text{—}(N_v)_A \qquad (VI)$$

where $S_p$ is a multivalent spacer covalently bonded to the quantity "A" independently selected nucleic acid moieties, $N_v$, and at least one nucleic acid moiety $N_1$ bound to a spacer moiety $S_1$, where A is at least 2. In one embodiment, A is 2. In various embodiments, A is 3, is 4, is 5, or is an integer between 3 and 100 (inclusive). In some embodiments, A is an integer in a range defined by a lower limit of 5, 10, 50, or 100 and an independently selected upper limit of 10, 50, 100, 150, 200, 250, or 500. It is also contemplated that in some embodiments, A is greater than 500. In some embodiments of the invention, the CIC has the structure of formula I, II or III. However, according to the invention, branched CICs comprise, but are not limited to, the structures provided in formulas IV, V and VI. That is, formulas IV, V and VI define core structures in which a multivalent spacer moiety ($S_p$) is covalently bound to at least three (3) nucleic acid moieties. It is contemplated that, in some embodiments, additional chemical moieties (e.g., phosphate, mononucleotide, additional nucleic acid and/or spacer moieties) are covalently bound at the termini of the core structures. For example, if all nucleic acid moieties in a CIC are 5'TCGTCGA 3' and all spacer moieties are glycerol or HEG, CICs having a core structure of formula IV include:

| | |
|---|---|
| (TCGTCGA)2-glycerol-TCGTCGA | (IVa) |
| (TCGTCGA-HEG)2-glycerol-TCGTCGA | (IVb) |
| (TCGTCGA-HEG-TCGTCGA)2-glycerol-TCGTCGA | (IVc) |
| [(TCGTCGA)2-glycerol-TCGTCGA]2-glycerol-TCGTCGA | (IVd) |

It will be immediately apparent, for example, that the genus of CICs comprising a core structure of formula IV encompasses CICs comprising a core structure of formula V or VI. In a preferred embodiment of the invention, the CIC comprises at least two different (i.e., different sequence) nucleic acid moieties.

In some embodiments, one or more spacers comprises smaller units (e.g., HEG, TEG, glycerol, C3 alkyl, and the like) linked together. In one embodiment, the linkage is an ester linkage (e.g., phosphodiester or phosphorothioate ester).

C. Single-Spacer CICs

In a different aspect of the invention, the CIC comprises a structure in which there is a single nucleic acid moiety covalently conjugated to a single spacer moiety, i.e., $$N_1\text{—}S_1 \qquad (VII)$$

In one embodiment, $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIa, infra. The multimer can be heteromeric or homomeric. In one embodiment, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIIb, infra.

For example, if the nucleic acid moiety is 5'TCGTCGA 3' and the spacer moiety is a phosphorothioate-linked multimer of hexaethylene glycol ["(HEG)$_{15}$"], a CIC having a core structure of formula VII includes:

| | |
|---|---|
| TCGTCGA-(HEG)15 | (VIIa) |

Similarly, if the nucleic acid moiety is 5'TCGTCGA 3' and the spacer moiety is a phosphorothioate-linked multimer of alternating hexaethylene glycol and propyl subunits, a CIC having a core structure of formula VI includes:

| | |
|---|---|
| TCGTCGA-HEG-propyl-HEG-propyl-HEG | (VIIb). |

2. Immunomodulatory Activity of CICs

The CICs of the invention have immunomodulatory activity. The terms "immunomodulatory," "immunomodulatory activity," or "modulating an immune response," as used herein, include immunostimulatory as well as immunosuppressive effects. An immune response that is immunomodulated according to the present invention is generally one that is shifted towards a "Th2-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen. Th1-type responses can be detected at the biochemical level by increased levels of Th1-associated cytokines such as IFN-γ, IFN-α, IL-2, IL-12, and TNF-β, as well as IL-6, although IL-6 may also be associated with Th2-type responses as well. Th2-type immune responses are generally associated with higher levels of antibody production, including IgE production, an absence of or minimal CTL production, as well as expression of Th2-associated cytokines such as IL-4 and IL-5.

Immunomodulation in accordance with the invention may be recognized by measurements (assays) in vitro, in vivo and/or ex vivo. Examples of measurable immune responses indicative of immunomodulatory activity include, but are not limited to, antigen-specific antibody production, secretion of cytokines, activation or expansion of lymphocyte populations such as NK cells, CD4+ T lymphocytes, CD8+ T lymphocytes, B lymphocytes, and the like. See, e.g., WO 97/28259; WO 98/16247; WO 99/11275; Krieg et al. (1995) *Nature* 374:546-549; Yamamoto et al. (1992) *J. Immunol.* 148:4072-4076; Ballas et al. (1996) *J. Immunol.* 157:1840-1845; Klinman et al. (1997) *J. Immunol.* 158:3635-3639; Sato et al. (1996) *Science* 273:352-354; Pisetsky (1996) *J. Immunol.* 156:421-423; Shimada et al. (1986) *Jpn. J. Cancer Res.* 77:808-816; Cowdery et al. (1996) *J. Immunol.* 156:4570-4575; Roman et al. (1997) *Nat. Med.* 3:849-54; Lipford et al. (1997) *Eur. J. Immunol.* 27:2340-2344; WO 98/55495, WO 00/61151, Pichyangkul et al. (2001) *J. Imm. Methods* 247:83-94. See also the Examples, infra. Certain useful assays are described herein below for purposes of illustration and not for limitation.

Assays are generally carried out by administering or contacting a cell, tissue, animal or the like with a test sample (e.g., containing a CIC, polynucleotide, and/or other agent) and measuring a response. The test samples containing CICs or polynucleotides can be in a variety of forms or concentrations, which will be understood by the ordinarily skilled practitioner to be appropriate for the assay type. For example, for purposes of a cell-based assay, CICs or polynucleotides are often used at a concentration of 20 μg/ml or 10 μg/ml or 2 μg/ml. Typically, for the purposes of the assay, concentration is determined by measuring absorbance at 260 nm and using the conversion 0.5 $OD_{260}$/ml=20 μg/ml. This normalizes the amount of total nucleic acid in the test sample and may be used, for example, when the spacer moiety does not have a significant absorbance at 260 nm. Alternatively, concentration or weight can be measured by other methods known in the art. If desired, the amount of nucleic acid moiety can be determined by measuring absorbance at 260 nm, and the weight of the CIC calculated using the molecular formula of the CIC. This method is sometimes used when the ratio of weight contributed by the spacer moiety(s) to weight contributed by the nucleic acid moieties in a CIC is high (i.e., greater than 1).

It will similarly be understood that positive and negative controls are useful in assays for immunomodulatory activity. A suitable positive control for immunomodulatory activity is the immunomodulatory phosphorothioate DNA having the sequence 5'-TGACTGTGAACGTTCGAGATGA-3' (SEQ ID NO:2), although other suitable positive controls with immunomodulatory activity will be apparent to the ordinarily skilled practitioner. One suitable negative control is no test agent (i.e., excipient or media alone, also referred to as "cells alone" for certain in vitro assays). Alternatively, a phosphorothioate DNA having the sequence 5'-TGACTGTGAACCTTAGAGATGA-3' (SEQ ID NO:3) is used as a negative control in some embodiments. Other negative controls can be designed by the practitioner guided by the disclosure herein and ordinary assay design.

One useful class of assays are "cytokine response assays." An exemplary assay for immunomodulatory activity measures the cytokine response of human peripheral blood mononuclear cells ("PBMCs") (e.g., as described in Bohle et al. [1999], *Eur. J. Immunol.* 29:2344-53; Verthelyi et al. [2001] *J. Immunol.* 166:2372-77). In one embodiment of this assay, peripheral blood is collected from one or more healthy human volunteers and PBMCs are isolated. Typically blood is collected by venipuncture using a heparinized syringe, layered onto a FICOLL® (Amersham Pharmacia Biotech) cushion and centrifuged. PBMCs are then collected from the FICOLL® interface and washed twice with cold phosphate buffered saline (PBS). The cells are resuspended and cultured (e.g., in 48- or 96-well plates) at $2 \times 10^6$ cells/mL in RPMI 1640 with 10% heat-inactivated human AB serum, 50 units/mL penicillin, 50 μg/mL streptomycin, 300 μg/mL glutamine, 1 mM sodium pyruvate, and 1×MEM non-essential amino acids (NEAA) in the presence and absence of test samples or controls for 24 hours.

Cell-free medium is collected from each well and assayed for IFN-γ and/or IFN-α concentration. Immunomodulatory activity is detected when the amount of IFN-γ secreted by PBMCs contacted with the test compound is significantly greater (e.g., at least about 3-fold greater, usually at least about 5-fold greater) than the amount secreted by the PBMCs in the absence of the test compound or, in some embodiments, in the presence of an inactive control compound (e.g., 5'-TGACTGTGAACCTTAGAGATGA-3' (SEQ ID NO:3)). Conversely, a test compound does not have immunomodulatory activity if the amount of IFN-γ secreted by PBMCs contacted with the test compound is not significantly greater (e.g., less than 2-fold greater) than in the absence of the test compound or, alternatively, in the presence of an inactive control compound (e.g., 5'-TGACTGTGAACCTTAGAGATGA-3' (SEQ ID NO:3)).

When IFN-α concentration is assayed, the amount of IFN-α secreted by PBMCs contacted with the test compound is often significantly greater (e.g., in the case of IFN-α sometimes at least about 2-fold or at least about 3-fold greater) than the amount secreted by the PBMCs in the absence of the test compound or, in some embodiments, in the presence of an inactive control compound (e.g., 5'-TGACTGTGAACCTTAGAGATGA-3' (SEQ ID NO:3)). In some embodiments, the significantly increased IFN-α secretion level is at least about 5-fold, at least about 10-fold, or even at least about 20-fold greater than controls. Conversely, a test compound does not have immunomodulatory activity if the amount of IFN-α secreted by PBMCs contacted with the test compound is not significantly greater (e.g., less than 2-fold greater) than in the absence of the test compound or, alternatively, in the presence of an inactive control compound (e.g., 5'-TGACTGTGAACCTTAGAGATGA-3' (SEQ ID NO:3)).

As illustrated in the examples, infra, administration of some CICs results in significant secretion of both IFN-γ and IFN-α, while administration of other CICs has a lesser effect on secretion of IFN-α or, conversely, a lesser effect on secretion of IFN-γ. See, e.g., Example 49.

Another useful class of assays are cell proliferation assays, e.g., B cell proliferation assays. The effect of an agent (e.g. a CIC) on B cell proliferation can be determined using any of a variety of assays known in the art. An exemplary B cell proliferation assay is provided in Example 41.

To account for donor variation, e.g., in cell-based assays, such as cytokine and proliferation assays, preferably assays are carried out using cells (e.g., PBMCs) from multiple different donors. The number of donors is usually at least 2 (e.g. 2), preferably at least 4 (e.g. 4), sometimes at least 10 (e.g. 10). Immunomodulatory activity is detected when the amount of IFN-γ secreted in the presence of the test compound (e.g. in at least half of the healthy donors tested, preferably in at least 75%, most preferably in at least 85%) is at least about 3-fold greater or at least about 5-fold greater than secreted in the absence of the test compound, or in some embodiments, than in the presence of an inactive control compound such as described supra.

In vitro assays can also be carried out using mouse cells, as described, for example, in Example 42, infra, and in other mammalian cells.

Exemplary in vivo assays are described in Examples 43, 44, and 46 (mice) and Example 45 (non-human primates).

Except where otherwise indicated or apparent, the cytokine assays described in the Examples, infra, are conducted using human PBMCs using essentially the protocol described in Example 28. Large numbers of test compounds can be assayed simultaneously, e.g., using multi-well plates or other multi-chamber assay materials. If desired, the assays can be carried out by computer-controlled robotic mechanisms well known in the art.

3. Nucleic Acid Moieties

The CICs of the invention comprise one or more nucleic acid moieties. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In a CIC comprising more than one nucleic acid moiety, the nucleic acid moieties may be the same or different.

The next three sections describe characteristics of nucleic acid moieties such as length, the presence, and the position of sequences or sequence motifs in the moiety, as well as describing (without intending to limit the invention) the properties and structure of nucleic acid moieties and CICs containing the moieties.

A. Length

Usually, a nucleic acid moiety is from 1 to 100 nucleotides in length, although longer moieties are possible in some embodiments. In some embodiments, the length of one or more of the nucleic acid moieties in a CIC is less than 8 nucleotides (i.e., 1, 2, 3, 4, 5, 6 or 7 nucleotides). In various embodiments, a nucleic acid moiety (such as a nucleic acid moiety fewer than 8 nucleotides in length) is at least 2 nucleotides in length, often at least 3, at least 4, at least 5, at least 6, or at least 7 nucleotides in length. In other embodiments, the nucleic acid moiety is at least 10, at least 20, or at least 30 nucleotides in length.

As shown in the Examples infra, CICs containing only heptameric, hexameric, pentameric, tetrameric, and trimeric nucleic acid moieties were active in assays for immunostimulatory activity (e.g., Examples 36 and 37). Thus, it is contemplated that, in some embodiments, a CIC will comprise at least one nucleic acid moiety shorter than 8 nucleotides. In some embodiments, all of the nucleic acid moieties in a CIC will be shorter than 8 nucleotides (e.g., having a length in a range defined by a lower limit of 2, 3, 4, 5, of 6 and an independently selected upper limit of 5, 6, or 7 nucleotides, where the upper limit is higher than the lower limit). For example, in one embodiment, specified nucleic acid moieties in a CIC (including all of the nucleic acid moieties in the CIC) may be either 6 or 7 nucleotides in length. In one embodiment, the CIC comprises two spacer moieties and an intervening nucleic acid moiety that is less than 8 bases in length (e.g., 5, 6, or 7 bases in length).

It is contemplated that in a CIC comprising multiple nucleic acid moieties, the nucleic acid moieties can be the same or different lengths. In one embodiment, the length of one or more, or most (e.g., at least about 2, at least about 4, or at least about 25%, at least about 50%, at least about 75%) or all of the nucleic acid moieties in a CIC is fewer than 8 nucleotides, in some embodiments fewer than 7 nucleotides, in some embodiments fewer than 6 nucleotides, in some embodiments between 2 and 6 nucleotides, in some embodiments between 2 and 7 nucleotides, in some embodiments between 3 and 7 nucleotides, in some embodiments between 4 and 7 nucleotides, in some embodiments between 5 and 7 nucleotides, and in some embodiments between 6 and 7 nucleotides.

As is discussed in greater detail infra, often at least one nucleic acid moiety of a CIC includes the sequence CG, e.g. TCG, or a CG-containing motif described herein. In one embodiment, at least one nucleic acid moiety comprises a CG-containing nucleic acid motif and is less than 8 nucleotides in length (e.g., has a specified length as described supra less than 8 nucleotides). In a related embodiment, none of the nucleic acid moieties in a CIC that are longer than 8 nucleotides comprise the sequence "CG" or optionally the sequence "TCG" or "ACG" (i.e., all of the nucleic acid moieties in the CIC that comprise the sequence CG are less than 8 nucleotides in length). In an embodiment, at least one nucleic acid moiety in the CIC does not comprise a CG sequence.

B. Sequences and Motifs

As noted supra, a particular nucleic acid moiety can have a variety of lengths. In one embodiment, the nucleic acid moiety has a length shorter than 8 nucleotides. In one embodiment, the nucleic acid moiety has a length of 8 nucleotides or longer. In various embodiments at least one nucleic acid moiety of a CIC of the invention comprises a sequence as disclosed infra.

In the formulas provided below, all sequences are in the 5'→3' direction and the following abbreviations are used: B=5-bromocytosine; bU=5-bromouracil; a-A=2-amino-adenine; g=6-thio-guanine; t=4-thio-thymine. H=a modified cytosine comprising an electron-withdrawing group, such as halogen in the 5 position. In various embodiments, a cytosine (C) in a sequence referred to infra is replaced with N4-ethylcytosine or N4-methylcytosine or 5-hydroxycytosine. In various embodiments, a guanosine (G) in the formula is replaced with 7-deazaguanosine.

In CICs tested thus far, the presence of CG correlates with cytokine-inducing activity. Thus, in one embodiment, at least one nucleic acid moiety of a CIC comprises at least one 5'-cytosine, guanine-3' (5'-CG-3') sequence. The cytosine is not methylated at the C-5 position and, preferably is not methylated at any position.

In one embodiment, one or more nucleic acid moieties comprises 3 to 7 bases. In one embodiment, the nucleic acid moiety comprises 3 to 7 bases and has the sequence 5'-[(X)$_{0-2}$]TCG[(X)$_{2-4}$]-3', or 5'-TCG[(X)$_{2-4}$]-3', or 5'-TCG(A/T)[(X)$_{1-3}$]-3', or 5'-TCG(A/T)CG(A/T)-3', or 5'-TCGACGT-3' or 5'-TCGTCGA-3', wherein each X is an independently selected nucleotide. In some embodiments, the CIC contains at least 3, at least 10, at least 30 or at least 100 nucleic acid moieties having an aforementioned sequence.

In an embodiment, the nucleic acid moiety comprises the sequence 5'-thymidine, cytosine, guanine-3' (5'-TCG-3'), for example (without limitation), the 3-mer TCG, the 4-mer TCGX (e.g., TCGA), the 5-mers TCGXX (e.g., TCGTC and TCGAT), the 6-mers TCGXXX, XTCGXX and TCGTCG, and the 7-mers TCGXXXX, XTCGXXX, XXTCGXX and TCGTCGX, where X is any base. Often, at least one nucleic acid moiety comprises the sequence 5'-thymidine, cytosine, guanine, adenosine-3' (5'-TCGA-3'), e.g., comprises a sequence 5'-TCGACGT-3'.

In some embodiments, a nucleic acid moiety comprises the sequence 5'-ACGTTCG-3'; 5'-TCGTCG-3'; 5'-AACGTTC-3'; 5'-AACGTT-3'; 5'-TCGTT-3'; 5'-CGTTCG-3'; 5'-TCGTCGA-3'; 5'-TCGXXX-3'; 5'-XTCGXX-3'; 5'-XX-TCGX-3'; 5'-TCGAGA-3'; 5'-TCGTTT-3'; 5'-TTCGAG-3'; 5'-TTCGT-3'; 5'-TTCGC-3'; 5'-GTCGT-3'; 5'-ATCGT-3'; 5'-ATCGAT-3'; 5'-GTCGTT-3'; 5'-GTCGAC-3'; 5'-ACCGGT-3'; 5'-AABGTT-3'; 5'-AABGUT-3',5'-TCGTBG-3' where X is any nucleotide.

In some embodiments, a nucleic acid moiety comprises the sequence 5'-X$_1$X$_2$CGX$_3$X$_4$-3', where X$_1$ is zero to ten nucleotides; X$_2$ is absent or is A, T, or U; X$_3$ is absent or is A and X$_4$ is zero to ten nucleotides. In an embodiment, the nucleic acid moiety is conjugated to a spacer moiety at the 3' end. In some embodiments, X$_1$ is zero to five nucleotides, alternatively zero to two nucleotides, and X$_4$ is zero to five nucleotides, alternatively zero to two nucleotides.

In some embodiments, a nucleic acid moiety comprises a sequence that is 5'-purine, purine, C, G, pyrimidine, pyrimidine-3'; 5'-purine, purine, C, G, pyrimidine, pyrimidine, C, G-3'; or 5'-purine, purine, C, G, pyrimidine, pyrimidine, C, C-3'; for example (all 5'→3'), GACGCT; GACGTC; GACGTT; GACGCC; GACGCU; GACGUC; GACGUU; GACGUT; GACGTU; AGCGTT; AGCGCT; AGCGTC; AGCGCC; AGCGUU; AGCGCU; AGCGUC; AGCGUT; AGCGTU; AACGTC; AACGCC; AACGTT; AACGCT; AACGUC; AACGUU; AACGCU; AACGUT; AACGTU; GGCGTT; GGCGCT; GGCGTC; GGCGCC; GGCGUU; GGCGCU; GGCGUC; GGCGUT; GGCGTU, AACGTT, AGCGTC, GACGTT, GGCGTT, AACGTC, GACGTC, GGCGTC, AACGCC, AGCGCC, GACGCC, GGCGCC, AGCGCT, GACGCT, GGCGCT, GGCGTT, and AACGCC.

In embodiments, a nucleic acid moiety comprises the sequence: 5'-purine, purine, cytosine, guanine, pyrimidine, pyrimidine, cytosine, cytosine-3' or 5'-purine, purine, cytosine, guanine, pyrimidine, pyrimidine, cytosine, guanine-3'

In some embodiments, a nucleic acid moiety comprises a sequence (all 5'→3') AACGTTCG; AACGTTCC; AACGUTCG; AABGTTCG; AABGUTCG and/or AABGTTBG.

In various embodiments, a nucleic acid moiety comprises the motif 5'-X$_1$ X$_2$ A X$_3$ C G X$_4$ T C G-3' (SEQ ID NO:4) wherein X$_1$ is T, G, C or B, wherein X$_2$ is T, G, A or U, wherein X$_3$ is T, A or C, wherein X$_4$ is T, G or U and wherein the sequence is not 5'-TGAACGTTCG-3' (SEQ ID NO:5) or 5'-GGAACGTTCG-3' (SEQ ID NO:6). Examples include (all 5'→3'): TGAACGUTCG (SEQ ID NO:7); TGACCGTTCG (SEQ ID NO:8); TGATCGGTCG (SEQ ID NO:9); TGATCGTTCG (SEQ ID NO:10); TGAACGGTCG (SEQ ID NO:11); GTAACGTTCG (SEQ ID NO:12); GTATCGGTCG (SEQ ID NO:13); GTACCGTTCG (SEQ ID NO:14); GAACCGTTCG (SEQ ID NO:15); BGACCGTTCG (SEQ ID NO:16); CGAACGTTCG (SEQ ID NO:17); CGACCGTTCG (SEQ ID NO:18); BGAACGTTCG (SEQ ID NO:19); TTAACGUTCG (SEQ ID NO:20); TUAACGUTCG (SEQ ID NO:21) and TTAACGTTCG (SEQ ID NO:22).

In various embodiments, a nucleic acid moiety comprises a sequence:

```
5'-TCGTCGAACGTTCGTTAACGTTCG-3';      (SEQ ID NO: 23)
5'-TGACTGTGAACGUTCGAGATGA-3';         (SEQ ID NO: 24)
5'-TCGTCGAUCGUTCGTTAACGUTCG-3';       (SEQ ID NO: 25)
5'-TCGTCGAUCGTTCGTUAACGUTCG-3';       (SEQ ID NO: 26)
5'-TCGTCGUACGUTCGTTAACGUTCG-3';       (SEQ ID NO: 27)
5'-TCGTCGAa-ACGUTCGTTAACGUTCG-3';     (SEQ ID NO: 28)
5'-TGATCGAACGTTCGTTAACGTTCG-3;        (SEQ ID NO: 29)
5'-TGACTGTGAACGUTCGGTATGA-3';         (SEQ ID NO: 30)
5'-TGACTGTGACCGTTCGGTATGA-3';         (SEQ ID NO: 31)
5'-TGACTGTGATCGGTCGGTATGA-3';         (SEQ ID NO: 32)
5'-TCGTCGAACGTTCGTT-3';               (SEQ ID NO: 33)
5'-TCGTCGTGAACGTTCGAGATGA-3';         (SEQ ID NO: 34)
5'-TCGTCGGTATCGGTCGGTATGA-3';         (SEQ ID NO: 35)
5'-CTTCGAACGTTCGAGATG-3';             (SEQ ID NO: 36)
5'-CTGTGATCGTTCGAGATG-3';             (SEQ ID NO: 37)
5'-TGACTGTGAACGGTCGGTATGA-3';         (SEQ ID NO: 38)
5'-TCGTCGGTACCGTTCGGTATGA-3';         (SEQ ID NO: 39)
5'-TCGTCGGAACCGTTCGGAATGA-3';         (SEQ ID NO: 40)
5'-TCGTCGAACGTTCGAGATG-3';            (SEQ ID NO: 41)
5'-TCGTCGTAACGTTCGAGATG-3';           (SEQ ID NO: 42)
5'-TGACTGTGACCGTTCGGAATGA-3';         (SEQ ID NO: 43)
5'-TCGTCGAACGTTCGAACGTTCG-3';         (SEQ ID NO: 44)
5'-TBGTBGAACGTTCGAGATG-3';            (SEQ ID NO: 45)
5'-TCGTBGAACGTTCGAGATG-3';            (SEQ ID NO: 46)
5'-TCGTCGACCGTTCGGAATGA-3';           (SEQ ID NO: 47)
5'-TBGTBGACCGTTCGGAATGA-3';           (SEQ ID NO: 48)
5'-TCGTBGACCGTTCGGAATGA-3';           (SEQ ID NO: 49)
5'-TTCGAACGTTCGTTAACGTTCG-3';         (SEQ ID NO: 50)
5'-CTTBGAACGTTCGAGATG-3';             (SEQ ID NO: 51)
5'-TGATCGTCGAACGTTCGAGATG-3'.         (SEQ ID NO: 52)
```

In some embodiments, a nucleic acid moiety comprises the sequence: 5'-X$_1$ X$_2$ A X$_3$ B G X$_4$ T C G-3' (SEQ ID NO:53), wherein X$_1$ is T, G, C or B, wherein X$_2$ is T, G, A or U, wherein X$_3$ is T, A or C, wherein X$_4$ is T, G or U. In some embodiments, the nucleic acid moiety is not 5'-TGAABGTTCG-3' (SEQ ID NO:54). Examples include (all 5'→3'): TGAABGUTCG (SEQ ID NO:55); TGACBGTTCG (SEQ ID NO:56); TGATBGGTCG (SEQ ID NO:57); GTATBGGTCG (SEQ ID NO:58); GTACBGTTCG (SEQ ID NO:59); GAACBGTTCG (SEQ ID NO:60); GAAABGUTCG (SEQ ID NO:61); BGACBGTTCG (SEQ ID NO:62); CGAABGTTCG (SEQ ID NO:63); BGAABGTTCG (SEQ ID NO:64);

BGAABGUTCG (SEQ ID NO:65); TTAABGUTCG (SEQ ID NO:66); TUAABGUTCG (SEQ ID NO:67) and TTAABGTTCG (SEQ ID NO:68).

In some embodiments, a nucleic acid moiety comprises the sequence:

| | |
|---|---|
| 5'-TGACTGTGAABGUTCGAGATGA-3'; | (SEQ ID NO: 69) |
| 5'-TCGTCGAABGTTCGTTAABGTTCG-3'; | (SEQ ID NO: 70) |
| 5'-TGACTGTGAABGUTCGGTATGA-3'; | (SEQ ID NO: 71) |
| 5'-TGACTGTGAABGUTCGGAATGA-3'; | (SEQ ID NO: 72) |
| 5'-TCGTCGAAABGUTCGGAATGA-3'; | (SEQ ID NO: 73) |
| 5'-TCGTBGAABGUTCGGAATGA-3'. | (SEQ ID NO: 74) |

In some embodiments, a nucleic acid moiety comprises the sequence: 5'-$X_1 X_2$ A $X_3$ C G $X_4$ T C G-3' (SEQ ID NO:75) wherein $X_1$ is T, C or B, wherein $X_2$ is T, G, A or U, wherein $X_3$ is T, A or C, wherein $X_4$ is T, G or U. In some embodiments, the formula is not 5'-TGAACGTTCG-3' (SEQ ID NO:5)

In other embodiments, the nucleic acid moiety comprises the sequence:

| | |
|---|---|
| 5'-TGACTGTGAABGTTCGAGATGA-3'; | (SEQ ID NO: 76) |
| 5'-TGACTGTGAABGTTBGAGATGA-3'; | (SEQ ID NO: 77) |
| 5'-TGACTGTGAABGTTCCAGATGA-3'; | (SEQ ID NO: 78) |
| 5'-TGACTGTGAACGTUCGAGATGA-3'; | (SEQ ID NO: 79) |
| 5'-TGACTGTGAACGbUTCGAGATGA-3'; | (SEQ ID NO: 80) |
| 5'-TGACTGTGAABGTTCGTUATGA-3'; | (SEQ ID NO: 81) |
| 5'-TGACTGTGAABGTTCGGTATGA-3'; | (SEQ ID NO: 82) |
| 5'-CTGTGAACGTTCGAGATG-3'; | (SEQ ID NO: 83) |
| 5'-TBGTBGTGAACGTTCGAGATGA-3'; | (SEQ ID NO: 84) |
| 5'-TCGTBGTGAACGTTCGAGATGA-3'; | (SEQ ID NO: 85) |
| 5'-TGACTGTGAACGtTCGAGATGA-3'; | (SEQ ID NO: 86) |
| 5'-TGACTGTGAACGTTCgAGATGA-3'; | (SEQ ID NO: 87) |
| 5'-TGACTGTGAACGTTCGTUATGA-3'; | (SEQ ID NO: 88) |
| 5'-TGACTGTGAACGTTCGTTATGA-3'; | (SEQ ID NO: 89) |
| 5'-TCGTTCAACGTTCGTTAACGTTCG-3'; | (SEQ ID NO: 90) |
| 5'-TGATTCAACGTTCGTTAACGTTCG-3'; | (SEQ ID NO: 91) |
| 5'-CTGTCAACGTTCGAGATG-3'; | (SEQ ID NO: 92) |
| 5'-TCGTCGGAACGTTCGAGATG-3'; | (SEQ ID NO: 93) |
| 5'-TCGTCGGACGTTCGAGATG-3'; | (SEQ ID NO: 94) |
| 5'-TCGTCGTACGTTCGAGATG-3'; | (SEQ ID NO: 95) |
| 5'-TCGTCGTTCGTTCGAGATG-3'. | (SEQ ID NO: 96) |

In some embodiments, with respect to any of the sequences disclosed supra, the nucleic acid moiety further comprises one, two, three or more TCG and/or TBG and/or THG, sequences, preferably 5' to the sequence provided supra. The TCG(s) and/or TBG(s) may or may not be directly adjacent to the sequence shown. For example, in some embodiments, a nucleic acid moiety includes any of the following: 5'-TCGT-GAACGTTCG-3' (SEQ ID NO:97); 5'-TCGTCGAACGT-TCG-3' (SEQ ID NO:98); 5'-TBGTGAACGTTCG-3' (SEQ ID NO:99); 5-TBGTBGAACGTTCG-3' (SEQ ID NO:100); 5'-TCGTTAACGTTCG-3' (SEQ ID NO:101). In some embodiments, the additional TCG and/or TBG sequence(s) is immediately 5' and adjacent to the reference sequence. In other embodiments, there is a one or two base separation.

In some embodiments, a nucleic acid moiety has the sequence: 5'-$(TCG)_w N_y$ A $X_3$ C G $X_4$ T C G-3' (SEQ ID NO:102) wherein w is 1-2, wherein y is 0-2, wherein N is any base, wherein $X_3$ is T, A or C, wherein $X_4$ is T, G or U.

In some embodiments, the nucleic acid moiety comprises any of the following sequences: TCGAACGTTCG (SEQ ID NO:103); TCGTCGAACGTTCG (SEQ ID NO:104); TCGT-GAACGTTCG (SEQ ID NO:105); TCGGTATCGGTCG (SEQ ID NO:106); TCGGTACCGTTCG (SEQ ID NO:107); TCGGAACCGTTCG (SEQ ID NO:108); TCGGAACGT-TCG (SEQ ID NO:109); TCGTCGGAACGTTCG (SEQ ID NO:110); TCGTAACGTTCG (SEQ ID NO:111); TCGAC-CGTTCG (SEQ ID NO:112); TCGTCGACCGTTCG (SEQ ID NO:113); TCGTTAACGTTCG (SEQ ID NO:114).

In some embodiments, a nucleic acid moiety comprises any of the following sequences: 5'-$(TBG)_z N_y$ A $X_3$ C G $X_4$ T C G-3' (SEQ ID NO:115) wherein z is 1-2, wherein y is 0-2, wherein B is 5-bromocytosine, wherein N is any base, wherein $X_3$ is T, A or C, wherein $X_4$ is T, G or U.

In some embodiments, a nucleic acid moiety comprises:

| | |
|---|---|
| TBGTGAACGTTCG; | (SEQ ID NO: 116) |
| TBGTBGTGAACGTTCG; | (SEQ ID NO: 117) |
| TBGAACGTTCG; | (SEQ ID NO: 118) |
| TBGTBGAACGTTCG; | (SEQ ID NO: 100) |
| TBGACCGTTCG; | (SEQ ID NO: 119) |
| TBGTBGACCGTTCG. | (SEQ ID NO: 120) |

In some embodiments, a nucleic acid moiety comprises any of the following sequences: 5'-T C G T B G $N_y$ A $X_3$ C G $X_4$ T C G-3' (SEQ ID NO:121) wherein y is 0-2, wherein B is 5-bromocytosine, wherein N is any base, wherein $X_3$ is T, A or C, wherein $X_4$ is T, G or U. In some embodiments, the nucleic acid moiety comprises any of the following sequences: TCGTBGTGAACGTTCG (SEQ ID NO:122); TCGTB-GAACGTTCG (SEQ ID NO:123); TCGTBGACCGTTCG (SEQ ID NO:124).

In some embodiments, a nucleic acid moiety comprises any of the following sequences: 5'-$(TCG)_w N_y$ A $X_3$ B G $X_4$ T C G-3' (SEQ ID NO:125) wherein w is 1-2, wherein y is 0-2, wherein N is any base, wherein $X_3$ is T, A or C, wherein $X_4$ is T, G or U. In some embodiments, the nucleic acid moiety comprises any of the following sequences: TCGGAAABGT-TCG (SEQ ID NO:126) or TCGAABGTTCG (SEQ ID NO:127).

In some embodiments, a nucleic acid moiety comprises any of the following sequences: 5'-$(TBG)_z N_y$ A $X_3$ B G $X_4$ T C G-3' (SEQ ID NO:128) wherein z is 1-2, wherein y is 0-2, wherein B is 5-bromocytosine, wherein N is any base, wherein $X_3$ is T, A or C, wherein $X_4$ is T, G or U. In some embodiments, the nucleic acid moiety comprises any of the following sequences: TBGAABGUTCG (SEQ ID NO:129) or TBGAABGTTCG (SEQ ID NO:130).

In some embodiments, a nucleic acid moiety comprises any of the following sequences: 5'-T C G T B G $N_y$ A $X_3$ B G X₄ T C G-3' (SEQ ID NO:131) wherein y is 0-2, wherein B is 5-bromocytosine, wherein N is any base, wherein X₃ is T, A or C, wherein X₄ is T, G or U. In some embodiments, the nucleic acid moiety comprises any of the following sequences: TCGTBGAABGUTCG (SEQ ID NO:132) or TCGTB-GAABGTTCG (SEQ ID NO:133).

In some embodiments, a nucleic acid moiety comprises the sequence:

AACGTTCC, AACGTTCG, GACGTTCC, GACGTTCG.

In some embodiments, a nucleic acid moiety comprises the sequence:

GGCGTTCG; GGCGCTCG; GGCGTCCG; GGCGCCCG; GACGTTCC;

GACGCTCC; GACGTCCC; GACGCCCC; AGCGTTCC; AGCGCTCC;

AGCGTCCC; AGCGCCCC; AACGTTCC; AACGCTCC; AACGTCCC;

AACGCCCC; GGCGTTCC; GGCGCTCC; GGCGTCCC; GGCGCCCC;

GACGTTCG; GACGCTCG; GACGTCCG; GACGCCCG; AGCGTTCG;

AGCGCTCG; AGCGTCCG; AGCGCCCG; AACGTTCG; AACGCTCG;

AACGTCCG; AACGCCCG; GACGCTCC; GACGCCC; AGCGTTCC;

AGCGCTCC; AGCGTCCC; AGCGCCCC; AACGTCCC; AACGCCCC;

GGCGTTCC; GGCGCTCC; GGCGTCCC; GGCGCCCC; GACGCTCG;

GACGTCCG; GACGCCCG; AGCGTTCG; AGCGTCCG; AGCGCCCG;

AACGTCCG; AACGCCCG.

In some embodiments, a nucleic acid moiety comprises the sequence:

(5'→3') TCGTCGA; TCGTCG; TCGTTT; TTCGTT; TTTTCG;

ATCGAT; GTCGAC; GTCGTT; TCGCGA; TCGTTTT; TCGTC;

TCGTT; TCGT; TCG; ACGTTT; CCGTTT; GCGTTT; AACGTT;

TCGAAAA; TCGCCCC; TCGGGGG.

In some embodiments, a nucleic acid moiety comprises an RNA of the sequence AACGUUCC, AACGUUCG, GACGUUCC, and GACGUUCG.

In some embodiments, a nucleic acid moiety has a sequence comprising a sequence or sequence motif described in copending coassigned U.S. patent applications 09/802,685 (published as U.S. Application Publication No. 20020028784A1 on Mar. 7, 2002 and as WO 01/68077 on Sep. 20, 2001); 09/802,359 (published as WO 01/68144 on Sep. 20, 2001), and copending U.S. application Ser. No. 10/033,243, or in PCT publications WO 97/28259, WO 98/16247; WO 98/55495; WO 99/11275; WO 99/62923; and WO 01/35991. The nucleic acid moiety can also have a sequence comprising any or several of the sequences previously reported to be correlated with immunostimulatory activity when administered as a polynucleotide greater (often substantially greater) than 8 nucleotides in length, e.g., Kandimalla et al., 2001, *Bioorg. Med. Chem.* 9:807-13; Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem. (Tokyo)* 116:991-994; Krieg et al. (1995) *Nature* 374: 546-549; Pisetsky et al. (1995) *Ann. N.Y. Acad. Sci.* 772:152-163; Pisetsky (1996a) *J. Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156: 558-564; Krieg (1996) *Trends Microbiol.* 4(2):73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996) *J. Lab. Clin. Med.* 128:329-338; Sonehara et al. (1996) *J. Interferon and Cytokine Res.* 16:799-803; Klinman et al. (1997) *J. Immunol.* 158:3635-3639; Sparwasser et al. (1997) *Eur. J. Immunol.* 27:1671-1679; Roman et al. (1997) *Nat Med.* 3:849-54; Carson et al. (1997) *J. Exp. Med.* 186:1621-1622; Chace et al. (1997) *Clin. Immunol. and Immunopathol.* 84:185-193; Chu et al. (1997) *J. Exp. Med.* 186:1623-1631; Lipford et al. (1997a) *Eur. J. Immunol.* 27:2340-2344; Lipford et al. (1997b) *Eur. J. Immunol.* 27:3420-3426; Weiner et al. (1997) *Proc. Natl. Acad. Sci. USA* 94:10833-10837; Macfarlane et al. (1997) *Immunology* 91:586-593; Schwartz et al. (1997) *J. Clin. Invest.* 100:68-73; Stein et al. (1997) *Antisense Technology*, Ch. 11 pp. 241-264, C. Lichtenstein and W. Nellen, Eds., IRL Press; Wooldridge et al. (1997) *Blood* 89:2994-2998; Leclerc et al. (1997) *Cell. Immunol.* 179:97-106; Kline et al. (1997) *J. Invest. Med.* 45(3):282A; Yi et al. (1998a) *J. Immunol.* 160:1240-1245; Yi et al. (1998b) *J. Immunol.* 160:4755-4761; Yi et al. (1998c) *J. Immunol.* 160: 5898-5906; Yi et al. (1998d) *J. Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J. Immunol.* 161:2428-2434; Krieg et al. (1998c) *Proc. Natl. Acad. Sci. USA* 95:12631-12636; Spiegelberg et al. (1998) *Allergy* 53(45S):93-97; Horner et al. (1998) *Cell Immunol.* 190:77-82; Jakob et al. (1998) *J. Immunol.* 161:3042-3049; Redford et al. (1998) *J. Immunol.* 161: 3930-3935; Weeratna et al. (1998) *Antisense & Nucleic Acid Drug Development* 8:351-356; McCluskie et al. (1998) *J. Immunol.* 161(9):4463-4466; Gramzinski et al. (1998) *Mol. Med.* 4:109-118; Liu et al. (1998) *Blood* 92:3730-3736; Moldoveanu et al. (1998) *Vaccine* 16:1216-1224; Brazolot Milan et al. (1998) *Proc. Natl. Acad. Sci. USA* 95:15553-15558; Briode et al. (1998) *J. Immunol.* 161:7054-7062; Briode et al. (1999) *Int. Arch. Allergy Immunol.* 118:453-456; Kovarik et al. (1999) *J. Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291-2298, WO 98/52962, WO 99/33488, WO 99/33868, WO 99/51259 and WO 99/62923. See also Zimmermann et al. (1998) *J. Immunol.* 160:3627-3630; Krieg (1999) *Trends Microbiol.* 7:64-65 and U.S. Pat. Nos. 5,663,153, 5,723,335 and 5,849,719. See also Liang et al. (1996) *J. Clin. Invest.* 98:1119-1129; Bohle et al. (1999) *Eur. J. Immunol.* 29:2344-2353 and WO 99/56755. See also WO 99/61056; WO 00/06588; WO 00/16804; WO 00/21556; WO 00/54803; WO 00/61151; WO 00/67023; WO 00/67787 and U.S. Pat. No. 6,090,791. In one embodiment, at least one nucleic acid moiety of a CIC comprises a TG sequence or a pyrimidine-rich (e.g., T-rich or C-rich) sequence, as described in PCT publication WO 01/22972.

In some embodiments, the nucleic acid moiety is other than one or more of the hexamers 5'-GACGTT-3',5'-GAGCTT-3', 5'-TCCGGA-3',5'-AACGTT-3', 5'-GACGTT-3',5'-TACGTT-3, '5'-CACGTT-3',5'-AGCGTT-3',5'-ATCGTT-3', 5'-ACCGTT-3',5'-AACGGT-3',5'-AACGAT-3',5'-AACGCT-3',5'-AACGTG-3', 5'-AACGTA-3', and 5'-AACGTC-3'.

In some embodiments, the CIC contains at least 3, at least 10, at least 30 or at least 100 nucleic acid moieties having a sequence described above.

C. Nucleic Acid Moiety Sequences: Heterogeneity and Position Effects

It is contemplated that in a CIC comprising multiple nucleic acid moieties, the nucleic acid moieties can be the same or different.

In one embodiment, all of the nucleic acid moieties in a CIC have the same sequence. In one embodiment, a CIC comprises nucleic acid moieties with at least 2, at least 3, at least 4, at least 5, or at least 6 or more different sequences. In one embodiment, a CIC has fewer than 10 different nucleic acid moieties. In one embodiment each of the nucleic acid moieties in a CIC has a different sequence.

In some embodiments, a single nucleic acid moiety contains more than one iteration of a sequence motif listed above in §3(B), or two or more different sequence motifs. The motifs within a single nucleic acid moiety can be adjacent, overlapping, or separated by additional nucleotide bases within the nucleic acid moiety. In an embodiment, a nucleic acid moiety includes one or more palindromic regions. In the context of single-stranded oligonucleotides, the term "palindromic" refers to a sequence that would be palindromic if the oligonucleotide were complexed with a complementary sequence to form a double-stranded molecule. In another embodiment, one nucleic acid moiety has a sequence that is palindromic or partially palindromic in relation to a second nucleic acid moiety in the CIC. In an embodiment of the invention, the sequence of one or more of the nucleic acid moieties of a CIC is not palindromic. In an embodiment of the invention, the sequence of one or more of the nucleic acid moieties of a CIC does not include a palindromic sequence greater than four bases, optionally greater than 6 bases.

As described supra, in various embodiments, one or more (e.g., all) of the nucleic acid moieties in a CIC comprises a 5'-CG-3' sequence, alternatively a 5'-TCG-3' sequence. In one embodiment, the nucleic acid moiety is 5, 6 or 7 bases in length. In an embodiment, the nucleic acid moiety has the formula 5'-TCG[(X)$_{2-4}$]-3' or 5'-TCG(A/T)[(X)$_{1-3}$] or 5'-TCG(A/T)CG(A/T)-3' or 5'-TCGACGT-3' (where each X is an independently selected nucleotide). In one embodiment, the aformentioned nucleic acid moiety is a 5-prime moiety.

In one embodiment, a nucleic acid moiety comprises a sequence 5'-TCGTCGA-3'. In one embodiment, a nucleic acid moiety comprises a sequence selected from (all 5'→3): TCGXXXX, TCGAXXX, XTCGXXX, XTCGAXX, TCGACGT, TCGAACG, TCGAGAT, TCGACTC, TCGAGCG, TCGATTT, TCGCTTT, TCGGTTT, TCGTTTT, TCGTCGT, ATCGATT, TTCGTTT, TTCGATT, ACGTTCG, AACGTTC, TGACGTT, TGTCGTT, TCGXXX, TCGAXX, GTCGTT, GACGTT, ATCGAT, TCGTCG; TCGTTT; TCGAGA; TTCGAG; TTCGTT; AACGTT; AACGTTCG; AACGUTCG, ABGUTCG, TCGXX, TCGAX, TCGAT, TCGTT, TCGTC; TCGA, TCGT, and TCGX (where X is A, T, G or C; U is 2'-deoxyuridine and B is 5-bromo-2'-deoxycytidine).

In one embodiment, the nucleic acid moiety is a 7-mer having the sequence TCGXXXX, TCGAXXX, XTCGXXX, XTCGAXX, TCGTCGA, TCGACGT, TCGAACG, TCGAGAT, TCGACTC, TCGAGCG, TCGATTT, TCGCTTT, TCGGTTT, TCGTTTT, TCGTCGT, ATCGATT, TTCGTTT, TTCGATT, ACGTTCG, AACGTTC, TGACGTT, or TGTCGTT; or is a 6-mer having the sequence TCGXXX, TCGAXX, TCGTCG, AACGTT, ATCGAT, GTCGTT, or GACGTT; or is a 5-mer having the sequence TCGXX, TCGAX, TCGAT, TCGTT, or TCGTC; or is a 4-mer having the sequence TCGA, TCGT, or TCGX, or is a 3-mer having the sequence TCG, where X is A, T, G or C.

In one embodiment, at least about 25%, preferably at least about 50%, or at least about 75%, and sometimes all of the nucleic acid moieties in the CIC comprise at least one of the aforementioned sequences. In one embodiment, at least one nucleic acid moiety does not comprise a CG motif. In other embodiments, at least about 25%, sometimes at least about 50%, and sometimes at least about 75% of the nucleic acid moieties in the CIC are nucleic acid moieties that do not have a CG motif or, alternatively, a TCG motif.

The position of a sequence or sequence motif in a CIC can influence the immunomodulatory activity of the CIC, as is illustrated in the Examples, infra. In referring to the position of a sequence motif in a nucleic acid moiety of a CIC, the following terminology is useful: (1) In a CIC containing multiple nucleic acid moieties, a moiety with a free-5' end is referred to as "a 5-prime moiety." It will be appreciated that a single CIC may have multiple 5-prime moieties. (2) Within any particular nucleic acid moiety, a sequence or motif is in "the 5-prime position" of the moiety when there are no nucleotide bases 5' to the reference sequence in that moiety. Thus, in the moiety with the sequence 5'-TCGACGT-3', the sequences T, TC, TCG and TCGA, are in "the 5-prime position," while the sequence GAC is not. By way of illustration, a CIC containing the sequence TCG in the 5-prime position of a nucleic acid moiety can render the CIC more active than an otherwise similar CIC with a differently positioned TCG motif. A CIC with a TCG sequence in a 5-prime moiety, e.g., at the 5-prime position of the 5-prime moiety can render a CIC particularly active. See e.g. Example 38. A nucleic acid moiety with a free 5' end can be designated using the symbol "5'$^F$" to the left of the formula for the base sequence of the nucleic acid moiety (e.g., 5'$^F$-TACG-3'). As used herein, the term "free 5' end" in the context of a nucleic acid moiety has its usual meaning and means that the 5' terminus of the nucleic acid moiety is not conjugated to a blocking group or a non-nucleotide spacer moiety.

Immunostimulatory activity can also be influenced by the position of a CG motif in a nucleic acid moiety (e.g., in a 5'-moiety). For example, in one useful embodiment the CIC contains at least one nucleic acid moiety with the sequence 5'-X-CG-Y-3' where X is zero, one, or two nucleotides and Y is 3, 4, 5, 6, 7, 8, 9, 10, 11, 12, 13, 14, 15 or more than 15 nucleotides in length. In an embodiment, the 5'-X-CG-Y-3' sequence is in a 5'-moiety of the CIC, e.g., the 5-prime position of the CIC. In an embodiment, the CIC contains 2, 3 or more nucleic acid moieties with a sequence having the formula 5'-X-CG-Y-3' sequence. For example, in an embodiment, all of the nucleic acid moieties of the CIC have sequences of the formula 5'-X-CG-Y-3' sequence.

Similarly, a CIC including the sequence TCGA (e.g., a sequence including TCGACGT) in a nucleic acid moiety has immunomodulatory activity, and is effective in IFN-α induction. A TCGA (e.g., a sequence including TCGACGT) in a 5-prime moiety, e.g., at the 5-prime position of the 5-prime moiety, renders the CIC particularly active. See examples 38 and 49. Thus, in one embodiment, a CIC comprises a core structure with the formula (5'-N$_1$-3')—S$_1$—N$_2$ (Ia) where N$_1$ has the sequence 5'-TCGAX-3' and X is 0 to 20 nucleotide bases, often 0 to 3 bases. In one embodiment, X is CGT. The sequence TCGTCGA is also particularly effective in IFN-α induction.

In addition, the presence of free (unconjugated) nucleic acid 5'-ends can affect immunostimulatory activity. See, e.g., Example 39. In various embodiments, a CIC of the invention comprises at least 1, at least 2, at least 3, at least 4, or at least 5 free 5' ends. In some embodiments, the number of free 5'-ends is from 1 to 10, from 2 to 6, from 3 to 5, or from 4-5. In one embodiment, the number of free 5' ends is at least about 50 or at least about 100.

D. "Isolated Immunomodulatory Activity"

One property of a nucleic acid moiety is the "isolated immunomodulatory activity" associated with the nucleotide sequence of the nucleic acid moiety. As noted supra, the present inventors have discovered that, surprisingly, CICs exhibit immunomodulatory activity even when none of the nucleic acid moieties of the CIC has a sequence that, if presented as a polynucleotide alone, exhibits comparable immunomodulatory activity.

In some embodiments, a nucleic acid moiety of a CIC does not have "isolated immunomodulatory activity," or has "inferior isolated immunomodulatory activity," (i.e., when compared to the CIC), as described below.

The "isolated immunomodulatory activity" of a nucleic acid moiety is determined by measuring the immunomodulatory activity of an isolated polynucleotide having the primary sequence of the nucleic acid moiety, and having the same nucleic acid backbone (e.g., phosphorothioate, phosphodiester, chimeric). For example, a CIC having the structure "5'-TCGTCG-3'-HEG-5'-ACGTTCG-3'-HEG-5'-AGATGAT-3'" contains three nucleic acid moieties. To determine the independent immunomodulatory activity of, for example, the first nucleic acid moiety in the CIC, a test polynucleotide having the same sequence (i.e., 5'-TCGTCG-3') and same backbone structure (e.g., phosphorothioate) is synthesized using routine methods, and its immunomodulatory activity (if any) is measured. Immunomodulatory activity can be determined using standard assays which indicate various aspects of the immune response, such as those described in §2, supra. Preferably the human PBMC assay described in §2, supra, is used. As discussed supra, to account for donor variation, typically the assay is carried out using cells obtained from multiple donors. A polynucleotide does not have immunomodulatory activity (and the corresponding nucleic acid moiety does not have "isolated immunomodulatory activity") when the amount of IFN-γ secreted by PBMCs contacted with the polynucleotide is not significantly greater (e.g., less than about 2-fold greater) in the majority of donors than in the absence of the test compound or, (in some embodiments) in the presence of an inactive control compound (e.g., 5'-TGACTGTGAACCTTAGAGATGA-3' (SEQ ID NO:3).)

To compare the immunomodulatory activity of a CIC and an isolated polynucleotide, immunomodulatory activity is measured, preferably using the human PBMC assay described in §2, supra. Usually, the activity of two compounds is compared by assaying them in parallel under the same conditions (e.g., using the same cells), usually at a concentration of about 20 µg/ml. As noted supra, typically, concentration is determined by measuring absorbance at 260 nm and using the conversion 0.5 OD$_{260}$/ml=20 µg/ml. This normalizes the amount of total nucleic acid in the test sample. Alternatively, concentration or weight can be measured by other methods known in the art. If desired, the amount of nucleic acid moiety can be determined by measuring absorbance at 260, and the weight of the CIC calculated using the molecular formula of the CIC. This method is sometimes used when the ratio of weight contributed by the spacer moiety(s) to weight contributed by the nucleic acid moieties in a CIC is high (i.e., greater than 1).

Alternatively, a concentration of 3 µM may be used, particularly when the calculated molecular weights of two samples being compared differ by more than 20%.

A nucleic acid moiety of a CIC is characterized as having "inferior immunomodulatory activity," when the test polynucleotide has less activity than the CIC to which it is compared. Preferably the isolated immunomodulatory activity of the test polynucleotide is no more than about 50% of the activity of the CIC, more preferably no more than about 20%, most preferably no more than about 10% of the activity of the CIC, or in some embodiments, even less.

For CICs with multiple (e.g., multiple different) nucleic acid moieties, it is also possible to determine the immunomodulatory activity (if any) of a mixture of test polynucleotides corresponding to the multiple nucleic acid moieties. The assay can be carried out using a total amount of test polynucleotide (i.e., in the mixture) which equals the amount of CIC used. Alternatively, an amount of each test polynucleotide, or each different test polynucleotide, in the mixture can be equal to the amount of the CIC in the assay. As noted in §2, to account for donor variation, preferably assays and analysis use PMBCs from multiple donors.

In one embodiment, one or more (e.g., at least about 2, at least about 4, or at least about 25%, at least about 50%, or all, measured individually or, alternatively, in combination) of the nucleic acid moieties in a CIC do not have isolated immunomodulatory activity. In one embodiment, one or more (e.g., at least about 2, at least about 4, or at least about 25%, at least about 50%, or all, measured individually or, alternatively, in combination) has inferior isolated immunomodulatory activity compared to the CIC.

In a related embodiment, a CIC comprises one or more nucleic acid moieties with isolated immunomodulatory activity. For example, in some embodiments, all or almost all (e.g., at least 90%, preferably at least 95%) of the nucleic acid moieties has isolated immunomodulatory activity. For example, a CIC comprising a multivalent spacer(s) can comprise more than 4, often more than 10, frequently at least about 20, at least about 50, at least about 100, at least about 400 or at least about 1000 nucleic acid moieties (e.g., at least about 2500) with isolated immunostimulatory activity (e.g., having the sequence 5'-TGA CTG TGA ACG TTC GAG ATG A-3' (SEQ ID NO:2)).

Thus, in a particular CIC, the number of nucleic acid moieties that have isolated immunomodulatory activity can be zero (0), one (1), 2 or more, 3 or more, fewer than 3, 4 or more, fewer than 4, 5 or more, fewer than 5, at least 10, at least about 20, at least about 50, at least about 100, at least about 400 or at least about 1000, all, or less than all, of the nucleic acid moieties of the CIC.

E. Structure of the Nucleic Acid Moiety

A nucleic acid moiety of a CIC may contain structural modifications relative to naturally occurring nucleic acids. Modifications include any known in the art for polynucleotides, but are not limited to, modifications of the 3'OH or 5'OH group, modifications of the nucleotide base, modifications of the sugar component, and modifications of the phosphate group. Various such modifications are described below.

The nucleic acid moiety may be DNA, RNA or mixed DNA/RNA, single stranded, double stranded or partially double stranded, and may contain other modified polynucleotides. Double stranded nucleic acid moieties and CICs are contemplated, and the recitation of the term "base" or "nucleotide" is intended to encompass basepair or basepaired nucleotide, unless otherwise indicated. A nucleic acid moiety may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, CICs and nucleic acid moieties of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications (discussed further below) include, but are not limited to, addition of an electron-withdrawing moiety to C-5 and/or C-6 of a cytosine (e.g., 5-bromocytosine, 5-chlorocytosine, 5-fluorocytosine, 5-iodocytosine) and C-5 and/or C-6 of a uracil (e.g., 5-bromouracil, 5-chlorouracil, 5-fluorouracil, 5-iodouracil). See, for example, PCT Application No. WO 99/62923.

The nucleic acid moiety can also contain phosphate-modified nucleotides. Synthesis of nucleic acids containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the nucleic acids of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidates (Nelson et al. (1997) *JOC* 62:7278-7287) and phosphorodithioates (U.S. Pat. No. 5,453,496) has also been described. Other non-phosphorous based modified nucleic acids can also be used (Stirchak et al. (1989) *Nucleic Acids Res.* 17:6129-6141). Nucleic acids with phosphorothioate backbones appear to be more resistant to degradation after injection into the host. Braun et al. (1988) *J. Immunol.* 141:2084-2089; and Latimer et al. (1995) *Mol. Immunol.* 32:1057-1064.

Nucleic acid moieties used in the invention can comprise ribonucleotides (containing ribose as the only or principal sugar component), and/or deoxyribonucleotides (containing deoxyribose as the principal sugar component). Modified sugars or sugar analogs can be incorporated in the nucleic acid moiety. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. The sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. For example, a sugar modification in the CIC includes, but is not limited to, 2'-amino-2'-deoxyadenosine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of a CIC.

The heterocyclic bases, or nucleic acid bases, which are incorporated in the nucleic acid moiety can be the naturally-occurring principal purine and pyrimidine bases, (namely uracil, thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the nucleic acid moiety can include one or several heterocyclic bases other than the principal five base components of naturally-occurring nucleic acids. Preferably, however, the heterocyclic base is, without limitation, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, or 2-amino-4-oxopyrrolo[2,3-d]pyrimidin-3-yl groups, where the purines are attached to the sugar moiety of the nucleic acid moiety via the 9-position, the pyrimidines via the 1-position, the pyrrolopyrimidines via the 7-position and the pyrazolopyrimidines via the 1-position.

The nucleic acid moiety may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the nucleic acid moiety. Preferably, the electron-withdrawing moiety is a halogen. Such modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidin, 5,6-dihydrocytosine, 5-iodocytosine, 5-nitrocytosine, and any other pyrimidine analog or modified pyrimidine. Other examples of base modifications include, but are not limited to, addition of an electron-withdrawing moiety to C-5 and/or C-6 of a uracil of the nucleic acid moiety. Preferably, the electron-withdrawing moiety is a halogen. Such modified uracils can include, but are not limited to, 5-bromouracil, 5-chlorouracil, 5-fluorouracil, 5-iodouracil. Also see, Kandimalla et al., 2001, *Bioorg Med. Chem.* 9:807-13.

Other examples of base modifications include the addition of one or more thiol groups to the base including, but not limited to, 6-thio-guanine, 4-thio-thymine and 4-thio-uracil.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

4. Non-Nucleic Acid Spacer Moieties

The CIC compounds of the invention comprise one or more non-nucleic acid spacer moieties covalently bound to the nucleic acid moieties. For convenience, non-nucleic acid spacer moieties are sometimes referred to herein simply as "spacers" or "spacer moieties."

Spacers are generally of molecular weight about 50 to about 500,000 (e.g. about 50 to about 50,000), sometimes from about 75 to about 5000, sometimes from about 75 to about 500, which are covalently bound, in various embodiments, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in a CIC. A spacer moiety is said to comprise a particular spacer component (e.g., hexaethylene glycol) when the spacer includes the component (or a substituted derivative) as a subunit or portion of the spacer. For example, the spacer shown in Example 49 can be described as comprising a polysaccharide component, a hexaethylene glycol component, and a derivatized thioether linker component. As described infra, in certain embodiments, a spacer comprises multiple covalently connected subunits and may have a homopolymeric or heteropolymeric structure. Often the subunits are connected by a linker, phosphodiester linkage, and/or phosphorothioate ester linkage. See the Examples, infra. Nonnucleotide spacer moieties of a CIC comprising or derived from such multiple units can be referred to as "compound spacers." In one embodiment, for illustration and not limitation, the CIC comprises a compound spacer comprising any two or more (e.g., 3 or more, 4 or more, or 5 or more) of the following compounds in phosphodiester linkage and/or phosphorothioate ester linkage: oligoethylene glycol unit (e.g., triethylene glycol spacer; hexaethylene glycol spacer); alkyl unit (e.g., propyl spacer; butyl spacer; hexyl spacer); branched spacer (e.g., 2-(hydroxymethyl)ethyl spacer; glycerol spacer; trebler spacer; symmetrical doubler spacer).

It will be appreciated that mononucleotides and polynucleotides are not included in the definition of non-nucleic acid spacers, without which exclusion there would be no difference between nucleic acid moiety and an adjacent non-nucleic acid spacer moiety.

A variety of spacers are described herein, for illustration and not limitation. It will be appreciated by the reader that, for convenience, a spacer moiety (or component of a spacer moiety) is sometimes referred to by the chemical name of the compound (e.g., hexaethylene glycol) from which the spacer moiety or component is derived, with the understanding that the CIC actually comprises the conjugate of the compound(s) to nucleic acid moieties. As will be understood by the ordinarily skilled practitioner (and as described in greater detail hereinbelow), the non-nucleic acid spacer can be (and usually is) formed from a spacer moiety precursor(s) that include reactive groups to permit coupling of one more nucleic acid (e.g., oligonucleotides) to the spacer moiety precursor to form the CIC and protecting groups may be included. The reactive groups on the spacer precursor may be the same or different.

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), symmetric or asymmetric spacers derived from glycerol, pentaerythritol, 1,3,5-trihydroxycyclohexane or 1,3-diamino-2-propanol (e.g., symmetrical doubler and trebler spacer moieties described herein). Optionally these spacer components are substituted. For example, as will be understood by one of ordinary skill in the art, glycerol and 1,3-diamino-2-propanol may be substituted at the 1, 2, and/or 3 position (e.g., replacement of one or more hydrogens attached to carbon with one of the groups listed below). Similarly, pentaerythritol may be substituted at any, or all, of the methylene positions with any of the groups described below. Substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, phosphoramidate, phosphorodithioate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, ether, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O)CH=CHC(=O) (maleimide), thioether, cyano, sugar (such as mannose, galactose, and glucose), α,β-unsaturated carbonyl, alkyl mercurial, α,β-unsaturated sulfone.

In one embodiment, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxarabinose and polymers thereof.

Spacers can comprise heteromeric or homomeric oligomers and polymers of the nonnucleic acid components described herein (e.g., linked by a phosphodiester or phosphorothioate linkage or, alternatively an amide, ester, ether, thioether, disulfide, phosphoramidate, phosphotriester, phosphorodithioate, methyl phosphonate or other linkage). For example, in one embodiment, the spacer moiety comprises a branched spacer component (e.g., glycerol) conjugated via a phosphodiester or phosphorothioate linkage to an oligoethylene glycol such as HEG (see, e.g., C-94). Another example, is a spacer comprising a multivalent spacer component conjugated to an oligoethylene glycol such as HEG.

Other suitable spacers comprise substituted alkyl, substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, ether, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O)CH=CHC(=O) (maleimide), thioether, cyano, sugar (such as mannose, galactose, and glucose), α,β-unsaturated carbonyl, alkyl mercurial, α,β-unsaturated sulfone.

Other suitable spacers may comprise polycyclic molecules, such as those containing phenyl or cyclohexyl rings. The spacer may be a polyether such as polyphosphopropanediol, polyethylene glycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenanthrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one embodiment, the spacer comprises (1-phosphopropane)-$_3$-phosphate or (1-phosphopropane)-$_4$-phosphate (also called tetraphosphopropanediol and pentaphosphopropanediol). In one embodiment, the spacer comprises derivatized 2,2'-ethylenedioxydiethylamine (EDDA).

Other examples of non-nucleic acid spacers useful in CICs include "linkers" described by Cload and Schepartz, *J. Am. Chem. Soc.* (1991), 113:6324; Richardson and Schepartz, *J. Am. Chem. Soc.* (1991), 113:5109; Ma et al., *Nucleic Acids Research* (1993), 21:2585; Ma et al., *Biochemistry* (1993), 32:1751; McCurdy et al., *Nucleosides & Nucleotides* (1991), 10:287; Jaschke et al., *Tetrahedron Lett.* (1993), 34:301; Ono et al., *Biochemistry* (1991), 30:9914; and Arnold et al., International Publication No. WO 89/02439 and EP0313219B1 entitled "Non-nucleic acid Linking Reagents for Nucleotide Probes," linkers described by Salunkhe et al., *J. Am. Chem. Soc.* (1992), 114:8768; Nelson et al., *Biochemistry* 35:5339-5344 (1996); Bartley et al., *Biochemistry* 36:14502-511 (1997); Dagneaux et al. *Nucleic Acids Research* 24:4506-12 (1996); Durand et al., *Nucleic Acids Research* 18:6353-59 (1990); Reynolds et al., *Nucleic Acids Research*, 24:760-65 (1996); Hendry et al. *Biochemica et Biophysica Acta*, 1219: 405-12 (1994); Altmann et al., *Nucleic Acids Research*, 23:4827-35 (1995), and U.S. Pat. No. 6,117,657 (Usman et al.).

Suitable spacer moieties can contribute charge and/or hydrophobicity to the CIC, contribute favorable pharmacokinetic properties (e.g., improved stability, longer residence time in blood) to the CIC, and/or result in targeting of the CIC to particular cells or organs. Spacer moieties can be selected or modified to tailor the CIC for desired pharmacokinetic properties, induction of a particular immune response, or suitability for desired modes of administration (e.g., oral administration).

In a CIC comprising more than one spacer moiety, the spacers may be the same or different. Thus, in one embodiment all of the non-nucleic acid spacer moieties in a CIC have the same structure. In one embodiment, a CIC comprises non-nucleic acid spacer moieties with at least 2, at least 3, at least 4, at least 5, or at least 6 or more different structures.

In some contemplated embodiments of the invention, the spacer moiety of a CIC is defined to exclude certain structures. Thus, in some embodiments of the invention, a spacer is other than an abasic nucleotide or polymer of abasic nucleotides. In some embodiments of the invention, a spacer is other than a oligo(ethyleneglycol) (e.g., HEG, TEG and the like) or poly(ethyleneglycol). In some embodiments a spacer is other than a C3 alkyl spacer. In some embodiments a spacer is other than an alkyl or substituted spacer. In some embodiments, a spacer is other than a polypeptide. Thus, in some embodiments, an immunogenic molecule, e.g., a protein or polypeptide, is not suitable as a component of spacer moieties. However, as discussed infra, it is contemplated that in certain embodiments, a CIC is a "proteinaceous CIC" i.e., comprising a spacer moiety comprising a polypeptide (i.e., oligomer or polymer of amino acids). For example, as discussed infra, in some embodiments, a polypeptide antigen can be used as a platform (multivalent spacer) to which a plurality of nucleic acid moieties are conjugated. However, in some embodiments, the spacer moiety is not proteinaceous and/or is not an antigen (i.e., the spacer moiety, if isolated from the CIC, is not an antigen).

Suitable spacer moieties do not render the CIC of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility<5 mg/ml when measured as dialcohol precursor 1,12-dihydroxydodecane) is not preferred because it can reduce the hydrophilicity and activity of the CIC. Preferably, spacer moieties have solubility much greater than 5 mg/ml (e.g., solubility at least about 20 mg/ml, at least about 50 mg/ml or at least about 100 mg/ml), e.g., when measured as dialcohol precursors. The form of the spacer moiety used for testing its water solubility is generally its most closely related unactivated and unprotected spacer precursor molecule. For example, C-19 contains a spacer moiety including a dodecyl group with phosphorothioate diester linkages at the C-1 and C-12 positions, thereby connecting the spacer moiety to the nucleic acid moieties. In this case, the water solubility of the dialcohol version of the dodecyl spacer, 1,12-dihydroxydodecane, was tested and found to be less than 5 mg/ml. Spacers with higher water solubility, when tested as their dialcohol precursors, resulted in more immunostimulatory CICs. These higher water solubility spacers include, without limitation, propane 1,3 diol; glycerol; butane-1,4-diol; pentane-1,5-diol; hexane-1,6-diol; triethylene glycol, tetraethylene glycol and HEG.

A. Charged and Multiunit Spacer Moieties

The charge of a CIC may be contributed by phosphate, thiophosphate, or other groups in the nucleic acid moieties as well as groups in non-nucleic acid spacer moieties. In some embodiments of the invention, a non-nucleic acid spacer moiety carries a net charge (e.g., a net positive charge or net negative charge when measured at pH 7). In one useful embodiment, the CIC has a net negative charge. In some embodiments, the negative charge of a spacer moiety in a CIC is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain embodiments the negative charge contributed by the non-nucleic acid spacer moieties in a CIC (i.e., the sum of the charges when there is more than one spacer) is greater than the negative charge contributed by the nucleic acid moieties of the CIC. Charge can be calculated based on molecular formula, or determined experimentally, e.g., by capillary electrophoresis (Li, ed., 1992, *Capillary Electrophoresis, Principles, Practice and Application* Elsevier Science Publishers, Amsterdam, The Netherlands, pp 202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one embodiment the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

For illustration, CICs containing multiunit spacers include

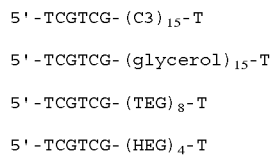

where $(C3)_{15}$ means 15 propyl linkers connected via phosphorothioate esters; $(glycerol)_{15}$ means 15 glycerol linkers connected via phosphorothioate esters; $(TEG)_8$ means 8 triethyleneglycol linkers connected via phosphorothioate esters; and $(HEG)_4$ means 4 hexaethyleneglycol linkers connected via phosphorothioate esters. It will be appreciated that certain multiunit spacers have a net negative charge, and that the negative charge can be increased by increasing the number of e.g., ester-linked monomeric units.

B. Multivalent Spacer Moiety

In certain embodiments, a spacer moiety is a multivalent non-nucleic acid spacer moiety (i.e., a "multivalent spacer"). As used in this context, a CIC containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinyl-glycerol); tetraminobenzene, heptaminobetacyclodextrin, 1,3,5-trihydroxycyclohexane, pentaerythritol and derivatives of pentaerythritol, tetraminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives (e.g., "symmetrical doubler"), [propyloxymethyl] ethyl compounds (e.g., "trebler"), polyethylene glycol derivatives such as so-called "Star PEGs" and "bPEG" (see, e.g., Gnanou et al., 1988, *Makromol. Chem.* 189:2885; Rein et al., 1993, *Acta Polymer* 44:225, Merrill et al., U.S. Pat. No. 5,171,264; Shearwater Polymers Inc., Huntsville Ala.), dendrimers and polysaccharides.

Dendrimers are known in the art and are chemically defined globular molecules, generally prepared by stepwise or reiterative reaction of multifunctional monomers to obtain a branched structure (see, e.g., Tomalia et al., 1990, *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful in the present invention include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use within the present invention include chemically-defined, non-polymeric valency platform molecules such as those disclosed in U.S. Pat. No. 5,552,391; and PCT applications PCT/US00/15968 (published as WO 00/75105); PCT/US96/09976 (published as WO 96/40197), PCT/US97/10075 (published as WO 97/46251); PCT/US94/10031 (published as WO 95/07073); and PCT/US99/29339 (published as WO 00/34231). Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques.

Multivalent spacers with a variety of valencies are useful in the practice of the invention, and in various embodiments the multivalent spacer of a CIC is bound to between about 3 and about 400 nucleic acid moieties, sometimes about 100 to about 500, sometimes about 150 to about 250, sometimes 3-200, sometimes from 3 to 100, sometimes from 3-50, frequently from 3-10, and sometimes more than 400 nucleic acid moieties. In various embodiments, the multivalent spacer is conjugated to more than 10, more than 25, more than 50, more than 100 or more than 500 nucleic acid moieties (which may be the same or different). It will be appreciated that, in certain embodiments in which a CIC comprises a multivalent spacer, the invention provides a population of CICs with slightly different molecular structures. For example, when a CIC is prepared using a dendrimer, polysaccharide or other multivalent spacer with a high valency, a somewhat heterogeneous mixture of molecules is produced, i.e., comprising different numbers (within or predominantly within a determinable range) of nucleic acid moieties joined to the multivalent spacer moiety. When a dendrimer, polysaccharide or the like is used as an element of a multivalent spacer, the nucleic acid moieties can be joined directly or indirectly to the element (e.g., dendrimer). For example, a CIC can comprise nucleic acid moietied joined to a dendrimer via an oligoethyleneglycol element (where the dendrimer+oligoethyleneglycol constitute the spacer moiety). It will be recognized that the nucleic acid moieties may be conjugated to more than one spacer moiety, as described in § III (1) B, supra.

Polysaccharides derivatized to allow linking to nucleic acid moieties can be used as multivalent spacers in CICs. Suitable polysaccharides may be naturally occurring polysaccharides or synthetic polysaccharides. Exemplary polysaccharides include, e.g., dextran, mannin, chitosan, agarose, and starch. Mannin may be used, for example, because there are mannin (mannose) receptors on immunologically relevant cell types, such as monocytes and alveolar macrophages, and so the polysaccharide spacer moiety may be used for targeting particular cell types. In an embodiment, the polysaccharide is cross-linked. One suitable compound is epichlorohydrin-crosslinked sucrose (e.g., FICOLL®). FICOLL® is synthesized by cross-linking sucrose with epichlorohydrin which results in a highly branched structure. For example, as shown in Example 49, aminoethylcarboxymethyl-ficoll (AECM-Ficoll) can be prepared by the method of Inman, 1975, *J. Imm.* 114:704-709. The number of nucleic acid moieties in a CIC comprising a polysaccharide can be any range described herein for a CIC (e.g., a multivalent CIC). For example, in one embodiment, the polysaccharide comprises between about 150 and about 250 nucleic acid moieties. AECM-Ficoll can then be reacted with a heterobifunctional crosslinking reagent, such as 6-maleimido caproic acyl N-hydroxysuccinimide ester, and then conjugated to a thiol-derivatized nucleic acid moiety (see Lee, et al., 1980, *Mol. Imm.* 17:749-56). Other polysaccharides may be modified similarly.

5. Synthesis of CICs

It will be well within the ability of one of skill, guided by this specification and knowledge in the art, to prepare CICs using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) *DNA* 3:401; Tang et al. (2000) *Org. Process Res. Dev.* 4:194-198; Wyrzykiewica et al. (1994) *Bioorg. & Med. Chem. Lett.* 4:1519-1522; Radhakrishna et al. (1989) *J. Org. Chem.* 55:4693-4699 and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.)

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O—(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O—(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Conjugation of the nucleic acid moieties and spacer moieties can be carried out in a variety of ways, depending on the particular CIC being prepared. Methods for addition of particular spacer moieties are known in the art and, for example, are described in the references cited supra. See, e.g., Durand et al., *Nucleic Acids Research* 18:6353-59 (1990). The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. As noted supra, spacer moiety precursors can optionally be modified with terminal activating groups for coupling to nucleic acids. Examples of activated spacer moieties can be seen in FIG. 1 where protecting groups suitable for automated synthesis have been added. Other spacer moiety precursors include, for example and not for limitation, (1) $HOCH_2CH_2$—O—$(CH_2CH_2O)_n CH_2CH_2OH$, where n=0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 or is greater than 45; (2) $HOCH_2CHOHCH_2OH$; (3) $HO(CH_2)_n OH$, where n=1, 2, 3, 4, 5, 6, 7, 8, 9, 10, or 11.

In one embodiment, a spacer moiety precursor is used that includes first and second reactive groups to permit conjugation to nucleic acid moieties in a stepwise fashion, in which the first reactive group has the property that it can couple efficiently to the terminus of a growing chain of nucleic acids and the second reactive group is capable of further extending, in a step-wise fashion the growing chain of mixed nucleotide and non-nucleotide moieties in the CIC. It will often be convenient to combine a spacer moiety(s) and a nucleic acid moiety(s) using the same phosphoramidite-type chemistry used for synthesis of the nucleic acid moiety. For example, CICs of the invention can be conveniently synthesized using an automated DNA synthesizer (e.g., Expedite 8909; Perseptive Biosystems, Framington, Mass.) using phosphoramidite chemistry (see, e.g., Beaucage, 1993, supra; *Current Protocols in Nucleic Acid Chemistry*, supra). However, one of skill will understand that the same (or equivalent) synthesis steps carried out by an automated DNA synthesizer can also be carried out manually, if desired. The resulting linkage between the nucleic acid and the spacer precursors can be a phosphorothioate or phosphodiester linkage. In such a synthesis, typically, one end of the spacer (or spacer subunit for multimeric spacers) is protected with a 4,4'-dimethoxytrityl group, while the other end contains a phosphoramidite group.

A variety of spacers with useful protecting and reacting groups are commercially available, for example:

triethylene glycol spacer or "TEG spacer" 9-O-(4,4'-dimethoxytrityl)triethyleneglycol-1-O-[(2-cyanoethyl) N,N-diisopropylphosphoramidite] (Glen Research, 22825 Davis Drive, Sterling, Va.);

hexaethylene glycol spacer or "HEG spacer" 18-O-(4,4'-dimethoxytrityl)hexaethyleneglycol-1-O-[(2-cyanoethyl) N,N-diisopropylphosphoramidite] (Glen Research, Sterling, Va.);

propyl spacer 3-(4,4'-dimethoxytrityloxy)propyloxy-1-O-[(2-cyanoethyl) N,N-diisopropylphosphoramidite] (Glen Research, Sterling, Va.);

butyl spacer 4-(4,4'-dimethoxytrityloxy)butyloxy-1-O-[(2-cyanoethyl) N,N-diisopropylphosphoramidite] (Chem Genes Corporation, Ashland Technology Center, 200 Homer Ave, Ashland, Mass.);

Hexyl spacer: 6-(4,4'-dimethoxytrityloxy)hexyloxy-1-O-[(2-cyanoethyl) N,N-diisopropylphosphoramidite] (Biosearch Technologies, Novoto, Calif.)

Figure 2:
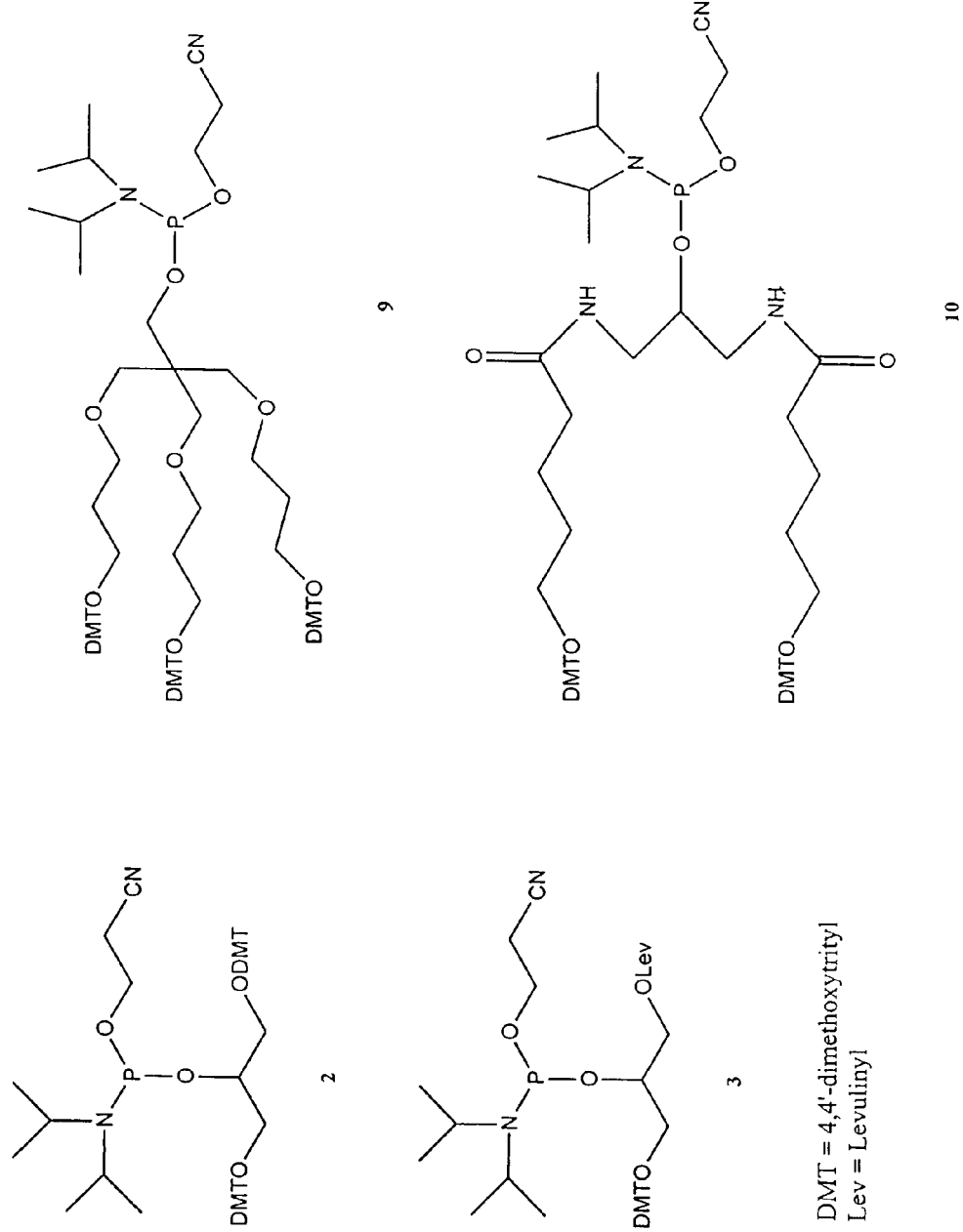
FIG. 2 shows the structure of certain reagents useful for synthesis of symmetric or asymmetric non-nucleic acid spacer moieties of CICs. Shown are dimethoxytrityl-protected phosphoramidite spacer moiety precursors for glycerol [2] "symmetrical branched"), levulinyl-glycerol [3] ("asymmetrical branched"), "trebler" [9] and "symmetrical doubler" [10] spacer moieties.

2-(hydroxymethyl)ethyl spacer or "HME spacer" 1-(4,4'-dimethoxytrityloxy)-3-(levulinyloxy)-propyloxy-2-O-[(2-cyanoethyl) N,N-diisopropylphosphoramidite]; also called "asymmetrical branched" spacer (see FIG. 2) (Chem Genes Corp., Ashland Technoklgy Center, Ashland Mass.);

"abasic nucleotide spacer" or "abasic spacer" 5-O-(4,4'-dimethoxytrityl)-1,2-dideoxyribose-3-O-[(2-cyanoethyl) N,N-diisopropylphosphoramidite] (Glen Research, Sterling, Va.);

"symmetrical branched spacer" or "glycerol spacer" 1,3-O,O-bis(4,4'-dimethoxytrityl)glycerol-2-O-[(2-cyanoethyl) N,N-diisopropylphosphoramidite] (Chem Genes, Ashland, Mass.) (see FIG. 2);

"trebler spacer" (see FIG. 2) 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, Va.);

"symmetrical doubler spacer" (see FIG. 2) 1,3-O,O-bis[5-O-(4,4'-dimethoxytrityloxy)pentylamido]propyl-2-O-[(2-cyanoethyl) N,N-diisopropylphosphoramidite] (Glen Research, Sterling, Va.);

"dodecyl spacer" 12-(4,4'-dimethoxytrityloxy)dodecyloxy-1-O-[(2-cyanoethyl) N,N-diisopropylphosphoramidite] (Glen Research, Sterling, Va.).

These and a large variety of other protected spacer moiety precursors (e.g., comprising DMT and phosphoramidite group protecting groups) can be purchased or can be synthesized using routine methods for use in preparing CICs disclosed herein. The instrument is programmed according to the manufacturer's instructions to add nucleotide monomers and spacers in the desired order.

CICs prepared "in situ" on a DNA synthesizer require protected nucleoside and protected spacer monomers, both containing reactive or activatable functional groups. The reactive and/or protected form of the spacer moiety can be described as a "spacer precursor component." It will be appreciated by those with skill in the art that the reactive groups in the spacer precursors form stable linkages after coupling and the protecting groups on the spacer precursor are removed in the resultant spacer moiety in the CIC. The protecting groups are generally removed during the step-wise synthesis of the CIC, in order to allow reaction at that site. In cases where there are protecting groups on additional reactive groups, the protecting groups are removed after the step-wise synthesis of the CIC (such as the levulinyl group on the spacer precursor shown in FIG. 2, structure 3, used to make C-25).

An example of a spacer precursor with no additional reactive functionality is 18-O-(4,4'-dimethoxytrityl)hexaethyleneglycol-1-O-[(2-cyanoethyl)N,N-diisopropylphosphoramidite], which contains a protecting group, the 4,4'-dimethoxytrityl group, and a reactive group, the (2-cyanoethyl)N,N-diisopropylphosphoramidite group. During preparation of the CIC using phosphoramidite chemistry on a DNA synthesizer, the (2-cyanoethyl)N,N-diisopropylphosphoramidite group in the spacer precursor is activated by a weak acid, such as 1H-tetrazole, and reacted with the free 5'-hydroxyl of the nucleobase-protected nucleic acid moiety to form a phosphite triester. The phosphite triester group is then either oxidized or sulfurized to a stable phosphotriester or phosphorothioate triester group, respectively. The resultant triester group is stable to the rest of the CIC synthesis and remains in that form until the final deprotection. In order to couple either another spacer precursor or an activated nucleoside monomer, which will become part of the next nucleic acid moiety, the 4,4'-dimethoxytrityl group on the spacer precursor is removed. After coupling and either oxidation or sulfurization, this group also becomes either a stable phosphotriester or phosphorothioate triester group, respectively. Once the protected CIC is fully assembled, the CIC is cleaved from the solid support, the cyanoethyl groups on the phosphotriester or phosphorothioate triester groups are removed, and the nucleobase protection is removed. In this example, the CIC contains spacer moieties including stable phosphodiester or phosphorothioate diester linkages to the nucleic acid moieties. Both the reactive phosphoramidite group and the protected hydroxyl group of the spacer precursor are converted to stable phosphodiester or phosphorothioate diester linkages in the spacer moiety. Because the reaction of each end of the spacer may be independent, one linkage may be phosphodiester and the other linkage phosphorothioate diester, or any combination thereof. CICs with other phosphate modifications, such as phosphorodithioate, methyl phosphonate, and phosphoramidate, may also be prepared in this manner by using a spacer precursor with the appropriate reactive group, the correct ancillary reagents, and protocols designed for that type of linkage. These protocols are analogous to those described for preparing nucleic acid moieties with modified phosphate linkages.

Although use of phosphoramidite chemistry is convenient for the preparation of certain CICs, it will be appreciated that the CICs of the invention are not limited to compounds prepared by any particular method of synthesis or preparation. For example, nucleic acid moieties containing groups not compatible with DNA synthesis and deprotection conditions, such as (but not limited to) hydrazine or maleimide, can be prepared by reacting a nucleic acid moiety containing an amino linker with the appropriate heterobifunctional crosslinking reagent, such as SHNH (succinimidyl hydrazinium nicotinate) or sulfo-SMCC (sulfosuccinimidyl 4-[N-maleimidomethyl]-cyclohexane-1-carboxylate).

Methods for conjugating protein, peptides, oligonucleotides, and small molecules in various combinations are described in the literature and can be adapted to achieve conjugation of a nucleic acid moiety containing a reactive linking group to a spacer moiety precursor. See, for example, Bioconjugate Techniques, Greg T. Hermanson, Academic Press, Inc., San Diego, Calif., 1996. In some embodiments, a nucleic acid moiety(s) is synthesized, and a reactive linking group (e.g., amino, carboxylate, thio, disulfide, and the like) is added using standard synthetic chemistry techniques. The reactive linking group (which is considered to form a portion of the resulting spacer moiety) is conjugated to additional non-nucleic acid compounds (for example, without limitation, a compound listed in §4, supra) to form a portion of the spacer moiety. Reactive linking groups are added to nucleic acids using standard methods for nucleic acid synthesis, employing a variety of reagents known in the art. Examples include reagents that contain a protected amino group, carboxylate group, thiol group, disulfide group, aldehyde group, diol group, diene group and a phosphoramidite group. Once these compounds are incorporated into the nucleic acids, via the activated phosphoramidite group, and are deprotected, they provide nucleic acids with amino, carboxylate, aldehyde, diol, diene or thiol reactivity. Examples of reactive groups for conjugating a nucleic acid moiety containing a reactive linker group to a spacer moiety precursor that contains a reactive group are shown below.

| nucleic acid reactive group | Spacer moiety precursor reactive group | Stable linkage formed |
|---|---|---|
| thiol | maleimide, haloacetyl | thioether |
| maleimide | thiol | thioether |
| thiol | pyridine disulfide | disulfide |
| pyridine disulfide | thiol | disulfide |
| amine | NHS or other active ester | amide |
| amine | carboxylate | amide |
| carboxylate | amine | amide |
| aldehyde, ketone | hydrazine, hydrazide | hydrazone, hydrazide |
| hydrazine, hydrazide | aldehyde, ketone | hydrazone, hydrazide |
| diene | dienophile | aliphatic or heterocyclic ring |

The reactive linking group and the spacer precursor react to form a stable bond and the entire group of atoms between the two (or more) nucleic acid moieties is defined as the spacer moiety. For example, a nucleic acid moiety synthesized with a mercaptohexyl group linked to the nucleic acid moiety via a phosphorothioate group can be reacted with a spacer precursor containing one (or more) maleimide group(s), forming a thioether linkage(s). The spacer moiety of this CIC includes the phosphorothioate group and hexyl group from the linker on the nucleic acid moiety, the new thioether linkage, and the rest of the spacer that was part of the spacer precursor.

Although linear CICs can be made using these conjugation strategies, these methods are most often applied for the preparation of branched CICs. Additionally, spacer precursor molecules can be prepared with several orthogonal reactive groups to allow for the addition of more than one type nucleic acid moiety (e.g., different sequence motif).

In one embodiment, CICs with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT/US94/10031, published as WO 95/07073). These two activated groups can be reacted independently of each other. This would result in a CIC containing a total of 4 nucleic acid moieties, two of each sequence.

CICs with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step). This procedure is described in detail in Example 15, infra.

A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one embodiment, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized. This procedure is described in detail in Example 17, infra.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS(N-[ε-maleimidocaproyloxyl sulfosuccinimide ester) Pierce Chemical Co. product 22307; Sulfo-GMBS (N-[γ-maleimidobutyryloxyl] sulfosuccinimide ester) Pierce Chemical Co. product 22324 (Pierce Chemical Company, Rockford, Ill.), and similar compounds of the general formula maleimido-R—C(O)NHS ester, where R=alkyl, cyclic alkyl, polymers of ethylene glycol, and the like.

Particularly useful methods for covalently joining nucleic acid moieties to multivalent spacers are described in the references cited supra, and in the examples.

Thus, in an aspect, the invention provides a method for preparing a CIC useful for modulating an immune response in a mammal by covalently joining a polynucleotide(s) to a compound thereby resulting in a chimeric compound comprising a nucleic acid moiety and a spacer moiety region, and having immunomodulatory activity. In various embodiments, the nucleic acid region can have the structure and sequence of any nucleic acid moiety described herein and the spacer region can have the structure of any spacer moiety described herein. Often, there is more than one joining step, e.g., the joining is repeated at least once to provide two polynucleotides covalently joined to one or two spacers, and is often repeated at least twice or thrice. The method further comprises combining the CIC with a pharmaceutically acceptable excipient to form a composition. In an embodiment, the composition is sterile, e.g., suitable for administration to a human patient, e.g., manufactured or formulated under GMP standards. In an embodiment, the CIC is combined with a microcarrier and/or antigen, as described herein. It is also contemplated that, in some embodiments, a CIC formulation of the invention will be free from one or more of (i) a colloidal dispersion system, (ii) liposomes, (iii) microcarriers, (iv) polypeptides, (v) antigens, and (vi) endotoxin.

6. Proteinaceous CICs

In certain embodiments, a polypeptide, such as a protein antigen or antigen fragment, is used as a multivalent spacer moiety to which a plurality of nucleic acid moieties are covalently conjugated, directly or via linkers, to form a "proteinaceous CIC." The polypeptide can be an antigen or immunogen to which an adaptive immune response is desired, or a carrier (e.g., albumin). Typically, a proteinaceous CIC comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity or do not have isolated immunomodulatory activity. Methods of making a proteinaceous CIC will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the CIC to a peptide.

7. Purification

The CICs of the invention are purified using any conventional means, such as high performance liquid chromatography, electrophoretic methods, nucleic acid affinity chromatography, size exclusion chromatography, and ion exchange chromatography. In some embodiments, a CIC is substantially pure, e.g., at least about 80% pure by weight, often at least about 90% pure by weight, more often at least about 95% pure, most often at least about 85% pure.

8. Compositions

In various embodiments, compositions of the invention comprise one or more CICs, (i.e. a single CIC or a combination of two or more CICs) optionally in conjunction with another immunomodulatory agent, such as a peptide, an antigen (described below) and/or an additional adjuvant. Compositions of the invention may comprise a CIC and pharmaceutically acceptable excipient. By "pharmaceutically acceptable" it is meant the carrier, diluent or excipient must be compatible with the other ingredients of the formulation and not deleterious to the recipient thereof. Pharmaceutically acceptable excipients are well known in the art and include sterile water, isotonic solutions such as saline and phosphate buffered saline, and other excipients known in the art. See, e.g., *Remington: The Science and Practice of Pharmacy* (19th edition, 1995, Gennavo, ed.). Adjuvants (an example of which is alum) are known in the art. CIC formulations may be prepared with other immunotherapeutic agents, such as cytokines and antibodies. In some embodiments the composition is isotonic and/or sterile, e.g., suitable for administration to a human patient, e.g., manufactured or formulated under GMP standards.

A. CIC/MC Complexes

CICs may be administered in the form of CIC/microcarrier (CIC/MC) complexes. Accordingly, the invention provides compositions comprising CIC/MC complexes.

CIC/MC complexes comprise a CIC bound to the surface of a microcarrier (i.e., the CIC is not encapsulated in the MC), and preferably comprise multiple molecules of CIC bound to each microcarrier. In certain embodiments, a mixture of different CICs may be complexed with a microcarrier, such that the microcarrier is bound to more than one CIC species. The bond between the CIC and MC may be covalent or non-covalent (e.g. mediated by ionic and/or hydrophobic interactions). As will be understood by one of skill in the art, the CIC may be modified or derivatized and the composition of the microcarrier may be selected and/or modified to accommodate the desired type of binding desired for CIC/MC complex formation.

Covalently bonded CIC/MC complexes may be linked using any covalent crosslinking technology known in the art. Typically, the CIC portion will be modified, either to incorporate an additional moiety (e.g., a free amine, carboxyl or sulfhydryl group) or incorporate modified (e.g., phosphorothioate) nucleotide bases to provide a site at which the CIC portion may be linked to the microcarrier. The link between the CIC and MC portions of the complex can be made at the 3' or 5' end of the CIC, or at a suitably modified base at an internal position in the CIC. The microcarrier is generally also modified to incorporate moieties through which a covalent link may be formed, although functional groups normally present on the microcarrier may also be utilized. The CIC/MC is formed by incubating the CIC with a microcarrier under conditions which permit the formation of a covalent complex (e.g., in the presence of a crosslinking agent or by use of an activated microcarrier comprising an activated moiety which will form a covalent bond with the CIC).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the CIC and the microcarrier as well as the desired final configuration of the CIC/MC complex. The crosslinker may be either homobifunctional or heterobifunctional. When a homobifunctional crosslinker is used, the crosslinker exploits the same moiety on the CIC and MC (e.g., an aldehyde crosslinker may be used to covalently link a CIC and MC where both the CIC and MC comprise one or more free amines). Heterobifunctional crosslinkers utilize different moieties on the CIC and MC, (e.g., a maleimido-N-hydroxysuccinimide ester may be used to covalently link a free sulfhydryl on the CIC and a free amine on the MC), and are preferred to minimize formation of inter-microcarrier bonds. In most cases, it is preferable to crosslink through a first crosslinking moiety on the microcarrier and a second crosslinking moiety on the CIC, where the second crosslinking moiety is not present on the microcarrier. One preferred method of producing the CIC/MC complex is by 'activating' the microcarrier by incubating with a heterobifunctional crosslinking agent, then forming the CIC/MC complex by incubating the CIC and activated MC under conditions appropriate for reaction. The crosslinker may incorporate a "spacer" arm between the reactive moieties, or the two reactive moieties in the crosslinker may be directly linked.

In one preferred embodiment, the CIC portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the CIC to form the CIC/MC complex.

Non-covalent CIC/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the CIC and MC.

Preferred non-covalent CIC/MC complexes are typically complexed by hydrophobic or electrostatic (ionic) interactions, or a combination thereof, (e.g., through base pairing between a CIC and a polynucleotide bound to an MC). Due to the hydrophilic nature of the backbone of polynucleotides, CIC/MC complexes which rely on hydrophobic interactions to form the complex generally require modification of the CIC portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the CIC will, of course, depend on the configuration of the CIC and the identity of the hydrophobic moiety. The hydrophobic moiety may be added at any convenient site in the CIC, preferably at either the 5' or 3' end; in the case of addition of a cholesterol moiety to a CIC, the cholesterol moiety is preferably added to the 5' end of the CIC, using conventional chemical reactions (see, for example, Godard et al. (1995) *Eur. J. Biochem.* 232:404-410). Preferably, microcarriers for use in CIC/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the CIC/MC complex is formed by mixing the CIC and the MC after preparation of the MC, in order to avoid encapsulation of the CIC during the MC preparation process.

Non-covalent CIC/MC complexes bound by electrostatic binding typically exploit the highly negative charge of the polynucleotide backbone. Accordingly, microcarriers for use in non-covalently bound CIC/MC complexes are generally positively charged at physiological pH (e.g., about pH 6.8-7.4). The microcarrier may intrinsically possess a positive charge, but microcarriers made from compounds not normally possessing a positive charge may be derivatized or otherwise modified to become positively charged. For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles). See, e.g., Examples 28 and 34, infra.

Non-covalent CIC/MC complexes linked by nucleotide base pairing may be produced using conventional methodologies. Generally, base-paired CIC/MC complexes are produced using a microcarrier comprising a bound, preferably a covalently bound, polynucleotide (the "capture polynucleotide") that is at least partially complementary to the CIC. The segment of complementarity between the CIC and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the CIC at the 5' or 3' end.

In other embodiments, a binding pair may be used to link the CIC and MC in a CIC/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes. When using a binding pair to mediate CIC/MC complex binding, the CIC is derivatized, typically by a covalent linkage, with one member of the binding pair, and the MC is derivatized with the other member of the binding pair. Mixture of the two derivatized compounds results in CIC/MC complex formation.

Many CIC/MC complex embodiments do not include an antigen, and certain embodiments exclude antigen(s) associated with the disease or disorder which is the object of the CIC/MC complex therapy. In further embodiments, the CIC is also bound to one or more antigen molecules. Antigen may be coupled with the CIC portion of a CIC/MC complex in a variety of ways, including covalent and/or non-covalent interactions. Alternately, the antigen may be linked to the microcarrier. The link between the antigen and the CIC in CIC/MC complexes comprising an antigen bound to the CIC can be made by techniques described herein and known in the art.

B. Co-Administered Antigen

In some embodiments, the CIC is coadministered with an antigen. Any antigen may be co-administered with a CIC and/or used for preparation of compositions comprising a CIC and antigen.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet vl (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). Preparation of protein antigens from grass pollen for in vivo administration has been reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrimp allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hev b 7 (Sowka et al. (1998) *Eur. J. Biochem.* 255:213-219). Table 1 shows a list of allergens that may be used.

TABLE 1

RECOMBINANT ALLERGENS

| Group | Allergen | Reference |
|---|---|---|
| ANIMALS: | | |
| CRUSTACEA | | |
| Shrimp/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 Hakkaart et al. Clin Exp Allergy, 1998, 28: 169-74 Hakkaart et al. Clin Exp Allergy, 1998, 28: 45-52 Hakkaart et al. Int Arch Allergy Immunol, 1998, 115 (2): 150-6 |
| | | Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 |
| | | Yasue et al. Cell Immunol, 1997, 181: 30-7 |
| | Der p10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. (1997) J Allergy Clin Immunol 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987, 109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 23 9: 197 |
| | rBet v 1 Bet v 2: (profilin) | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76 |
| | | Vrtala et al. J Immunol Jun. 15, 1998, 160: 6137-44 |
| | | Niederberger et al. J Allergy Clin Immun., 1998, 101: 258-64 |
| | Hol l 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |

TABLE 1-continued

RECOMBINANT ALLERGENS

| Group | Allergen | Reference |
|---|---|---|
| | Cyn d 12 (a profilin) | Asturias et al. Clin Exp Allergy, 1997, 27: 1307-13 |
| | | Fuchs et al. J Allergy Clin Immunol, 1997, 100: 356-64 |
| Japanese Cedar | Jun a 2 (Juniperus ashei) | Yokoyama et al. Biochem. Biophys. Res. Commun., 2000, 275: 195-202 |
| | Cry j 1, Cry j 2 (Cryptomeria japonica) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9 |
| | | Fuchs et al. J Allergy Clin Immunol, 1997, 100: 356-64 |
| Mercurialis | Mer a I (profilin) | Vallverdu et al. J Allergy Clin Immunol, 1998, 101: 363-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
| | | Burks et al. J Clin Invest, 1995, 96: 1715-21 |
| | | Burks et al. Int Arch Allergy Immunol, 1995, 107: 248-50 |
| *Poa pratensis* | Poa p9 | Parronchi et al. Eur J Immunol, 1996, 26: 697-703 |
| | | Astwood et al. Adv Exp Med Biol, 1996, 409: 269-77 |
| Ragweed | Amb a I | Sun et al. Biotechnology August, 1995, 13: 779-86 |
| | | Hirschwehr et al. J Allergy Clin Immunol, 1998, 101: 196-206 |
| | | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
| | | Donovan et al. Electrophoresis, 1993, 14: 917-22 |
| FUNGI: | | |
| *Aspergillus* | Asp f 1, Asp f 2, Asp f3, Asp f 4, rAsp f6 | Crameri et al. Mycoses, 1998, 41 Suppl 1: 56-60 |
| | | Hemmann et al. Eur J Immunol, 1998, 28: 1155-60 |
| | | Banerjee et al. J Allergy Clin Immunol, 1997, 99: 821-7 |
| | | Crameri Int Arch Allergy Immunol, 1998, 115: 99-114 |
| | | Crameri et al. Adv Exp Med Biol, 1996, 409: 111-6 |
| | | Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza*, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) Proc. Natl. Acad. Sci. USA 85:4446-4450; Scherle and Gerhard (1986) J. Exp. Med. 164:1114-1128; Granoff et al. (1993) Vaccine 11:S46-51; Kodihalli et al. (1997) J. Virol. 71:3391-3396; Ahmeida et al. (1993) Vaccine 11:1302-1309; Chen et al. (1999) Vaccine 17:653-659; Govorkova and Smirnov (1997) Acta Virol. (1997) 41:251-257; Koide et al. (1995) Vaccine 13:3-5; Mbawuike et al. (1994) Vaccine 12:1340-1348; Tamura et al. (1994) Vaccine 12:310-316; Tamura et al. (1992) Eur. J. Immunol. 22:477-481; Hirabayashi et al. (1990) Vaccine 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with CICs. Lea et al. (1996) Biochim. Biophys. Acta 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

CICs can be administered in combination with antigen in a variety of ways. In some embodiments, a CIC and antigen are administered spatially proximate with respect to each other. As described below, spatial proximation can be accomplished in a number of ways, including conjugation, encapsidation, via affixation to a platform or adsorption onto a surface. In one embodiment, a CIC and antigen are administered as an admixture (e.g., in solution). It is specifically contemplated that, in certain embodiments, the CIC is not conjugated to an immunogen or antigen.

In some embodiments, the CIC is linked to a polypeptide, e.g., an antigen. The CIC portion can be linked with the antigen portion of a conjugate in a variety of ways, including covalent and/or non-covalent interactions, via the nucleic acid moiety or non-nucleic acid spacer moiety. In some embodiments, linkage is via a reactive group such as, without limitation, thio, amine, carboxylate, aldehyde, hydrizine, hydrizone, disulfide and the like.

The link between the portions can be made at the 3' or 5' end of a nucleic acid moiety, or at a suitably modified base at an internal position in the nucleic acid moiety. For example, if the antigen is a peptide and contains a suitable reactive group (e.g., an N-hydroxysuccinimide ester) it can be reacted directly with the $N^4$ amino group of cytosine residues. Depending on the number and location of cytosine residues in the CIC, specific coupling at one or more residues can be achieved.

Alternatively, modified oligonucleosides, such as are known in the art, can be incorporated at either terminus, or at internal positions in the CIC. These can contain blocked functional groups which, when deblocked, are reactive with a variety of functional groups which can be present on, or attached to, the antigen of interest.

Where the antigen is a peptide, this portion of the conjugate can be attached to the nucleic acid moiety or spacer moiety through solid support chemistry. For example, a nucleic acid portion of a CIC can be added to a polypeptide portion that has been pre-synthesized on a support. Haralambidis et al. (1990) *Nucleic Acids Res.* 18:493-499; and Haralambidis et al. (1990) *Nucleic Acids Res.* 18:501-505.

Alternatively, the CIC can be synthesized such that it is connected to a solid support through a cleavable linker extending from the 3'-end of a nucleic acid moiety. Upon chemical cleavage of the CIC from the support, a terminal thiol group or a terminal amino group is left at the 3'-end of the nucleic acid moiety (Zuckermann et al., 1987, *Nucleic Acids Res.* 15:5305-5321; Corey et al., 1987, *Science* 238: 1401-1403; Nelson et al., 1989, *Nucleic Acids Res.* 17:1781-1794). Conjugation of the amino-modified CIC to amino groups of the peptide can be performed as described in Benoit et al. (1987) *Neuromethods* 6:43-72. Conjugation of the thiol-modified CIC to carboxyl groups of the peptide can be performed as described in Sinah et al. (1991) *Oligonucleotide Analogues. A Practical Approach*, IRL Press. Coupling of a nucleic acid moiety or spacer carrying an appended maleimide to the thiol side chain of a cysteine residue of a peptide has also been described. Tung et al. (1991) *Bioconjug. Chem.* 2:464-465.

The peptide portion of the conjugate can be attached to a free 5'-end of a nucleic acid moiety through an amine, thiol, or carboxyl group that has been incorporated into nucleic acid moiety or spacer (e.g., via a free 5'-end, a 3'-end, via a modified base, and the like).

Conveniently, a linking group comprising a protected amine, thiol, or carboxyl at one end, and a phosphoramidite can be covalently attached to a hydroxyl group of a CIC. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015, 733, 5,118,800, and 5,118,802. Subsequent to deprotection, the amine, thiol, and carboxyl functionalities can be used to covalently attach the CIC to a peptide. Benoit et al. (1987); and Sinah et al. (1991).

A CIC-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of a CIC. Roget et al. (1989) *Nucleic Acids Res.* 17:7643-7651.

Incorporation of a streptavidin moiety into the peptide portion allows formation of a non-covalently bound complex of the streptavidin conjugated peptide and the biotinylated oligonucleotide.

Non-covalent associations can also occur through ionic interactions involving a CIC and residues within the antigen, such as charged amino acids, or through the use of a linker portion comprising charged residues that can interact with both the oligonucleotide and the antigen. For example, non-covalent conjugation can occur between a generally negatively-charged CIC and positively-charged amino acid residues of a peptide, e.g., polylysine, polyarginine and polyhistidine residues.

Non-covalent conjugation between CIC and antigens can occur through DNA binding motifs of molecules that interact with DNA as their natural ligands. For example, such DNA binding motifs can be found in transcription factors and anti-DNA antibodies.

The linkage of the CIC to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

A CIC may be proximately associated with an antigen(s) in other ways. In some embodiments, a CIC and antigen are proximately associated by encapsulation. In other embodiments, a CIC and antigen are proximately associated by linkage to a platform molecule. A "platform molecule" (also termed "platform") is a molecule containing sites which allow for attachment of the a CIC and antigen(s). In other embodiments, a CIC and antigen are proximately associated by adsorption onto a surface, preferably a carrier particle.

In some embodiments, the methods of the invention employ an encapsulating agent that can maintain the proximate association of the a CIC and first antigen until the complex is available to the target (or compositions comprising such encapsulating agents). Preferably, the composition comprising a CIC, antigen and encapsulating agent is in the form of adjuvant oil-in-water emulsions, microparticles and/or liposomes. More preferably, adjuvant oil-in-water emulsions, microparticles and/or liposomes encapsulating a CIC are in the form of particles from about 0.04 μm to about 100 μm in size, preferably any of the following ranges: from about 0.1 μm to about 20 μm; from about 0.15 μm to about 10 μm; from about 0.05 μm to about 1.00 μm; from about 0.05 μm to about 0.5 μm.

Colloidal dispersion systems, such as microspheres, beads, macromolecular complexes, nanocapsules and lipid-based systems, such as oil-in-water emulsions, micelles, mixed micelles and liposomes can provide effective encapsulation of CIC-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect a CIC-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

One colloidal dispersion system useful in the administration of CICs is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular*

*Biology* by J. Kendrew (1994). For suitable lipids see e.g., Lasic (1993) "Liposomes: from Physics to Applications" Elsevier, Amsterdam.

Processes for preparing liposomes containing CIC-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In some embodiments a CIC and antigen are proximately associated by linkage to a platform molecule, such as a proteinaceous or non-proteinaceous (e.g., synthetic) valency platform. Examples of suitable platforms are described supra, in the discussion of valency platforms used as a spacer moiety in a CIC. Attachment of antigens to valency platforms can be carried out using routine methods. As an example, polypeptides contain amino acid side chain moieties with functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

In another embodiment, a CIC and antigen are coadministered by adsorbing both to a surface, such as a nanoparticle or microcarrier. Adsorption of a CIC and/or antigen to a surface may occur through non-covalent interactions, including ionic and/or hydrophobic interactions. Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable.

In general, characteristics of nanoparticles, such as surface charge, particle size and molecular weight, depend upon polymerization conditions, monomer concentration and the presence of stabilizers during the polymerization process (Douglas et al., 1987, supra). The surface of carrier particles may be modified, for example, with a surface coating, to allow or enhance adsorption of the CIC and/or antigen. Carrier particles with adsorbed CIC and/or antigen may be further coated with other substances. The addition of such other substances may, for example, prolong the half-life of the particles once administered to the subject and/or may target the particles to a specific cell type or tissue, as described herein.

Nanocrystalline surfaces to which a CIC and antigen may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 μm, that carry an inner layer of CIC and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987, supra). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Polypeptides may also be adsorbed to polyalkylcyanoacrylate nanoparticles. See, for example, Douglas et al., 1987; Schroeder et al. (1998) *Peptides* 19:777-780.

Another adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

C. Additional Adjuvants

A CIC may also be administered in conjunction with an adjuvant. Administration of an antigen with a CIC and an adjuvant leads to a potentiation of a immune response to the antigen and thus, can result in an enhanced immune response compared to that which results from a composition comprising the CIC and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMS) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

IV. Methods of the Invention

The invention provides methods of modulating an immune response in an individual, preferably a mammal, more preferably a human, comprising administering to the individual a CIC as described herein. Immunomodulation may include stimulating a Th1-type immune response and/or inhibiting or reducing a Th2-type immune response. The CIC is administered in an amount sufficient to modulate an immune response. As described herein, modulation of an immune response may be humoral and/or cellular, and is measured using standard techniques in the art and as described herein.

A number of individuals are suitable for receiving the CIC(s) described herein. Preferably, but not necessarily, the individual is human.

In certain embodiments, the individual suffers from a disorder associated with a Th2-type immune response, such as (without limitation) allergies, allergy-induced asthma, atopic dermatitis, eosinophilic gastrointestinal inflammation, eosinophilic esophagitis, and allergic bronchopulmonary aspergillosis. Administration of a CIC results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. The CIC may be given in conjunction with the vaccine (e.g., in the same injection or a contemporaneous, but separate, injection) or the CIC may be administered separately (e.g., at least 12 hours before or after administration of the vaccine). In certain embodiments, the antigen(s) of the vaccine is part of the CIC, by either covalent or non-covalent linkage to the CIC. Administration of CIC therapy to an individual receiving a vaccine results in an immune response to the vaccine that is shifted towards a Th1-type response as compared to individuals which receive vaccine not containing a CIC. Shifting towards a Th1-type response may be recognized by a delayed-type hypersensitivity (DTH) response to the antigen(s) in the vaccine, increased IFN-γ and other Th1-type response associated cytokines, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of CIC and vaccine also results in amelioration of one or more symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, CIC treatment with vaccine results in reduced coughing, pleural or chest wall pain, fever, and/or other symptoms known in the art. Where the vaccine is an allergen used in allergy desensitization therapy, the treatment results in a reduction in the symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and a reduction in symptoms. Administration of a CIC to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system including macrophages and natural killer (NK) cells. See, for example, Cho et al. (2000) *Nat. Biotechnol.* 18:509-514. In treatment of a pre-existing disease or disorder, the CIC can be administered in conjunction with other immunotherapeutic agents such as cytokines, adjuvants and antibodies. For example, a CIC can be administered as part of a therapeutic regimen that includes administration of a binding agent that binds an antigen displayed by tumor cells. Exemplary binding agents include polyclonal and monoclonal antibodies. Examples of target antigens include CD20, CD22, HER2 and others known in the art or to be discovered in the future. Without intending to be bound by theory, it is believed that the CIC enhances killing of tumor cells to which the binding agent is associated (e.g., by enhancing antibody dependent cellular cytotoxicity and/or effector function). The binding agent can optionally be labeled, e.g., with a radioisotope or toxin that damages a cell to which the binding agent is bound. The CIC may be given in conjunction with the agent (e.g., at the same time) or before or after (e.g., less than 24 hours before or after administration of the agent). For example, in the case of cancer, the CIC can be administered in conjunction with a chemotherapeutic agent know or suspected of being useful for the treatment of cancer. As another example, the CIC can be administered in conjunction with radiation therapy, gene therapy, or the like. The CIC may be any of those described herein.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). CIC therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. CIC therapy is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi,* and/or *L. aethiopica*), and toxoplasmosis (i.e., infection by *Toxoplasmosis gondii*) also benefit from CIC therapy. CIC therapy is also useful for treatment of parasitic diseases such as schistosomiasis (i.e., infection by blood flukes of the genus *Schistosoma* such as *S. haematobium, S. mansoni, S. japonicum,* and *S. mekongi*) and clonorchiasis (i.e., infection by *Clonorchis sinensis*). Administration of a CIC to an individual suffering from an infectious disease results in an amelioration of symptoms of the infectious disease. In some embodiments, the infectious disease is not a viral disease.

The invention further provides methods of increasing or stimulating at least one Th1-associated cytokine in an individual, including IL-2, IL-12, TNF-β, IFN-γ and IFN-α. In certain embodiments, the invention provides methods of increasing or stimulating IFN-γ in an individual, particularly in an individual in need of increased IFN-γ levels, by administering an effective amount of a CIC to the individual such that IFN-γ. Individuals in need of increased IFN-γ are those having disorders which respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of a CIC in accordance with the invention results in an increase in IFN-γ levels, and results in amelioration of one or more symptoms, stabilization of one or more symptoms, or prevention of progression (e.g., reduction or elimination of additional lesions or symptoms) of the disorder which responds to IFN-γ. The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of a CIC to the individual such that IFN-α levels are increased. Individuals in need of increased IFN-α are those having disorders which respond to the administration of IFN-α, including recombinant IFN-α, including, but not limited to, viral infections and cancer.

Administration of a CIC in accordance with the invention results in an increase in IFN-α levels, and results in amelioration of one or more symptoms, stabilization of one or more symptoms, or prevention of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

As will be apparent upon review of this disclosure, the spacer composition of a CIC can affect the immune response elicited by administration of the CIC. Virtually all of the spacers tested (with the exception of dodecyl) can be used in CICs to efficiently induce IFN-γ in human PBMCs. However, the spacer composition of linear CICs has been observed to have differential effects on induction of IFN-α. For example, CICs containing, for example, HEG, TEG or C6 spacers tend to cause higher IFN-α induction (and reduced B cell proliferation) in PBMCs than did CICs containing C3, C4 or abasic spacers (see, e.g., Example 34, infra).

Also provided are methods of reducing levels, particularly serum levels, of IgE in an individual having an IgE-related disorder by administering an effective amount of a CIC to the individual. In such methods, the CIC may be administered alone (e.g., without antigen) or administered with antigen, such as an allergen. An IgE-related disorder is a condition, disorder, or set of symptoms ameliorated by a reduction in IgE levels. Reduction in IgE results in an amelioration of symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of an allergic response.

Methods of the invention includes embodiments in which CICs are administered in the form of a CIC/microcarrier complex(s).

In some embodiments, the invention provides methods of stimulating CTL production in an individual, comprising administering an effective amount of a CIC to the individual such that CTL production is increased.

As will be apparent to one of skill in the art, the methods of the invention may be practiced in combination with other therapies for the particular indication for which the CIC is administered. For example, CIC therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

A. Administration and Assessment of the Immune Response

The CIC can be administered in combination with pharmaceutical and/or immunogenic and/or other immunostimulatory agents, as described herein, and can be combined with a physiologically acceptable carrier thereof.

For example, a CIC or composition of the invention can be administered in conjunction with other immunotherapeutic agents such as cytokines, adjuvants and antibodies. The CIC may be given in conjunction with the agent (e.g., at the same time, or before or after (e.g., less than 24 hours before or after administration of the agent). The CIC may be any of those described herein.

As with all immunostimulatory compositions, the immunologically effective amounts and method of administration of the particular CIC formulation can vary based on the individual, what condition is to be treated and other factors evident to one skilled in the art. Factors to be considered include the presence of a coadministered antigen, whether or not the CIC will be administered with or covalently attached to an adjuvant or delivery molecule, route of administration and the number of immunizing doses to be administered. Such factors are known in the art and it is well within the skill of those in the art to make such determinations without undue experimentation. A suitable dosage range is one that provides the desired modulation of immune response to the antigen. Generally, dosage is determined by the amount of CIC administered to the patient, rather than the overall quantity of CIC. Useful dosage ranges of the CIC, given in amounts of CIC delivered, may be, for example, from about any of the following: 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. The absolute amount given to each patient depends on pharmacological properties such as bioavailability, clearance rate and route of administration.

The effective amount and method of administration of the particular CIC formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient CIC-containing composition to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the CIC. Thus, administration of CIC to mammalian skin and/or mucosa, where APCs are present in relatively high concentration, is preferred.

The present invention provides CIC formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein a CIC are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the CIC to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up CIC transferred from the end of the tines. For example, the MONO-VACC old tuberculin test manufactured by Pasteur Merieux of Lyon, France contains a device suitable for introduction of CIC-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of a CIC formulation. Use of the device is preferably according to the manufacturer's written instructions included with the device product. Similar devices which can also be used in this embodiment are those which are currently used to perform allergy tests.

Another suitable approach to epidermal administration of CIC is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The CIC can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. Formulations of CIC suitable for parenteral administration are generally formulated in USP water or water for injection and may further comprise pH buffers, salts bulking agents, preservatives, and other pharmaceutically acceptable excipients. CICs for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations CIC suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations of CIC suitable for administration by inhalation including, but not limited to, liquid suspensions for forming aerosols as well as powder forms for dry powder inhalation delivery systems. Devices suitable for administration by inhalation of CIC formulations include, but are not limited to, atomizers, vaporizers, nebulizers, and dry powder inhalation delivery devices.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the formulations of CIC of the invention. The methods of producing the various compositions and devices are within the ability of one skilled in the art and are not described in detail here.

Analysis (both qualitative and quantitative) of the immune response to CIC can be by any method known in the art, including, but not limited to, measuring antigen-specific antibody production (including measuring specific antibody+ subclasses), activation of specific populations of lymphocytes such as CD4+ T cells, NK cells or CTLs, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity and CTL assays can be performed for instance as described in Raz et al. (1994) *Proc. Natl. Acad. Sci. USA* 91:9519-9523 and Cho et al. (2000). Cytokine concentrations can be measured, for example, by ELISA. These and other assays to evaluate the immune response to an immunogen are well known in the art. See, for example, SELECTED METHODS IN CELLULAR IMMUNOLOGY (1980) Mishell and Shiigi, eds., W.H. Freeman and Co.

Preferably, a Th2-type response is stimulated, i.e., elicited and/or enhanced. With reference to the invention, stimulating a Th1-type immune response can be determined in vitro or ex vivo by measuring cytokine production from cells treated with a CIC as compared to control cells not treated with CIC. Methods to determine the cytokine production of cells include those methods described herein and any known in the art. The type of cytokines produced in response to CIC treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IFN-γ and IFN-α. In contrast, "Th2-type biased cytokines" refers to those associated with a Th2-type immune response, and include, but are not limited to, IL-4, IL-5, and IL-13. Cells useful for the determination of CIC activity include cells of the immune system, primary cells isolated from a host and/or cell lines, preferably APCs and lymphocytes, even more preferably macrophages and T cells.

Stimulating a Th1-type immune response can also be measured in a host treated with a CIC can be determined by any method known in the art including, but not limited to: (1) a reduction in levels of IL-4 or IL-5 measured before and after antigen-challenge; or detection of lower (or even absent) levels of IL-4 or IL-5 in a CIC treated host as compared to an antigen-primed, or primed and challenged, control treated without CIC; (2) an increase in levels of IL-12, IL-18 and/or IFN (α, β or γ) before and after antigen challenge; or detection of higher levels of IL-12, IL-18 and/or IFN (α, β or γ) in a CIC treated host as compared to an antigen-primed or, primed and challenged, control treated without CIC; (3) "Th1-type biased" antibody production in a CIC treated host as compared to a control treated without CIC; and/or (4) a reduction in levels of antigen-specific IgE as measured before and after antigen challenge; or detection of lower (or even absent) levels of antigen-specific IgE in a CIC treated host as compared to an antigen-primed, or primed and challenged, control treated without CIC. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to CIC treatment indicate a Th1-type or a Th2-type biased immune response by the cells. As used herein, the term "Th1-type biased" antibody production refers to the measurable increased production of antibodies associated with a Th2-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of administration of CIC produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction and reduction in histamine release in response to allergen.

V. Kits of the Invention

The invention provides kits. In certain embodiments, the kits of the invention comprise one or more containers comprising a CIC. The kits may further comprise a suitable set of instructions, generally written instructions, relating to the use of the CIC for the intended treatment (e.g., immunomodulation, ameliorating symptoms of an infectious disease, increasing IFN-γ levels, increasing IFN-α levels, or ameliorating an IgE-related disorder).

The kits may comprise CIC packaged in any convenient, appropriate packaging. For example, if the CIC is a dry formulation (e.g., freeze dried or a dry powder), a vial with a resilient stopper is normally used, so that the CIC may be easily resuspended by injecting fluid through the resilient stopper. Ampoules with non-resilient, removable closures (e.g., sealed glass) or resilient stoppers are most conveniently used for liquid formulations of CIC. Also contemplated are packages for use in combination with a specific device, such as an inhaler, nasal administration device (e.g., an atomizer) or an infusion device such as a minipump.

The instructions relating to the use of CIC generally include information as to dosage, dosing schedule, and route of administration for the intended treatment. The containers of CIC may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kits further comprise an antigen (or one or more antigens), which may or may not be packaged in the same container (formulation) as the CIC(s). Antigen have been described herein.

In certain embodiments, the kits of the invention comprise a CIC in the form of a CIC/microcarrier complex (CIC/MC) and may further comprise a set of instructions, generally written instructions, relating to the use of the CIC/MC complex for the intended treatment (e.g., immunomodulation, ameliorating symptoms of an infectious disease, increasing IFN-γ levels, increasing IFN-α levels, or ameliorating an IgE-related disorder).

In some embodiments, kits of the invention comprise materials for production of CIC/MC complex generally include separate containers of CIC and MC, although in certain embodiments materials for producing the MC are supplied rather than preformed MC. The CIC and MC are preferably supplied in a form which allows formation of CIC/MC complex upon mixing of the supplied CIC and MC. This configuration is preferred when the CIC/MC complex is linked by non-covalent bonding. This configuration is also preferred when the CIC and MC are to be crosslinked via a heterobifunctional crosslinker; either CIC or the MC is supplied in an "activated" form (e.g., linked to the heterobifunctional crosslinker such that a moiety reactive with the CIC is available).

Kits for CIC/MC complexes comprising a liquid phase MC preferably comprise one or more containers including materials for producing liquid phase MC. For example, a CIC/MC kit for oil-in-water emulsion MC may comprise one or more containers containing an oil phase and an aqueous phase. The contents of the container are emulsified to produce the MC, which may be then mixed with the CIC, preferably a CIC which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

VI. Examples

The following Examples are provided to illustrate, but not limit, the invention.

Example 1

Structure of Polynucleotides and Chimeric Compounds

Table 2 shows the structures of polynucleotides and chimeric molecules referred to in the Examples. "HEG" is a hexa(ethylene glycol) spacer moiety; "TEG" is triethylene glycol; "C3" is a propyl spacer moiety; "C4" is a butyl spacer; "C6" is a hexyl spacer; "C12" is a dodecyl spacer; "HME" is 2-hydroxymethylethyl; "abasic" or "ab" is 1'2'-dideoxyribose. Other spacers are described in this specification and in the figures.

Except where noted in Table 2 or in specific examples, all nucleotide linkages and linkages between nucleic acid moieties and spacer moieties are phosphorothioate ester. For example, in CICs comprising compound (multiple subunits) spacer moieties with multiple HEG or C3 units (e.g., C-13, C-14, C-15, C-15, C-91, C-92, C-36, C-37, and C-38) the C3 or HEG units are linked with a phosphorothioate linker. Similarly, the branched CICs shown (e.g., C-93, C-94, C-95, C-96, C-97, C-98, C-100, C-101, C-103, C-104, C-121, C-122, C-123, C-124, C-125, C-126, C-127, C-129, C-130) comprise phosphorothioate linkers between the branching subunit and the linear subunit of the spacer. Other branched CICs shown (e.g., C-26, C-99, C-102, C-105, and C-137) are prepared by conjugation strategies and have linking groups as described in the Examples.

Table 2 also includes CICs (e.g., C-128, C-106-C-113) with an end linking group (e.g., HS(CH$_2$)$_6$— and HO(CH$_2$)$_6$SS(CH$_2$)$_6$) useful to link these molecules with branched spacer moieties to create branched CICs. See, e.g., Example 18. These linking groups are connected to the CIC with a phosphorothioate linkage.

TABLE 2

TEST COMPOUNDS AND POLYNUCLEOTIDES

| Compound Designation Number(s) | Structure |
|---|---|
| P-1 | 5'-TCGTCGA-3' |
| P-2 | 5'-TCGTCG-3' |
| P-3 | 5'-ACGTTCG-3' |
| P-4 | 5'-AGATGAT-3' |
| P-5 | 5'-ATCTCGA-3' |
| P-6 | 5'-TGA CTG TGA ACG TTC GAG ATG A-3' (SEQ ID NO: 134) |
| P-7 | 5'-TGA CTG TGA ACC TTA GAG ATG A-3' (SEQ ID NO: 135) |
| P-8 | 5'-TGACTGTGAAGGTTAGAGATGA-3' (SEQ ID NO: 136) |
| P-9 | 5'-CTGTGAACGTTCGAGATG-3' (SEQ ID NO: 83) |
| P-10 | 5'-TCGTCGAACGTTCGAGATG-3' (SEQ ID NO: 41) |
| P-11 | 5'-AACGTT-3' |
| P-12 | 5'-TCGTCGT-3' |
| P-13 | 5'-TCGAGAT-3' |
| P-14 | 5'-TCGACGT-3' |
| P-15 | HO(CH$_2$)$_6$SS(CH$_2$)$_6$-5'-TGACTGTGAACCTTAGAGATGA-3' (SEQ ID NO: 137) |
| P-16 | HS(CH$_2$)$_6$-5'-TGACTGTGAACCTTAGAGATGA-3' (SEQ ID NO: 138) |
| M-1 | 5'-TGCTGC-3'-HEG-5'-AGCTTGC-3'-HEG-5'-AGATGAT-3' |
| C-8 | 5'-TCGTCGA-3'-HEG-5'-ACGTTCG-3'-HEG-5'-AGATGAT-3' |
| C-9 | 5'-TCGTCGA-3'- C3-5'-ACGTTCG-3'-C3-5'-AGATGAT-3' |
| C-10 | 5'-TCGTCG-3'-HEG-5'-ACGTTCG-3'-HEG-5'-AGATGAT-3' |
| C-11 | 5'-TCGTCG-3'-C3-5'-ACGTTCG-3'-C3-5'-AGATGAT-3' |
| C-12 | (5'-TCGTCGA-3')$_2$-glycerol-3'-AGCTGCT-5' |
| C-13 | 5'-TCGTCG-3'-(C3)$_{15}$-5'-T-3' |
| C-14 | 5'-TCGTCG-3'-(HME)$_{15}$-5'-T-3' |
| C-15 | 5'-TCGTCG-3'-(TEG)$_8$-5'-T-3' |
| C-16 | 5'-TCGTCG-3'-(HEG)$_4$-5'-T-3' |
| C-17 | 5'-TCGTCG-3'-C4-5'-ACGTTCG-3'-C4-5'-AGATGAT-3' |
| C-18 | 5'-TCGTCG-3'-TEG-5'-ACGTTCG-3'-TEG-5'-AGATGAT-3' |
| C-19 | 5'-TCGTCG-3'-C12-5'-ACGTTCG-3'-C12-5'-AGATGAT-3' |
| C-20 | 5'-TCGTCG-3'-abasic-5'-ACGTTCG-3'-abasic-5'-AGATGAT-3' |
| C-21 | 5'-TCGTCGA-3'-HEG-5'-TCGTCGA-3'-HEG-5'-TCGTCGA-3' |
| C-22 | 5'-TCGTCG-3'-HEG-5'-TCGTCG-3'-HEG-5'-TCGTCG-3' |
| C-23 | 5'-TCGTCG-3'-HEG-5'-AACGTT-3'-HEG-5'-AGATGAT-3' |
| C-24 | 5'-ACGTTCG-3'-HEG-5'-ACGTTCG-3'-HEG-5'-AGATGAT-3' |
| C-25 | 5'-TCGTCG-3'-HME-5'-ACGTTCG-3'-HME-5'-AGATGAT-3' |
| C-26 | (5'-TCGTCGA-3')$_4$-R where R = Starburst Dendrimer ® (See Ex. 18) |
| C-27 | (5'-TCGTCGA-3')$_2$-glycerol-5'-AACGTTC-3' |
| C-28 | (5'-TCGTCGA-3')$_2$-glycerol-5'-TCGTCGA-3' |
| C-29 | 5'-TCGTCG-3'-HEG-5'-ACGTTCG-3'-HEG-5'-AGATGAT-3'-TEG |
| C-30 | HEG-5'-TCGTCG-3'-HEG-5'-ACGTTCG-3'-HEG-5'-AGATGAT-3'-TEG |
| C-31 | HEG-5'-TCGTCG-3'-HEG-5'-ACGTTCG-3'-HEG-5'-AGATGAT-3'-TEG (phosphodiester linkages) |
| C-32 | 5'-TCG-3'-HEG-5'-TCG-3'-HEG-5'-TCG-3'-HEG-5'-TCG-3'-HEG-5'-TCG-3' |
| C-33 | 5'-TCGTCGA-3'-C3-5'-TCGTCGA-3'-C3-5'-TCGTCGA-3' all phosphorothioate linkages |
| C-34 | HS(CH$_2$)$_6$-5'-TCGTCGA-3'-C3-5'-ACGTTCG-3'-C3-5'-AGATGAT-3' |
| C-35 | 5'-TCGTCGA-3'\\glycerol-5'-AGATGAT-3' / 5'-AACGTTC-3' |
| C-36 | 5'-TCGTCGA-3'-(HEG)$_6$-5'-TCGTCGA-3' (phosphodiester linkages) |
| C-37 | 5'-TCGTCGA-3'-(HEG)$_4$-3'-AGCTGCT-5' |
| C-38 | 5'-TCGTCGA-3'-(HEG)$_4$-5'-TCGTCGA-3' |
| C-39 | 5'-TCGTCGA-3'-HEG-5'-TCGTCGA-3' |
| C-40 | 5'-TCGTCG-3'-HEG-5'-TCGA-3' |
| C-41 | 5'-TCGTTTT-3'-HEG-5'-TCGTTTT-3'-HEG-5'-TCGTTTT-3' |
| C-42 | 5'-TCGTCGT-3'-HEG-5'-TCGTCGT-3'-HEG-5'-TCGTCGT-3' |
| C-43 | 5'-TCGTC-3'-HEG-5'-TCGTC-3'-HEG-5'-TCGTC-3'-HEG-5'-TCGTC-3' |
| C-44 | 5'-TCGT-3'-HEG-5'-TCGT-3'-HEG-5'-TCGT-3'-HEG-5'-TCGT-3'-HEG-5'-TCGT-3' |
| C-45 | 5'-TCGAGAT-3'-HEG-5'-TCGAGAT-3'-HEG-5'-TCGAGAT-3' |
| C-46 | 5'-TTCGTTT-3'-HEG-5'-TTCGTTT-3'-HEG-5'-TTCGTTT-3' |
| C-47 | 5'-TCGTCGT-3'-HEG-5'-TGTCGTT-3'-HEG-5'-TGTCGTT-3' |
| C-48 | 5'-TCGTCGA-3'-HEG-5'-ACGTTCG-3'-HEG-5'-TCGTCGA-3' |
| C-49 | 5'-TCGTCGA-3'-HEG-5'-ACGTTCG-3'-HEG-5'-GGGGGG-3' |
| C-50 | 5'-TCGAACG-3'-HEG-5'-TCGAACG-3'-HEG-5'-TCGAACG-3' |
| C-51 | 5'-TCGACGT-3'-HEG-5'-TCGACGT-3'-HEG-5'-TCGACGT-3' |
| C-52 | 5'-CGTTCGA-3'-HEG-5'-CGTTCGA-3'-HEG-5'-CGTTCGA-3' |
| C-53 | 5'-TGACTGTGA-3'-HEG-5'-ACGTTCG-3'-HEG-5'-AGATGAT-3' |
| C-54 | 5'-TCGTCGA-3'-HEG-5'-AACGTTC-3'-HEG-5'-AGATGAT-3 |
| C-55 | 5'-TCGTCGA-3'-HEG-5'-AACGTTC-3'-HEG-5'-TCGTCGA-3 |
| C-56 | 5'-TCGTCGA-3'-HEG-5'-AGATGAT-3'-HEG-5'-ACGTTCG-3' |
| C-57 | 5'-ACGTTCG-3'-HEG-5'-TCGTCGA-3'-HEG-5'-AGATGAT-3' |
| C-58 | 5'-ACGTTCG-3'-HEG-5'-AGATGAT-3'-HEG-5'-TCGTCGA-3' |
| C-59 | 5'-AGATGAT-3'-HEG-5'-TCGTCGA-3'-HEG-5'-ACGTTCG-3' |
| C-60 | 5'-AGATGAT-3'-HEG-5'-ACGTTCG-3'-HEG-5'-TCGTCGA-3' |
| C-61 | 5'-TCCATTT-3'-HEG-5'-AACGTTC-3'-HEG-5'-TGACGTT-3' |
| C-62 | 5'-TGACGTT-3'-HEG-5'-AACGTTC-3'-HEG-5'-TCCATTT-3' |
| C-63 | 5'-TCGACTC-3'-HEG-5'-TCGAGCG-3'-HEG-5'-TTCTCTT-3' |
| C-64 | 5'-CTGTGAACGTTCGAGATG-3' (SEQ ID NO: 83)-HEG-5'-CTGTGAACGTTCGAGATG-3' (SEQ ID NO: 83) |
| C-65 | 5'-TCGTCGA-3'-HEG-5'-TCGTCGA-3'-HEG-5'-AGCTGCT-3' |
| C-66 | 5'-TCGTCGAACGTTCGAGATG-3' (SEQ ID NO: 41)-HEG-5'-TCGTCGAACGTTCGAGATG-3' (SEQ ID NO: 41) |
| C-67 | 5'-TCGTCGAACGTTCGAGATG-3' (SEQ ID NO: 41)-HEG-3'-GTAGAGCTTGCAAGCTGCT-5' (SEQ ID NO: 41) |
| C-68 | 5'-TCG-3'-HEG-5'-T-3' |
| C-69 | 5'-TCGAT-3'-HEG-5'-TCGAT-3'-HEG-5'-TCGAT-3'-HEG-5'-TCGAT-3' |
| C-70 | 5'-TCGTCGA-3'-HEG-5'-TCGTCGA-3'-HEG-5'-AACGTTC-3'-HEG-5'-AGAT-3' |
| C-71 | 5'-TCGACGT-3'-HEG-5'-TCGACGT-3'-HEG-5'-TCGACGT-3'-HEG-5'-TCGACGT-3' |
| C-72 | 5'-TCCTCCA-3'-HEG-5'-ACCTTAG-3'-HEG-5'-AGATGAT-3' (no CG) |
| C-73 | 5'-ACGTCGA-3'-HEG-5'-ACGTCGA-3'-HEG-5'-ACGTCGA-3' |
| C-74 | 5'-TCGATTT-3'-HEG-5'-TCGATTT-3'-HEG-5'-TCGATTT-3' |
| C-75 | 5'-TTCGATT-3'-HEG-5'-TTCGATT-3'-HEG-5'-TTCGATT-3' |
| C-76 | 5'-TTTCGAT-3'-HEG-5'-TTTCGAT-3'-HEG-5'-TTTCGAT-3' |
| C-77 | 5'-TTTTCGA-3'-HEG-5'-TTTTCGA-3'-HEG-5'-TTTTCGA-3' |
| C-78 | 5'-TCGCTTT-3'-HEG-5'-TCGCTTT-3'-HEG-5'-TCGCTTT-3' |
| C-79 | 5'-TCGGTTT-3'-HEG-5'-TCGGTTT-3'-HEG-5'-TCGGTTT-3' |
| C-80 | 5'-ACGATTT-3'-HEG-5'-ACGATTT-3'-HEG-5'-ACGATTT-3' |
| C-81 | 5'-ATCGAT-3'-HEG-5'-ATCGAT-3'-HEG-5'-ATCGAT-3' |
| C-82 | 5'-ATCGATT-3'-HEG-5'-ATCGATT-3'-HEG-5'-ATCGATT-3' |
| C-83 | 5'-AACGTT-3'-HEG-5'-AACGTT-3'-HEG-5'-AACGTT-3' |
| C-84 | C397: 5'-GsGs-3'-C3-5'-TGC-3'-C3-5'-ATCGAT-3'-C3-5'-GCA-3'-C3-5'-GGsGsGsG-3' (s = phosphorothioate linkages, otherwise linkages are phosphodiester) |
| C-85 | 5'-GsGs-3'-C3-5'-TCGTGC-3'-C3-5'-ATCGAT-3'-C3-5'-GCACGA-3'-C3-5'-GGsGsGsG-3' (s = phosphorothioate linkages, otherwise linkages are phosphodiester) |
| C-86 | 5'-TGCTGCA-3'-C3-5'-AGCTTGC-3'-C3-5'-AGATGAT-3' (No CG) |
| C-87 | 5'-GsGsGsGs-3'-C3-5'-ATCGAT-3'-C3-5'-TGATGCATCA-3'-C3-5'-ATCGAT-3'-C3-5'-GsGsGsGsG-3' (s = phosphorothioate linkages, otherwise linkages are phosphodiester) |

TABLE 2-continued

TEST COMPOUNDS AND POLYNUCLEOTIDES

| Compound Designation Number(s) | Structure |
|---|---|
| C-88 | 5'-TCCA-3'-C3-5'-TGACGTT-3'-C3-5'-CCTGATGCT-3' |
| C-89 | 5'-TGACTGTGA-3'-C3-5'-ACGTTCG-3'-C3-AGATGAT-3' |
| C-90 | 5'-TCGTCGA-3'-C3-5'-TCGTCGA-3'-C3-5'-TCGTCGA-3' |
| C-91 | 5'-TCG-3'-(ab)$_3$-5'-T-3' |
| C-92 | (ab)-5'-TCG-3'-(ab)$_2$-5'-T-3' |
| C-93 | (5'-TCGTCGA-3'-HEG)$_2$-glycerol-HEG-5'-TCGTCGA-3' (phosphodiester) |
| C-94 | (5'-TCGTCGA-3'-HEG)$_2$-glycerol-HEG-5'-TCGTCGA-3' |
| C-95 | (5'-TCGTCGA-3'-HEG)$_2$-glycerol-HEG-3'-AGCTGCT-5' |
| C-96 | (5'-TCGTCGA-3'-HEG)$_2$-glycerol-HEG-5'-AACGTTC-3' |
| C-97 | (5'-TCGTCGA-3'-HEG)$_2$-glycerol-HEG-5'-AACGTTC-3'-HEG-5'-TCGA-3' |
| C-98 | (5'-TCGTCGA-3'-HEG)$_3$-trebler-HEG-5'-AACGTTC-3'-HEG-5'-TCGA-3' |
| C-99 | TMEA-(5'-TGACTGTGAACGTTCGAGATGA-3')$_3$ (SEQ ID NO: 139) (See Ex. 23) |
| C-100 | (5'-TCGTCGA-3'-HEG)$_2$-glycerol-HEG-5'-AACGTTC-3'-HEG-5'-TCGACGT-3' |
| C-101 | (5'-TCGACGT-3'-HEG)$_2$-glycerol-HEG-5'-TCGACGT-3' |
| C-102 | Starburst Dendrimer ®-(5'-TGACTGTGAACGTTCGAGATGA-3')$_x$ (X range = 3-16) (SEQ ID NO: 2) (See Ex. 24) |
| C-103 | (5'-TCGTCGA-3'-TEG)$_2$-glycerol-TEG-5'-TCGTCGA-3' |
| C-104 | (5'-TCGTCGA-3'-C3)$_2$-glycerol-C3-5'-TCGTCGA-3' |
| C-105 | TMEA-(S-(CH$_2$)$_3$-3'-TAGTAGA-5'-HEG-3'-GCTTGCA-5'-HEG-3'-AGCTGCT-5')$_3$(See Ex. 23) |
| C-106 | HO(CH$_2$)$_6$SS(CH$_2$)$_6$-5'-TGACTGTGAACGTTCGAGATGA-3' (SEQ ID NO: 140) |
| C-107 | HS(CH$_2$)$_6$-5'-TGACTGTGAACGTTCGAGATGA-3' (SEQ ID NO: 141) |
| C-110 | HO(CH$_2$)$_6$SS(CH$_2$)$_6$-5'-TCGTCG-3'-C3-5'-ACGTTCG-3'-C3-5'-AGATGAT-3' |
| C-111 | HS(CH$_2$)$_6$-5'-TCGTCG-3'-C3-5'-ACGTTCG-3'-C3-5'-AGATGAT-3' |
| C-112 | HO(CH$_2$)$_6$SS(CH$_2$)$_6$-5'-TCGTCGA-3'-HEG-5'-ACGTTCG-3'-HEG-5'-AGATGAT-3' |
| C-113 | HS(CH$_2$)$_6$-5'-TCGTCGA-3'-HEG-5'-ACGTTCG-3'-HEG-5'-AGATGAT-3' |
| C-114 | 5'-TCGTCGA-3'-C3-5'-ACGTTCG-3'-C3-5'-AGATGAT-3'-C3-(CH$_2$)$_3$SS(CH$_2$)$_3$OH |
| C-115 | 5'-TCGTCGA-3'-C3-5'-ACGTTCG-3'-C3-5'-AGATGAT-3'-C3-(CH$_2$)$_3$SH |
| C-116 | 5'-TCGTCGA-3'-HEG-5'-ACGTTCG-3'-HEG-5'-AGATGAT-3'-(CH$_2$)$_3$SS(CH$_2$)$_3$OH |
| C-117 | 5'-TCGTCGA-3'-HEG-5'-ACGTTCG-3'-HEG-5'-AGATGAT-3'-(CH$_2$)$_3$SH |
| C-118 | 5'-TCGTCGA-3'-HEG-C3-5'-ACGTTCG-3'-HEG-5'-AGATGAT-3' |
| C-119 | 5'-TCGA-3'-HEG-5'-TCGA-3'-HEG-5'-TCGA-3'-HEG-5'-TCGA-3'-HEG-5'-TCGA-3' |
| C-120 | 5'-TCGTCG-3'-C6-5'-ACGTTCG-3'-C6-5'-AGATGAT-3' |
| C-121 | (5'-AACGTT-3'-HEG)$_2$-glycerol-HEG-5'-AACGTT-3' |
| C-122 | (5'-TCAACGTT-3'-HEG)$_2$-glycerol-HEG-5'-TCAACGTT-3' |
| C-123 | (5'-TCGTCGA-3'-HEG-HEG)$_2$-glycerol-HEG-HEG-5'-TCGTCGA-3 |
| C-124 | (5'-TCGACGT-3'-HEG)$_2$-symmetrical doubler-HEG-5'-TCGACGT-3' |
| C-125 | (5'-TCGACGT-3'-HEG)$_3$-trebler-HEG-5'-TCGACGT-3' |
| C-126 | ((5'-TCGACGT-3'-HEG)$_2$-glycerol-HEG)$_2$-glycerol-HEG-5'-TCGACGT-3' |
| C-127 | (5'-TCGACGT-3'-HEG)$_2$-glycerol-HEG-5'-AACGTTC-3' |
| C-128 | HO(CH$_2$)$_6$SS(CH$_2$)$_6$-5'-TCGTCGA-3'-C3-5'-ACGTTCG-3'-C3-5'-AGATGAT-3' |
| C-129 | ((5'-TCGACGT-3'-HEG)2-glycerol-HEG)2-glycerol-HEG-5'-T-3' |
| C-130 | (5'-TCGACGT-3'-HEG)3-trebler-HEG-5'-T-3' |
| C-131 | 5'-TCGTCGA-3'-C4-5'-ACGTTCG-3'-C4-5'-AGATGAT-3' |
| C-132 | 5'-TCGTCGA-3'-C6 -5'-ACGTTCG-3'-C6-5'-AGATGAT-3' |
| C-133 | 5'-TCGTCGA-3'-TEG-5'-ACGTTCG-3'-TEG-5'-AGATGAT-3' |
| C-134 | 5'-TCGTCGA-3'-PEG-5'-ACGTTCG-3'-PEG-5'-AGATGAT-3 [PEG = (CH2CH2O)$_{45}$] |
| C-135 | 5'-TCGACGT-3'-HEG-(CH$_2$)$_3$SS(CH$_2$)$_3$OH |
| C-136 | 5'-TCGACGT-3'-HEG-(CH$_2$)$_3$SH |
| C-137 | (5'-TCGACGT-3'-HEG)$_x$-Ficoll$_{400}$ (X range = 150-250, ave. 185) See example 49 |

Example 2

Synthesis of a Chimeric Compound with a Linear Structure and Hexaethylene Glycol Spacers C-10, having the structure shown below, was synthesized. The nucleic acid moieties are DNA with phosphorothioate linkages, and the spacer moieties are hexaethylene glycol (HEG), connected to the nucleic acid moieties via phosphorothioate linkages.

C-10:
5'-TCGTCG-3'-HEG-5'-ACGTTCG-3'-HEG-5'-AGATGAT-3'

The C-10 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 4,4'-O-dimethoxytrityl-hexaethylene glycol-O—(N,N-diisopropyl) 2-cyanoethylphosphoramidite (obtained from Glen Research, Sterling, Va.) were dissolved in anhydrous acetonitrile to a final concentration of 0.05 M. (As will be apparent to the ordinarily skilled reader, the terms "nucleoside monomer" or "spacer moiety" are sometimes used herein, e.g., in the context of synthesis of CICs, to refer to the precursor reagents that when deprotected and linked to other components using synthetic methods such as those disclosed herein, give rise to the nucleic acid and nonnucleic acid moieties of the CICs.) The HEG spacer precursor was placed in an auxiliary monomer site on the instrument. The instrument was programmed to add the nucleotide monomers and HEG spacers in the desired order, with synthesis of the nucleic acid moieties occurring in the 3' to 5' direction.

1. Use a 3'-support bound "T" solid support
2. Synthesis of 5'-AGATGA-3' moiety
3. Addition of HEG spacer
4. Synthesis of 5'-ACGTTCG-3' moiety
5. Addition of HEG spacer
6. Synthesis of 5'-TCGTCG-3' moiety The synthesis cycle consisted of a detritylation step, a coupling step (phosphoramidite monomer plus 1H-tetrazole), a capping step, a sulfurization step using 0.05 M 3H-1,2-benzodithiol-3-one 1,1-dioxide (Beaucage reagent), and a final capping step. At the completion of assembly, the 'trityl-off' compound was cleaved from the controlled-pore glass and the bases were deprotected with concentrated aqueous ammonia at 58° C. for 16 hours. The compound was purified by preparative polyacrylamide electrophoresis, desalted on a SEP-PAK® Plus cartridge (Waters, Milford, Mass.), and precipitated from 1 M aqueous sodium chloride with 2.5 volumes of 95% ethanol. The molecule was dissolved in MILLI-Q® water and the yield was determined from the absorbance at 260 nm. Finally, the compound was lyophilized to a powder. The compound was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg compound (i.e., essentially endotoxin free).

C-8, C-21, C-22, C-23, C-24, C-32 and M-1 and other linear HEG-CICs were synthesized analogously.

Example 3

Synthesis of a Chimeric Compound with a Linear Structure and Propyl Spacers

C-11, having the structure shown below, was synthesized. The nucleic acid moieties are DNA with phosphorothioate linkages, and the spacer moieties are propyl (C3), connected to the nucleic acid moieties via phosphorothioate linkages.

C-11:

5'-TCGTCG-3'-C3-5'-ACGTTCG-3'-C3-5'-AGATGAT-3'

The C-11 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 4,4'-O-dimethoxytrityl-propyl-O—(N,N-diisopropyl) 2-cyanoethylphosphoramidite (obtained from Glen Research, Sterling, Va.) were dissolved in anhydrous acetonitrile to a final concentration of 0.05 M. The C3 spacer precursor was placed in an auxiliary monomer site on the instrument. The instrument was programmed to add the nucleotide monomers and C3 spacers in the desired order, with synthesis of the nucleic acid moieties occurring in the 3' to 5' direction.

1. Use a 3'-support bound "T" solid support
2. Synthesis of 5'-AGATGA-3' moiety
3. Addition of C3 spacer
4. Synthesis of 5'-ACGTTCG-3' moiety
5. Addition of C3 spacer
6. Synthesis of 5'-TCGTCG-3' moiety The synthesis, deprotection, workup, and analysis were performed as described in Example 2.

C-9 and other C3-containing CICs were synthesized analogously.

Example 4

Synthesis of a Chimeric Compound with a Linear Structure and with Butyl Spacers

C-17, having the structure shown below, was synthesized. The nucleic acid moieties are DNA with phosphorothioate linkages, and the spacer moieties are butyl (C4), connected to the nucleic acid moieties via phosphorothioate linkages.

C-17:
5'-TCGTCG-3'-C4-5'-ACGTTCG-3'-C4-5'-AGATGAT-3'

The C-17 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 4,4'-O-dimethoxytrityl-butyl-O—(N,N-diisopropyl) 2-cyanoethylphosphoramidite (obtained from ChemGenes, Ashland, Mass.) were dissolved in anhydrous acetonitrile to a final concentration of 0.05 M. The C4 spacer precursor was placed in an auxiliary monomer site on the instrument. The instrument was programmed to add the nucleotide monomers and C4 spacers in the desired order, with synthesis of the nucleic acid moieties occurring in the 3' to 5' direction.

1. Use a 3'-support bound "T" solid support
2. Synthesis of 5'-AGATGA-3' moiety
3. Addition of C4 spacer
4. Synthesis of 5'-ACGTTCG-3' moiety
5. Addition of C4 spacer
6. Synthesis of 5'-TCGTCG-3' moiety The synthesis, deprotection, workup, and analysis were performed as described in Example 2.

Example 5

Synthesis of a Chimeric Compound with a Linear Structure and Triethylene Glycol Spacers C-18, having the structure shown below, was synthesized. The nucleic acid moieties are DNA with phosphorothioate linkages, and the spacer moieties are triethylene glycol (TEG), connected to the nucleic acid moieties via phosphorothioate linkages.

C-18:
5'-TCGTCG-3'-TEG-5'-ACGTTCG-3'-TEG-5'-AGATGAT-3'

The C-18 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 4,4'-O-dimethoxytrityl-triethylene glycol-O—(N,N-diisopropyl) 2-cyanoethylphosphoramidite (obtained from Glen Research, Sterling, Va.) were dissolved in anhydrous acetonitrile to a final concentration of 0.05 M. The TEG spacer precursor was placed in an auxiliary monomer site on the instrument. The instrument was programmed to add the nucleotide monomers and TEG spacers in the desired order, with synthesis of the nucleic acid moieties occurring in the 3' to 5' direction.

1. Use a 3'-support bound "T" solid support
2. Synthesis of 5'-AGATGA-3' moiety
3. Addition of TEG spacer
4. Synthesis of 5'-ACGTTCG-3' moiety
5. Addition of TEG spacer
6. Synthesis of 5'-TCGTCG-3' moiety The synthesis, deprotection, workup, and analysis were performed as described in Example 2.

Example 6

Synthesis of a Chimeric Compound with a Linear Structure and Dodecyl Spacers

C-19, having the structure shown below, was synthesized. The nucleic acid moieties are DNA with phosphorothioate linkages, and the spacer moieties are dodecyl (C12), connected to the nucleic acid moieties via phosphorothioate linkages.

C-19:
5'-TCGTCG-3'-C12-5'-ACGTTCG-3'-C12-5'-AGATGAT-3'

The C-19 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 4,4'-O-dimethoxytrityl-dodecyl-O—(N,N-diisopropyl) 2-cyanoethylphosphoramidite (obtained from Glen Research, Sterling, Va.) were dissolved in anhydrous acetonitrile to a final concentration of 0.05 M. The C12 spacer precursor was placed in an auxiliary monomer site on the instrument. The instrument was programmed to add the nucleotide monomers and C12 spacers in the desired order, with synthesis of the nucleic acid moieties occurring in the 3' to 5' direction.
1. Use a 3'-support bound "T" solid support
2. Synthesis of 5'-AGATGA-3' moiety
3. Addition of C12 spacer
4. Synthesis of 5'-ACGTTCG-3' moiety
5. Addition of C12 spacer
6. Synthesis of 5'-TCGTCG-3' moiety The synthesis, deprotection, workup, and analysis were performed as described in Example 2.

Example 7

Synthesis of a Chimeric Compound with a Linear Structure and Abasic Spacers

C-20, having the structure shown below, was synthesized. The nucleic acid moieties are DNA with phosphorothioate linkages, and the spacer moieties are 1',2'-dideoxyribose (abasic), connected to the nucleic acid moieties via phosphorothioate linkages.

C-20: 5'-TCGTCG-3'-abasic-5'-ACGTTCG-3'-abasic-5'-AGATGAT-3'

The C-20 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 5'-O-(4,4'-dimethoxytrityl)-1',2'-dideoxyribose-3'-O—(N,N-diisopropyl) 2-cyanoethylphosphoramidite (obtained from Glen Research, Sterling, Va.) were dissolved in anhydrous acetonitrile to a final concentration of 0.05 M. The abasic spacer precursor was placed in an auxiliary monomer site on the instrument. The instrument was programmed to add the nucleotide monomers and abasic spacers in the desired order, with synthesis of the nucleic acid moieties occurring in the 3' to 5' direction.
1. Use a 3'-support bound "T" solid support
2. Synthesis of 5'-AGATGA-3' moiety
3. Addition of abasic spacer
4. Synthesis of 5'-ACGTTCG-3' moiety
5. Addition of abasic spacer
6. Synthesis of 5'-TCGTCG-3' moiety The synthesis, deprotection, workup, and analysis were performed as described in Example 2.

Example 8

Synthesis of a Chimeric Compound with a Linear Structure and Hexaethylene Glycol and Triethylene Glycol Spacers C-29, having the structure shown below, was synthesized. The nucleic acid moieties are DNA with phosphorothioate linkages, the spacer moieties are hexaethylene glycol (HEG), connected to the nucleic acid moieties via phosphorothioate linkages, and the 3'-end group is triethylene glycol (TEG), connected to the nucleic acid moiety via a phosphorothioate linkage.

C-29:
5'-TCGTCG-3'-HEG-5'-ACGTTCG-3'-HEG-5'-AGATGAT-3'-TEG

The C-29 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The triethylene glycol-controlled-pore glass, used as the solid support for the synthesis, was from Glen Research (Sterling, Va.). The nucleoside monomers and the spacer moiety precursor, 4,4'-O-dimethoxytrityl-hexaethylene glycol-O—(N,N-diisopropyl) 2-cyanoethylphosphoramidite (obtained from Glen Research, Sterling, Va.) were dissolved in anhydrous acetonitrile to a final concentration of 0.05 M. The HEG spacer was placed in an auxiliary monomer site on the instrument. The instrument was programmed to add the nucleotide monomers and HEG spacers in the desired order, with synthesis of the nucleic acid moieties occurring in the 3' to 5' direction.
1. Use a triethylene glycol solid support
2. Synthesis of 5'-AGATGAT-3' moiety
3. Addition of HEG spacer
4. Synthesis of 5'-ACGTTCG-3' moiety
5. Addition of HEG spacer
6. Synthesis of 5'-TCGTCG-3' moiety The synthesis, deprotection, workup, and analysis were performed as described in Example 2.

Example 9

Synthesis of a Chimeric Compound with a Linear Structure and Hexaethylene Glycol and Triethylene Glycol Spacers C-30, having the structure shown below, was synthesized. The nucleic acid moieties are DNA with phosphorothioate linkages, the spacer moieties and 5'-end group are hexaethylene glycol (HEG), connected to the nucleic acid moieties via phosphorothioate linkages, and the 3'-end group is triethylene glycol (TEG), connected to the nucleic acid moiety via a phosphorothioate linkage.

C-30:
HEG-5'-TCGTCG-3'-HEG-5'-ACGTTCG-3'-HEG-5'-AGATGAT-3'-TEG

The C-30 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The triethylene glycol-controlled-pore glass, used as the solid support for the synthesis, was from Glen Research (Sterling, Va.). The nucleoside monomers and the spacer moiety precursor, 4,4'-O-dimethoxytrityl-hexaethylene glycol-O—(N, N-diisopropyl) 2-cyanoethylphosphor amidite (obtained from Glen Research, Sterling, Va.) were dissolved in anhydrous acetonitrile to a final concentration of 0.05 M. The HEG spacer precursor was placed in an auxiliary monomer site on the instrument. The instrument was programmed to add the nucleotide monomers and HEG spacers in the desired order, with synthesis of the nucleic acid moieties occurring in the 3' to 5' direction.
1. Use a triethylene glycol solid support
2. Synthesis of 5'-AGATGAT-3' moiety 3. Addition of HEG spacer
4. Synthesis of 5'-ACGTTCG-3' moiety
5. Addition of HEG spacer
6. Synthesis of 5'-TCGTCG-3' moiety
7. Addition of the HEG spacer The synthesis, deprotection, workup, and analysis were performed as described in Example 2.

Example 10

Synthesis of a Chimeric Compound with a Linear Structure and Hexaethylene Glycol and Triethylene Glycol Spacers, and with Phosphodiester Linkages C-31, having the structure shown below, was synthesized. The nucleic acid moieties are DNA with phosphodiester linkages, the spacer moieties and 5'-end group are hexaethylene glycol (HEG), connected to the nucleic acid moieties via phosphodiester linkages, and the 3'-end group is triethylene glycol (TEG), connected to the nucleic acid moiety via a phosphodiester linkage.

C-31:
HEG-5'-TCGTCG-3'-HEG-5'-ACGTTCG-3'-HEG-5'-AGATGAT-3'-TEG

The C-31 molecule was synthesized by TriLink BioTechnologies (San Diego, Calif.) on a Perseptive Biosystems Expedite 8909 automated DNA synthesizer using the manufacturer's protocol for 1 umol phosphodiester DNA. The triethylene glycol-controlled-pore glass, used as the solid support for the synthesis, was from Glen Research (Sterling, Va.). The nucleoside monomers and the spacer moiety, 4,4'-O-dimethoxytrityl-hexaethylene glycol-O—(N,N-diisopropyl) 2-cyanoethylphosphor amidite (obtained from Glen Research, Sterling, Va.) were dissolved in anhydrous acetonitrile to a final concentration of 0.05 M. The HEG spacer was placed in an auxiliary monomer site on the instrument. The instrument was programmed to add the nucleotide monomers and HEG spacers in the desired order, with synthesis of the nucleic acid moieties occurring in the 3' to 5' direction.
1. Use a triethylene glycol solid support
2. Synthesis of 5'-AGATGAT-3' moiety
3. Addition of HEG spacer
4. Synthesis of 5'-ACGTTCG-3' moiety
5. Addition of HEG spacer
6. Synthesis of 5'-TCGTCG-3' moiety
7. Addition of the HEG spacer The synthesis cycle consisted of a detritylation step, a coupling step (phosphoramidite monomer plus 1H-tetrazole), a capping step, an oxidation step, and a final capping step. At the completion of assembly, the 'trityl-off' compound was cleaved from the controlled-pore glass and the bases were deprotected with concentrated aqueous ammonia at 58° C. for 16 hours. The compound was purified by preparative polyacrylamide electrophoresis, desalted on a SEP-PAK® Plus cartridge (Waters, Milford, Mass.), and precipitated from 1 M aqueous sodium chloride with 2.5 volumes of 95% ethanol. The compound was dissolved in MILLI-Q® water and the yield was determined from the absorbance at 260 nm. Finally, the compound was lyophilized to a powder. The compound was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg compound.

C-25, having the structure shown below, was synthesized. The nucleic acid moieties are DNA with phosphorothioate linkages, and the spacer moieties are 2-(hydroxymethyl)ethyl (HME), connected to the nucleic acid moieties via phosphorothioate linkages.

C-25:
5'-TCGTCG-3'-HME-5'-ACGTTCG-3'-HME-5'-AGATGAT-3'

The C-25 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The nucleoside monomers and the spacer moiety precursor, 1-O-(4,4'-dimethoxytrityl)-3-O-levulinyl-glycerol-2-O—(N,N-diisopropyl) 2-cyanoethylphosphoramidite (obtained from ChemGenes, Ashland, Mass.) were dissolved in anhydrous acetonitrile to a final concentration of 0.05 M. The HME spacer was placed in an auxiliary monomer site on the instrument. The instrument was programmed to add the nucleotide monomers and HME spacers in the desired order, with synthesis of the nucleic acid moieties occurring in the 3' to 5' direction.
1. Use a 3'-support bound "T" solid support
2. Synthesis of 5'-AGATGA-3' moiety
3. Addition of HME spacer
4. Synthesis of 5'-ACGTTCG-3' moiety
5. Addition of HME spacer
6. Synthesis of 5'-TCGTCG-3' moiety The synthesis, deprotection, workup, and analysis were performed as described in Example 2. The levulinyl group is removed during the treatment with ammonia.

Example 12

Synthesis of a Chimeric Compound with a Linear Structure and a Negatively Charged Spacer Moiety C-13, having the structure shown below, was synthesized. The nucleic acid moieties are DNA with phosphorothioate linkages, and the spacer moiety is a propyl (C3) polymer linked via phosphorothioate linkages.

C-13: 5'-TCGTCG-3'-(C3)$_{15}$-5'-T-3'

The C-13 molecule was synthesized on a Perseptive Biosystems Expedite 8909 automated DNA synthesizer using the manufacturers protocol for 1 umol phosphorothioate DNA. The nucleoside monomers and the spacer moiety precursor, 4,4'-O-dimethoxytrityl-propyl-O—(N,N-diisopropyl) 2-cyanoethylphosphoramidite (obtained from Glen Research, Sterling, Va.) were dissolved in anhydrous acetonitrile to a final concentration of 0.1 M. The C3 spacer was placed in an auxiliary monomer site on the instrument. The instrument was programmed to add the nucleotide monomers and C3 spacers in the desired order, with synthesis of the nucleic acid moieties occurring in the 3' to 5' direction.
1. Use a 3'-support bound "T" solid support
2. Addition of 15 C3 spacers
3. Synthesis of 5'-TCGTCG-3' moiety The synthesis cycle consisted of a detritylation step, a coupling step (phosphoramidite monomer plus 1H-tetrazole), a capping step, a sulfurization step using 0.02 M 3-amino-1, 2,4-dithiazole-5-thione (ADTT) in 9:1 acetonitrile:pyridine, and a final capping step. At the completion of assembly, the 'trityl-on' compound was cleaved from the controlled-pore glass and the bases were deprotected with concentrated aqueous ammonia at 58° C. for 16 hours. The compound was purified by HPLC on a Hamilton PRP-1 column using an increasing gradient of acetonitrile in 0.1 M triethylammonium acetate. The purified compound was concentrated to dryness, the 4,4'-dimethoxytrityl group was removed with 80% aqueous acetic acid, and then the compound was precipitated two times from 1 M aqueous sodium chloride with 2.5 volumes of 95% ethanol. The compound was dissolved in MILLI-Q® water and the yield was determined from the absorbance at 260 nm. Finally, the compound was lyophilized to a powder.

The compound was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg compound.

C-14, C-15 and C-16 were synthesized analogously.

Example 13

Synthesis of a Chimeric Compound with a Linear Structure and a Negatively Charged Spacer Moiety C-38, having the structure shown below, was synthesized. The nucleic acid moieties are DNA with phosphorothioate linkages, and the spacer moieties are hexaethylene glycol (HEG), connected via phosphorothioate linkages.

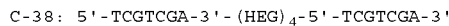

C-38: 5'-TCGTCGA-3'-(HEG)₄-5'-TCGTCGA-3'

The C-38 molecule was synthesized as described in Example 2. The spacer moiety precursor is 4,4'-O-dimethoxytrityl-hexaethylene glycol-O—(N,N-diisopropyl) 2-cyanoethylphosphoramidite (obtained from Glen Research, Sterling, Va.). The synthesis was accomplished by carrying out the following steps:

1. Use a 3'-support bound "A" solid support
2. Synthesis of 5'-TCGTCG-3' moiety
3. Addition of 4 HEG spacers
4. Synthesis of 5'-TCGTCGA-3' moiety The compound was purified using HPLC as described in Example 12. The compound was characterized and the endotoxin content determined as described in Example 2.

Example 14

Synthesis of a Chimeric Compound with a Linear Structure and a Negatively Charged Spacer Moiety with Both Nucleic Acid Moieties Attached Via the 3'-End C-37, having the structure shown below, was synthesized. The nucleic acid moieties are DNA with phosphorothioate linkages, and the spacer moieties are hexaethylene glycol (HEG), connected via phosphorothioate linkages.

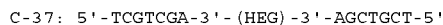

C-37: 5'-TCGTCGA-3'-(HEG)-3'-AGCTGCT-5'

The C-37 molecule was synthesized as described in Example 2, except that a 5'-support bound nucleoside and 3'-O-(4,4'-dimethoxytrityl)-protected nucleoside-5'-O—(N,N-diisopropyl) 2-cyanoethylphosphoramidites were used (Glen Research, Sterling, Va.) to synthesize the first nucleic acid moiety. The spacer moiety precursor is 4,4'-O-dimethoxytrityl-hexaethylene glycol-O—(N,N-diisopropyl) 2-cyanoethylphosphor amidite (obtained from Glen Research, Sterling, Va.). The synthesis was accomplished by carrying out the following steps:

1. Use a 5'-support bound "T" solid support
2. Synthesis of 3'-AGCTGC-5' moiety with 3'-O-(4,4'-dimethoxytrityl)-protected nucleoside-5'-O—(N,N-diisopropyl) 2-cyanoethylphosphoramidites (5' to 3' synthesis)
3. Addition of 4 HEG spacers
4. Synthesis of 5'-TCGTCGA-3' moiety with 5'-O-(4,4'-dimethoxytrityl)-protected nucleoside-3'-O—(N,N-diisopropyl) 2-cyanoethylphosphoramidites (3' to 5' synthesis)

The compound was purified using HPLC as described in Example 12. The compound was characterized and the endotoxin content determined as described in Example 2.

Example 15

Synthesis of a Chimeric Compound with a Branched Structure

C-27, having the structure shown below, was synthesized. The nucleic acid moieties are DNA with phosphorothioate linkages and the spacer moiety is glycerol, connected to the nucleic acid moieties via phosphorothioate linkages.

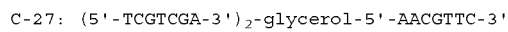

C-27: (5'-TCGTCGA-3')₂-glycerol-5'-AACGTTC-3'

The C-27 molecule was synthesized by TriLink BioTechnologies (San Diego, Calif.) on a Perseptive Biosystems Expedite 8909 automated DNA synthesizer using the manufacturers protocol for 1 umol phosphorothioate DNA. The nucleoside monomers and the spacer moiety precursor, 1,3-di-(4,4'-O-dimethoxytrityl)-glycerol-2-O—(N,N-diisopropyl) 2-cyanoethylphosphoramidite (symmetrical branched phosphoramidite obtained from ChemGenes, Ashland, Mass., FIG. 2) were dissolved in anhydrous acetonitrile to a final concentration of 0.05 M. The glycerol spacer was placed in an auxiliary monomer site on the instrument. The instrument was programmed to add the nucleotide monomers and the glycerol spacer in the desired order, with synthesis of the nucleic acid moieties occurring in the 3' to 5' direction.

1. Use a 3'-support bound "C" solid support
2. Synthesis of 5'-AACGTT-3' moiety
3. Addition of the symmetrical branched phosphoramidite based on glycerol
4. Synthesis of two 5'-TCGTCGA-3' moieties simultaneously The preparation of this branched compound followed the same protocol described in Example 2, except that in step 4, each reagent delivery in the synthesis cycle was doubled because two nucleic acid chains were built simultaneously. The symmetrical branched phosphoramidite shown in FIG. 2 requires the nucleic acid sequences synthesized after the addition of the symmetrical branched phosphoramidite to be the same, although the nucleic acid sequence synthesized before its addition may be the same or different from the later sequences.

The branched compound was purified and characterized as described in Example 2.

C-28 was synthesized analogously.

Example 16

Synthesis of a Chimeric Compound with a Branched Structure and with All Nucleic Acid Moieties Attached Via the 3'-End C-95, having the structure shown below, was synthesized. The nucleic acid moieties are DNA with phosphorothioate linkages and the spacer moieties are glycerol and HEG, connected to the nucleic acid moieties via phosphorothioate linkages.

C-95:
(5'-TCGTCGA-3'-HEG)$_2$-glycerol-HEG-3'-AGCTGCT-5'

The C-95 molecule was synthesized as described in Example 2, except that a 5'-support bound nucleoside and 3'-O-(4,4'-dimethoxytrityl)-protected nucleoside-5'-O—(N,N-diisopropyl) 2-cyanoethylphosphoramidites were used (Glen Research, Sterling, Va.) to synthesize the first nucleic acid moiety. The branched spacer moiety precursor is 1,3-di-(4,4'-O-dimethoxytrityl)-glycerol-2-O—(N,N-diisopropyl) 2-cyanoethylphosphoramidite (symmetrical branched phosphoramidite obtained from ChemGenes, Ashland, Mass., FIG. 2). The synthesis was accomplished by carrying out the following steps:

1. Use a 5'-support bound "T" solid support
2. Synthesis of 3'-AGCTGC-5' moiety with 3'-O-(4,4'-dimethoxytrityl)-protected nucleoside-5'-O—(N,N-diisopropyl) 2-cyanoethyl phosphoramidites (5' to 3' synthesis)
3. Addition of a HEG spacer
4. Addition of the symmetrical branched phosphoramidite based on glycerol
5. Addition of two HEG spacers simultaneously
6. Synthesis of two 5'-TCGTCGA-3' moieties simultaneously with 5'-O-(4,4'-dimethoxytrityl)-protected nucleoside-3'-O—(N,N-diisopropyl) 2-cyanoethylphosphoramidites (3' to 5' synthesis)

The preparation of this branched compound followed the same protocol described in Example 2, except that in steps 5 and 6, each reagent delivery in the synthesis cycle was doubled because two nucleic acid chains were built simultaneously. The symmetrical branched phosphoramidite shown in FIG. 2 requires the nucleic acid sequences synthesized after the addition of the symmetrical branched phosphoramidite to be the same, although the nucleic acid sequence synthesized before its addition may be the same or different from the later sequences.

The compound was purified using HPLC as described in Example 12. The compound was characterized and the endotoxin content determined as described in Example 2.

Example 17

Synthesis of a Chimeric Compound with a Branched Structure, Containing Three Different Nucleic Acid Moieties C-35, having the formula shown below, is synthesized. The nucleic acid moieties are DNA with phosphorothioate linkages and the spacer moiety is glycerol, connected to the nucleic acid moieties via phosphorothioate linkages.

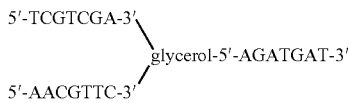

C-35:

The C-35 molecule is synthesized as described in Example 2. The nucleoside monomers and the spacer moiety precursor, 1-(4,4'-O-dimethoxytrityl)-3-O-levulinyl-glycerol-2-O—(N,N-diisopropyl) 2-cyanoethylphosphoramidite (asymmetrical branched phosphoramidite obtained from ChemGenes, Ashland, Mass., FIG. 2) are dissolved in anhydrous acetonitrile to a final concentration of 0.05 M. The glycerol spacer is placed in an auxiliary monomer site on the instrument. The instrument is programmed to add the nucleotide monomers and the glycerol spacer in the desired order, with synthesis of the nucleic acid moieties occurring in the 3' to 5' direction.

1. Use a 3'-support bound "T" solid support
2. Synthesis of 5'-AGATGA-3' moiety
3. Addition of the asymmetrical branched phosphoramidite based on glycerol
4. Synthesis of the 5'-AACGTTC-3' moiety at the dimethoxytrityl end
5. Detritylation and capping of the AACGTTC moiety
6. Removal of the levulinyl protecting group
7. Synthesis of the 5'-TCGTCGA-3' moiety Synthesis takes place essentially as described in Example 2, except that after step 4, the 5'-AACGTTC-3' moiety is detritylated and capped with acetic anhydride/N-methylimidazole in order to terminate that nucleic acid moiety. Next, the levulinyl protecting group is removed with 0.5 M hydrazine hydrate in 3:2 pyridine:acetic acid/pH 5.1 for 5 min. The compound-containing solid support is washed well with anhydrous acetonitrile, and the 5'-TCGTCGA-3' moiety is added using the protocol described in Example 2.

The branched compound is purified and characterized as described in Example 2.

Example 18

Figure 3A:
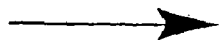
FIGS. 3A and 3B diagram the synthesis of a branched CIC.
Figure 3B:
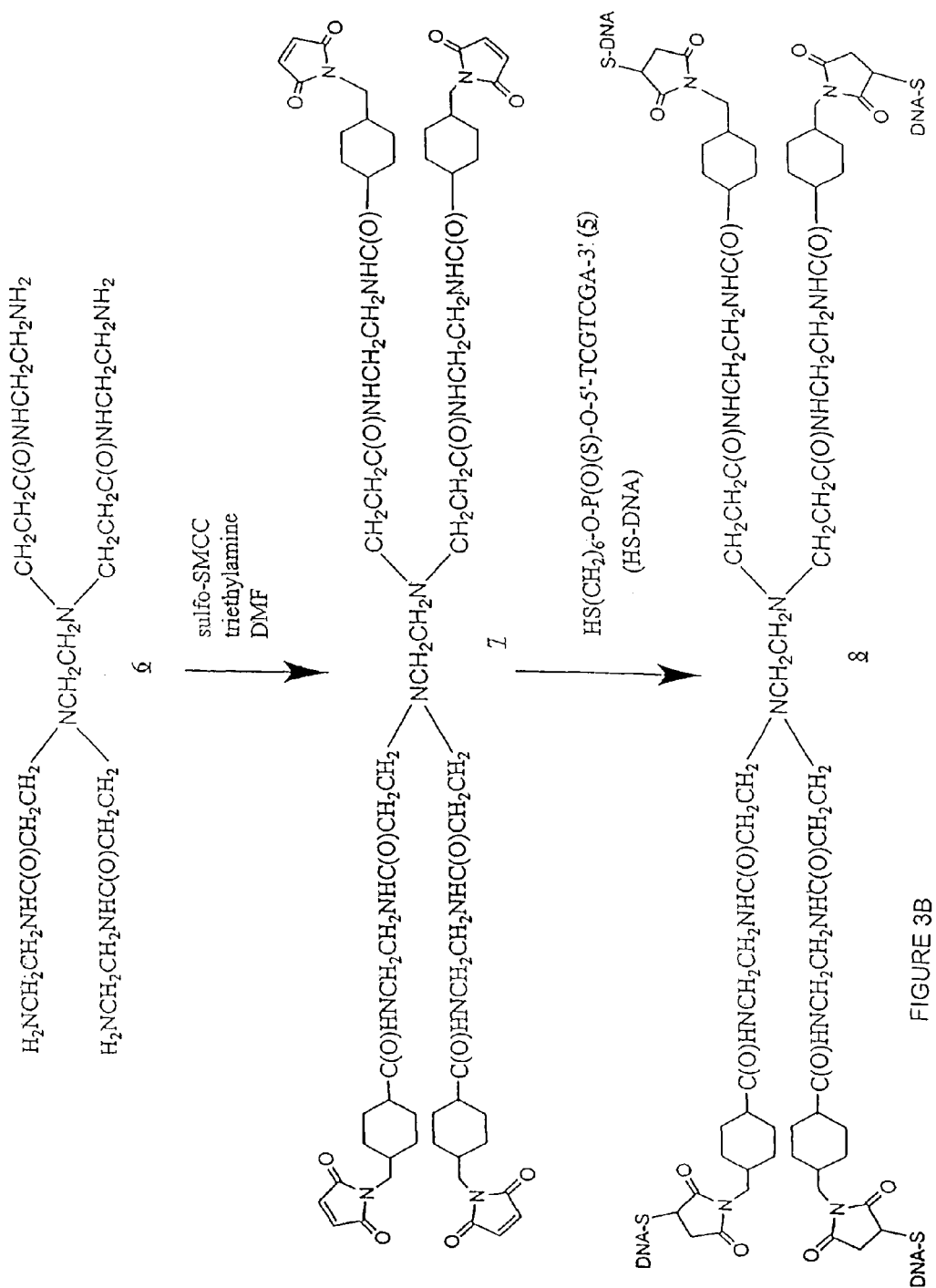

Synthesis of a Chimeric Compound with a Branched Structure by a Conjugation Strategy C-36 is synthesized as shown in FIG. 3. The nucleic acid moieties are DNA with phosphorothioate linkages and the spacer moiety is based on a STARBURST® dendrimer. The nucleic acid moiety is synthesized with a 5'-C6-disulfide spacer (thiol-modifier C6 S—S, Glen Research, Sterling, Va. product no. 10-1926-xx), which upon reduction, provides a thiol group that can react with the maleimide groups on the dendrimer.

Synthesis of 5'-C6-disulfide-TCGTCGA (4)

The 5'-C6-disulfide-TCGTCGA is synthesized using a Perseptive Biosystems Expedite 8909 automated DNA synthesizer using the manufacturer's protocol for 1 umol phosphorothioate DNA. The nucleoside monomers and the thiol-modifier C6 S—S (Glen Research, Sterling, Va.) are dissolved in anhydrous acetonitrile to a final concentration of 0.1 M. The thio-modifier is placed in an auxiliary monomer site on the instrument. The instrument is programmed to add the nucleotide monomers and the thiol modifier in the desired order, with synthesis of the nucleic acid moieties occurring in the 3' to 5' direction.

1. Use a 3'-support bound "A" solid support
2. Synthesis of 5'-TCGTCG-3' moiety
3. Addition of the thiol modifier precursor (S-trityl-6-mercaptohexyl)-(2-cyanoethyl)-(N,N-diisopropyl)-phosphoramidite)

The synthesis cycle consists of a detritylation step, a coupling step (phosphoramidite monomer plus 1H-tetrazole), a capping step, a sulfurization step using 0.02 M 3-amino-1,2,4-dithiazole-5-thione (ADTT) in 9:1 acetonitrile:pyridine, and a final capping step. At the completion of assembly, the 'trityl-on' compound is cleaved from the controlled-pore glass and the bases are deprotected with concentrated aqueous ammonia at 58° C. for 16 hours. The compound is purified by HPLC on a Hamilton PRP-1 column using an increasing gradient of acetonitrile in 0.1 M triethylammonium acetate. The purified compound is concentrated to dryness, the 4,4'-dimethoxytrityl group is removed with 80% aqueous acetic acid, and then the compound is precipitated two times from 1 M aqueous sodium chloride with 2.5 volumes of 95% ethanol. The compound is dissolved in MILLI-Q® water and the yield is determined from the absorbance at 260 nm. Finally, the compound is lyophilized to a powder.

The compound is characterized by capillary gel electrophoresis, electrospray mass spectrometry, and RP-HPLC to confirm composition and purity. An endotoxin content assay (LAL assay, Bio Whittaker) is also conducted, showing endotoxin levels were <5 EU/mg compound.

Synthesis of 5'-thiol-C6-TCGTCGA (5)

The disulfide modified nucleic acid (4) is reduced to a thiol using tris(2-carboxyethylphosphine) hydrochloride (TCEP; Pierce, Rockford, Ill.). The nucleic acid is dissolved at a concentration of 20 mg/ml in buffer containing 0.1 M sodium phosphate/0.15 M sodium chloride/pH 7.5. In a separate vial, the TCEP is dissolved to a concentration of 0.17 M in 0.1 M sodium phosphate/0.15 M sodium chloride/pH 7.5. Add 5 equivalents of TCEP to the nucleic acid and mix gently. Incubate the solution for 120 min at 40° C. and then purify by size exclusion chromatography (Pharmacia P2 column) to yield the 5'-thiol-C6-TCGTCGA (5).

Synthesis of the Maleimide-Modified STARBURST® dendrimer (7)

STARBURST® dendrimers with various numbers of amines (4, 8, 16, 32, 64, etc.) are available from Aldrich (Milwaukee, Wis.). A Starburst® dendrimer (6), having four amino groups, is dissolved in dimethylformamide (DMF) at a concentration of 0.2 M. Triethylamine (10 equivalents) and sulfosuccinimidyl 4-(N-maleimidomethyl)-cyclohexane-1-carboxylate (sulfo-SMCC; Pierce, Rockford, Ill., 8 equivalents) are then added and the solution is stirred for 2 hours or until complete, as determined by thin layer chromatography (TLC; 10% methanol/dichloromethane). The reaction is quenched with water for 30 min and then the DMF is removed in vacuo. The residue is dissolved in dichloromethane and washed two times with aqueous saturated sodium bicarbonate and then water. The organic phase is dried over $MgSO_4$, filtered, and concentrated to dryness in vacuo. The product is purified by silica gel chromatography to yield 7.

Synthesis of STARBURST® dendrimer-(5'-TCGTCGA-3')$_4$ (8)

The maleimide-modified STARBURST® dendrimer (6) is dissolved in DMSO (5 mg/ml) and the purified 5'-C6-thiol-TCGTCGA (5) (10 equivalents), dissolved at a concentration of 10 mg/ml in 0.1 M sodium phosphate/0.15 M sodium chloride/pH 7.5, is added drop-wise. The resulting mixture is stirred at 40° C. overnight. The conjugate is purified by size exclusion chromatography (SEPHADEX® G-25) to yield compound 8.

Example 19

Synthesis of a Chimeric Compound with a Branched Structure

C-94, having the structure shown below, was synthesized. The nucleic acid moieties are DNA with phosphorothioate linkages and the spacer moiety is glycerol, connected to the nucleic acid moieties via phosphorothioate linkages.

C-94:
(5'-TCGTCGA-3'-HEG)$_2$-glycerol-HEG-5'-TCGTCGA-3'

The C-94 molecule was synthesized by TriLink BioTechnologies (San Diego, Calif.) on a Perseptive Biosystems Expedite 8909 automated DNA synthesizer using the manufacturers protocol for 1 umol phosphorothioate DNA. The nucleoside monomers and the spacer moiety precursors [1,3-di-(4,4'-O-dimethoxytrityl)-glycerol-2-O—(N,N-diisopropyl) 2-cyanoethylphosphoramidite (symmetrical branched phosphoramidite obtained from ChemGenes, Ashland, Mass., FIG. 2) and 4,4'-O-dimethoxytrityl-hexaethylene glycol-O—(N,N-diisopropyl) 2-cyanoethylphosphoramidite (obtained from Glen Research, Sterling, Va.)] were dissolved in anhydrous acetonitrile to a final concentration of 0.05 M. The glycerol and HEG spacers were placed in auxiliary monomer sites on the instrument. The instrument was programmed to add the nucleotide monomers, HEG spacers, and the glycerol spacer in the desired order, with synthesis of the nucleic acid moieties occurring in the 3' to 5' direction.

1. Use a 3'-support bound "A" solid support
2. Synthesis of 5'-TCGTCGA-3'-moiety
3. Addition of HEG spacer
4. Addition of the symmetrical branched phosphoramidite based on glycerol
5. Addition of two HEG spacers simultaneously
6. Synthesis of two 5'-TCGTCGA-3' moieties simultaneously The preparation of this branched compound followed the same protocol described in Example 2, except that in steps 5 and 6, each reagent delivery in the synthesis cycle was doubled because two nucleic acid chains were built simultaneously. The symmetrical branched phosphoramidite shown in FIG. 2 requires the nucleic acid sequences synthesized after the addition of the symmetrical branched phosphoramidite to be the same, although the nucleic acid sequence synthesized before its addition may be the same or different from the later sequences.

The branched compound was purified by HPLC as described in Example 12 and characterized as described in Example 2.

C-96 and C-101 were synthesized analogously.

C-103 and C-104 were also synthesized by the same method, except that either triethylene glycol or propyl spacers were used, respectively, in place of the hexaethylene glycol spacers.

Example 20

Synthesis of a Chimeric Compound with a Branched Structure

C-98, having the structure shown below, was synthesized. The nucleic acid moieties are DNA with phosphorothioate linkages and the spacer moiety is glycerol, connected to the nucleic acid moieties via phosphorothioate linkages.

C-98:
(5'-TCGTCGA-3'-HEG)$_3$-trebler-HEG-5'-AACGTTC-3'-HEG-5'-TCGA-3'

The C-98 molecule was synthesized by TriLink BioTechnologies (San Diego, Calif.) on a Perseptive Biosystems Expedite 8909 automated DNA synthesizer using the manufacturers protocol for 1 umol phosphorothioate DNA. The nucleoside monomers and the spacer moieties [trebler phosphoramidite (obtained from Glen Research, Sterling, Va.) and 4,4'-O-dimethoxytrityl-hexaethylene glycol-O—(N,N-diisopropyl) 2-cyanoethylphosphoramidite (obtained from Glen Research, Sterling, Va.)] were dissolved in anhydrous acetonitrile to a final concentration of 0.05 M. The trebler and HEG spacers were placed in auxiliary monomer sites on the instrument. The instrument was programmed to add the nucleotide monomers, HEG spacer and the trebler spacer in the desired order, with synthesis of the nucleic acid moieties occurring in the 3' to 5' direction.

1. Use a 3'-support bound "A" solid support
2. Synthesis of 5'-TCGA-3'-moiety
3. Addition of HEG spacer
4. Synthesis of the 5'-AACGTTC-3' moiety
5. Addition of HEG spacer
6. Addition of the trebler phosphoramidite (see FIG. 2)
7. Addition of three HEG spacers simultaneously
8. Synthesis of three 5'-TCGTCGA-3' moieties simultaneously The preparation of this branched compound followed the same protocol described in Example 2, except that in steps 7 and 8, each reagent delivery in the synthesis cycle was tripled because 3 nucleic acid chains were built simultaneously. The symmetrical treblerphosphoramidite shown in FIG. 2 requires the nucleic acid sequences synthesized after the addition of the symmetrical treblerphosphoramidite to be the same, although the nucleic acid sequence synthesized before its addition may be the same or different from the later sequences.

The branched compound was purified by HPLC as described in Example 12, and characterized as described in Example 2.

Example 21

Synthesis of a Linear Chimeric Compound with Hexaethylene Glycol Spacers and a 3'-Thiol Linker CICs containing 3'-thiol linkers are first synthesized and purified as their disulfide derivatives. The disulfide group is then reduced to yield the reactive thiol group. For example, to synthesize C-116, C-8 was synthesized as in Example 2, except that 3'-Thiol Modifier C3 S—S CPG (Glen Research, Sterling, Va.) was used as the solid support instead of the "T" solid support.

C-116:
5'-TCGTCGA-3'-HEG-5'-ACGTTCG-3'-HEG-5'-AGATGAT-3'-(CH$_2$)$_3$SS(CH$_2$)$_3$OH

It will be appreciated that C-116 can be described as [C-8]-3'-disulfide. The CIC was purified by HPLC as described in Example 12. The compound was characterized as described in Example 2.

C-116 was reduced to the thiol using tris(2-carboxyethylphosphine) hydrochloride (TCEP; Pierce, Rockford, Ill.). C-116 was dissolved to a concentration of 30.5 mg/ml (0.8 ml, 24.4 mg; 3.14 umol) in 100 mM sodium phosphate/150 mM sodium chloride/1 mM EDTA/pH 7.4 buffer. In a separate vial, TCEP was dissolved to a concentration of 0.167 M in 100 mM sodium phosphate/150 mM sodium chloride/1 mM EDTA/pH 7.4 buffer. 5 equivalents (100 ul, 4.8 mg, 17 umol) of the TCEP stock solution were added to the CIC solution. The solution was mixed gently, incubated for 120 min at 40° C., and purified on a SEPHADEX® G-25 column (5 ml, Amersham Pharmacia, Piscataway, N.J.) to yield C-117 (13.2 mg). It will be appreciated that C-117 can be described as [C-8]-3'-thio. The CIC was purified by HPLC as described in Example 12.

C-115 was synthesized analogously from C-114.

Example 22

Synthesis of a Linear Chimeric Compound with Propyl Spacers and a 5'-Thiol Linker CICs containing 5'-thiol linkers are first synthesized and purified as their disulfide derivatives. The disulfide group is then reduced to yield the reactive thiol group. Compound C-110 (below) can be described as 5'-disulfide-C-11. Compound C-111 can be described as 5'-thiol-C-11.

C-110:
HO(CH$_2$)$_6$SS(CH$_2$)$_6$-5'-TCGTCG-3'-C3-5'-ACGTTCG-3'-C3-5'-AGATGAT-3'

C-110 was synthesized as described in Example 3, except that the final coupling was with the thiol modifier C6 S—S (Glen Research, Sterling, Va.). The CIC was purified by HPLC as described in Example 12. The compound was characterized as described in Example 2. C-110 was reduced to the thiol using tris(2-carboxyethylphosphine) hydrochloride (TCEP; Pierce, Rockford, Ill.) as described in Example 22.

C-107, C-113 and P-16 were synthesized analogously.

Example 23

Figure 4:
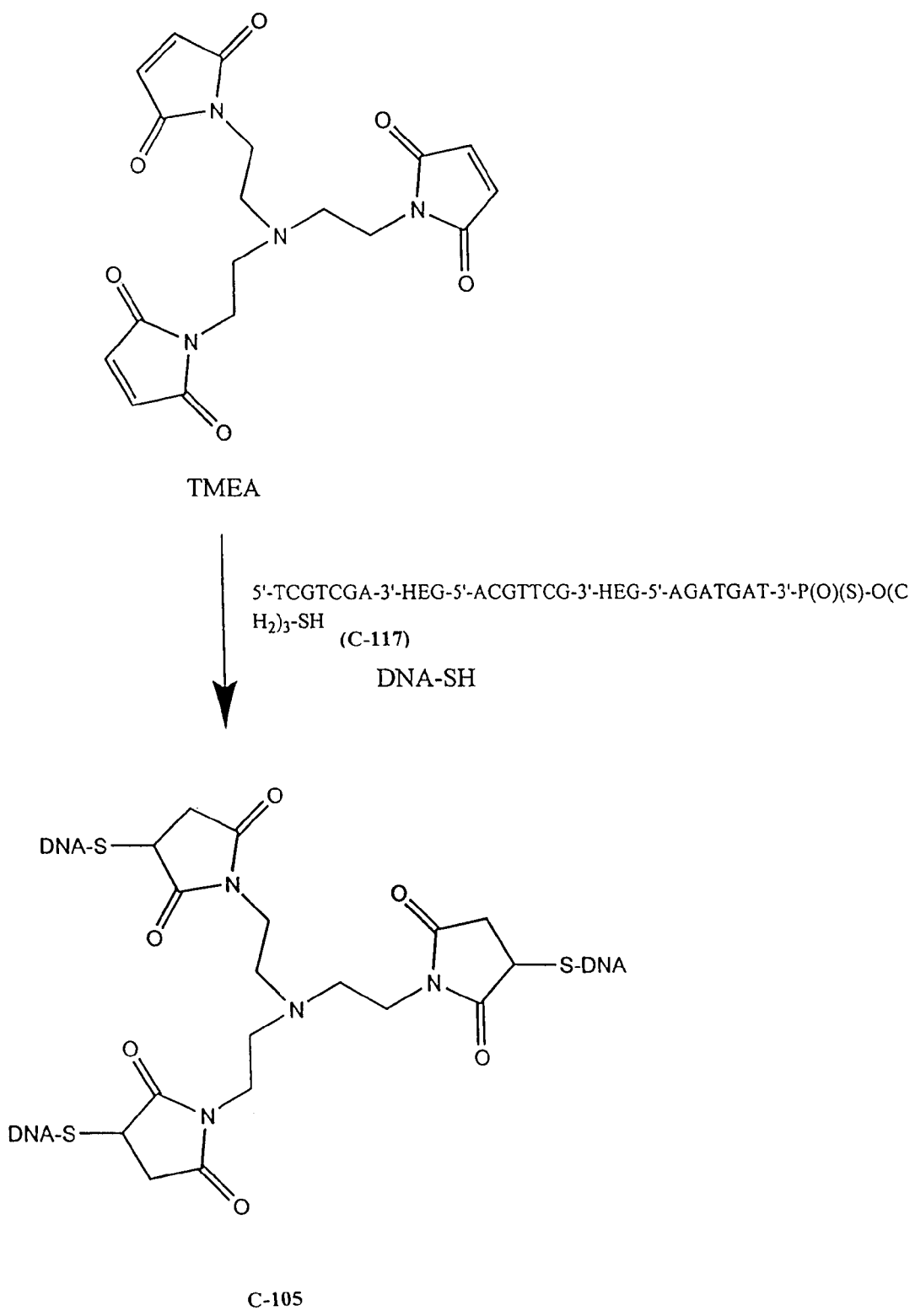
FIG. 4 shows the synthetic scheme for C-105.

Synthesis of a Chimeric Compound with a Branched Structure by a Conjugation Strategy C-105 was synthesized as shown in FIG. 4. Tris(2-maleimidoethyl)amine (TMEA, Pierce, Rockford, Ill.) was dissolved to a concentration of 4.3 mg/ml in dimethylformamide (DMF). The TMEA solution (12 ul, 52 ug, 1.0 eq) was added to a solution of C-117 (237 ul, 4.0 mg, 4.0 eq) in 100 mM sodium phosphate/150 mM sodium chloride/1 mM EDTA/pH 7.4 buffer and mixed well. The solution was left at room temperature overnight and was purified on a Superdex 200 column (24 ml, Amersham Pharmacia, Piscataway, N.J.) in 10 mM sodium phosphate/141 mM sodium chloride/pH 7.0 buffer. The product was dried in vacuo, dissolved in 0.4 ml of MILLI-Q® water, and precipitated with 1.0 ml of 95% ethanol. After freezing at −20° C. for 1 hour, the mixture was centrifuged (2 min at 14 K RPM), and the supernatant was carefully removed. The pellet was dissolved in 0.35 ml of MILLI-Q® water and the concentration of C-105 was measured (0.4 mg isolated). The compound was analyzed as described in Example 2.

C-99 was synthesized analogously.

Example 24

Synthesis of a Chimeric Compound with a Branched Structure by a Conjugation Strategy A. Synthesis of Maleimido-STARBURST DENDRIMER® Generation 2

The STARBURST Dendrimer®, Generation 2, containing 16 hydroxyl groups, was purchased as a 20% solution in methanol from Aldrich (Milwaukee, Wis.). The dendrimer (191 ul, 38.2 mg, 11.7 umol) was dried in vacuo, re-dissolved in 200 ul of DMF and re-dried in vacuo to remove the last traces of methanol. To prepare the maleimido-dendrimer, N-(p-maleimidophenyl)isocyanate (PMPI, 50 mg, 233.5 umol) was dissolved in 200 ul of DMF in a separate glass vial and then quickly added to the dendrimer. The mixture was vortexed until the dendrimer dissolved. The solution was put on a rotating mixer overnight at room temperature. The solution was concentrated in vacuo, dissolved in 20% methanol/dichloromethane (1 ml), and purified on a 7.5 g silica gel column (70-230 mesh, 60 A) in 20% methanol/dichloromethane. The maleimido-dendrimer product eluted from the column in the first fraction (due to the presence of residual DMF) and was free of the PMPI by-products. The product was concentrated to a tan solid (10 mg, 13% yield).

B. Synthesis of STARBURST DENDRIMER®-(5'-TGACT-GTGAACGT TCGAGATGA)$_{x=3-16}$ (SEQ ID NO:2)(C-102)

The maleimido-dendrimer (5.7 mg) was dissolved in dimethylsulfoxide (DMSO) to form a stock solution at a concentration of 2.5 mg/ml. The maleimido-dendrimer stock solution (100 ul, 0.25 mg, 0.0375 umol) was added to a solution of C-107 (9.1 mg, 1.2 umol) in 100 mM sodium phosphate/150 mM sodium chloride/1 mM EDTA/pH 7.4 buffer (0.7 ml). The solution was placed on a rotating mixer overnight at room temperature and the product was purified on a Superdex 200 column (24 ml, Amersham Pharmacia, Piscataway, N.J.) in 10 mM sodium phosphate/141 mM sodium chloride/pH 7.0 buffer. The product eluted in the void volume at 10.4 min (1.3 mg). The product was found to be a mixture of high molecular weight species, representing different loadings of polynucleotide on the dendrimer, by analysis on a 1.2% agarose E-gel (Invitrogen, Carlsbad, Calif.). C-102 ran as a mixture of products between 1 kb to greater than 15 kb (effective size compared to double-stranded DNA markers).

Example 25

Synthesis of a Linear Chimeric Compound with Propyl Spacers and Mixed Phosphodiester/Phosphorothioate Linkages C-84, having the structure shown below, was synthesized. The nucleic acid moieties are DNA with either phosphorothioate linkages, indicated by a lower case "s", or phosphodiester linkages (all other linkages), and the spacer moieties are propyl (C3), connected to the nucleic acid moieties via phosphodiester linkages.

C-84:
5'-GsGs-3'-C3-5'-TGC-3'-C3-5'-ATCGAT-3'-C3-5'-GCA-3'-C3-5'-GGsGsGsGsG-3'

(where a lower case "s" indicates a phosphorothioate linkage and the other linkages are phosphodiester)

The C-84 molecule was synthesized by TriLink BioTechnologies (San Diego, Calif.) on a Perseptive Biosystems Expedite 8909 automated DNA synthesizer using the manufacturer's protocol for 1 umol phosphorothioate DNA. The phosphorothioate linkages were programmed using upper case letters for the bases and the phosphodiester linkages were programmed using lower case letters for the bases and auxiliary positions containing the propyl spacer phosphoramidite. The nucleoside monomers and the spacer moiety precursor, 4,4'-O-dimethoxytrityl-propyl-O—(N,N-diisopropyl) 2-cyanoethylphosphoramidite (obtained from Glen Research, Sterling, Va.) were dissolved in anhydrous acetonitrile to a final concentration of 0.05 M. The C3 spacer was placed in an auxiliary monomer site on the instrument. The instrument was programmed to add the nucleotide monomers and C3 spacers in the desired order, with synthesis of the nucleic acid moieties occurring in the 3' to 5' direction.

1. Use a 3'-support bound "G" solid support
2. Synthesis of 5'-GGsGsGsGsG-3'
3. Addition of C3 spacer
4. Synthesis of 5'-GCA-3'
5. Addition of C3 spacer
6. Synthesis of 5'-ATCGAT-3'
7. Addition of C3 spacer
8. Synthesis of 5'-TGC-3'
9. Addition of C3 spacer
10. Synthesis of 5'-GsGs-3'

The synthesis, deprotection, workup, and analysis were performed as described in Example 2.

C-85 and C-87 were synthesized analogously.

Example 26

Synthesis of Oligonucleotides Containing Fewer Than Eight (8) Nucleotides

Polynucleotides containing fewer than eight bases and containing phosphorothioate linkages were synthesized on a Perseptive Biosystems Expedite 8909 automated DNA synthesizer. Polynucleotides were purified by RP-HPLC on a Polymer Labs PLRP—S column using an increasing gradient of acetonitrile in 0.1 M triethylammonium acetate. The purified polynucleotides were concentrated to dryness, the 4,4'-dimethoxytrityl group was removed with 80% aqueous acetic acid, and then the compounds were precipitated two times from 0.6 M aqueous sodium acetate/pH 5.0 with 3 volumes of isopropanol. The polynucleotides were dissolved in MILLI-Q® water and the yield was determined from the absorbance at 260 nm. Finally, the polynucleotides were lyophilized to a powder. The polynucleotides were characterized, and the endotoxin content determined, as described in Example 2.

Example 27

Preparation of Cationic Biodegradable Microcarriers

Cationic poly(lactic acid, glycolic acid) microcarriers (cPLGA) were prepared as follows. 0.875 g of poly(D,L-lactide-co-glycolide) 50:50 polymer (Boehringer Mannheim, Indianapolis, Ind.) with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of PVA aqueous solution (0.35% w/v) by homogenization at 4000 rpm for 30 minutes at room temperature using a laboratory mixer (Silverson L4R, Silverson Instruments). System temperature was then raised to 40° C. by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

Microcarriers were separated by centrifugation at 8000 rpm for 10 minutes at room temperature (Beckman Instruments) and resuspended in deionized water by gentle bath sonication. The centrifugal wash was repeated two additional times to remove excess PVA from the particle surface. Final centrifugal pellets of particles were suspended in approximately 10 ml of water, and lyophilized overnight. The dried cationic microcarrier powder was characterized for size and surface charge: mean size (number weighted, μ)=1.4; zeta potential (mV)=32.4.

Example 28

Immunomodulation of Human Cells by CICs

Tests were conducted to assess the immunomodulatory activity of (1) chimeric molecules containing spacer moieties and (2) polynucleotides.

The chimeric compounds and polynucleotides were synthesized as described supra or by conventional phosphorothioate chemistry. Polynucleotides P-6 and P-7 were synthesized by Hybridon Specialty Products (Milford Mass.). Immuno-modulatory activity was determined by routine assays as disclosed herein.

Peripheral blood was collected from volunteers by venipuncture using heparinized syringes. Blood was layered onto a FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 48 well plates (Examples 29-32) or 96-well plates (Examples 33-40) at $2\times10^6$ cells/mL at 37° C. in RPMI 1640 with 10% heat-inactivated human AB serum plus 50 units/mL penicillin, 50 μg/mL streptomycin, 300 μg/mL glutamine, 1 mM sodium pyruvate, and 1×MEM non-essential amino acids (NEAA).

The cells were cultured in the absence of test samples, in the presence of test samples at 20 μg/ml (0.5 OD/ml), or in the presence of test samples at 20 μg/ml premixed with 100 μg/ml cPLGA (when used) for 24 hours. Cell-free medium was then collected from each well and assayed for IFN-γ and IFN-α concentrations. SAC (Pansorbin CalBiochem, 1/5000 dilution) was used as a positive control. SAC contains is *Staph. aureus* (cowan) cell material.

IFN-γ and IFN-α were assayed using CYTOSCREEN™ ELISA kits from BioSource International, Inc., according to the manufacturer's instructions.

In the human PBMC assay, background levels of IFN-γ can vary, even significantly, with the donor. Levels of IFN-α generally exhibit low background levels under unstimulated conditions.

Examples of results from such assays are shown in Examples 29-40 below.

In each of the experiments shown, "medium alone" and "P-7" are negative controls. "P-7" has been previously shown not to have immunostimulatory activity. SAC and "P-6" are positive controls. P-6 has been previously shown to have significant immunostimulatory activity.

Example 29

Immunostimulatory Activity of CICs

This example shows that four different CICs had significant immunomodulatory activity as evidenced by stimulation of IFN-γ and IFN-α secretion (Table 3). As expected, P-7 had no activity. In addition, P-1, a TCG-containing 7-mer, had no activity. Interestingly, CICs with HEG and propyl spacer moieties showed different degrees of stimulation of IFN-α secretion. Although both types of CICs stimulated IFN-α secretion, the effect was more marked for the HEG-containing CICs.

TABLE 3

| | IFN-γ (pg/ml) | | | IFN-α (pg/ml) | | |
|---|---|---|---|---|---|---|
| Test compound | Donor 1 | Donor 2 | mean | Donor 1 | Donor 2 | mean |
| medium alone | 8 | 0 | 4 | 0 | 0 | 0 |
| P-7 | 410 | 51 | 231 | 0 | 0 | 0 |
| SAC | 2040 | 1136 | 1588 | 393 | 43 | 218 |
| P-6 | 2180 | 669 | 1425 | 401 | 39 | 220 |
| P-1 | 8 | 0 | 4 | 0 | 0 | 0 |
| C-8 | 1916 | 696 | 1306 | 1609 | 44 | 827 |
| C-9 | 2157 | 171 | 1164 | 142 | 0 | 71 |
| C-10 | 1595 | 952 | 1273 | 1662 | 50 | 856 |
| C-11 | 2308 | 270 | 1289 | 119 | 0 | 59 |

Example 30

Activity of Polynucleotides

This example shows that polynucleotides P-1, P-2, P-3, P-4 and P-5 did not have immunomodulatory activity (Table 4). These polynucleotides have the sequences of the nucleic acid moieties of C-10 and C-11, shown in Example 29 to have immunomodulatory activity.

TABLE 4

| | IFN-γ (pg/ml) | | | IFN-α (pg/ml) | | |
|---|---|---|---|---|---|---|
| Test compound | Donor 3 | Donor 4 | mean | Donor 3 | Donor 4 | mean |
| medium alone | 0 | 3 | 2 | 0 | 18 | 9 |
| P-7 | 3 | 8 | 5 | 0 | 31 | 15 |
| SAC | 1179 | 2000 | 1589 | 50 | 969 | 510 |
| P-6 | 99 | 223 | 161 | 28 | 106 | 67 |
| P-1 | 1 | 4 | 2 | 0 | 32 | 16 |
| P-3 | 1 | 3 | 2 | 0 | 32 | 16 |
| P-4 | 0 | 3 | 1 | 0 | 58 | 29 |
| P-5 | 0 | 3 | 2 | 0 | 57 | 29 |
| P-2 | 0 | 4 | 2 | 0 | 40 | 20 |

Example 31

Activity of Polynucleotide Mixtures

This example shows a mixture of polynucleotides P-1 and P-3, or P-1, P-3, P-4 and P-5 did not have immunomodulatory activity (Table 5). These polynucleotides have the sequences of the nucleic acid moieties of C-10 and C-11 which did have immunomodulatory activity. The mixtures contained equal amounts of each polynucleotide, at a total concentration of 20 µg/ml total polynucleotide.

TABLE 5

| Test compound | IFN-γ (pg/ml) | | | IFN-α (pg/ml) | | |
|---|---|---|---|---|---|---|
| | Donor 5 | Donor 6 | mean | Donor 5 | Donor 6 | mean |
| medium alone | 3 | 52 | 28 | 20 | 20 | 20 |
| P-7 | 7 | 66 | 37 | 20 | 94 | 57 |
| SAC | 903 | 284 | 593 | 458 | 8215 | 4337 |
| P-6 | 73 | 1170 | 621 | 54 | 482 | 268 |
| (P-1) + (P-3) | 3 | 36 | 19 | 20 | 40 | 30 |
| (P-1) + (P-3) + (P-4) + (P-5) | 1 | 99 | 50 | 70 | 65 | 68 |
| C-10 | 102 | 806 | 454 | 91 | 1700 | 896 |
| C-11 | 25 | 792 | 409 | 76 | 175 | 126 |

Example 32

Immunomodulatory Activity of CICs

This example shows the immunomodulatory activity of C-10 and C-11, in an assay with different donors than Examples 29 and 31 (Table 6).

TABLE 6

| Test compound | IFN-γ (pg/ml) | | | IFN-α (pg/ml) | | |
|---|---|---|---|---|---|---|
| | Donor 7 | Donor 8 | mean | Donor 7 | Donor 8 | mean |
| medium alone | 1 | 0 | 1 | 0 | 0 | 0 |
| P-7 | 2 | 2 | 2 | 0 | 0 | 0 |
| SAC | 594 | 1100 | 847 | 22 | 303 | 163 |
| P-6 | 15 | 367 | 191 | 4 | 59 | 32 |
| C-10 | 23 | 198 | 111 | 46 | 539 | 293 |
| C-11 | 5 | 419 | 212 | 6 | 56 | 31 |

Example 33

Immunomodulatory Activity of CICs

This example shows immunomodulatory activity of C-8 and C-9, in an assay with different donors than Example 29 (Table 7). P-2, a TCG-containing 6-mer, had no activity.

TABLE 7

| | IFN-γ | | | | | IFN-α | | | | |
|---|---|---|---|---|---|---|---|---|---|---|
| | Donor 9 | Donor 10 | Donor 11 | Donor 12 | mean | Donor 9 | Donor 10 | Donor 11 | Donor 12 | mean |
| medium alone | 17 | 1 | 1 | 10 | 7 | 4 | 2 | 2 | 15 | 6 |
| P-7 | 5 | 2 | 3 | 2 | 3 | 0 | 3 | 1 | 5 | 2 |
| SAC | 380 | 688 | 159 | 73 | 325 | 2246 | 364 | 1129 | 1029 | 1192 |
| P-6 | 66 | 20 | 72 | 23 | 45 | 12 | 28 | 12 | 12 | 16 |
| P-2 | 2 | 3 | 1 | 2 | 2 | 0 | 2 | 1 | 4 | 2 |
| C-8 | 312 | 35 | 31 | 28 | 102 | 58 | 30 | 18 | 49 | 39 |
| C-9 | 134 | 7 | 56 | 30 | 56 | 8 | 10 | 1 | 15 | 8 |

Example 34

Immunomodulatory Activity of CICs

The assays shown in Table 8 demonstrate immunostimulatory activity of several CICs of the invention, i.e., CICs characterized by a variety of different short nucleic acid moieties and a variety of different spacer moieties. Table 8 also shows that compound M-1, which has a mixed HEG/nucleic acid structure but lacks any 5'-C,G-3' sequence (see Table 2), as well as certain other compounds (C-19), did not show activity. The formulation of the CICs with cPLGA significantly enhanced induction of IFN-α. IFN-γ levels were also increased in some cases. The numbers "28—" represent individual donors.

TABLE 8

| stim | Conc ug/ml | IFN-γ (pg/ml) | | | | | IFN-α (pg/ml) | | | | |
|---|---|---|---|---|---|---|---|---|---|---|---|
| | | 28065 | 28066 | 28067 | 28068 | mean | 28065 | 28066 | 28067 | 28068 | mean |
| cells alone | 0 | 96 | 2 | 1 | 2 | 25 | 0 | 4 | 0 | 6 | 3 |
| P-6 | 20 | 439 | 12 | 28 | 906 | 346 | 14 | 17 | 45 | 126 | 50 |
| P-7 | 20 | 397 | 1 | 8 | 15 | 105 | 0 | 8 | 0 | 3 | 3 |
| P-2 | 20 | 79 | 1 | 1 | 0 | 20 | 0 | 3 | 0 | 0 | 1 |
| P-3 | 20 | 94 | 27 | 1 | 0 | 31 | 0 | 0 | 5 | 0 | 1 |
| P-4 | 20 | 93 | 1 | 1 | 1 | 24 | 0 | 0 | 9 | 0 | 2 |
| P-2 + P-3 + P-4 | 20 tot; 6.7 ea | 99 | 0 | 1 | 0 | 25 | 0 | 0 | 8 | 0 | 2 |

TABLE 8-continued

| stim | Conc ug/ml | IFN-γ (pg/ml) | | | | | IFN-α (pg/ml) | | | | |
|---|---|---|---|---|---|---|---|---|---|---|---|
| | | 28065 | 28066 | 28067 | 28068 | mean | 28065 | 28066 | 28067 | 28068 | mean |
| C-8 | 20 | 1000 | 19 | 56 | 419 | 373 | 123 | 6 | 96 | 358 | 146 |
| C-9 | 20 | 1000 | 8 | 57 | 510 | 394 | 13 | 0 | 22 | 64 | 25 |
| C-10 | 20 | 1000 | 9 | 51 | 559 | 405 | 116 | 6 | 107 | 340 | 142 |
| C-17 | 20 | 1000 | 6 | 32 | 459 | 374 | 21 | 0 | 22 | 95 | 34 |
| C-18 | 20 | 1000 | 102 | 27 | 695 | 456 | 51 | 9 | 16 | 162 | 59 |
| C-19 | 20 | 84 | 8 | 1 | 2 | 24 | 0 | 1 | 0 | 13 | 4 |
| C-20 | 20 | 354 | 13 | 16 | 505 | 222 | 21 | 5 | 13 | 64 | 26 |
| C-21 | 20 | 653 | 16 | 24 | 960 | 413 | 227 | 24 | 183 | 769 | 300 |
| C-23 | 20 | 438 | 5 | 6 | 238 | 172 | 52 | 3 | 19 | 137 | 53 |
| C-24 | 20 | 337 | 2 | 4 | 116 | 115 | 28 | 0 | 8 | 67 | 26 |
| C-25 | 20 | 541 | 6 | 19 | 337 | 226 | 11 | 0 | 22 | 79 | 28 |
| M-1 | 20 | 157 | 1 | 40 | 2 | 50 | 0 | 0 | 3 | 0 | 1 |
| C-27 | 20 | 475 | 3 | 24 | 226 | 182 | 3 | 0 | 24 | 16 | 11 |
| C-28 | 20 | 1082 | 5 | 42 | 410 | 385 | 3 | 0 | 29 | 52 | 21 |
| PLGA | 0 | 55 | 1 | 1 | 5 | 16 | 0 | 2 | 12 | 10 | 6 |
| P-6 + PLGA | 20 | 975 | 191 | 287 | 573 | 506 | 388 | 194 | 565 | 2000 | 787 |
| P-7 + PLGA | 20 | 19 | 27 | 6 | 11 | 15 | 0 | 5 | 0 | 0 | 1 |
| P-2 + PLGA | 20 | 357 | 138 | 104 | 443 | 261 | 982 | 708 | 2100 | 2336 | 1532 |
| P-3 + PLGA | 20 | 134 | 1 | 1 | 4 | 35 | 307 | 0 | 0 | 0 | 77 |
| P-4 + PLGA | 20 | 19 | 1 | 0 | 3 | 6 | 34 | 5 | 0 | 0 | 10 |
| P-2 + P-3 + P-4 + PLGA | 20 tot; 6.7 ea | 122 | 4 | 14 | 70 | 53 | 1820 | 0 | 435 | 106 | 590 |
| C-8 + PLGA | 20 | 527 | 280 | 245 | 357 | 352 | 2395 | 538 | 4380 | 4625 | 2985 |
| C-9 + PLGA | 20 | 334 | 139 | 343 | 456 | 318 | 1093 | 130 | 1686 | 2045 | 1239 |
| C-10 + PLGA | 20 | 619 | 152 | 557 | 420 | 437 | 2049 | 369 | 3515 | 3586 | 2380 |
| C-17 + PLGA | 20 | 508 | 184 | 587 | 355 | 408 | 1914 | 240 | 2729 | 2774 | 1914 |
| C-18 + PLGA | 20 | 732 | 108 | 355 | 448 | 411 | 2188 | 375 | 3513 | 7141 | 3304 |
| C-19 + PLGA | 20 | 1000 | 780 | 730 | 466 | 744 | 5997 | 3753 | 14359 | 7079 | 7797 |
| C-20 + PLGA | 20 | 1055 | 256 | 270 | 488 | 517 | 1044 | 191 | 1265 | 2000 | 1125 |
| C-21 + PLGA | 20 | 682 | 874 | 390 | 481 | 607 | 2468 | 784 | 3372 | 4962 | 2897 |
| C-23 + PLGA | 20 | 216 | 161 | 120 | 377 | 219 | 789 | 189 | 1573 | 2000 | 1138 |
| C-24 + PLGA | 20 | 236 | 47 | 188 | 707 | 295 | 31 | 20 | 772 | 340 | 291 |
| C-25 + PLGA | 20 | 427 | 179 | 289 | 499 | 348 | 414 | 87 | 1082 | 1335 | 730 |
| M-1 + PLGA | 20 | 7 | 1 | 3 | 5 | 4 | 0 | 0 | 8 | 5 | 3 |
| C-27 + PLGA | 20 | 888 | 205 | 235 | 466 | 448 | 136 | 44 | 388 | 259 | 207 |
| C-28 + PLGA | 20 | 860 | 88 | 489 | 415 | 463 | 216 | 73 | 401 | 520 | 303 |
| SAC | 0 | 1000 | 339 | 511 | 355 | 551 | 284 | 156 | 1544 | 350 | 583 |

It will be apparent from review of Table 8 that Donor 28065 exhibited high background in the IFN-gamma assay. Values rendered as "1000" indicate a measurement outside the limits of sensitivity of the assay.

Example 42

Immunomodulation of Mouse Cells by CIC

Polynucleotides and chimeric compounds were tested for immunostimulatory activity on mouse splenocytes. Immunostimulation was assessed by measurement of cytokine secretion into the culture media. Cytokine levels in the culture supernatant were determined by enzyme-linked immunosorbent assay (ELISA) tests.

Cells were isolated and prepared using standard techniques. Spleens of 8 to 20 week-old BALB/c mice were harvested and the splenocytes isolated using standard teasing and treatment with ACK lysing buffer from BioWhittaker, Inc. Four spleens were pooled in this experiment. Isolated cells were washed in RPMI 1640 media supplemented with 2% heat-inactivated fetal calf serum (FCS), 50 µM 2-mercaptoethanol, 1% penicillin-streptomycin, and 2 mM L-glutamine and resuspended at approximately $7 \times 10^5$ cells/ml in 10% FCS/RPMI (RPMI 1640 media with 10% heat-inactivated FCS, 50 µM 2-mercaptoethanol, 1% penicillin-streptomycin, and 2 mM L-glutamine).

Cell cultures were set up in triplicate with approximately $7 \times 10^5$ cells/well in a 96-well flat microtiter plate in 100 µl 10% FCS/RPMI with the cells allowed to rest for at lest 1 hour after plating. The indicated test compounds were incubated (at the indicated concentrations) for 24 hours at 37° C. Cell supernatants were harvested and frozen at −80° C. Cytokine production by the cells was determined by ELISAs, as shown in Table 9.

TABLE 9

| Test Compound | Dose | IL-6 | IL-12 | IFNγ |
|---|---|---|---|---|
| P-6 | 5.0 µg/ml | 9311 | 5374 | 2505 |
| | 1.0 µg/ml | 5760 | 4565 | 2175 |
| | 0.1 µg/ml | 121 | 1665 | 187 |
| C-10 | 5.0 µg/ml | 3342 | 2329 | 199 |
| | 1.0 µg/ml | 1761 | 1738 | 104 |
| | 0.1 µg/ml | 9 | 122 | 9 |
| C-11 | 5.0 µg/ml | 10098 | 4279 | 3342 |
| | 1.0 µg/ml | 11814 | 4914 | 3220 |
| | 0.1 µg/ml | 458 | 3359 | 960 |
| P-7 | 5.0 µg/ml | 9 | 177 | 23 |
| | 1.0 µg/ml | 7 | 143 | 30 |
| SAC | | 734 | 1343 | 18843 |
| media alone | | 9 | 124 | 9 |

Example 35

Activity of CIC Containing 3-Nucleotide Nucleic Acid Moieties and Enhancement of Activity by cPLGA This example shows immunostimulatory activity of several CICs in the presence and absence of cPLGA as assayed using human PBMCs. Interestingly, the phosphodiester version of C-30 (C-31) was inactive as a CIC alone, but had good activity when formulated with cPLGA. In fact, the general trend was that while the CICs containing all phosphodiester linkages (C-31, C-36, and C-93) were inactive as CICs alone, they became significantly more active when formulated with cPLGA.

C-32, a CIC containing only trimeric nucleic acid moieties, had activity when used alone and demonstrated more activity when formulated with cPLGA. See Table 10.

TABLE 10

|        | IFN-γ (pg/ml) |       |       |       |       | IFN-α (pg/ml) |       |       |       |       |
|--------|-------|-------|-------|-------|-------|-------|-------|-------|-------|-------|
| stim   | 28089 | 28090 | 28098 | 28099 | mean  | 28089 | 28090 | 28098 | 28099 | mean  |
| cells alone | 0   | 0   | 0   | 4   | 1   | 25  | 79  | 33  | 28  | 41  |
| P-6    | 84  | 255 | 745 | 125 | 302 | 0   | 62  | 105 | 105 | 68  |
| P-7    | 0   | 4   | 0   | 2   | 1   | 0   | 27  | 19  | 37  | 21  |
| C-10   | 35  | 44  | 174 | 140 | 98  | 17  | 61  | 187 | 304 | 142 |
| C-21   | 61  | 68  | 218 | 124 | 118 | 56  | 157 | 286 | 466 | 241 |
| C-22   | 31  | 15  | 110 | 91  | 62  | 0   | 46  | 97  | 247 | 97  |
| C-8    | 62  | 52  | 205 | 116 | 109 | 21  | 124 | 314 | 362 | 205 |
| C-9    | 12  | 7   |     |     | 10  | 10  | 67  |     |     | 39  |
| C-29   | 63  | 50  | 150 | 177 | 110 | 75  | 92  | 359 | 332 | 214 |
| C-30   | 0   | 6   | 12  | 20  | 9   | 134 | 29  | 52  | 47  | 65  |
| C-31   | 0   | 0   | 0   | 2   | 0   | 158 | 26  | 62  | 29  | 69  |
| C-32   | 0   | 5   | 11  | 35  | 13  | 285 | 31  | 46  | 59  | 106 |
| C-33   | 0   | 0   | 0   | 3   | 1   | 56  | 22  | 34  | 30  | 36  |
| C-93   | 0   | 0   | 0   | 3   | 1   | 0   | 30  | 25  | 29  | 21  |
| C-28   | 14  | 15  | 183 | 45  | 64  | 0   | 64  | 42  | 67  | 43  |
| PLGA   | 15  | 2   | 16  | 10  | 11  | 8   | 38  | 39  | 49  | 33  |
| P-6 + PLGA | 606 | 144 | 3277 | 160 | 1047 | 197 | 103 | 340 | 91  | 183 |
| P-7 + PLGA | 121 | 3   | 91  | 5   | 55  | 7   | 85  | 36  | 47  | 44  |
| C-10 + PLGA | 804 | 373 | 1501 | 301 | 745 | 523 | 256 | 509 | 1317 | 651 |
| C-21 + PLGA | 1138 | 454 | 1612 | 630 | 958 | 1347 | 1020 | 1001 | 2302 | 1418 |
| C-22 + PLGA | 772 | 244 | 1271 | 357 | 661 | 619 | 386 | 604 | 1339 | 737 |
| C-8 + PLGA | 668 | 332 | 1863 | 506 | 842 | 1005 | 683 | 934 | 1680 | 1075 |
| C-9 + PLGA | 1036 | 330 |     |     | 683 | 308 | 363 |     |     | 335 |
| C-29 + PLGA | 825 | 477 | 1536 | 341 | 795 | 909 | 711 | 855 | 1419 | 973 |
| C-30 + PLGA | 97  | 233 | 447 | 41  | 205 | 44  | 116 | 49  | 33  | 60  |
| C-31 + PLGA | 256 | 327 | 1597 | 406 | 647 | 696 | 912 | 1028 | 1361 | 999 |
| C-32 + PLGA | 454 | 192 | 259 | 57  | 240 | 281 | 289 | 218 | 131 | 230 |
| C-33 + PLGA | 171 | 186 | 249 | 96  | 176 | 658 | 1220 | 1764 | 1304 | 1237 |
| C-93 + PLGA | 427 | 628 | 1707 | 323 | 771 | 990 | 1738 | 2681 | 4000 | 2352 |
| C-28 + PLGA | 683 | 306 | 2252 | 224 | 866 | 136 | 155 | 141 | 70  | 126 |
| SAC    | 195 | 489 | 101 | 306 | 273 | 67  | 239 | 92  | 70  | 117 |

Example 36

Immunostimulatory Activity of CICs Containing 5' TCG

This example shows immunomodulation by CICs containing various nucleic acid moieties (see Table 11). In general, sequences containing a 5'-TCG-3' (C-8, C-21, C-50, C-51, etc.) or 5'-NTCG (C-46), where N is any nucleoside, were more active than other CG-containing CICs (C-24, C-52). Additionally, while most of the CICs induced a significant amount of IFN-γ, the results were more variable for the induction of IFN-α, suggesting the motif requirements for IFN-α induction may be more stringent than those for IFN-γ induction. In particular, CICs containing a 5'-TCGA-3' (C-50, C-51, C-45) generated more IFN-α than CICs containing a 5'-TCGT-3' (C-41, C-42, C-52).

With the exception of C-8 and C-21 (including the motif 5'-TCGTCGA-3'), the best IFN-α induction was generated by CICs with the TCGA in the 5' position.

CICs containing only hexameric (C-22), pentameric (C-43), and tetrameric (C-44) nucleic acid moieties were found to induce IFN-γ when used alone. In addition, each of these CICs, as well as C-32 containing only trimeric nucleic acid moieties, induced considerable IFN-γ and IFN-α when formulated with cPLGA. C-39, a CIC with two heptameric nucleic acid moieties, was active when used alone, while C-40, a CIC with one hexameric and one tetrameric nucleic acid moiety, was inactive in this experiment. Both of these CICs exhibited significant activity when formulated with cPLGA.

TABLE 11

|        | IFN-γ (pg/ml) |       |       |       |       | IFN-α (pg/ml) |       |       |       |       |
|--------|-------|-------|-------|-------|-------|-------|-------|-------|-------|-------|
| stim   | 28042 | 28043 | 28044 | 28045 | mean  | 28042 | 28043 | 28044 | 28045 | mean  |
| cells alone | 15 | 4   | 3   | 5   | 7   | 0   | 44  | 9   | 0   | 13  |
| P-6    | 495 | 1189 | 925 | 212 | 705 | 27  | 85  | 36  | 21  | 42  |
| P-7    | 66  | 76  | 26  | 13  | 45  | 0   | 11  | 22  | 20  | 13  |
| C-8    | 468 | 939 | 1000 | 234 | 660 | 20  | 51  | 32  | 5   | 27  |

TABLE 11-continued

| | IFN-γ (pg/ml) | | | | | IFN-α (pg/ml) | | | | |
|---|---|---|---|---|---|---|---|---|---|---|
| stim | 28042 | 28043 | 28044 | 28045 | mean | 28042 | 28043 | 28044 | 28045 | mean |
| C-24 | 148 | 156 | 312 | 26 | 161 | 0 | 0 | 8 | 0 | 2 |
| C-21 | 790 | 1519 | 1198 | 177 | 921 | 57 | 72 | 79 | 15 | 56 |
| C-42 | 198 | 1067 | 4000 | 37 | 1326 | 0 | 29 | 24 | 0 | 13 |
| C-41 | 174 | 1075 | 841 | 45 | 534 | 0 | 3 | 23 | 0 | 7 |
| C-45 | 590 | 1466 | 984 | 253 | 823 | 62 | 123 | 152 | 14 | 88 |
| C-46 | 399 | 814 | 480 | 63 | 439 | 24 | 73 | 26 | 3 | 31 |
| C-47 | 112 | 537 | 142 | 17 | 202 | 20 | 0 | 0 | 0 | 5 |
| C-50 | 1324 | 1292 | 509 | 192 | 829 | 36 | 137 | 193 | 35 | 100 |
| C-51 | 795 | 1349 | 1114 | 411 | 917 | 112 | 245 | 240 | 36 | 158 |
| C-52 | 238 | 214 | 212 | 28 | 173 | 0 | 3 | 35 | 48 | 22 |
| M-1 | 45 | 29 | 7 | 3 | 21 | 0 | 0 | 13 | 2 | 4 |
| C-22 | 206 | 343 | 736 | 40 | 331 | 12 | 18 | 67 | 30 | 32 |
| C-43 | 128 | 536 | 566 | 16 | 312 | 0 | 14 | 20 | 0 | 8 |
| C-44 | 238 | 359 | 484 | 51 | 283 | 0 | 12 | 60 | 1 | 18 |
| C-32 | 91 | 19 | 78 | 17 | 51 | 0 | 0 | 8 | 0 | 2 |
| C-39 | 343 | 488 | 281 | 137 | 312 | 31 | 187 | 46 | 36 | 75 |
| C-40 | 26 | 55 | 20 | 23 | 31 | 0 | 26 | 31 | 2 | 15 |
| PLGA | 192 | 82 | 55 | 3 | 83 | 0 | 0 | 0 | 8 | 2 |
| P-6 + PLGA | 1382 | 1538 | 2581 | 178 | 1420 | 106 | 387 | 371 | 38 | 226 |
| P-7 + PLGA | 152 | 324 | 174 | 12 | 166 | 0 | 2 | 0 | 2 | 1 |
| C-8 + PLGA | 1367 | 2547 | 1490 | 286 | 1423 | 2182 | 2193 | 716 | 211 | 1325 |
| C-24 + PLGA | 1017 | 1380 | 1362 | 52 | 953 | 0 | 31 | 65 | 0 | 24 |
| C-21 + PLGA | 4000 | 1204 | 1870 | 325 | 1850 | 2959 | 2024 | 886 | 191 | 1515 |
| C-42 + PLGA | 1515 | 1417 | 2190 | 372 | 1374 | 425 | 1081 | 295 | 69 | 468 |
| C-41 + PLGA | 710 | 1940 | 1910 | 496 | 1264 | 535 | 1987 | 534 | 119 | 794 |
| C-45 + PLGA | 1380 | 2292 | 1920 | 634 | 1557 | 2408 | 4000 | 1693 | 642 | 2186 |
| C-46 + PLGA | 2201 | 2352 | 1432 | 472 | 1614 | 502 | 1309 | 257 | 100 | 542 |
| C-47 + PLGA | 3579 | 4000 | 1137 | 161 | 2219 | 46 | 271 | 30 | 0 | 87 |
| C-50 + PLGA | 2969 | 1209 | 1465 | 402 | 1511 | 1548 | 2818 | 1242 | 327 | 1484 |
| C-51 + PLGA | 2018 | 4000 | 1000 | 463 | 1870 | 1837 | 3241 | 1154 | 536 | 1692 |
| C-52 + PLGA | 1172 | 1726 | 1551 | 117 | 1142 | 12 | 34 | 34 | 0 | 20 |
| M-1 + PLGA | 215 | 159 | 23 | 3 | 100 | 0 | 1 | 0 | 0 | 0 |
| C-22 + PLGA | 4000 | 2975 | 1085 | 136 | 2049 | 325 | 1186 | 226 | 42 | 445 |
| C-43 + PLGA | 2210 | 2594 | 1354 | 194 | 1588 | 358 | 1293 | 402 | 49 | 526 |
| C-44 + PLGA | 1452 | 4000 | 2006 | 276 | 1934 | 986 | 4000 | 1768 | 192 | 1736 |
| C-32 + PLGA | 2211 | 4000 | 2759 | 133 | 2276 | 204 | 1142 | 771 | 12 | 532 |
| C-39 + PLGA | 1800 | 4000 | 2275 | 274 | 2087 | 2167 | 4000 | 2613 | 736 | 2379 |
| C-40 + PLGA | 1438 | 498 | 1813 | 160 | 977 | 2758 | 4000 | 1556 | 370 | 2171 |
| SAC | 1618 | 1271 | 1053 | 123 | 1016 | 285 | 110 | 57 | 0 | 113 |

Example 37

Immunostimulatory Activity of CICs

This example shows immunomodulation assays for additional linear CICs (some containing both phosphorothioate (PS) and phosphodiester (PO) linkages) and branched CICs (Tables 12 and 13). Comparison of C-94, a branched CIC, with C-21, a linear CIC containing the same nucleic acid moieties, showed that the branched CIC induced 4-fold more IFN-α than the linear CIC. The amounts of IFN-γ and IFN-α induced were significantly increased for each CIC by formulation with cPLGA. The phosphodiester versions of C-94 and C-93 were active only when formulated. C-87 showed remarkable induction of IFN-α.

TABLE 12

| | IFN-γ (pg/ml) | | | | | IFN-α (pg/ml) | | | | |
|---|---|---|---|---|---|---|---|---|---|---|
| stim | 28042 | 28043 | 28044 | 28045 | mean | 28042 | 28043 | 28044 | 28045 | mean |
| cells alone | 11 | 4 | 0 | 13 | 7 | 8 | 2 | 3 | 64 | 19 |
| P-6 | 324 | 1036 | 529 | 653 | 636 | 9 | 34 | 22 | 108 | 43 |
| P-7 | 34 | 19 | 48 | 35 | 34 | 0 | 0 | 4 | 54 | 15 |
| C-8 | 623 | 753 | 646 | 604 | 656 | 78 | 25 | 52 | 256 | 103 |
| C-53 | 39 | 27 | 38 | 26 | 32 | 0 | 0 | 0 | 5 | 1 |
| C-49 | 367 | 433 | 767 | 353 | 480 | 30 | 8 | 100 | 88 | 57 |
| C-84 | 29 | 23 | 69 | 232 | 88 | 0 | 0 | 5 | 222 | 57 |
| C-85 | 17 | 13 | 315 | 134 | 120 | 0 | 0 | 28 | 24 | 13 |
| C-94 | 443 | 198 | 1417 | 888 | 736 | 302 | 252 | 664 | 1855 | 768 |
| C-93 | 8 | 1 | 41 | 17 | 17 | 7 | 3 | 81 | 61 | 38 |
| C-21 | 572 | 460 | 4000 | 1644 | 1669 | 146 | 94 | 191 | 349 | 195 |
| C-9 | 691 | 268 | 590 | 1306 | 714 | 39 | 0 | 11 | 64 | 29 |
| PLGA | 9 | 5 | 59 | 72 | 36 | 7 | 0 | 98 | 112 | 54 |
| P-6 + PLGA | 601 | 358 | 1474 | 1941 | 1093 | 115 | 116 | 515 | 1298 | 511 |
| P-7 + PLGA | 13 | 13 | 46 | 65 | 34 | 5 | 0 | 0 | 43 | 12 |
| C-8 + PLGA | 284 | 551 | 1781 | 3113 | 1432 | 595 | 396 | 1013 | 2259 | 1066 |
| C-53 + PLGA | 21 | 12 | 217 | 210 | 115 | 19 | 0 | 0 | 42 | 15 |

TABLE 12-continued

| | IFN-γ (pg/ml) | | | | | IFN-α (pg/ml) | | | | |
|---|---|---|---|---|---|---|---|---|---|---|
| stim | 28042 | 28043 | 28044 | 28045 | mean | 28042 | 28043 | 28044 | 28045 | mean |
| C-49 + PLGA | 1471 | 1219 | 4000 | 2061 | 2188 | 904 | 460 | 4000 | 1040 | 1601 |
| C-84 + PLGA | 235 | 232 | 291 | 956 | 428 | 1777 | 914 | 4000 | 3641 | 2583 |
| C-85 + PLGA | 313 | 294 | 554 | 1167 | 582 | 2116 | 921 | 4000 | 2413 | 2362 |
| C-94 + PLGA | 2412 | 755 | 4000 | 3379 | 2637 | 1883 | 1640 | 4000 | 4000 | 2881 |
| C-93 + PLGA | 880 | 316 | 869 | 1251 | 829 | 778 | 471 | 2045 | 988 | 1071 |
| C-21 + PLGA | 4000 | 690 | 4000 | 2533 | 2806 | 712 | 577 | 2572 | 1571 | 1358 |
| C-9 + PLGA | 1451 | 763 | 4000 | 1804 | 2005 | 389 | 199 | 397 | 477 | 366 |

TABLE 13

| | IFN-g (pg/ml) | | | | | IFN-a (pg/ml) | | | | |
|---|---|---|---|---|---|---|---|---|---|---|
| stim | 28218 | 28219 | 28220 | 28221 | mean | 28218 | 28219 | 28220 | 28221 | mean |
| cells alone | 5 | 5 | 5 | 5 | 5 | 32 | 32 | 32 | 32 | 32 |
| P-6 | 13 | 7 | 25 | 141 | 47 | 32 | 32 | 32 | 32 | 32 |
| P-7 | 5 | 5 | 5 | 5 | 5 | 32 | 32 | 32 | 32 | 32 |
| C-87 | 83 | 24 | 38 | 977 | 281 | 3075 | 32 | 4269 | 265 | 1910 |
| C-94 | 15 | 39 | 44 | 269 | 92 | 32 | 167 | 633 | 412 | 311 |
| SAC | 2552 | 621 | 1383 | 647 | 1301 | 483 | 105 | 32 | 452 | 268 |

Example 38

Position Effect of Sequence Motif in CIC

This example describes immunomodulation assays for a number of CICs (some of which were assayed in different donors in previous examples) and illustrates the effect of nucleic acid sequence position in a CIC.

The CICs tested included CICs containing two different CG-containing nucleic acid sequences in nucleic acid moieties (TCGTCGA and ACGTTCG) along with one nucleic acid moiety not containing a CG sequence (AGATGAT). Of the CG-containing nucleic acid sequences, CIC's containing a TCGTCGA sequence have greater activity than CIC's containing only ACGTTCG. Of these two, CICs with TCGTCGA were more active. The general structure of the CICs used in this example, $N_1$—$S_1$—$N_2$—$S_2$—$N_3$, can be used to describe the placement of the motifs within the CIC. Placing the most active motif, TCGTCGA, in the $N_1$ position led to the most active CICs (C-8, C-56). Placement in the $N_2$ position also conferred activity. For instance, C-57 with the TCGTCGA in the $N_2$ position was somewhat more active than C-58, with the TCGTCGA in the $N_3$ position. A CIC with a ACGTTCG sequence in the $N_1$ position, while being less active than a similar CIC with a TCGTCGA sequence, was more active than a CIC with the sequence AGATGAT, in the $N_1$ position (compare C-57 and C-58 to C-59 and C-60). In this experiment, C-61, which contained nucleic acid moieties that comprise CG motifs, but not TCG motifs, induced IFN-γ when formulated with cPLGA. See Table 14.

TABLE 14

| | IFN-γ (pg/ml) | | | | | IFN-α (pg/ml) | | | | |
|---|---|---|---|---|---|---|---|---|---|---|
| stim | 28156 | 28157 | 28158 | 28159 | mean | 28156 | 28157 | 28158 | 28159 | mean |
| cells alone | 125 | 3 | 4 | 5 | 34 | 3 | 3 | 1 | 8 | 4 |
| P-6 | 1132 | 872 | 207 | 231 | 611 | 52 | 484 | 7 | 32 | 144 |
| P-8 | 255 | 20 | 31 | 31 | 84 | 16 | 9 | 24 | 8 | 14 |
| C-8 | 1612 | 742 | 340 | 197 | 723 | 102 | 755 | 61 | 160 | 270 |
| C-9 | 1162 | 729 | 192 | 329 | 603 | 26 | 142 | 78 | 20 | 67 |
| C-23 | 733 | 576 | 202 | 295 | 452 | 26 | 235 | 59 | 169 | 122 |
| C-54 | 297 | 378 | 88 | 218 | 245 | 8 | 96 | 8 | 13 | 31 |
| C-55 | 511 | 566 | 55 | 186 | 329 | 9 | 5 | 63 | 3 | 20 |
| C-56 | 1223 | 543 | 203 | 563 | 633 | 98 | 415 | 57 | 131 | 175 |
| C-57 | 419 | 323 | 67 | 262 | 268 | 5 | 52 | 61 | 42 | 40 |
| C-58 | 404 | 288 | 59 | 84 | 209 | 13 | 30 | 29 | 23 | 24 |
| C-60 | 304 | 209 | 26 | 38 | 144 | 5 | 22 | 3 | 1 | 8 |
| C-61 | 92 | 179 | 35 | 63 | 92 | 3 | 0 | 47 | 0 | 13 |
| PLGA | 43 | 63 | 5 | 11 | 30 | 85 | 246 | 0 | 3 | 83 |
| P-6 + PLGA | 1070 | 2643 | 251 | 496 | 1115 | 582 | 2948 | 418 | 359 | 1077 |
| P-8 + PLGA | 95 | 115 | 26 | 34 | 67 | 43 | 8 | 2 | 23 | 19 |
| C-8 + PLGA | 1083 | 1862 | 269 | 1129 | 1086 | 4000 | 4877 | 857 | 1573 | 2827 |
| C-9 + PLGA | 814 | 1412 | 307 | 992 | 881 | 1398 | 1778 | 418 | 483 | 1019 |

TABLE 14-continued

| | IFN-γ (pg/ml) | | | | | IFN-α (pg/ml) | | | | |
|---|---|---|---|---|---|---|---|---|---|---|
| stim | 28156 | 28157 | 28158 | 28159 | mean | 28156 | 28157 | 28158 | 28159 | mean |
| C-23 + PLGA | 825 | 865 | 182 | 1423 | 824 | 1020 | 1621 | 240 | 597 | 869 |
| C-54 + PLGA | 838 | 1150 | 157 | 1751 | 974 | 752 | 1265 | 147 | 278 | 611 |
| C-55 + PLGA | 1048 | 960 | 247 | 2356 | 1153 | 505 | 801 | 78 | 211 | 399 |
| C-56 + PLGA | 792 | 604 | 321 | 4000 | 1429 | 4000 | 4000 | 852 | 2433 | 2821 |
| C-57 + PLGA | 1027 | 814 | 101 | 3056 | 1250 | 555 | 1476 | 10 | 252 | 573 |
| C-58 + PLGA | 804 | 1065 | 135 | 1021 | 756 | 179 | 932 | 3 | 139 | 313 |
| C-60 + PLGA | 650 | 858 | 56 | 1014 | 645 | 71 | 118 | 32 | 50 | 68 |
| C-61 + PLGA | 1265 | 1508 | 238 | 864 | 969 | 4 | 80 | 1 | 63 | 37 |
| SAC | 780 | 1184 | 83 | 659 | 677 | 208 | 55 | 6 | 34 | 76 |

This experiment also compared immunomodulatory activity of two types of branched CICs: C-94 has HEG moieties between the branching glycerol component and the nucleic acid moieties, while C-28 has the nucleic acid moieties attached directly to the glycerol spacer. See Table 15. Interestingly, while the induction of IFN-γ was similar for both branched CICs, the induction of IFN-α was dramatically higher for the CIC containing the HEG spacers. A branched CIC, containing three P-6 sequences attached via their 5-ends to a maleimido-activated triethylamine spacer (C-99), induced IFN-γ only when formulated with cPLGA and did not induce IFN-α. In general, the greatest IFN-α production was produced using CICs with nucleic acid moieties attached via a branched structure and having multiple unattached or "free" 5'-ends of nucleic acid moieties, and including spacers that provide conformational flexibility and distance between the nucleic acid moieties.

TABLE 15

| | IFN-γ (pg/ml) | | | | | IFN-α (pg/ml) | | | | |
|---|---|---|---|---|---|---|---|---|---|---|
| stim | 110 | 112 | 119 | 120 | mean | 110 | 112 | 119 | 120 | mean |
| cells alone | 44 | 24 | 20 | 28 | 29 | 20 | 200 | 2 | 2 | 56 |
| P-6 | 1508 | 344 | 144 | 104 | 525 | 50 | 172 | 234 | 72 | 132 |
| P-7 | 124 | 24 | 16 | 40 | 51 | 2 | 32 | 474 | 2 | 128 |
| C-8 | 1152 | 540 | 136 | 48 | 469 | 196 | 30 | 264 | 42 | 133 |
| C-59 | 256 | 52 | 28 | 40 | 94 | 2 | 6 | 2 | 2 | 3 |
| C-63 | 1536 | 376 | 80 | 60 | 513 | 294 | 38 | 464 | 228 | 256 |
| C-50 | 1096 | 264 | 52 | 48 | 365 | 716 | 84 | 838 | 636 | 569 |
| C-51 | 1528 | 240 | 52 | 40 | 465 | 1408 | 72 | 2200 | 622 | 1076 |
| C-45 | 880 | 192 | 52 | 36 | 290 | 446 | 130 | 1074 | 428 | 520 |
| C-41 | 512 | 100 | 32 | 32 | 169 | 58 | 2 | 182 | 6 | 62 |
| C-42 | 1508 | 204 | 56 | 56 | 456 | 250 | 26 | 156 | 36 | 117 |
| C-46 | 1224 | 400 | 68 | 36 | 432 | 58 | 2 | 208 | 48 | 79 |
| C-52 | 472 | 48 | 40 | 28 | 147 | 2 | 2 | 292 | 2 | 75 |
| C-39 | 604 | 116 | 108 | 32 | 215 | 674 | 26 | 444 | 250 | 349 |
| C-40 | 180 | 12 | 4 | 20 | 54 | 6 | 198 | 152 | 2 | 90 |
| C-94 | 5168 | 284 | 104 | 120 | 1419 | 1608 | 144 | 2610 | 878 | 1310 |
| C-28 | 5564 | 52 | 44 | 60 | 1430 | 38 | 4 | 56 | 26 | 31 |
| C-99 | 276 | 12 | 16 | 40 | 86 | 22 | 4 | 86 | 2 | 29 |
| PLGA | 32 | 8 | 72 | 120 | 58 | 10 | 2 | 60 | 92 | 41 |
| P-6 + PLGA | 1640 | 968 | 960 | 2300 | 1467 | 948 | 260 | 1298 | 1470 | 994 |
| P-7 + PLGA | 72 | 16 | 32 | 316 | 109 | 14 | 14 | 22 | 2 | 13 |
| C-8 + PLGA | 1948 | 1220 | 1188 | 2384 | 1685 | 6674 | 1138 | 2130 | 2650 | 3148 |
| C-59 + PLGA | 680 | 824 | 620 | 1828 | 988 | 234 | 2 | 76 | 278 | 148 |
| C-63 + PLGA | 1208 | 1580 | 2340 | 2092 | 1805 | 4148 | 738 | 2796 | 2298 | 2495 |
| C-50 + PLGA | 812 | 3684 | 1432 | 992 | 1730 | 3768 | 1414 | 4161 | 3402 | 3186 |
| C-51 + PLGA | 1240 | 11216 | 2896 | 924 | 4069 | 5244 | 1260 | 5104 | 6148 | 4439 |
| C-45 + PLGA | 2736 | 3024 | 3056 | 2472 | 2822 | 5532 | 1544 | 5474 | 4206 | 4189 |
| C-41 + PLGA | 3168 | 1808 | 16000 | 3656 | 6158 | 3542 | 746 | 2074 | 2094 | 2114 |
| C-42 + PLGA | 1612 | 2032 | 10212 | 1908 | 3941 | 3462 | 1030 | 2118 | 2054 | 2166 |
| C-46 + PLGA | 3048 | 2012 | 3720 | 3608 | 3097 | 2372 | 638 | 2372 | 2682 | 2016 |
| C-52 + PLGA | 1032 | 1236 | 2344 | 1724 | 1584 | 64 | 20 | 252 | 206 | 136 |
| C-39 + PLGA | 2024 | 1332 | 8228 | 1244 | 3207 | 3764 | 846 | 3078 | 2658 | 2587 |
| C-40 + PLGA | 1360 | 1244 | 5364 | 1864 | 2458 | 2362 | 684 | 3794 | 2616 | 2364 |
| C-94 + PLGA | 2668 | 3188 | 8840 | 3396 | 4523 | 5658 | 1838 | 8000 | 6346 | 5461 |
| C-28 + PLGA | 2104 | 2568 | 3572 | 1320 | 2391 | 302 | 2 | 284 | 198 | 197 |
| C-99 + PLGA | 768 | 672 | 5316 | 472 | 1807 | 114 | 80 | 344 | 260 | 200 |

Example 39

Activity of Branched CICs

This example demonstrates that branched CICs with multiple free 5'-ends and conformational flexibility provided by HEG spacers induced more IFN-α relative to linear CICs with HEG spacers (compare C-94 with C-21 and C-96 with C-23) or branched CICs without additional (HEG) spacers (compare C-94 with C-28 and C-96 with C-27). Adding another HEG spacer and a 4-base nucleic acid moiety to C-96 caused a reduction of IFN-α induction (compare C-96 with C-97). See Table 16.

Immunostimulatory activity of two CICs containing trimeric 5'-TCG-3' motifs was tested (C-91 and C-68). While neither CIC was active on its own, C-91 had significant activity when formulated on cPLGA.

A hydrophilic polyamide-containing STARBURST Dendrimer® with multiple P-6 sequences conjugated to it (C-102), had significantly more IFN-α activity than the P-6 sequence alone, when compared with an equal amount of P-6 (on a P-6 strand per strand basis). This result confirms, using a different composition and synthetic protocol from that demonstrated above, the utility of a multimeric delivery of 5'-CG-3'-containing nucleic acid moieties on a flexible, hydrophilic core for significantly increased induction of IFN-α.

TABLE 16

| stim | IFN-g (pg/ml) | | | | | | IFN-a (pg/ml) | | | | | |
|---|---|---|---|---|---|---|---|---|---|---|---|---|
| | 28185 | 28186 | 28187 | 28188 | mean | x4 | 28185 | 28186 | 28187 | 28188 | mean | x2 |
| cells alone | 5 | 1 | 13 | 1 | 5 | 20 | 36 | 4 | 32 | 4 | 19 | 38 |
| P-6 | 205 | 17 | 148 | 8 | 94 | 378 | 120 | 41 | 4 | 4 | 42 | 84 |
| P-7 | 0 | 4 | 19 | 2 | 6 | 25 | 4 | 25 | 5 | 31 | 16 | 32 |
| C-8 | 154 | 25 | 123 | 9 | 78 | 311 | 196 | 31 | 202 | 4 | 108 | 217 |
| C-94 | 181 | 61 | 384 | 17 | 161 | 644 | 1895 | 239 | 136 | 13 | 571 | 1142 |
| C-28 | 162 | 24 | 75 | 5 | 66 | 266 | 14 | 4 | 0 | 4 | 6 | 11 |
| C-21 | 244 | 37 | 125 | 7 | 103 | 413 | 443 | 64 | 1 | 4 | 128 | 256 |
| C-23 | 42 | 14 | 29 | 3 | 22 | 88 | 83 | 27 | 59 | 55 | 56 | 112 |
| C-27 | 49 | 3 | 21 | 3 | 19 | 75 | 4 | 4 | 39 | 4 | 13 | 25 |
| C-96 | 163 | 22 | 195 | 12 | 98 | 392 | 2550 | 446 | 118 | 40 | 788 | 1577 |
| C-97 | 259 | 16 | 125 | 5 | 101 | 405 | 307 | 71 | 4 | 2 | 96 | 192 |
| C-9 | 189 | 24 | 95 | 11 | 80 | 319 | 25 | 16 | 4 | 146 | 48 | 95 |
| C-86 | 1 | 4 | 30 | 5 | 10 | 40 | 7 | 4 | 4 | 31 | 11 | 22 |
| C-91 | 3 | 4 | 6 | 7 | 5 | 20 | 9 | 46 | 37 | 4 | 24 | 48 |
| C-68 | 0 | 4 | 2 | 1 | 2 | 7 | 4 | 13 | 25 | 4 | 11 | 23 |
| C-102 | 158 | 43 | 101 | 6 | 77 | 307 | 1880 | 187 | 109 | 4 | 545 | 1090 |
| PLGA | 10 | 4 | 13 | 4 | 8 | 30 | 4 | 4 | 0 | 4 | 3 | 6 |
| P-6 + PLGA | 315 | 64 | 128 | 39 | 137 | 546 | 710 | 116 | 78 | 4 | 227 | 454 |
| P-7 + PLGA | 7 | 3 | 15 | 2 | 7 | 27 | 4 | 4 | 4 | 9 | 5 | 10 |
| C-8 + PLGA | 319 | 127 | 242 | 24 | 178 | 712 | 1599 | 646 | 601 | 35 | 720 | 1441 |
| C-94 + PLGA | 391 | 118 | 280 | 34 | 206 | 823 | 6761 | 19553 | 3949 | 207 | 7618 | 15235 |
| C-28 + PLGA | 395 | 65 | 175 | 13 | 162 | 649 | 84 | 145 | 15 | 13 | 64 | 128 |
| C-21 + PLGA | 333 | 49 | 177 | 20 | 145 | 579 | 3581 | 3169 | 1340 | 64 | 2038 | 4077 |
| C-23 + PLGA | 199 | 67 | 102 | 15 | 96 | 382 | 599 | 250 | 110 | 21 | 245 | 490 |
| C-27 + PLGA | 292 | 170 | 95 | 14 | 142 | 570 | 54 | 58 | 4 | 39 | 39 | 78 |
| C-96 + PLGA | 400 | 186 | 244 | 41 | 218 | 872 | 27504 | 5572 | 2464 | 173 | 8928 | 17857 |
| C-97 + PLGA | 356 | 177 | 124 | 39 | 174 | 696 | 2264 | 668 | 285 | 48 | 816 | 1632 |
| C-9 + PLGA | 384 | 82 | 93 | 19 | 145 | 579 | 479 | 451 | 193 | 35 | 290 | 579 |
| C-86 + PLGA | 11 | 3 | 84 | 4 | 25 | 101 | 33 | 4 | 4 | 4 | 11 | 22 |
| C-91 + PLGA | 161 | 101 | 114 | 1 | 94 | 377 | 880 | 494 | 316 | 4 | 423 | 847 |
| C-68 + PLGA | 31 | 8 | 24 | 4 | 17 | 67 | 14 | 51 | 4 | 4 | 18 | 37 |
| C-102 + PLGA | 774 | 132 | 380 | 7 | 323 | 1293 | 2094 | 397 | 221 | 26 | 684 | 1369 |
| SAC | 195 | 22 | 274 | 15 | 127 | 506 | 73 | 4 | 151 | 102 | 82 | 165 |

Example 40

This experiment examined the activity of a series of CICs containing a hexameric nucleic acid motif, 5'-TCGTCG-3', and multiple spacers attached to the 3'-end of the nucleic acid moiety (C-13, C-14, C-15 and C-16). See Table 17. None of the CICs was active when used alone, however all had significant activity when formulated on cPLGA.

TABLE 17

| stim | IFN-γ (pg/ml) | | | | | IFN-α (pg/ml) | | | | |
|---|---|---|---|---|---|---|---|---|---|---|
| | 28057 | 28058 | 28059 | 28060 | mean | 28057 | 28058 | 28059 | 28060 | mean |
| cells alone | 1 | 2 | 1 | 39 | 11 | 0 | 0 | 0 | 0 | 0 |
| P-6 | 83 | 103 | 1230 | 85 | 375 | 621 | 396 | 145 | 123 | 321 |
| P-7 | 1 | 2 | 3 | 4 | 2 | 0 | 0 | 0 | 0 | 0 |
| C-13 | 2 | 3 | 12 | 5 | 6 | 31 | 0 | 249 | 0 | 70 |

TABLE 17-continued

| | IFN-γ (pg/ml) | | | | | IFN-α (pg/ml) | | | | |
|---|---|---|---|---|---|---|---|---|---|---|
| stim | 28057 | 28058 | 28059 | 28060 | mean | 28057 | 28058 | 28059 | 28060 | mean |
| C-14 | 3 | 1 | 1 | 3 | 2 | 0 | 0 | 0 | 0 | 0 |
| C-15 | 5 | 3 | 0 | 1 | 2 | 0 | 0 | 0 | 0 | 0 |
| C-16 | 1 | 2 | 0 | 6 | 2 | 0 | 0 | 0 | 0 | 0 |
| PLGA | 40 | 32 | 49 | 254 | 94 | 35 | 222 | 41 | 0 | 74 |
| P-6 + PLGA | 2000 | 2000 | 2000 | 452 | 1613 | 2000 | 2000 | 1747 | 403 | 1537 |
| P-7 + PLGA | 40 | 271 | 16 | 40 | 92 | 0 | 527 | 161 | 108 | 199 |
| C-13 + PLGA | 2000 | 262 | 221 | 168 | 663 | 5865 | 7994 | 5912 | 1437 | 5302 |
| C-14 + PLGA | 2000 | 359 | 732 | 2000 | 1273 | 3937 | 6871 | 6371 | 2953 | 5033 |
| C-15 + PLGA | 2000 | 585 | 2000 | 258 | 1211 | 2991 | 6282 | 4138 | 1731 | 3786 |
| C-16 + PLGA | 172 | 207 | 277 | 71 | 182 | 1842 | 2529 | 2333 | 1362 | 2017 |
| SAC | 673 | 2000 | 2000 | 2000 | 1668 | 920 | 2000 | 387 | 146 | 863 |

Example 41

Effects of CICs in B-Cell Proliferation Assay

Human PBMCs were isolated from heparinized blood from two normal subjects. Some PBMCs were held in reserve while the remainder was incubated with CD19+ MACS beads (Miltenyi Biotec). These cells were then passed through a magnet, separating the CD19+ B cells through positive selection. This population was >98% CD19+ as determined by FACS analysis. B cells were then cultured at $1 \times 10^5/200$ μl/well in 96-well round-bottomed plates. In some cases, PBMCs were also cultured, but at $2 \times 10^5/200$ μl/well. Cells were stimulated in triplicate with 2 μg/ml polynucleotide or CIC. The culture period was 48 hours at 37° C. At the end of the culture period, the plates were pulsed with $^3$H-thymidine, 1 μCi/well, and incubated for an additional 8 hours. Then the plates were harvested using standard liquid scintillation techniques and data was collected in counts per minutes (cpm).

Experiment A: The results of Experiment A (Table 18) demonstrate that polynucleotides (P-6) and CICs (C-8, C-9, C-21, C-28) containing 5'-C,G-3' motifs cause B cells to proliferate. Control compounds, P-7 and M-1, and a heptameric polynucleotide, P-1, generated little to no B cell proliferation. The branched CIC, C-28, and the CIC containing the propyl spacers, C-9, induced more B cell proliferation than CICs containing hexaethylene glycol spacers, C-8 and C-21. The proliferation of PBMCs mirrored that of B cells.

TABLE 18

| | | Donor 146 | | | | Donor 147 | | | | mean |
|---|---|---|---|---|---|---|---|---|---|---|
| cell type | stim | cpm1 | cpm2 | cpm3 | mean | cpm1 | cpm2 | cpm3 | mean | of both |
| B cells | cells alone | 538 | 481 | 795 | 605 | 482 | 360 | 296 | 379 | 492 |
| B cells | P-6 | 29280 | 33430 | 30056 | 30922 | 35729 | 18032 | 21166 | 24976 | 27949 |
| B cells | P-7 | 4858 | 5810 | 7079 | 5916 | 4364 | 4066 | 2774 | 3735 | 4825 |
| B cells | P-1 | 761 | 608 | 721 | 697 | 569 | 460 | 687 | 572 | 634 |
| B cells | C-8 | 23815 | 30066 | 22969 | 25617 | 20914 | 22370 | 23659 | 22314 | 23966 |
| B cells | C-9 | 35365 | 42705 | 45231 | 41100 | 55543 | 49035 | 44985 | 49854 | 45477 |
| B cells | C-21 | 28467 | 16074 | 19258 | 21266 | 17604 | 18851 | 19887 | 18781 | 20024 |
| B cells | M-1 | 1514 | 2815 | 1173 | 1834 | 1679 | 1667 | 1436 | 1594 | 1714 |
| B cells | C-28 | 50999 | 54630 | 46418 | 50682 | 65593 | 51040 | 50357 | 55663 | 53173 |
| PBMCs | cells alone | 2744 | 2303 | 2284 | 2444 | 1301 | 2402 | 2143 | 1949 | 2196 |
| PBMCs | P-6 | 22067 | 23740 | 28099 | 24635 | 26436 | 23830 | 17531 | 22599 | 23617 |
| PBMCs | P-7 | 7620 | 8362 | 9686 | 8556 | 9783 | 9841 | 10476 | 10033 | 9295 |
| PBMCs | P-1 | 9724 | 3041 | 2425 | 5063 | 1706 | 1960 | 324 | 1330 | 3197 |
| PBMCs | C-8 | 47202 | 40790 | 44811 | 44268 | 38845 | 39733 | 27981 | 35520 | 39894 |
| PBMCs | C-9 | 55348 | 24857 | 39953 | 40053 | 88106 | 65413 | 90665 | 81395 | 60724 |
| PBMCs | C-21 | 30338 | 22685 | 22383 | 25135 | 28819 | 530 | 37088 | 22146 | 23641 |
| PBMCs | M-1 | 8753 | 5203 | 4496 | 6151 | 1034 | 3298 | 1674 | 2002 | 4076 |
| PBMCs | C-28 | 94977 | 121595 | 84977 | 100516 | 103916 | 91439 | 100905 | 98753 | 99635 |

Experiment B: Experiment B (Table 19) evaluated the effects of the spacer composition, as well as the CIC structure (linear vs. branched), on B cell proliferation. Linear CICs containing propyl, butyl, abasic, and hydroxymethylethyl spacers tended to induce more B cell proliferation than the corresponding CICs containing either hexaethylene glycol or triethylene glycol spacers (compare C-10, C-11, C-17, C-18, C-20, C-25). The dodecyl spacer rendered the CIC inactive (C-19). Notably, the B cell proliferation data does not necessarily mirror the cytokine data shown above, with particular differences see between B cell proliferation and IFN-α induction.

TABLE 19

PROLIFERATION ASSAY

| | | | 121 | | | | 194 | | | | mean |
|---|---|---|---|---|---|---|---|---|---|---|---|
| sample | cell | stim | cpm1 | cpm2 | cpm3 | mean | cpm1 | cpm2 | cpm3 | mean | of both |
| 1 | B cells | cells alone | 451 | 757 | 297 | 502 | 203 | 228 | 151 | 194 | 348 |
| 2 | B cells | P-6 | 19996 | 15031 | 19804 | 18277 | 13678 | 12732 | 9003 | 11804 | 15041 |
| 3 | B cells | P-7 | 1623 | 1821 | 2901 | 2115 | 1992 | 1593 | 1686 | 1757 | 1936 |
| 4 | B cells | C-8 | 2604 | 12078 | 17696 | 10793 | 9333 | 9391 | 7602 | 8775 | 9784 |
| 5 | B cells | C-9 | 21938 | 35400 | 23877 | 27072 | 13660 | 16717 | 17866 | 16081 | 21576 |
| 6 | B cells | C-10 | 15142 | 14136 | 16158 | 15145 | 7480 | 5458 | 5943 | 6294 | 10720 |
| 7 | B cells | C-11 | 30367 | 30412 | 18528 | 26436 | 16967 | 20898 | 11253 | 16373 | 21404 |
| 8 | B cells | C-22 | 17147 | 14014 | 6844 | 12668 | 6472 | 5540 | 3894 | 5302 | 8985 |
| 9 | B cells | C-94 | 11418 | 14406 | 11110 | 12311 | 7361 | 8505 | 5349 | 7072 | 9692 |
| 10 | B cells | C-28 | 35393 | 26954 | 26780 | 29709 | 21588 | 13691 | 15691 | 16990 | 23350 |
| 11 | B cells | C-17 | 27975 | 30426 | 9895 | 22765 | 17467 | 14890 | 10518 | 14292 | 18529 |
| 12 | B cells | C-18 | | 17085 | 14653 | 15869 | 10028 | 12217 | 10538 | 10928 | 13398 |
| 13 | B cells | C-19 | 858 | 1099 | 926 | 961 | 371 | 403 | 312 | 362 | 662 |
| 14 | B cells | C-20 | 31276 | 30851 | 28532 | 30220 | 18082 | 18705 | 17481 | 18089 | 24155 |
| 15 | B cells | C-23 | 10628 | 16221 | 20087 | 15645 | 8730 | 6532 | 9596 | 8286 | 11966 |
| 16 | B cells | C-24 | 8206 | 6789 | 2799 | 5931 | 3979 | 3407 | 3468 | 3618 | 4775 |
| 17 | B cells | C-25 | 34360 | 35016 | 26480 | 31952 | 16060 | 19509 | 17384 | 17651 | 24802 |

Example 43

Figure 5:
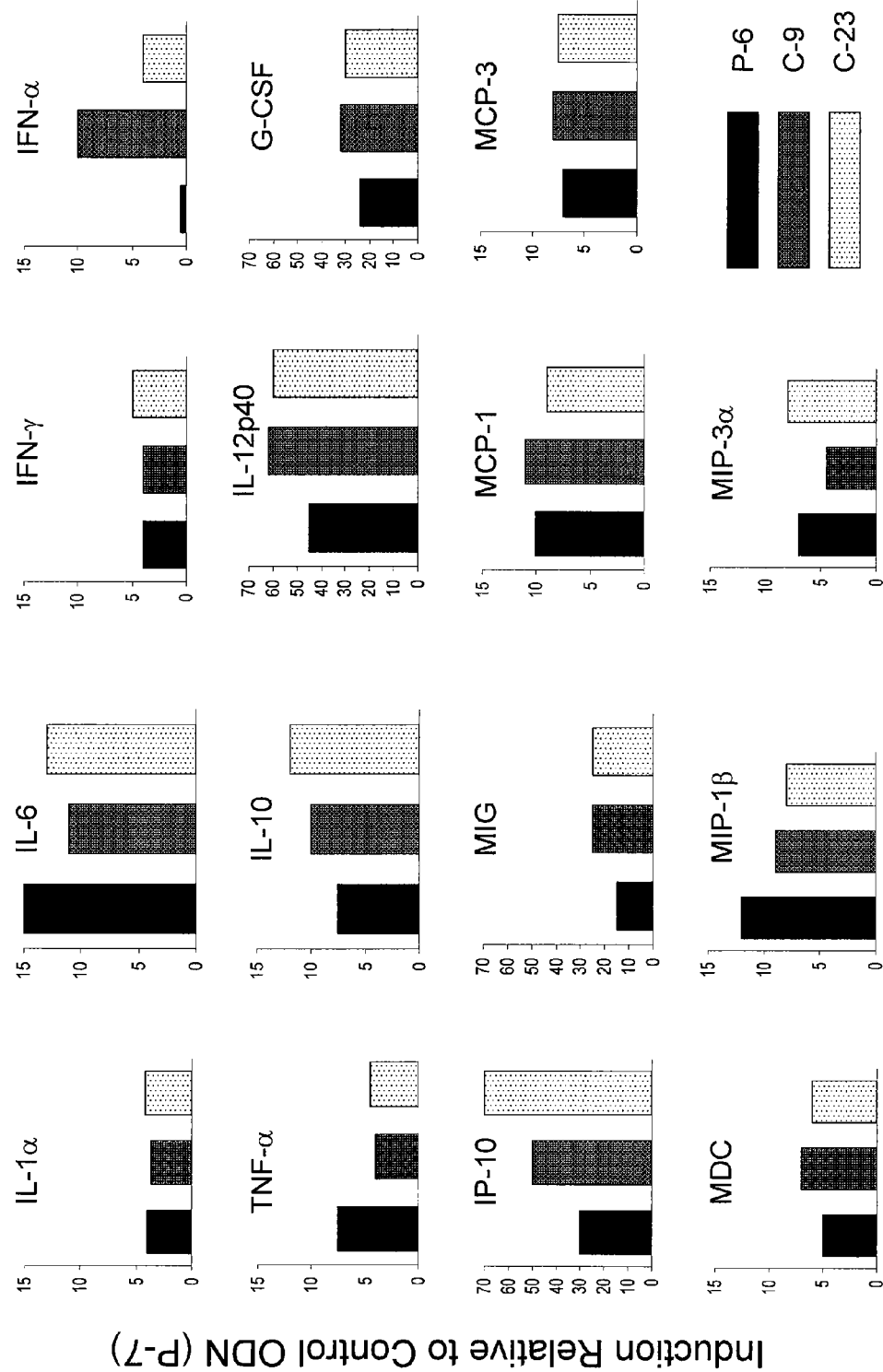
FIG. 5 shows induction of immune-associated genes in the mouse lung after intranasal treatment with CICs.

Induction of Immune-Associated Genes in the Mouse Lung After Intranasal Treatment with CICs The ability of C-9, C-23, and P-6 (positive control) to induce mRNA expression of 75 different genes in the mouse lung was investigated. The genes evaluated included genes encoding cytokines, chemokines, cell surface molecules, transcription factors, metalloproteases, and other molecules. The study was performed at Northview Pacific Laboratories (Hercules, Calif.) with 6-8 week old female BALB/c mice from Jackson Labs (Bar Harbor, Me.). Five mice per group were intranasally treated under light isoflorine anesthesia with 20 ug of C-9, C-23, P-6 (positive control) or P-7 (negative control) in 50 uL of saline. Previous experiments demonstrated that optimal induction of most genes was at 6 hrs after treatment. Therefore, at 6 hrs the lungs were harvested and snap-frozen in liquid nitrogen and stored at −80° C. for later use. Total RNA was isolated using RNeasy mini kits (Qiagen Inc., Valencia, Calif.). The RNA samples were DNAse-treated (Roche Diagnostics, Mannheim, Germany) and converted into cDNA using Superscript II Rnase H-Reverse Transcriptase (Invitrogen, Rockville Md.) as described in Scheerens et al., 2001, *Eur. J. of Immunology* 31:1465-74. The cDNA samples were pooled per group and in each pooled sample the expression of mRNA of 75 genes was measured using real-time quantitative PCR (ABI Prism 5700, Perkin Elmer Applied Biosystems) and syber green (Qiagen Inc.). In addition to the genes of interest, in each sample the mRNA expression of a housekeeping gene was measured (HPRT or ubiquitin). In order to correct for the amount of RNA in each sample, all data were calculated relative to the expression of the housekeeping gene. A selection of the most upregulated genes is shown in FIG. 5, with data expressed as fold-induction over the response in control-treated (P-7) mice. The data demonstrate that C-9, C-23, and P-6 potently induce the expression of a variety of genes including IL-6, IL-12p40, IFN-alpha, IP-10, and IL-10. Treatment of mice with C-9, however, induced considerably higher mRNA expression of IFN-alpha when compared to the C-23 or P-6 treated group.

Example 44

In Vivo Activity of CICs

An in vivo study was performed by injecting mice (10 mice/group) subcutaneously in the scruff of the neck with 20 ug (200 ul volume) of P-6 (positive control), P-7 (negative control), C-9, C-23, P-1 or P-11. Blood was collected 2 hours later. For the LPS positive control group, mice were injected intraperitoneally with a 200 ul volume, and blood was collected 1.5 hours later (i.e., at the peak of LPS induced TNF-α activity). The blood was clotted and the serum was prepared and stored at −80° C. until assayed. Serum cytokines were assayed using Biosource cytoscreen kits for TNF-α and Pharmingen antibody pairs for mIL-6 and mIL-12. All samples were assayed in duplicate.

Figure 6A:
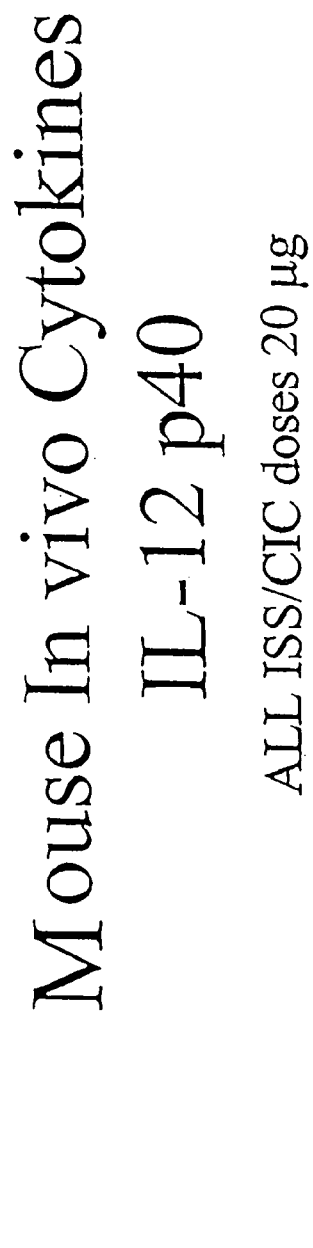
Figure 6B:
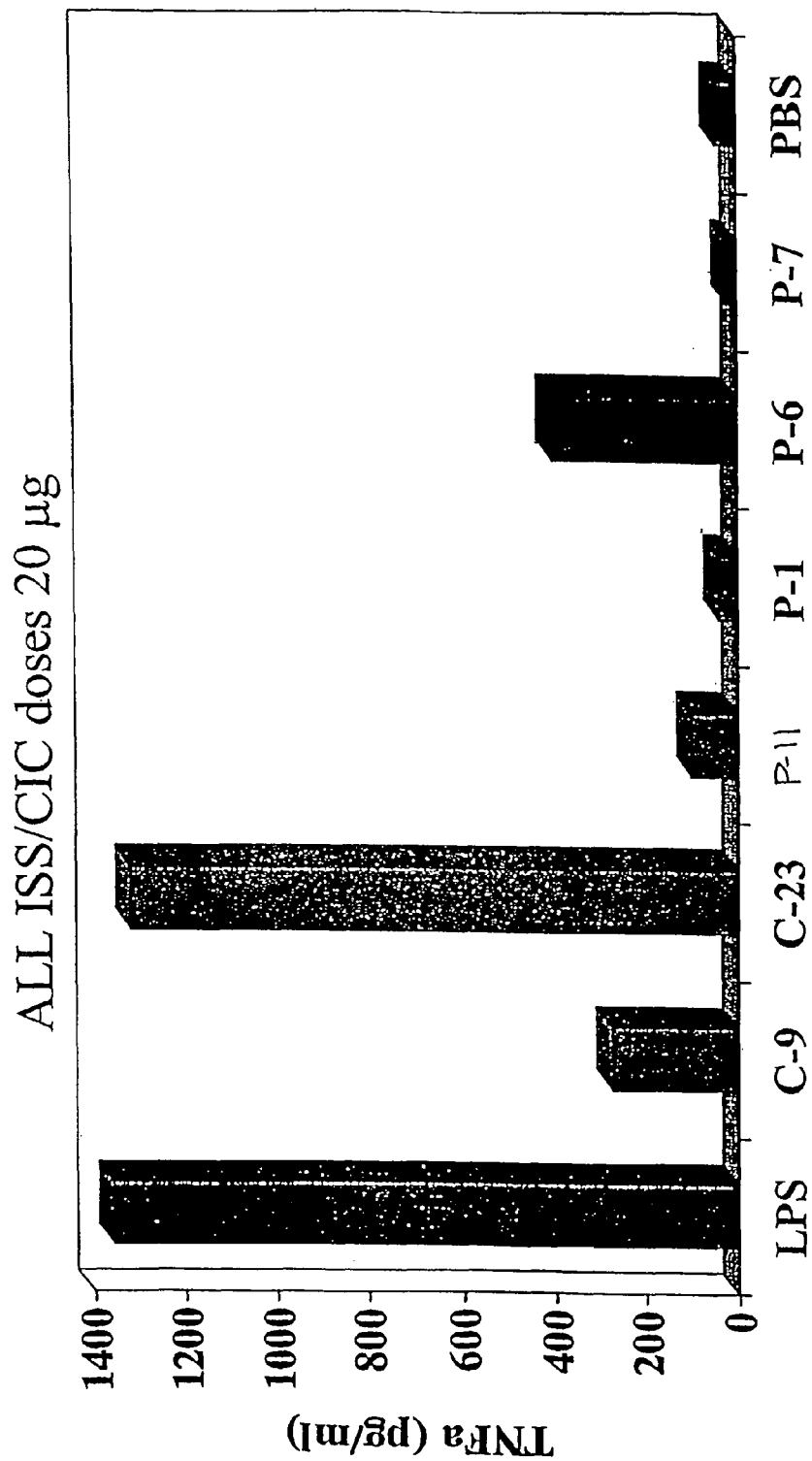
Figure 7A:
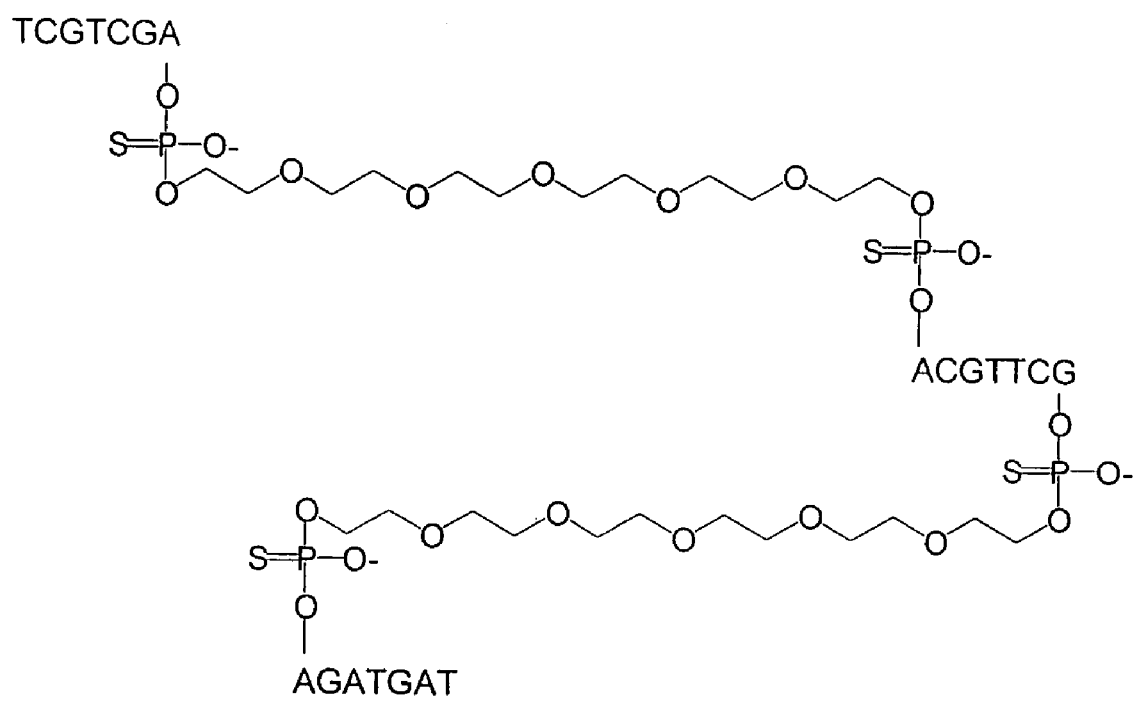
FIGS. 7A-B show the structures of C-8 (FIG. 7A) and C-101 (FIG. 7B).
Figure 7B:
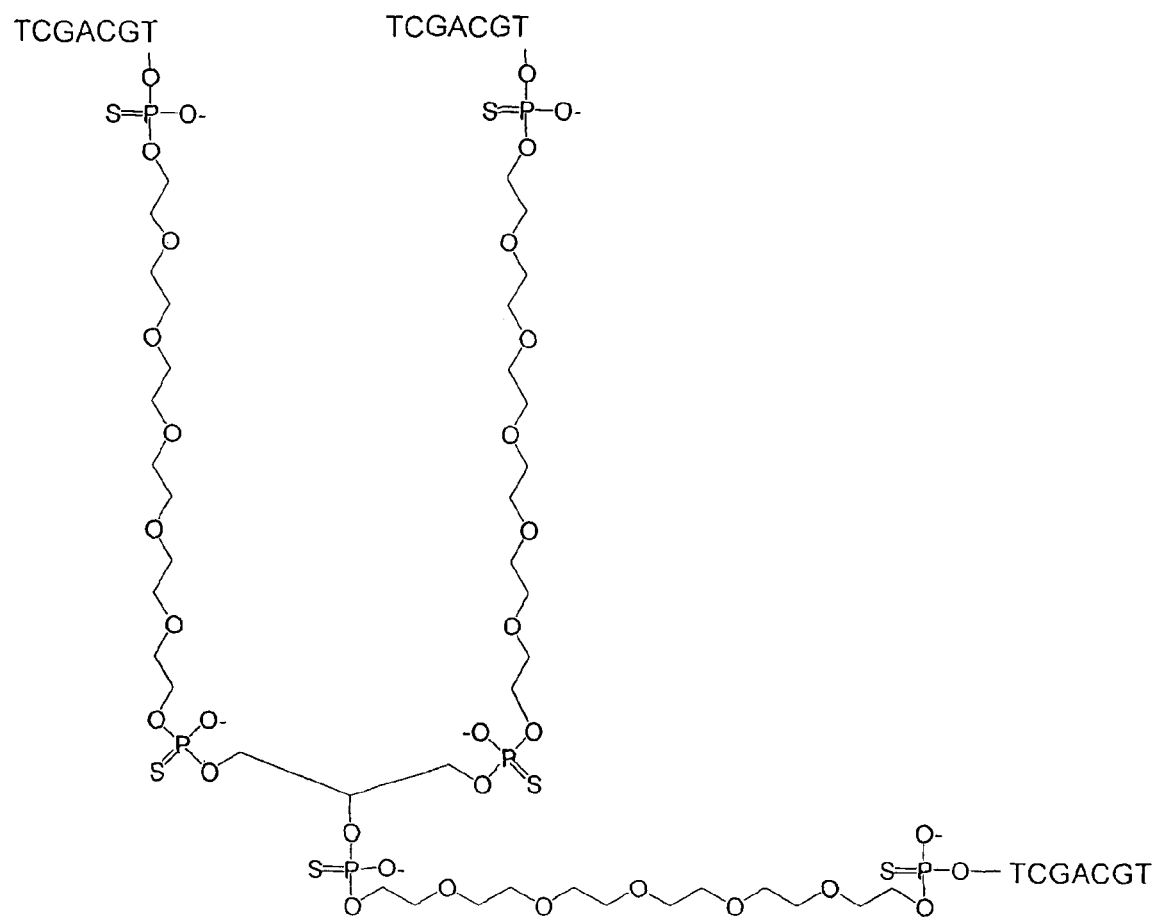

P-6 and the two CICs, C-9 and C-23, each induced IL-12 p40, IL-6, and TNF-α, while the control oligonucleotide, P-7, was inactive (FIG. 6A-C). CIC C-23 was more potent than C-9 and P-6 in this assay. As expected, the hexamer (P-11: 5'-AACGTT) and heptamer (P-1: 5'-TCGTCGA) were inactive.

Example 45

Primate Immune Response to Antigen and CICs

Immune responses to administration of hepatitis B surface antigen (HBsAg) in the presence of CICs were examined in baboons.

HBsAg was recombinant HBsAg produced in yeast. Groups of baboons (eight animals per group) included male and female baboons with weights ranging from 8-31 kg (group mean weights at 13-16 kg) at the start of the study.

The baboons were immunized two times, at a two-month interval (0 and 2 months), by intramuscular injection (IM) with 20 µg HBsAg in a 1 ml volume. As outlined below, some of the groups also received CICs (C-8 or C-9) or a positive control (P-6) with the HBsAg.

Bleeds on all animals were collected prior to immunization and at 2 weeks post-immunization. Anti-HBsAg IgG titers were measured as follows. Baboon serum samples were analyzed by AUSAB EIA commercial kit (Abbott Labs Cat. # 9006-24 and 1459-05) using human plasma derived HBsAg coated beads. Samples were tested along with a panel of human plasma derived HBsAg positive and negative standards ranging from 0-150 mIU/ml. Biotin conjugated HBsAg and rabbit anti-biotin-HRP conjugated antibody was used as the secondary antibody complex used for detection. The assay was developed with ortho-phenylenediamine (OPD) and the absorbance values were determined at 492 nm with background subtraction at 600 nm (Quantum II spectrophotometer, Abbott Labs). Using the specimen absorbance value the corresponding concentration of anti-HBsAg is expressed in milli-international units per ml (mIU/ml) as determined from the standard curve according to parameters established by the manufacturer. For diluted specimens, quantitation was based on the specimen absorbance that resulted in a value between 0-150 mIU/ml, multiplying by the dilution factor to arrive at the final concentration.

Statistical analysis was done with log-transformed data by analysis of variance (NCSS97 Statistical Software program, Kaysville, Utah) using One-Way ANOVA Planned Comparison ($\alpha$=0.05). $p \leqq 0.05$ was considered significant. The animal groups tested were immunized as follows:

Group 1-20 µg HBsAg;

Group 2-20 µg HBsAg+1000 µg P-6;

Group 3-20 µg HBsAg+1000 µg C-8;

Group 4-20 µg HBsAg+1000 µg C-9

Results from the study are shown in Table 20 below. Administration of CICs or the positive control P-6, in conjunction with HBsAg resulted in increased titers of anti-HBsAg antibodies as compared to administration of HBsAg alone. In a pairwise comparison, the immune response detected in Groups 2, 3, and 4 were significantly different from that detected in Group 1 (p<0.05 for Group 2 and p<0.005 for Groups 3 and 4, post-second immunization). There was no statistical difference found between groups 2, 3, and 4.

TABLE 20

Baboons Antibody Response (AUSAB EIA) HBsAg + CIC

| # | Group # Vaccine | Anti-HBsAg (mIU/ml) post-first | post-second |
|---|---|---|---|
| B339 | 1 | 0 | 7 |
| B340 | HBV | 0 | 63 |
| B341 | (20 ug) | 0 | 15 |
| B342 | | 0 | 80 |
| B343 | | 0 | 55 |
| B344 | | 0 | 50 |
| B345 | | 0 | 28 |
| B346 | | 0 | 24 |
| | Mean | 0 | 40 |
| | Stdev | 0 | 26 |
| B347 | 2 | 0 | 329 |
| B348 | HBV | 6 | 121 |
| B349 | (20 ug) | 0 | 108 |
| B350 | P-6 | 17 | 13,569 |
| B351 | (1000 ug) | 0 | 315 |
| B352 | | 0 | 38 |
| B353 | | 15 | 1,446 |
| B354 | | 21 | 1,675 |
| | Mean | 7 | 2200* |
| | Stdev | 9 | 4,637 |
| B379 | 3 | 2 | 184 |
| B380 | HBV | 0 | 3,038 |
| B381 | (20 ug) | 0 | 41,706 |
| B382 | C-8 | 125 | 3,718 |
| B383 | (1000 ug) | 0 | 250 |
| B384 | | 52 | 13,750 |
| B385 | | 0 | 11,626 |

TABLE 20-continued

Baboons Antibody Response (AUSAB EIA) HBsAg + CIC

| # | Group # Vaccine | Anti-HBsAg (mIU/ml) post-first | post-second |
|---|---|---|---|
| B386 | | 0 | 79 |
| | Mean | 22 | 9294** |
| | Stdev | 45 | 14,121 |
| B387 | 4 | 0 | 5,605 |
| B388 | HBV | 42 | 8,978 |
| B389 | (20 ug) | 0 | 312 |
| B390 | C-9 | 0 | 2,992 |
| B391 | (1000 ug) | 405 | 12,663 |
| B392 | | 26 | 112 |
| B393 | | 75 | 2,364 |
| B394 | | 0 | 52 |
| | Mean | 68 | 4135** |
| | Stdev | 139 | 4,633 |

*p < 0.05,
**p < 0.005 compared to HBV alone (Group 1)

Example 46

In Vivo Responses Generated by a CIC-Antigen Conjugate

This example shows the induction of an antibody-mediated immune response in mice by administration of a CIC-antigen conjugate.

As described below, 10 mice/group were immunized twice intradermally (in the tail) at two week intervals with C-11/Amb a 1 conjugate synthesized as described below (1 ug or 10 ug), P-6/Amb a 1 (1 ug) or Amb a 1 (1 ug). Anti-Amb a 1-specific IgG 1 and IgG2a titers were determined from sera taken 2 weeks post each injection. In vitro re-stimulations were done on spleen cells at 6 weeks post $2^{nd}$ immunization to determine Amb a 1-specific IFNγ and IL-5 responses.

Mice immunized with the C-11-Amb a 1 conjugate showed the characteristic immune response pattern seen with the P-6-Amb a 1 reference material, specifically, a switch from a Th2, toward a Th2-type Amb a 1-specific immune response. Mice immunized with either the C-11 or P-6 conjugates developed strong IgG2a responses and reduced IgG1 responses. The conjugate treated groups also demonstrated a shut down of the IL-5 response and elevation of the IFNγ response. Additionally, the immune responses to the C-11-Amb a 1 conjugate appear to increase in a dose dependant fashion, as demonstrated by comparing the 1 ug and 10 ug dose groups. The C-11-Amb a 1 conjugate elicits an immune response of similar quality to that seen with P-6-Amb a 1.

Results are shown in Tables 21-23.

General Procedure

The animal study was performed at Northview Pacific Laboratories (Hercules, Calif.) using 8-12 week old female BALB/c mice from Charles River Laboratories (Hollister, Calif.). 10 mice/group were injected twice intradermally in the tail (ID) at two-week intervals with one of the following materials: C-11/Amb a 1 conjugate (1 ug), C-11/Amb a 1 conjugate (10 ug), P-6/Amb a 1 conjugate (1 ug) or Amb a 1 antigen (1 ug). Bleeds were collected via the retro-orbital route two weeks after each of the injections and serum prepared for antibody determination. Six weeks after the $2^{nd}$ injection spleens were harvested for in vitro re-stimulation assays to determine cytokine response of IFNγ and IL-5. Spleens were assayed individually. Amb a 1 was used at 25 and 5 ug/ml for re-stimulation with $5 \times 10^5$ cells/well and supernatants harvested on Day 4 and stored at −80° C. until assayed. Controls for the in vitro assay included SAC at 0.01% and PMA/IO at 10 ng/ml and 1 uM, respectively.

Mouse Anti-Amb a 1 IgG1 and IgG2a Assays

Mouse serum samples were analyzed by ELISA in 96-well round-bottom plates that were coated with 50 μl/well Amb a 1 antigen at 1 μg/ml. Goat anti-mouse IgG1 (or IgG2a) biotin conjugated antibody was used as the secondary antibody. Streptavidin-horseradish peroxidase conjugate was used for detection. The assay was developed with TMB and the absorbance values were determined at 450 nm with background subtraction at 650 nm (Emax precision microplate reader, Molecular Devices, Sunnyvale, Calif.). The titer was defined as the reciprocal of the serum dilution that gave an ELISA absorbance of 0.5 OD using 4-parameter analysis (Softmax Pro97, Molecular Devices, Sunnyvale, Calif.). All samples were tested in duplicate wells on separate plates, and the titers were reported as the mean of the two values.

Mouse IL-5 and IFN-Gamma Assays

Supernatants were tested for IL-5 and IFNγ levels by capture ELISA on anti-cytokine monoclonal antibody coated plates. Biotinylated anti-cytokine MAbs were used as secondary antibodies. Streptavidin-horseradish peroxidase conjugate was used for detection and the assay was developed with TMB. Concentration was calculated from a standard curve assayed on each plate. The absorbance values were determined at 450 nm with background subtraction at 650 nm (Emax precision microplate reader, Molecular Devices, Sunnyvale, Calif.). All samples were tested in duplicate wells on separate plates, and the concentrations were reported as the mean of the two values.

Statistics were done on log transformed data with the NCSS97 program (NCSS Statistical Software, Kaysville, Utah) using One-Way ANOVA with Planned Comparisons, α=0.05. For the following study, $p<0.05$ is considered statistically significant.

Synthesis of the C-11/Amb a 1 Conjugate

Synthesis of Activated C-11 (C-111)

The 5'-disulfide-C-11 (C-110) was dissolved in activation buffer (100 mM sodium phosphate/150 mM sodium chloride/pH 7.5) and activated by reduction with TCEP. The activated CIC (C-111) was purified using a 5 ml SEPHADEX® G25 column (Pharmacia) using the same activation buffer as mobile phase. Fractions were collected manually at 0.5-minute intervals starting at baseline rise. After purification, the concentration of the various fractions was determined using A260 and an extinction coefficient of 25.6 OD/mg.

Amb a 1 was activated by first blocking the its free-sulfhydryls, and then adding a hetero-functional cross-linker. Excess reagents were removed by desalting using a HiTrap G-25 desalting column (Pharmacia Catalog #17-1408-01). The resulting activated Amb a 1 had an average of 9.3 sites per protein activated.

Synthesis of the C-11/Amb a 1 Conjugate

The activated C-11 (C-111) and activated Amb a 1 were combined and the resulting C-11/Amb a 1 conjugate was fractionated using a Superdex 200 size exclusion chromatography column (Pharmacia Cat. # 17-1088-01; 1 cm×30 cm). Formulation buffer (10 mM phosphate, 150 mM NaCl, pH 7.2) was used as mobile phase. Fractions were collected at 1-minute intervals, starting when the baseline began to rise.

The conjugate samples were analyzed by SDS-PAGE using a 4-12% NuPAGE gel (Invitrogen, Catalog #NPO322) using MOPS buffer (Invitrogen, Catalog #NP0001), and by Size Exclusion Chromatography (SEC-HPLC) using a Bio-Sep SEC-S3000 column (Phenomenex, Catalog #OOH-2146-E0). After SDS-PAGE the protein was visualized by using Coomassie blue stain (GelCode, Pierce Catalog #24596). Presence of the CIC was confirmed by using DNA-Silver stain (Pharmacia, Catalog #17-6000-30). Both SDS-PAGE and SEC-HPLC were used to define pooling criteria, and for characterization of the obtained pool. Protein concentration was measured by the Bicinchoninic acid method (BCA, Sigma Catalog #BCA-1).

TABLE 21

Activity of C-11/Amb a 1 Conjugate in Mice
IgG1 and IgG2a anti-Amb a 1 titers

| Group | Animal # | Immunization | 2 weeks post 1st Imm | | 2 weeks post 2nd Imm | |
|---|---|---|---|---|---|---|
| | | | IgG1 | IgG2a | IgG1 | IgG2a |
| 1 | 1 | C-11/Amb a 1 | 30 | 148 | 7,900 | 19,886 |
| | 2 | conjugate | 30 | 221 | 13,037 | 19,735 |
| | 3 | (1 ug) | 30 | 943 | 946 | 23,918 |
| | 4 | ID | 30 | 64 | 5,485 | 10,487 |
| | 5 | | 38 | 1,894 | 3,805 | 9,945 |
| | 6 | | 30 | 943 | 600 | 5,249 |
| | 7 | | 30 | 570 | 10,337 | 20,156 |
| | 8 | | 30 | 259 | 600 | 8,350 |
| | 9 | | 56 | 30 | 2,575 | 5,747 |
| | 10 | | 30 | 30 | 8,381 | 28,971 |
| | | mean | 33** | 510 | 5,367** | 15,244* |
| | | std dev | 8 | 599 | 4,400 | 8,285 |
| 2 | 11 | C-11/Amb a 1 | 51 | 345 | 8,982 | 27,877 |
| | 12 | conjugate | 30 | 667 | 201,008 | 612,739 |
| | 13 | (10 ug) | 77 | 445 | 6,739 | 86,672 |
| | 14 | ID | 30 | 1,662 | 22,578 | 121,770 |
| | 15 | | 30 | 67 | 190,835 | 88,745 |
| | 16 | | 30 | 450 | 5,971 | 17,600 |
| | 17 | | 55 | 1,137 | 29,646 | 105,398 |
| | 18 | | 99 | 1,119 | 70,159 | 183,152 |
| | 19 | | 99 | 8,227 | 80,052 | 250,206 |
| | 20 | | 30 | 1,613 | 6,235 | 63,616 |

TABLE 21-continued

Activity of C-11/Amb a 1 Conjugate in Mice
IgG1 and IgG2a anti-Amb a 1 titers

| Group | Animal # | Immunization | 2 weeks post 1st Imm IgG1 | 2 weeks post 1st Imm IgG2a | 2 weeks post 2nd Imm IgG1 | 2 weeks post 2nd Imm IgG2a |
|---|---|---|---|---|---|---|
| | | mean | 53* | 1,573 | 62,221 | 155,778* |
| | | std dev | 29 | 2,399 | 75,298 | 174,925 |
| 3 | 21 | P-6/Amb a 1 | 30 | 37 | 3,437 | 65,306 |
| | 22 | reference conjugate | 1,422 | 303 | 15,652 | 6,198 |
| | 23 | (1 ug) | 485 | 265 | 84,927 | 177,281 |
| | 24 | ID | 170 | 1,182 | 37,379 | 56,074 |
| | 25 | | 903 | 2,027 | 38,121 | 76,572 |
| | 26 | | 88 | 2,298 | 32,499 | 240,098 |
| | 27 | | 33 | 321 | 3,011 | 24,404 |
| | 28 | | 30 | 55 | 24,307 | 20,796 |
| | 29 | | 113 | 89 | 43,060 | 19,586 |
| | 30 | | 30 | 39 | 37,116 | 7,317 |
| | | mean | 330 | 662 | 31,951 | 69,363 |
| | | std dev | 475 | 862 | 23,568 | 78,697 |
| 4 | 31 | Amb a 1 | 3,405 | 349 | 172,827 | 6,244 |
| | 32 | (1 ug) | 7,331 | 30 | 164,673 | 1,003 |
| | 33 | ID | 2,847 | 35 | 112,766 | 7,174 |
| | 34 | | 4,021 | 30 | 100,281 | 1,399 |
| | 35 | | 8,333 | 212 | 156,037 | 4,969 |
| | 36 | | 1,214 | 286 | 118,407 | 2,125 |
| | 37 | | 1,279 | 30 | 396,404 | 600 |
| | 38 | | 4,332 | 80 | 187,335 | 4,599 |
| | 39 | | 569 | 30 | 63,536 | 600 |
| | 40 | | 2,696 | 30 | 161,039 | 902 |
| | | mean | 3,603** | 111* | 163,331** | 2,962** |
| | | std dev | 2,554 | 123 | 90,406 | 2,530 | a value of 30 was used for samples <30 post 1st immunization
a value of 600 was used for samples <600 post 2nd immunization
*p < 0.05,
**p < 0.005 compared to P-6/Amb a 1

TABLE 22

Activity of C-11/Amb a 1 Conjugate in Mice
In vitro IFNγ response (pg/ml)

| Animal | Immunization | Amb a 1 25 ug/ml | Amb a 1 5 ug/ml | PMA | Media Alone |
|---|---|---|---|---|---|
| 1 | | 22501 | 16320 | 12505 | 45 |
| 2 | C-11/Amb a 1 | 16291 | 10054 | 8433 | 45 |
| 3 | conjugate | 8534 | 5084 | 5835 | 45 |
| 4 | (1 ug) | 16925 | 8322 | 3796 | 45 |
| 5 | | 23136 | 11298 | 9225 | 45 |
| 6 | ID | 24900 | 25489 | 21525 | 185 |
| 7 | | 4383 | 2716 | 8855 | 45 |
| 8 | | DEAD | DEAD | DEAD | DEAD |
| 9 | | 16088 | 6285 | 27722 | 45 |
| 10 | | 25067 | 12431 | 28201 | 45 |
| | Mean | 17536 | 10889 | 14011 | 61 |
| | StDev | 7289 | 6839 | 9353 | 47 |
| 11 | | 19994 | 13466 | 33702 | 45 |
| 12 | C-11/Amb a 1 | 50732 | 25103 | 36467 | 45 |
| 13 | conjugate | 54752 | 28422 | 21770 | 123 |
| 14 | (10 ug) | 96417 | 78017 | 24601 | 1305 |
| 15 | | 83356 | 43505 | 20021 | 151 |
| 16 | ID | 88018 | 51299 | 40604 | 829 |
| 17 | | 87839 | 59079 | 31562 | 83 |
| 18 | | 49763 | 28468 | 58062 | 211 |
| 19 | | 102646 | 60332 | 32669 | 3366 |
| 20 | | 61939 | 29505 | 53393 | 756 |
| | Mean | 65868** | 39652 | 35576 | 394 |
| | StDev | 24860 | 20160 | 13331 | 455 |
| 21 | | 4275 | 3083 | 36550 | 45 |
| 22 | P-6/Amb a 1 | 4307 | 996 | 23742 | 45 |
| 23 | reference | 40761 | 16956 | 15407 | 45 |
| 24 | conjugate | 40764 | 23643 | 8961 | 118 |
| 25 | (1 ug) | 35645 | 30164 | 15915 | 209 |
| 26 | ID | 40895 | 31027 | 13355 | 308 |
| 27 | | 25538 | 14349 | 15515 | 73 |
| 28 | | 15884 | 12432 | 11623 | 45 |
| 29 | | 4215 | 4608 | 71066 | 45 |
| 30 | | 63276 | 46897 | 43680 | 734 |
| | Mean | 27556 | 18416 | 25581 | 167 |
| | StDev | 20099 | 14603 | 19548 | 218 |
| 31 | | 3016 | 2585 | 108000 | 452 |
| 32 | Amb a 1 | 1193 | 277 | 94345 | 104 |
| 33 | (1 ug) | 5112 | 6239 | 97567 | 461 |
| 34 | | 1301 | 251 | 89623 | 49 |
| 35 | | 6879 | 2972 | 77808 | 56 |
| 36 | ID | 1187 | 673 | 77299 | 89 |
| 37 | | 4492 | 2840 | 89253 | 282 |
| 38 | | 6170 | 3765 | 70169 | 187 |
| 39 | | 2099 | 1152 | 108000 | 132 |
| 40 | | 2209 | 3895 | 103131 | 309 |
| | Mean | 3366** | 2465 | 91520 | 212 |
| | StDev | 2143 | 1915 | 13239 | 156 | a value of 18 was used for values <18
▒ values were not included in calculations since value for media alone was >3 stdev + average of all media alone values (ie. 2014 pg/ml)
**p < 0.005 compared P-6/Amb a 1 for 25 ug/ml restimulation

TABLE 23

Activity of C-11/Amb a 1 Conjugate in Mice
In vitro IL-5 response (pg/ml)

| | | Amb a 1 | | | Media |
|---|---|---|---|---|---|
| Animal | Immunization | 25 ug/ml | 5 ug/ml | PMA | Alone |
| 1 | | 67 | 106 | 2202 | 41 |
| 2 | C-11/Amb a 1 | 49 | 53 | 2406 | 24 |
| 3 | conjugate | 264 | 24 | 968 | 24 |
| 4 | (1 ug) | 24 | 24 | 2979 | 24 |
| 5 | | 68 | 45 | 2851 | 46 |
| 6 | ID | 104 | 121 | 2547 | 129 |
| 7 | | 24 | 24 | 3935 | 24 |
| 8 | | DEAD | DEAD | DEAD | DEAD |
| 9 | | 24 | 24 | 1383 | 24 |
| 10 | | 24 | 203 | 1837 | 53 |
| | Mean | 68 | 63 | 2320 | 33 |
| | StDev | 86 | 63 | 948 | 12 |
| 11 | | 24 | 33 | 1655 | 24 |
| 12 | C-11/Amb a 1 | 41 | 73 | 2258 | 84 |
| 13 | conjugate | 169 | 137 | 892 | 24 |
| 14 | (10 ug) | 261 | 221 | 918 | 33 |
| 15 | | 134 | 221 | 658 | 24 |
| 16 | ID | 253 | 187 | 778 | 29 |
| 17 | | 72 | 109 | 966 | 24 |
| 18 | | 24 | 35 | 3656 | 24 |
| 19 | | 334 | 231 | 1238 | 145 |
| 20 | | 213 | 55 | 751 | 24 |
| | Mean | 153 | 130 | 1377 | 44 |
| | StDev | 111 | 80 | 940 | 40 |
| 21 | | 24 | 24 | 1514 | 24 |
| 22 | P-6/Amb a 1 reference | 24 | 60 | 3725 | 24 |
| 23 | conjugate | 157 | 277 | 1702 | 24 |
| 24 | (1 ug) | 96 | 152 | 4473 | 24 |
| 25 | | 88 | 36 | 1414 | 24 |
| 26 | ID | 39 | 372 | 1235 | 24 |
| 27 | | 218 | 176 | 1037 | 24 |
| 28 | | 103 | 54 | 1382 | 24 |
| 29 | | 24 | 459 | 2194 | 24 |
| 30 | | 110 | 102 | 2990 | 24 |
| | Mean | 88 | 171 | 2167 | 24 |
| | StDev | 64 | 151 | 1174 | 0 |
| 31 | | 724 | 331 | 1332 | 24 |
| 32 | Amb a 1 | 91 | 57 | 3186 | 24 |
| 33 | (1 ug) | 930 | 1259 | 1574 | 56 |
| 34 | | 375 | 674 | 2506 | 24 |
| 35 | | 1093 | 763 | 2197 | 24 |
| 36 | ID | 1206 | 490 | 3715 | 27 |
| 37 | | 2808 | 2115 | 1727 | 67 |
| 38 | | 1441 | 909 | 1655 | 58 |
| 39 | | 1240 | 1228 | 1367 | 24 |
| 40 | | 1373 | 481 | 1683 | 68 |
| | Mean | 1128** | 831 | 2094 | 40 |
| | StDev | 734 | 588 | 808 | 20 | a value of 24 was used for values <24

▓▓▓ values were not included in calculations since value for media alone was >3 stdev + average of all media alone values (ie. 124 pg/ml)

*p < 0.05,
**p < 0.005 compared to P-6/Amb a 1 for 25 ug/ml restimulation

Example 47

Effect of Spacer Moiety on CIC Activity

This example shows the effect of different spacer moieties on IFN-α induction. Comparison of C-90 (C3 CIC) and C-51 (HEG CIC) showed that C-51 induced 8-fold more IFN-α than C-90, although the amount of IFN-γ induced by each CIC was similar. Similarly, comparison of branched CICs containing different linkers showed that for IFN-α induction, HEG (C-94)>TEG (C-103)>C3 (C-104)=no linker (C-28).

TABLE 24

| | IFN-g (pg/ml) | | | | | IFN-g (pg/ml) | | | | |
|---|---|---|---|---|---|---|---|---|---|---|
| stim | 28234 | 28235 | 28236 | 28237 | mean | 28234 | 28235 | 28236 | 28237 | mean |
| cells alone | 4 | 4 | 4 | 4 | 4 | 16 | 16 | 16 | 16 | 16 |
| P-6 | 15 | 52 | 51 | 1167 | 321 | 58 | 16 | 16 | 74 | 41 |
| P-7 | 13 | 4 | 7 | 4 | 7 | 62 | 16 | 16 | 16 | 28 |
| C-90 | 7 | 118 | 497 | 1586 | 552 | 16 | 46 | 117 | 345 | 131 |
| C-51 | 17 | 123 | 193 | 1580 | 478 | 16 | 77 | 352 | 3798 | 1061 |
| C-71 | 30 | 168 | 448 | 1663 | 577 | 17 | 30 | 538 | 1665 | 563 |
| C-101 | 14 | 205 | 627 | 2612 | 865 | 16 | 249 | 1354 | 8566 | 2546 |
| C-96 | 21 | 239 | 354 | 1396 | 503 | 16 | 120 | 608 | 993 | 434 |
| C-97 | 10 | 119 | 269 | 980 | 345 | 16 | 16 | 140 | 16 | 47 |
| C-100 | 27 | 183 | 490 | 1907 | 652 | 16 | 16 | 398 | 193 | 156 |
| C-88 | 5 | 21 | 17 | 477 | 130 | 95 | 16 | 212 | 111 | 109 |
| C-33 | 23 | 86 | 247 | 2076 | 608 | 16 | 16 | 16 | 91 | 35 |
| C-21 | 4 | 107 | 308 | 1645 | 516 | 16 | 16 | 73 | 678 | 196 |
| C-28 | 10 | 14 | 88 | 1229 | 335 | 16 | 16 | 16 | 16 | 16 |
| C-94 | 7 | 161 | 239 | 1116 | 381 | 16 | 118 | 548 | 3631 | 1078 |
| C-103 | 21 | 44 | 250 | 1854 | 542 | 16 | 21 | 126 | 213 | 94 |
| C-104 | 14 | 4 | 87 | 125 | 58 | 16 | 29 | 16 | 16 | 19 |
| PLGA | 4 | 31 | 18 | 10 | 16 | 16 | 122 | 157 | 35 | 83 |
| P-6 + PLGA | 57 | 514 | 1052 | 3775 | 1350 | 16 | 694 | 1163 | 3444 | 1329 |
| P-7 + PLGA | 4 | 4 | 11 | 13 | 8 | 16 | 16 | 16 | 16 | 16 |
| C-90 + PLGA | 139 | 673 | 831 | 4618 | 1565 | 1175 | 696 | 4544 | 5103 | 2880 |
| C-51 + PLGA | 88 | 644 | 1064 | 3748 | 1386 | 3257 | 2168 | 8000 | 8000 | 5356 |
| C-71 + PLGA | 101 | 797 | 1254 | 3899 | 1513 | 3085 | 2244 | 8000 | 8000 | 5332 |
| C-101 + PLGA | 110 | 659 | 879 | 6944 | 2148 | 4679 | 4488 | 8000 | 8000 | 6292 |
| C-96 + PLGA | 143 | 1070 | 1167 | 5471 | 1963 | 4107 | 3237 | 6660 | 8000 | 5501 |
| C-97 + PLGA | 68 | 737 | 988 | 5327 | 1780 | 4742 | 4216 | 8000 | 8000 | 6240 |
| C-100 + PLGA | 176 | 1299 | 1742 | 7804 | 2755 | 1520 | 1092 | 4074 | 3777 | 2616 |

TABLE 24-continued

| | IFN-g (pg/ml) | | | | | IFN-g (pg/ml) | | | | |
|---|---|---|---|---|---|---|---|---|---|---|
| stim | 28234 | 28235 | 28236 | 28237 | mean | 28234 | 28235 | 28236 | 28237 | mean |
| C-88 + PLGA | 102 | 512 | 1148 | 5055 | 1704 | 803 | 613 | 2409 | 6412 | 2559 |
| C-33 + PLGA | 118 | 444 | 968 | 3947 | 1369 | 551 | 566 | 3514 | 6727 | 2840 |
| C-21 + PLGA | 159 | 411 | 1089 | 4056 | 1429 | 1369 | 1561 | 5366 | 8000 | 4074 |
| C-28 + PLGA | 28 | 131 | 1005 | 3868 | 1258 | 16 | 16 | 184 | 134 | 88 |
| C-94 + PLGA | 174 | 623 | 1352 | 4034 | 1546 | 4145 | 4653 | 7197 | 8000 | 5999 |
| C-103 + PLGA | 192 | 643 | 1388 | 5063 | 1822 | 895 | 1486 | 4456 | 5405 | 3061 |
| C-104 + PLGA | 40 | 73 | 641 | 4930 | 1421 | 16 | 16 | 128 | 92 | 63 |
| SAC | 1845 | 1250 | 924 | 5350 | 2342 | 2374 | 327 | 1149 | 3744 | 1899 |

Example 48

Assessment of Isolated Immunomodulatory Activity of Polynucleotides Corresponding in Sequence to CIC Nucleic Acid Moieties This example further illustrates the immunostimulatory activity of CICs that contain nucleic acid moieties that do not have isolated immunomodulatory activity. The activity of polynucleotides corresponding in sequence to the CIC nucleic acid moieties were assayed alone or in combination with free spacers, and compared to the activity of a CIC containing the same amount of nucleic acid and spacer. For instance, 3 uM of CIC C-101 was compared with 9 uM P-14 or a mixture of 9 uM P-14 and 9 uM hexaethylene glycol and 3 uM glycerol (because C-101 contains three equivalents of P-14, three equivalents of hexaethylene glycol, and one equivalent of glycerol.) In all cases, the CICs were active while the short polynucleotides, both alone and mixed with spacers, were inactive. See Table 25. The activity of the spacers alone was tested at a concentration of 9 uM and all were completely inactive.

TABLE 25

| | IFN-g (pg/ml) | | | | | IFN-a (pg/ml) | | | | |
|---|---|---|---|---|---|---|---|---|---|---|
| stim | 28250 | 28251 | 28252 | 28253 | mean | 28250 | 28251 | 28252 | 28253 | mean |
| cells alone | 18 | 5 | 9 | 1 | 8 | 16 | 16 | 30 | 19 | 20 |
| P-6 | 121 | 18 | 34 | 37 | 52 | 16 | 16 | 16 | 16 | 16 |
| P-7 | 104 | 1 | 39 | 1 | 36 | 16 | 16 | 16 | 16 | 16 |
| Propyl spacer | 13 | 1 | 1 | 1 | 4 | 16 | 16 | 16 | 16 | 16 |
| Butyl spacer | 8 | 5 | 1 | 1 | 4 | 16 | 16 | 16 | 16 | 16 |
| Triethylene glycol | 15 | 1 | 7 | 1 | 6 | 16 | 16 | 16 | 16 | 16 |
| Hexaethylene glycol | 12 | 1 | 1 | 15 | 7 | 16 | 16 | 16 | 35 | 21 |
| Glycerol | 16 | 12 | 2 | 1 | 8 | 16 | 16 | 16 | 16 | 16 |
| C-51 | 135 | 45 | 164 | 167 | 128 | 181 | 246 | 95 | 1226 | 437 |
| C-101 | 224 | 63 | 180 | 146 | 153 | 540 | 1472 | 509 | 2645 | 1291 |
| P-14 | 10 | 34 | 11 | 10 | 16 | 16 | 16 | 16 | 16 | 16 |
| P-14/HEG/glycerol | 14 | 19 | 10 | 10 | 13 | 16 | 16 | 16 | 16 | 16 |
| C-21 | 122 | 51 | 155 | 203 | 133 | 31 | 69 | 41 | 264 | 101 |
| C-94 | 340 | 60 | 287 | 128 | 204 | 245 | 645 | 323 | 1198 | 603 |
| P-1 | 54 | 21 | 56 | 1 | 33 | 16 | 16 | 16 | 16 | 16 |
| P-1/HEG/glycerol | 15 | 9 | 19 | 1 | 11 | 16 | 16 | 16 | 16 | 16 |
| C-45 | 107 | 26 | 95 | 8 | 59 | 16 | 109 | 55 | 382 | 140 |
| P-13 | 18 | 13 | 22 | 1 | 14 | 16 | 16 | 16 | 16 | 16 |
| P-13/HEG | 40 | 28 | 45 | 1 | 28 | 16 | 16 | 16 | 16 | 16 |
| C-10 | 337 | 163 | 776 | 898 | 544 | 16 | 23 | 25 | 124 | 47 |
| P-2 | 7 | 25 | 53 | 1 | 22 | 16 | 16 | 25 | 16 | 18 |
| P-3 | 32 | 21 | 72 | 1 | 31 | 16 | 29 | 38 | 31 | 29 |
| P-4 | 72 | 1 | 43 | 1 | 29 | 16 | 16 | 16 | 16 | 16 |
| P-2/P-3/P-4/HEG | 68 | 1 | 38 | 1 | 27 | 16 | 16 | 16 | 16 | 16 |

Example 49

Preparation of (5'-TCGACGT-3'-HEG)$_{ave=185}$-Ficoll$_{400}$(C-137)

A. Preparation of Maleimido-Ficoll$_{400}$

Aminoethylcarboxymethyl (AECM)$_{180}$-Ficoll$_{400}$ was prepared by the method of Inman (*J. Immunology*, 1975, 114: 704-709). On average there were 180 aminoethyl groups per mole of Ficoll (MW=400,000 Da). 27.6 mg (62.6 umol) of sulfosuccinimidyl 4-[N-maleimidomethyl]-cyclohexane-1-carboxylate dissolved in 300 ul of DMSO was added dropwise, with constant vortexing, to 23.2 mg (0.058 umol) of AECM$_{180}$-Ficoll$_{400}$ dissolved in 1.0 ml of 0.1 M sodium phosphate buffer (pH 6.66). The reaction mixture was placed on a shaker for 2 h and then desalted on a SEPHADEX® G-25 column to yield 20 mg of maleimido-Ficoll$_{400}$. On average, there were approximately 165 maleimide groups per mole of Ficoll.

B. Preparation of 5'-TCGACGT-3'-HEG-(CH$_2$)$_3$—OH(C-136)

5'-TCGACGT-3'-HEG-(CH$_2$)$_3$—SS—(CH$_2$)$_3$—OH(C-135) was synthesized analogously to C-116. To 10 mg (3.57 umol) of C-135 dissolved in 0.4 mL of 0.1 M sodium phosphate/150 mM sodium chloride/pH 7.5 buffer was added 5.7 mg (20 umol) of TCEP dissolved in 0.7 ml of the same buffer. The mixture was vortexed well and placed in a 40° C. water bath for 2 h. The thiol (C-136) was purified by RP—HPLC (Polymer Labs PLRP-S column) using an increasing gradient of acetonitrile in triethylammonium acetate buffer (TEAA)/pH 7.0 and used immediately in the next reaction.

C. Preparation of (5'-TCGACGT-3'-HEG)$_x$-Ficoll$_{400}$ (C-137)

To 5.5 mg (0.014 umol) of maleimido-Ficoll$_{400}$ dissolved in 0.7 ml of 0.1 M sodium phosphate/pH 6.66 was added 6.8 mg (2.5 umol) of C-136 dissolved in 3.45 mL of approximately 30% acetonitrile/TEAA/pH 7.0 buffer. The mixture was put on the shaker at RT overnight and the product was purified on a Superdex 200 column (Pharmacia). Calculations using the total weight of the isolated product and absorbance values at 260 nm showed the product contained, on average, approximately 185 oligonucleotides per mole of Ficoll. A second fraction containing a lower loading of oligonucleotides per mole of Ficoll was also obtained.

D. Activity of C-137

As shown in Table 26, the polysaccharide based CIC had striking activity in the cytokine response assays, in particular showing significant stimulation of IFN-α.

TABLE 26

| Compound stim | IFN-g (pg/ml) | | | | | | IFN-a (pg/ml) | | | | |
|---|---|---|---|---|---|---|---|---|---|---|---|
| | 28313 | 28314 | 28315 | 28316 | mean | ×4 | 28313 | 28314 | 28315 | 28316 | mean |
| cells alone | 1 | 9 | 11 | 11 | 8 | 32 | 31 | 122 | 100 | 98 | 88 |
| P6 | 1 | 38 | 47 | 309 | 99 | 395 | 31 | 130 | 122 | 134 | 104 |
| P7 | 1 | 11 | 12 | 20 | 11 | 43 | 31 | 176 | 107 | 121 | 109 |
| C-137 | 1 | 22 | 13 | 54 | 22 | 90 | 3612 | 5468 | 624 | 4000 | 3426 |
| SAC | 87 | 77 | 56 | 4000 | 1055 | 4220 | 346 | 192 | 114 | 1172 | 456 |

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

All patents, patent applications, and publications cited herein are hereby incorporated by reference in their entirety for all purposes to the same extent as if each individual publication, patent or patent application were specifically and individually indicated to be so incorporated by reference.

We claim:

1. A method of modulating an immune response in an individual comprising administering to an individual a linear chimeric immunomodulatory compound (CIC) in an amount sufficient to modulate an immune response in said individual, wherein the linear CIC comprises a structure $N_1$—$S_1$—$N_2$—$S_2$—$N_3$, wherein $N_1$, $N_2$, and $N_3$ are independently selected nucleic acid moieties comprising 3 to 7 bases, at least one of $N_1$, $N_2$, and $N_3$ has the sequence 5'-[(X)$_{0-2}$]TCG[(X)$_{2-4}$]-3', wherein each X is an independently selected nucleotide;

wherein $S_1$ is a non-nucleic acid spacer moiety covalently bound to $N_1$ and $N_2$; $S_2$ is a non-nucleic acid spacer moiety covalently bound to $N_2$ and $N_3$; $S_1$ and $S_2$ are the same or different; each of $S_1$ and $S_2$ comprises hexaethylene glycol (HEG), triethyleneglycol (TEG), propyl, butyl, or hexyl; and wherein said CIC has at least one immunomodulatory activity selected from the group consisting of (i) the ability to stimulate interferon-gamma (IFN-γ) production by human peripheral blood mononuclear cells and (ii) the ability to stimulate interferon-alpha (IFN-α) production by human peripheral blood mononuclear cells.

2. A method of modulating an immune response in an individual comprising administering to an individual a linear CIC in an amount sufficient to modulate an immune response in said individual, wherein the linear CIC is selected from the group consisting of:

5'-TCGTCGA-3'-HEG-5'-ACGTTCG-3'-HEG-5'-AGATGAT-3'

5'-TCGTCG-3'-HEG-5'-ACGTTCG-3'-HEG-5'-AGATGAT-3'

5'-TCGTCGA-3'-HEG-5'-TCGTCGA-3'-HEG-5'-TCGTCGA-3'

5'-TCGTCG-3'-HEG-5'-TCGTCG-3'-HEG-5'-TCGTCG-3'

5'-TCGTCG-3'-HEG-5'-AACGTT-3'-HEG-5'-AGATGAT-3'

5'-TCGTCG-3'-HEG-5'-ACGTTCG-3'-HEG-5'-AGATGAT-3'-TEG

HEG-5'-TCGTCG-3'-HEG-5'-ACGTTCG-3'-HEG-5'-AGATGAT-3'-TEG

5'-TCGTTTT-3'-HEG-5'-TCGTTTT-3'-HEG-5'-TCGTTTT-3'

5'-TCGTCGT-3'-HEG-5'-TCGTCGT-3'-HEG-5'-TCGTCGT-3'

5'-TCGAGAT-3'-HEG-5'-TCGAGAT-3'-HEG-5'-TCGAGAT-3'

5'-TCGTCGT-3'-HEG-5'-TGTCGTT-3'-HEG-5'-TGTCGTT-3'

5'-TCGTCGA-3'-HEG-5'-ACGTTCG-3'-HEG-5'-TCGTCGA-3'

5'-TCGTCGA-3'-HEG-5'-ACGTTCG-3'-HEG-5'-GGGGGG-3'

5'-TCGAACG-3'-HEG-5'-TCGAACG-3'-HEG-5'-TCGAACG-3'

5'-TCGACGT-3'-HEG-5'-TCGACGT-3'-HEG-5'-TCGACGT-3'

5'-TCGTCGA-3'-HEG-5'-AACGTTC-3'-HEG-5'-AGATGAT-3'

-continued
```
5'-TCGTCGA-3'-HEG-5'-AACGTTC-3'-HEG-5'-TCGTCGA-3'

5'-TCGTCGA-3'-HEG-5'-AGATGAT-3'-HEG-5'-ACGTTCG-3'

5'-TCGACTC-3'-HEG-5'-TCGAGCG-3'-HEG-5'-TTCTCTT-3'

5'-TCGTCGA-3'-HEG-5'-TCGTCGA-3'-HEG-3'-AGCTGCT-5'

5'-TCGAT-3'-HEG-5'-TCGAT-3'-HEG-5'-TCGAT-3'-HEG-
5'-TCGAT-3'

5'-TCGTCGA-3'-HEG-5'-TCGTCGA-3'-HEG-5'-AACGTTC-3'-
HEG-5'-AGAT-3'

5'-TCGACGT-3'-HEG-5'-TCGACGT-3'-HEG-5'-TCGACGT-3'-
HEG-5'-TCGACGT-3'

5'-TCGATTT-3'-HEG-5'-TCGATTT-3'-HEG-5'-TCGATTT-3'

5'-TCGCTTT-3'-HEG-5'-TCGCTTT-3'-HEG-5'-TCGCTTT-3'
and

5'-TCGGTTT-3'-HEG-5'-TCGGTTT-3'-HEG-5'-TCGGTTT-3'.
```

3. The method of claim 1, wherein said modulation comprises an increase in secretion of interferon-gamma (IFN-γ) or interferon-alpha (IFN-α) by blood cells from the individual.

4. The method of claim 1 wherein said modulation is determined by upregulation of immune-associated genes selected from the group consisting of interferon-alpha (IFN-α), interleukin-6 (IL-6), interleukin-12 (IL-12) p40, interferon gamma inducible protein 10 (IP-10) and interleukin-10 (IL-10).

5. The method of claim 1 wherein at least one nucleic acid moiety of the CIC comprises the sequence 5'-TCGACGT-3' or 5'-TCGTCGA-3'.

6. The method of claim 1 wherein the individual has a disorder selected from the group consisting of asthma, allergy, rhinitis, viral infection, bacterial infection, inflammatory disorder, idiopathic pulmonary fibrosis, and cancer.

* * * * *

UNITED STATES PATENT AND TRADEMARK OFFICE
CERTIFICATE OF CORRECTION

PATENT NO. : 8,003,115 B2
APPLICATION NO. : 11/891624
DATED : August 23, 2011
INVENTOR(S) : Karen L. Fearon et al.

It is certified that error appears in the above-identified patent and that said Letters Patent is hereby corrected as shown below:

On the Title Page

On page 4, item (56) under "Other Publications", column 1, line 17, replace "632" with -- 6324 --.

On page 4, item (56) under "Other Publications", column 2, line 62, replace ";" with -- : --.

In the Specification

At column 1, line 61, replace "*Naure*" with -- *Nature* --.

At column 4, lines 23-24, replace "5'-TCGA-3',5'-TCGACGT-3',5'-TCGTCGA-3'" with -- 5'-TCGA-3', 5'-TCGACGT-3', 5'-TCGTCGA-3' --.

At column 6, lines 30-31, replace "Cloning." with -- Cloning: --

At column 6, line 33, replace "jointly" with -- (jointly --.

At column 6, line 50, replace "Antibodies." with -- Antibodies: --.

At column 6, line 52, replace "(jointly," with -- (jointly --.

At column 7, lines 53-54, replace "*Hemophilus*" with -- *Haemophilus* --.

At column 8, line 49, replace "Formadley" with -- Fornadley --.

At column 15, line 1, replace ""Th2-type"" with -- "Th1-type" --.

At column 19, lines 48-49, replace "guanine-3'" with -- guanine-3'. --.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,003,115 B2

At column 25, line 51, replace "aformentioned" with -- aforementioned --.

At column 30, lines 32-33, replace "[2.3-d]" with -- [2,3-d] --.

At column 30, line 33, replace "[2.3-d]" with -- [2,3-d] --.

At column 30, lines 51-52, replace "fluoropyrimidin" with -- fluoropyrimidine --.

At column 30, line 60, replace "*Bioorg*" with -- *Bioorg.* --.

At column 35, lines 42-43, replace "tetraminobenzene" with -- tetraaminobenzene --.

At column 35, line 43, replace "heptaminobetacyclodextrin" with -- heptaaminobetacyclodextrin --.

At column 35, line 45, replace "tetraminopentaerythritol" with -- tetraaminopentaerythritol --.

At column 37, line 55, replace "Framington" with -- Framingham --.

At column 38, lines 34-35, replace "$HOCH_2CH_2—O—(CH_2CH_2O)_nCH_2CH_2OH$" with -- $HOCH_2CH_2O(CH_2CH_2O)_nCH_2CH_2OH$ --.

At column 38, line 55, replace "Framington," with -- Framingham, --.

At column 39, line 14, replace "Horner" with -- Homer --.

At column 39, line 18, replace "Novoto," with -- Novato, --.

At column 39, line 23, replace "Technoklgy" with -- Technology --.

At column 42, line 24, replace "maleiamide," with -- maleimide, --.

At column 42, line 34, replace "Rockford, Ill." with -- Rockford, IL --.

At column 46, line 60, replace "β-lactoglobin" with -- β-lactoglobulin --.

At columns 47-48, line 43, replace "topomyosin" with -- tropomyosin --.

At columns 49-50, line 35, replace "*Penicillinium*" with -- *Penicillium* --.

At column 49, line 41, replace "*Hemophilus*" with -- *Haemophilus* --.

At column 52, line 1, replace "hydrizine," with -- hydrazine, --.

At column 52, line 38, replace "Analogues. A" with -- Analogues: A --.

CERTIFICATE OF CORRECTION (continued)
U.S. Pat. No. 8,003,115 B2

At column 56, lines 51-52, replace "polyisohexlcyanoacrylate" with -- polyisohexylcyanoacrylate --.

At column 57, line 21, replace "(ISCOMS)" with -- (ISCOMs) --.

At column 64, line 12, replace "Th2-type" with -- Th1-type --.

At column 64, line 65, replace "Th2-type" with -- Th1-type --.

At column 69, line 53, replace "5'-TCGTCGA-3" with -- 5'-TCGTCGA-3' --.

At column 81, line 15, replace "C." with -- C --.

At column 81, line 34, replace "Rockford, Ill." with -- Rockford, IL --.

At column 81, line 52, replace "Rockford, Ill.," with -- Rockford, IL, --.

At column 82, line 4, replace "C." with -- C --.

At column 84, line 11, replace "Rockford, Ill." with -- Rockford, IL --.

At column 84, line 49, replace "Rockford, Ill." with -- Rockford, IL --.

At column 84, line 58, replace "Rockford, Ill." with -- Rockford, IL --.

At column 87, line 1, replace "C." with -- C --.

At column 87, line 7, replace "C." with -- C --.

At column 91, line 67, replace "at lest" with -- at least --.

At columns 97-98, line 12, replace "IFN-g" with -- IFN-γ --.

At columns 97-98, line 12, replace "IFN-a" with -- IFN-α --.

At columns 101-102, line 15, replace "IFN-g" with -- IFN-γ --.

At columns 101-102, line 15, replace "IFN-a" with -- IFN-α --.

At column 105, line 39, replace "isoflorine" with -- isoflurane --.

At column 105, line 44, replace "C." with -- C --.

At column 105, line 54, replace "syber green" with -- sybr green --.

At column 106, line 36, replace "C." with -- C --.

CERTIFICATE OF CORRECTION (continued)
U.S. Pat. No. 8,003,115 B2

At column 108, line 41, replace "Th2-type" with -- Th1-type --.

At column 108, line 67, replace "C." with -- C --.

At column 110, line 27, replace "#NPO322)" with -- #NP0322) --.

At column 113, line 39, replace "IFN-g" with -- IFN-γ --.

At column 114, line 39, replace "IFN-g" with -- IFN-α --.

At column 115, line 2, replace "IFN-g" with -- IFN-γ --.

At column 116, line 2, replace "IFN-g" with -- IFN-α --.

At columns 115-116, line 28, replace "IFN-g" with -- IFN-γ --.

At columns 115-116, line 28, replace "IFN-a" with -- IFN-α --.

At column 117, line 21, replace "–OH" with -- –SH --.

At column 118, line 22, replace "polysaccaride" with -- polysaccharide --.

At columns 117-118, line 26, replace "IFN-g" with -- IFN-γ --.

At columns 117-118, line 26, replace "IFN-a" with -- IFN-α --.